United States Patent [19]

Takatani et al.

[11] Patent Number: 5,561,147

[45] Date of Patent: Oct. 1, 1996

[54] PYRIDINE DERIVATIVES, THEIR PRODUCTION AND USE

[75] Inventors: Muneo Takatani, Kyoto; Taketoshi Saijo, Ikeda; Kiminori Tomimatsu, Minoo, all of Japan

[73] Assignee: Takeda Chemical Industries, Ltd., Osaka, Japan

[21] Appl. No.: 455,170

[22] Filed: May 31, 1995

Related U.S. Application Data

[62] Division of Ser. No. 334,221, Nov. 4, 1994, Pat. No. 5,457,106, which is a division of Ser. No. 81,181, Jun. 24, 1993, Pat. No. 5,389,658, which is a division of Ser. No. 880,641, May 7, 1992, Pat. No. 5,246,948.

[30] Foreign Application Priority Data

May 10, 1991 [JP] Japan ................... 3-105691

[51] Int. Cl.$^6$ ............. A61K 31/42; C02D 473/02
[52] U.S. Cl. ............. 514/340; 546/15; 546/271.4; 546/271.7
[58] Field of Search ............... 546/275; 514/340

[56] References Cited

U.S. PATENT DOCUMENTS

| | | |
|---|---|---|
| 3,687,959 | 8/1972 | Zielinski . |
| 4,514,408 | 4/1985 | Nisato et al. . |
| 4,691,017 | 9/1987 | Ezer et al. . |
| 4,711,961 | 12/1987 | Welter et al. . |
| 4,713,388 | 12/1987 | Ezer et al. . |
| 4,786,644 | 11/1988 | Glamkowski et al. . |
| 4,833,134 | 5/1989 | Kishimoto et al. . |
| 4,923,858 | 5/1990 | Engel et al. . |
| 5,036,083 | 7/1991 | Broneau . |
| 5,260,316 | 11/1993 | Van Duzer . |
| 5,270,309 | 12/1993 | Shiraishi et al. ............ 514/229.8 |
| 5,308,844 | 5/1994 | Rieu et al. ............ 514/230.5 |

FOREIGN PATENT DOCUMENTS 2034712   6/1980   United Kingdom .

OTHER PUBLICATIONS

Chemical Abstracts, vol. 85, No. 14, Oct. 4, 1976, p. 325, Abstract 99178d.

Chemical Abstracts, vol. 61, No. 1, Jul. 1, 1964, Abstract 638g.

*Primary Examiner*—Johann Richter
*Assistant Examiner*—John Peabody
*Attorney, Agent, or Firm*—Foley & Lardner

[57] ABSTRACT

There is disclosed a pharmaceutical composition for providing antiinflammatory, antipyretic, analgesic, antiallergic, immunosuppressing or immunomodulating activity which comprises a pyridine derivative of the formula (I):

$$R-X-A-N\begin{matrix}R_3\\ \diagdown\\ C-R_4\\ \diagup\\ Y\end{matrix}\qquad (I)$$

wherein R is an optionally substituted pyridine ring, X is a oxygen atom or $-S(O)_n-$, wherein n is 0, 1 or 2, A is a bivalent $C_{1-15}$ hydrocarbon residue whose branched moiety may have a substituent, Y is an oxygen or sulfur atom, $R_3$ is a hydrogen atom or an optionally substituted hydrocarbon residue, $R_4$ is an optionally substituted hydrocarbon residue or an optionally substituted monocyclic or bicyclic heterocyclic group, $R_3$ and $R_4$ may be joined together with the carbamoyl group or the thiocarbamoyl group to which they are attached to form an optionally substituted heterocyclic group, or $R_3$ or $R_4$ may be independently attached to A to form a ring, or a pharmaceutically acceptable salt or solvate thereof, and a pharmaceutically acceptable carrier or diluent.

5 Claims, No Drawings

PYRIDINE DERIVATIVES, THEIR PRODUCTION AND USE

This application is a division of application Ser. No. 08/334,221 filed Nov. 4, 1994 now U.S. Pat. No. 5,457,106 which is a division application of Ser. No. 08/081,181, filed Jun. 24, 1993 now U.S. Pat. No. 5,389,658 which is a division of application Ser. No. 07/880,641 filed May 7, 1992 now U.S. Pat. No. 5,246,948.

FIELD OF THE INVENTION

The present invention relates to pyridine derivatives which are useful as a medicament, their production and use.

BACKGROUND OF THE INVENTION

Treatment of autoimmune diseases such as rheumatoid arthritis and the like has been carried out by symptomatic therapy in which inflammation is relieved by a non-steroidal antiinflammatory drug (NSAID). The NSAID's are classified into acidic antiinflammatory drugs and basic antiinflammatory drugs.

On the other hand, recently, more attention has been paid to causal therapy in which immunopathy is improved by immunomodulatory activity. Examples of drugs used for causal therapy include D-penicillamine, levamisole, lobenzarit and the like.

Most of these NSAID's are acidic antiinflammatory drugs represented by aspirin, indomethacin and the like. They have disadvantage of causing serious side effects such as a stomach ulcer and there are difficulties in using them continuously for a long period for time. Further, although basic antiinflammatory drugs have strong analgesic activity, they have weak antiinflammatory action and therefore they are unsuitable for chronic diseases.

Furthermore, immunomodulators are insufficient in their pharmacological effects, side effects, toxicity and the like. Thus, it is desired to develop better drugs which are suitable for both symptomatic and causal therapy.

Recently, adhesion protein [e.g., intercellular adhesion molecule (ICAM)] inhibitors which inhibit infiltration of inflammatory cells or block attachment of immunocytes which participate in antigen or cell recognition have been noted [Masayuki Miyasaka, Jikken-Igaku, 9, 289 (1991); D. L. Thiele and P. E. Lipsky, Immunology Today, 10, 375 (1989)]. There are possibilities that these drugs inhibit or mitigate inflammation by a mechanism different from the conventional one. Therefore, such drugs are expected to be antiinflammatory drugs, antiallergic drugs or immunosuppressants of a new generation.

OBJECTS OF THE INVENTION

The main object of the present invention is to provide novel drugs which have immunomodulatory activity or adhesion protein expression inhibitory activity as well as improved antiinflammatory activity, antipyretic activity and analgesic activity.

Compounds having a structure similar to that of the compounds in the present invention have been disclosed as starting materials for synthesis of cephems in EP-A-256542, JP-A 61-194794 and JP-A 62-148377. Further, N-[2-(4-pyridylthio)-ethyl]acetamide and N-[2-(4-pyridylsulfonyl)-ethyl]acetamide has been disclosed in Tr. Leninger. Khim.-Farmatseut. Inst., 1962 (16), 17–20 [Chem. Abstr. 61, 638g].

However, there is no disclosure of biological activities of these compounds.

SUMMARY OF THE INVENTION

The present inventors have synthesized and studied various pyridine derivatives having substituents. As a result, it has been found that a specific class of pyridine derivatives has excellent antiinflammatory activity, antipyretic activity, analgesic activity, immunomodulatory activity, antiallergic activity and adhesion protein expression inhibitory activity.

That is, according to the present invention, there are provided:

1) A pharmaceutical composition for providing antiinflammatory, antipyretic, analgesic, antiallergic, immunosuppressing or immunomodulating activity which comprises a pyridine derivative of the formula (I):

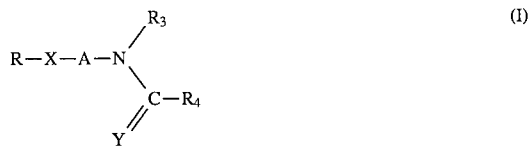

wherein R is an optionally substituted pyridine ring, X is a oxygen atom or $-S(O)_n-$, wherein n is 0, 1 or 2, A is a bivalent $C_{1-15}$ hydrocarbon residue whose branched moiety may have a substituent, Y is an oxygen or sulfur atom, $R_3$ is a hydrogen atom or an optionally substituted hydrocarbon residue, $R_4$ is an optionally substituted hydrocarbon residue or an optionally substituted monocyclic or bicyclic heterocyclic group, $R_3$ and $R_4$ may be joined together with the carbamoyl group or the thiocarbamoyl group to which they are attached to form an optionally substituted heterocyclic group or $R_3$ or $R_4$ may be independently attached to A to form a ring, or a pharmaceutically acceptable salt or solvate thereof, and a pharmaceutically acceptable carrier or diluent;

2) A pyridine derivative of the formula (II):

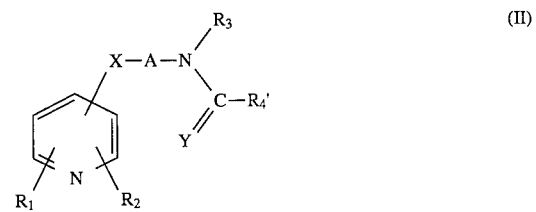

wherein $R_1$ and $R_2$ are the same or different and are a hydrogen atom, a halogen atom, a lower alkyl group, a lower alkenyl group, a lower alkoxy group, hydroxy group, nitro group, cyano group, amino group, carbamoyl group, an acylamino group, a lower alkylamino group, a lower alkenylamino or an aralkylamino group, X is an oxygen atom or $-S(O)_n-$, wherein n is 0, 1 or 2, A is a bivalent $C_{1-15}$ hydrocarbon residue whose branched moiety may have a substituent, Y is an oxygen or sulfur atom, $R_3$ is a hydrogen atom or an optionally substituted hydrocarbon residue, $R_4'$ is (1) a $C_{2-30}$ alkyl group, (2) a $C_{2-30}$ alkenyl group, (3) a lower alkyl group substituted with a halogen atom, an aryl group or a heterocyclic group, (4) a lower alkenyl group substituted with a halogen atom or a heterocyclic group, (5) an optionally substituted aralkyl group, (6) an optionally substituted aryl group or (7) an optionally substituted monocyclic or bicyclic heterocyclic group, or a salt or solvate thereof;

3) A pyridine derivative of the formula (III):

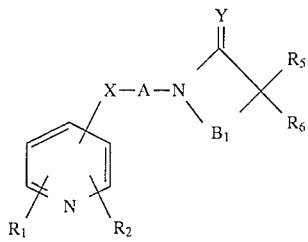 (III)

wherein $R_1$ and $R_2$ are the same or different and are a hydrogen atom, a halogen atom, a lower alkyl group, a lower alkenyl group, a lower alkoxy group, hydroxy group, nitro group, cyano group, amino group, carbamoyl group, an acylamino group, a lower alkylamino group, a lower alkenylamino group or an aralkylamino group, X is an oxygen atom or —S(O)$_n$—, wherein n is 0, 1 or 2; A is a bivalent $C_{1-15}$ hydrocarbon residue whose branched moiety may have a substituent, Y is an oxygen or sulfur atom, $R_5$ and $R_6$ are the same or different and are a hydrogen atom, a lower alkyl group, a lower alkenyl group, a halogeno lower alkyl group, a halogeno lower alkenyl group, an optionally substituted aralkyl group or an optionally substituted aryl group, or $R_5$ and $R_6$ are joined to form a group of the formula:

wherein $R_7$ and $R_8$ are the same or different and are a hydrogen atom, a lower alkyl group, a lower alkenyl group, a halogeno lower alkyl group, a halogeno lower alkenyl group, an optionally substituted aralkyl group, an optionally substituted aryl group or an optionally substituted monocyclic or a bicyclic heterocyclic group, or $R_7$ and $R_8$ are linked together to form a ring, $B_1$ is —(CH$_2$)$_p$—, wherein p is an integer of 1 to 4, or a group of the formula:

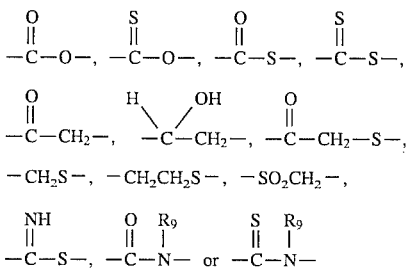

wherein $R_9$ is a hydrogen atom, an optionally substituted lower alkyl, lower alkenyl or aralkyl group, or a salt or solvate thereof, 4) A pyridine derivative of the formula (IV):

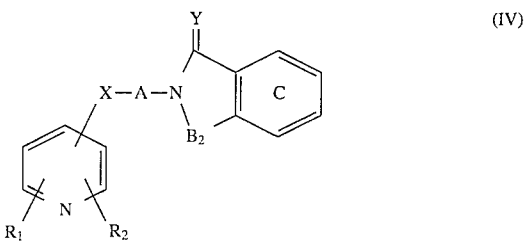 (IV)

wherein $R_1$ and $R_2$ are the same or different and are a hydrogen atom, a halogen atom, a lower alkyl group, a lower alkenyl group, a lower alkoxy group, hydroxy group, nitro group, cyano group, amino group, carbamoyl group, an acylamino group, a lower alkylamino group, a lower alkenylamino group or an aralkylamino group, X is an oxygen atom or —S(O)$_n$—, wherein n is 0, 1 or 2, A is a bivalent $C_{1-15}$ hydrocarbon residue whose branched moiety may have a substituent, Y is an oxygen or sulfur atom, a group of the formula:

is an optionally substituted benzene ring, $B_2$ is —(CH$_2$)$_p$—, wherein p is an integer of 1 to 4, or a group of the formula:

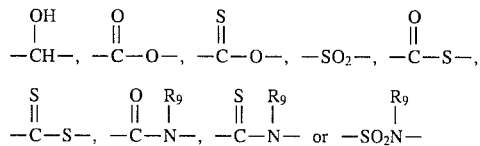

wherein $R_9$ is a hydrogen atom, an optionally substituted lower alkyl, lower alkenyl or aralkyl group, or a group of the formula:

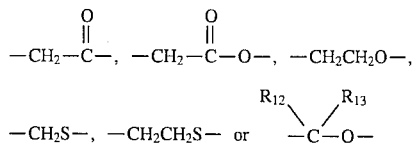

wherein $R_{12}$ and $R_{13}$ are the same or different and are a hydrogen atom, a lower alkyl group, a lower alkenyl group, a halogeno lower alkyl group, a halogeno lower alkenyl group, an optionally substituted aralkyl group or an aryl group, or $R_{12}$ and $R_{13}$ may be linked together to form a ring, or a salt or solvate thereof, and 5) A pyridine derivative of the formula (V):

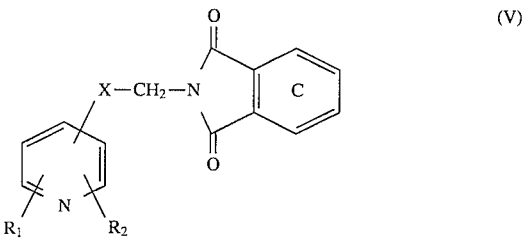 (V)

wherein $R_1$ and $R_2$ are the same or different and are a hydrogen atom, a halogen atom, a lower alkyl group, a lower alkenyl group, a lower alkoxy group, hydroxy group, nitro group, cyano group, amino group, carbamoyl group, an acylamino group, a lower alkylamino group, a lower alkenylamino group or an aralkylamino group, X is an oxygen atom or —S(O)$_n$—, wherein n is 0, 1 or 2, a group of the formula:

is an optionally substituted benzene ring, or a salt or solvate thereof.

DETAILED DISCLOSURE OF THE INVENTION

In the formula (I), the optionally substituted pyridine ring represented by R may be substituted by the same or different 1 to 4, preferably 1 to 2 substituents such as a halogen atom, a lower alkyl group, a lower alkenyl group, a lower alkoxy group, hydroxy group, nitro group, cyano group, amino group, carbamoyl group, an acylamino group, a lower alkylamino group, a lower alkenylamino group or an aralkylamino group.

Examples of the hydrocarbon residue represented by A in the above formula include a group of the formula:

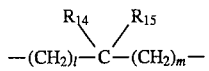

wherein l and m each are 0 or an integer of 1 to 6, $R_{14}$ and $R_{15}$ are a hydrogen atom, a lower alkyl group, a lower alkenyl group, an optionally substituted aralkyl group or an optionally substituted aryl group, and $R_{14}$ and $R_{15}$ may be linked together with the adjacent carbon atom to form a 3 to 6 membered ring, and $R_{14}$ or $R_{15}$ may be linked to $R_3$ or $R_4$ to form a ring, or a group of the formula:

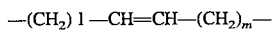

—(CH$_2$) l —CH=CH—(CH$_2$)$_m$— wherein l and m are as defined above.

Examples of the optionally substituted hydrocarbon residue of $R_3$ and $R_4$ include (1) a $C_{2-30}$ alkyl group, (2) a $C_{2-30}$ alkenyl group, (3) a lower alkyl group substituted with a halogen atom, an aryl group or a heterocyclic group, (4) a lower alkenyl group substituted with a halogen atom, an aryl group or a heterocyclic group, (5) an optionally substituted aralkyl group and (6) an optionally substituted aryl group.

The monocyclic heterocyclic group represented by $R_4$, $R_7$ and $R_8$ is a 5 to 6 membered monocyclic aromatic heterocyclic group or a saturated or unsaturated monocyclic non-aromatic heterocyclic group having 1 to 4 hetero atoms selected from the group consisting of oxygen, sulfur and nitrogen as its ring constituent atoms. Preferred examples thereof include thienyl (e.g., 2-thienyl, 3-thienyl, etc.), furyl (e.g., 2-furyl, 3-furyl, etc.), pyranyl, 2H-pyrrolyl, pyrrolyl (e.g., 2-pyrrolyl, 3-pyrrolyl, etc.), imidazolyl (e.g., 2-imidazolyl, 4-imidazolyl, etc.), pyrazolyl (e.g., 3-pyrazolyl, 4-pyrazolyl, etc.), isothiazolyl (e.g., 3-isothiazolyl, 4-isothiazolyl, etc.), isoxazolyl (e.g., 3-isoxazolyl, 4-isoxazolyl, etc.), pyridyl (e.g., 2-pyridyl, 3-pyridyl, 4-pyridyl, etc.), pyrazinyl, pyrimidinyl (e.g., 2-pyrimidinyl, 4-pyrimidinyl, etc.), pyridazinyl (e.g., 3-pyridazinyl, 4-pyridazinyl, etc.) and the like. The above monocyclic heterocyclic group may be partially saturated. Examples of the partially saturated monocyclic heterocyclic group include pyrrolidinyl (e.g., 2-pyrrolidinyl, 3-pyrrolidinyl, etc.), pyrrolinyl (e.g., 2-pyrrolin-3-yl, etc.), imidazolinyl (2-imidazolin-4-yl, etc.), piperidyl (e.g., 2-piperidyl, 3-piperidyl, etc.), piperazinyl (e.g., 2-piperazinyl, etc.), morpholinyl (e.g., 3-morpholinyl, etc.) and the like.

The above monocyclic heterocyclic group represented by $R_4$, $R_7$ and $R_8$ may have 1 to 4 substituents such as a halogen atom, a lower alkyl group, a lower alkenyl group, a lower alkoxy group, nitro group, cyano group, hydroxy group, a lower alkoxycarbonyl group, carboxyl group, carbamoyl group, a lower alkylcarbamoyl group, a lower alkenylcarbamoyl group or the like.

The bicyclic heterocyclic group represented by $R_4$, $R_7$ and $R_8$ is a condensed ring formed by a 5 to 6 membered aromatic heterocyclic group or a saturated or unsaturated non-aromatic heterocyclic group having 1 to 4 hetero atoms selected from the group consisting of oxygen, sulfur and nitrogen as ring constituent atoms. Preferred examples thereof include isobenzofuranyl (e.g., 1-benzofuranyl, etc.), chromenyl (e.g., 2H-chromen-3-yl, etc.), benzothienyl (e.g., 2-benzothienyl, etc.), indolizinyl (e.g., 2-indolizinyl, 3-indolizinyl, etc.), isoindolyl (e.g., 1-isoindolyl, etc.), 3H-indolyl (e.g., 3H-indol-2-yl, etc.), indolyl (e.g., 2-indolyl, etc.), 1H-indazolyl (e.g., 1H-indazol-3-yl, etc.), purinyl (e.g., 8-purinyl, etc.), isoquinolyl (e.g., 1-isoquinolyl, 3-isoquinolyl, etc.), quinolyl (2-quinolyl, 3-quinolyl, etc.), phthalazinyl (e.g., 1-phthalazinyl, etc.), naphthylidinyl (e.g., 1,8-naphthylidin-2-yl, etc.), quinoxalinyl (e.g., 2-quinoxalinyl, etc.), quinazolinyl (e.g., 2-quinazolinyl, etc.), cinnolinyl (e.g., 3-cinnolinyl, etc.) and the like. The above bicyclic heterocyclic group may be partially saturated. Examples of the partially saturated bicyclic heterocyclic group include isochromanyl (e.g., 3-isochromanyl, etc.), indolinyl (e.g., 2-indolinyl, etc.), isoindolinyl (e.g., 1-isoindolinyl, etc.), 1,2,3,4-tetrahydro-2-quinolyl, 1,2,3,4-teraydro-3-isoquinolyl and the like.

The above bicyclic heterocyclic group represented by $R_4$, $R_7$ and $R_8$ may have 1 to 4 substituents which are the same as those of the above monocyclic heterocyclic group represented by $R_4$, $R_7$ and $R_8$.

Examples of the heterocyclic group formed by $R_3$ and $R_4$ together with the carbamoyl group or the thiocarbamoyl group to which they are attached include a group of the formula (VI):

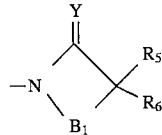

(VI)

wherein Y is an oxygen or sulfur atom; $R_5$ and $R_6$ are the same or different and are a hydrogen atom, a lower alkyl group, a lower alkenyl group, a halogeno lower alkyl group, a halogeno lower alkenyl group, an optionally substituted aralkyl group or an optionally substituted aryl group, or $R_5$ and $R_6$ are joined to form a group of the formula:

$R_7$ and $R_8$ are the same or different and are a hydrogen atom, a lower alkyl group, a lower alkenyl group, a halogeno lower alkyl group, a halogeno lower alkenyl group, an optionally substituted aralkyl group, an optionally substituted aryl group or an optionally substituted monocyclic or bicyclic heterocyclic group, or $R_7$ and $R_8$ are linked together to form a ring, $B_1$ is —$(CH_2)_p$—, wherein p is an integer of 1 to 4, or a group of the formula:

$$-\overset{O}{\underset{\|}{C}}-O-,\ -\overset{S}{\underset{\|}{C}}-O-,\ -\overset{O}{\underset{\|}{C}}-S-,\ -\overset{S}{\underset{\|}{C}}-S-,$$

$$-\overset{O}{\underset{\|}{C}}-CH_2-,\ -\overset{H}{\underset{\diagdown}{C}}\overset{OH}{\underset{\diagup}{\phantom{C}}}-CH_2-,\ -\overset{O}{\underset{\|}{C}}-CH_2-S-,$$

$$-CH_2S-,\ -CH_2CH_2S-,\ -SO_2CH_2-,$$

$$-\overset{NH}{\underset{\|}{C}}-S-,\ -\overset{O}{\underset{\|}{C}}-\overset{R_9}{\underset{|}{N}}-\ or\ -\overset{S}{\underset{\|}{C}}-\overset{R_9}{\underset{|}{N}}-$$

wherein $R_9$ is a hydrogen atom, an optionally substituted lower alkyl, lower alkenyl or aralkyl group, or $B_1$ is a group of the formula:

$$\underset{B_2}{\overset{Y}{\underset{\diagdown}{\overset{\|}{-N}}}}\diagdown\overset{\phantom{C}}{\underset{\phantom{C}}{C}}\bigcirc \qquad (VII)$$

wherein Y is a oxygen or sulfur atom, a group of the formula $$\overset{C}{\bigcirc}$$

is an optionally substituted benzene ring, $B_2$ is —$(CH_2)_p$—, wherein p is an integer of 1 to 4, or a group of the formula:

$$-\overset{OH}{\underset{|}{CH}}-,\ -\overset{O}{\underset{\|}{C}}-O-,\ -\overset{S}{\underset{\|}{C}}-O-,\ -SO_2-,$$

$$-\overset{O}{\underset{\|}{C}}-S-,\ -\overset{S}{\underset{\|}{C}}-S-,\ -\overset{O}{\underset{\|}{C}}-\overset{R_9}{\underset{|}{N}}-,$$

$$-\overset{S}{\underset{\|}{C}}-\overset{R_9}{\underset{|}{N}}-\ or\ -SO_2\overset{R_9}{\underset{|}{N}}-$$

wherein $R_9$ is a hydrogen atom, an optionally substituted lower alkyl, lower alkenyl or aralkyl group, or $B_2$ is a group of the formula:

$$-CH_2-\overset{O}{\underset{\|}{C}}-,\ -CH_2-\overset{O}{\underset{\|}{C}}-O-,\ -CH_2CH_2O-,$$

$$-CH_2S-,\ -CH_2CH_2S-\ or\ -\overset{R_{12}}{\underset{R_{13}}{\overset{\diagdown}{\underset{\diagup}{C}}}}-O-$$

wherein $R_{12}$ and $R_{13}$ are the same or different and are a hydrogen atom, a lower alkyl group, a lower alkenyl group, a halogeno lower alkyl group, a halogeno lower alkenyl group, an optionally substituted aralkyl or aryl group, or $R_{12}$ and $R_{13}$ may be linked together to form a ring.

Examples of the substituent of the optionally substituted benzene ring of the formula:

$$\overset{C}{\bigcirc},$$

include a lower alkyl group, a lower alkenyl group, a halogeno lower alkyl group, a halogeno lower alkenyl group, an optionally substituted aralkyl group or an aryl group, a halogen atom, nitro group, cyano group, a lower alkoxy group, amino group, a lower alkylamino group, a lower alkenylamino group, an acylamino group, acyl group, carbamoyl group and the like. The benzene ring may be substituted with 1 to 4, preferably 1 to 2 substituents which are the same or different.

When $R_3$ and $R_4$ are independently attached to A to form a ring, A is a group of the formula:

$$-(CH_2)_l-\overset{R_{14}}{\underset{R_{15}}{\overset{\diagdown}{\underset{\diagup}{C}}}}-(CH_2)_m-$$

wherein l, m, $R_{14}$ and $R_{15}$ are as defined above. Examples of a 3 to 6 membered ring formed by linkage between $R_{14}$ and $R_{15}$ included cyclopropyl, cyclobutyl, cyclopentyl, cyclohexyl and the like. Examples of the ring formed by linkage between $R_{14}$ or $R_{15}$ and $R_3$ include groups of the formulas:

$$-\left\langle\begin{array}{c}(CH_2)_q\\(CH_2)_r\end{array}\right.\overset{Y}{\underset{\diagup}{\overset{\|}{NC-R_4}}},\ -CH_2-\left\langle\begin{array}{c}(CH_2)_q\\(CH_2)_r\end{array}\right.\overset{Y}{\underset{\diagup}{\overset{\|}{NC-R_4}}},$$

$$and\ -CH_2CH_2-\left\langle\begin{array}{c}(CH_2)_q\\(CH_2)_r\end{array}\right.\overset{Y}{\underset{\diagup}{\overset{\|}{NC-R_4}}}$$

wherein q and r are 2 or 3, respectively and $R_4$ and Y are as defined above.

Examples of the ring formed by linkage between $R_{14}$ or $R_{15}$ and $R_4$ include groups of the formulas:

$$-\left\langle\begin{array}{c}(CH_2)_s\\(CH_2)_tC\\\|\\Y\end{array}\right.\overset{\phantom{x}}{\underset{\diagup}{N-R_3}},\ -CH_2-\left\langle\begin{array}{c}(CH_2)_s\\(CH_2)_tC\\\|\\Y\end{array}\right.\overset{\phantom{x}}{\underset{\diagup}{N-R_3}},$$

$$and\ -CH_2CH_2-\left\langle\begin{array}{c}(CH_2)_s\\(CH_2)_tC\\\|\\Y\end{array}\right.\overset{\phantom{x}}{\underset{\diagup}{N-R_3}}$$

wherein s and t are 1 or 2, respectively and $R_3$ and Y are as defined above.

Examples of the ring formed by linkage between $R_7$ and $R_8$ or between $R_{12}$ and $R_{13}$ include a monocyclic hydrocarbon residue having 3 to 6 carbon atoms such as cyclopropyl, cyclobutyl, cycloheptyl, cyclohexyl and the like.

Examples of the "halogen atom" in each group of the above formulas include fluoro, bromo, chloro and iodo.

Examples of the "lower alkyl group" in the each group of the above formulas include straight-chain or branched chain alkyl groups having 1 to 6 carbon atoms such as methyl, ethyl, propyl, isopropyl, butyl, isobutyl, sec-butyl, tert-butyl, pentyl, hexyl and the like.

Examples of the "lower alkenyl group" in each group of the above formulas include alkenyl groups having 2 to 6 carbon atoms such as vinyl, allyl, 2-butenyl, 3-butenyl and the like.

Examples of the substituent of the optionally substituted lower alkyl and lower alkenyl groups represented by $R_9$ include a halogen atom, a lower alkoxy group, hydroxy group, a lower alkoxycarbonyl group, carboxyl group, carbamoyl group, a lower alkylcarbamoyl group, pyridylthio group and the like.

Examples of the "lower alkoxy group" in each group of the above formulas include straight-chain or branched-chain alkoxy groups having 1 to 6 carbon atoms such as methoxy, ethoxy, propoxy, isopropoxy, butoxy, pentoxy and the like.

Examples of the "acylamino group" in each group of the above formulas include alkanoylamino groups and benzamide groups having 2 to 6 carbon atoms such as acetamide, propanoylamino, butyrylamino, pivaloylamino and the like Examples of the "lower alkylamino group" in each group of the above formulas include alkylamino groups whose alkyl moiety has 1 to 6 carbon atoms (e.g., methylamino, ethylamino, propylamino, butylamino, etc.), N,N-dialkylamino groups whose alkyl moieties have 1 to 6 carbon atoms, respectively (e.g., dimethylamino, diethylamino, dibutylamino, methylethylamino, etc.), groups wherein the alkyl moieties of the dialkyl moiety are joined to form a 5 or 6 membered ring structure (e.g., pyrrolidinyl, piperidino, etc.) and the like.

Examples of the "lower alkenylamino group" in each group of the above formulas include alkenylamino and N,N-dialkenylamino groups containing the "lower alkenyl groups" as exemplified above.

Examples of the "aralkylamino group" in each group in the above formulas include phenyl lower alkylamino groups whose alkyl moiety has 1 to 6 carbon atoms (e.g., benzylamino, phenethylamino, 3-phenylpropylamino, 4-phenylbutylamino, etc.), naphthyl lower alkylamino groups whose alkyl moiety has 1 to 6 carbon atoms [e.g., (1-naphthyl)methylamino, 2-(1-naphthyl)ethylamino, 2-(2-naphthyl)ethylamino, etc.], N,N-bis(phenyl lower alkyl)amino groups whose each alkyl moiety has 1 to 6 carbon atoms [e.g., dibenzylamino, diphenethylamino, bis(3-phenylpropyl)amino, etc.], N,N-bis (naphthyl lower alkyl)amino groups whose each alkyl moiety has 1 to 6 carbon atoms [e.g., bis[(1-naphthyl)methyl]amino, bis[(1-naphthyl)ethyl] amino, etc.] and the like.

The phenyl moiety of the phenyl lower alkylamino group and the N,N-bis(phenyl lower alkyl)amino group as well as the naphthyl moiety of the naphthyl lower alkylamino group and the N,N-bis(naphthyl lower alkyl)amino group may have 1 to 4 substituents such as a halogen atom, a lower alkyl group, a lower alkenyl group, a lower alkoxy group, nitro group, cyano group, hydroxy group, a lower alkoxycarbonyl group, carbamoyl group, a lower alkylcarbamoyl group, a lower alkenylcarbamoyl group and the like.

Examples of the "halogen atom", the "lower alkyl group" and the "lower alkoxy group" include the same groups as the "halogen atom", the "lower alkyl group", the "lower alkenyl group" and the "lower alkoxy group" in the groups of the above formulas, respectively.

Examples of the "lower alkenylcarbamoyl" group include N-alkenylcarbamoyl groups and N,N-dialkenylcarbamoyl groups containing the "lower alkenyl group" as exemplified above.

Examples of the lower alkoxycarbonyl group include alkoxycarbonyl groups having about 1 to 6 carbon atoms such as methoxycarbonyl, ethoxycarbonyl, propoxycarbonyl, butoxycarbonyl and the like. Examples of the lower alkylcarbamoyl group include N-alkylcarbamoyl groups whose alkyl moiety has 1 to 6 carbon atoms (e.g., methylcarbamoyl, ethylcarbamoyl, propylcarbamoyl, butylcarbamoyl, etc.), N,N-dialkylcarbamoyl groups whose each alkyl moiety has 1 to 6 carbon atoms (e.g, dimethylcarbamoyl, diethylcarbamoyl, dibutylcarbamoyl, methylethylcarbamoyl, etc.) and the like.

Examples of the "lower alkenylcarbamoyl" group include N-alkenylcarbamoyl groups and N,N-dialkenylcarbamoyl groups containing the "lower alkenyl group" as exemplified above.

Examples of the "optionally substituted aralkyl group" in each group of the above formulas include phenyl lower alkyl groups whose alkyl moiety has 1 to 6 carbon atoms (e.g., benzyl, phenethyl, 3-phenylpropyl, 4-phenylbutyl, etc.), naphtyl lower alkyl whose each alkyl moiety has 1 to 6 carbon atoms [e.g., (1-naphthyl)methyl, 2-(1-naphthyl)ethyl, 2-(2-naphthyl)ethyl, etc.] and the like. The phenyl moiety of the phenyl lower alkyl group and the naphthyl moiety of the naphthyl lower alkyl group may have 1 to 4 substituents such as a halogen atom, a lower alkyl group, a lower alkenyl, a lower alkoxy group, nitro group, cyano group, hydroxy group, a lower alkoxycarbonyl group, carbamoyl group, a lower alkylcarbamoyl group, a lower alkenylcarbamoyl group or the like. Examples of the halogen atom include fluoro, bromo, chloro and iodo. Examples of the lower alkyl group and the lower alkenyl groups include the same "lower alkyl group" and "lower alkenyl group" as exemplified above. Examples of the alkoxy group include straight-chain or branched-chain alkoxy groups having about 1 to 6 carbon atoms such as methoxy, ethoxy, propoxy, isopropoxy, butoxy, pentoxy and the like. Examples of the lower alkoxycarbonyl group include alkoxycarbonyl groups having about 1 to 6 carbon atoms such as methoxy carbonyl, ethoxycarbonyl, propoxycarbonyl, butoxycarbonyl and the like. Examples of the lower alkylcarbamoyl group include N-alkylcarbamoyl groups whose alkyl moiety has 1 to carbon atoms (e.g., methylcarbamoyl, ethylcarbamoyl, propylcarbamoyl, butylcarbamoyl, etc.), N,N-dialkylcarbamoyl groups whose each alkyl moiety has 1 to 6 carbon atoms (e.g., dimethylcarbamoyl, diethylcarbamoyl, dibutylcarbamoyl, methylethylcarbamoyl, etc.) and the like.

Examples of the "optionally substituted aryl group" in each group of the above formulas include aromatic monocyclic or bicyclic hydrocarbon residues such as phenyl, 1-naphthyl, 2-naphthyl, phenanthryl and the like. The aryl group may have 1 to 4, preferably 1 or 2 substituents such as a halogen atom, a lower alkyl group, a lower alkenyl group, a lower alkoxy group, nitro group, cyano group, oxo group, hydroxy group, amino group, an acylamino group, a lower alkoxycarbonyl group, carbamoyl group, a lower alkylcarbamoyl group, a lower alkenylcarbamoyl group or the like. Examples of the halogen atom include fluoro, bromo, chloro and iodo. Examples of the lower alkyl group include alkyl groups having 1 to 6 carbon atoms and examples of the lower alkenyl group include alkenyl groups having about 2 to 6 carbon atoms. As concrete examples of the alkyl group having 1 to 6 carbon atoms and the lower alkenyl group having 2 to 6 carbon atoms, there are such alkyl groups and alkenyl groups as exemplified above for the "lower alkyl group" and the "lower alkenyl group". Examples of the lower alkoxy group include alkoxy groups having 1 to 6 carbon atoms. Examples of the lower alkoxycarbonyl group include alkoxycarbonyl groups whose alkoxy moiety has 1 to 6 carbon atoms. Examples of the lower alkylcarbamoyl group include N-alkylcarbamoyl groups whose alkyl moiety has 1 to 6 carbon atoms and N,N-dialkylcarbamoyl groups whose each alkyl moiety has about 1 to 6 carbon atoms. As concrete examples of these groups, there are such groups as exemplified above for the lower alkoxy group, lower alkoxycarbonyl group and lower alkylcarbamoyl as the substituent of the phenyl moiety in the above aralkyl group. Examples of the "lower alkenylcarbamoyl group" include N-alkenylcarbamoyl groups and N,N-dialkenylcarbamoyl groups containing the "lower alkenyl group" as exemplified above. Examples of the aryl group having an oxo group include benzoquinonyl, naphthoquinolyl, anthraquinonyl and the like.

Examples of the "$C_{2-30}$ alkyl group" in the above each group include straight-chain or branched-chain alkyl groups having 2 to 30, preferably 2 to 10 carbon atoms (e.g., ethyl, propyl, butyl, pentyl, hexyl, heptyl, octyl, nonyl, decyl, undecyl, tridecyl, tetradecyl, pentadecyl, hexadecyl, heptadecyl, octadecyl, nonadecyl, icosanyl, henicosanyl, docosanyl, tricosanyl, tetracosanyl, pentacosanyl, hexacosanyl, heptacosanyl, octacosanyl, nonacosanyl, triacontanyl, farnesyl, dihydrophytyl, etc.), cycloalkyl groups having 3 to 8 carbon atoms (e.g., cyclopropyl, cyclobutyl, cyclopentyl, cyclohexyl, cycloheptyl, cyclooctyl, etc.), bicycloalkyl groups having 7 to 12 carbon atoms (e.g., norbornyl, bicyclo [2.2.2]octyl, bicyclo[3.3.1]nonyl, bicyclo[3.3.0]octyl, etc.), tricycloalkyl groups having 7 to 12 carbon atoms (e.g., adamantyl, etc.), bicyclic hydrocarbon residues in which a condensed ring is formed by 5 to 8-membered rings (e.g., perhydropentalenyl, perhydroindenyl, perhydroazulenyl, perhydrocyclopenta-cyclooctenyl, perhydronaphthyl, perhydrobenzocycloheptenyl, perhydrobenzocyclooctenyl, perhydroheptalenyl, perhydrocycloheptacyclooctenyl, etc.), tricyclic hydrocarbon residues in which a condensed ring is formed by 5 to 8 membered rings [e.g., perhydroindacenyl (as,s), perhydro-acenaphthylenyl, perhydrophenanthryl, perhydroanthryl, etc.] and the like.

Examples of the $C_{2-30}$ alkenyl group in the above each group include alkenyl groups having 2 to 30 carbon atoms (e.g., vinyl, allyl, 9-octadecenyl, etc.), cycloalkenyl groups having 5 to 8 carbon atoms (e.g., cyclopentenyl, cyclohexenyl, etc.), bicycloalkenyl groups having 7 to 12 carbon atoms [e.g., bicyclo[2.2.2]oct-2-enyl, etc.], tricycloalkenyl groups having about 7 to 12 carbon atoms, bicyclic hydrocarbon residues in which a condensed ring is formed by a benzene ring and a 5 to 8 membered ring [e.g., indanyl (e.g., 1-indanyl, 2-indanyl, etc.), indenyl (e.g., 1H-inden-1-yl, 1H-inden-2-yl, 1H-inden-3-yl, etc.), dihydronaphthyl (e.g., 1,2-dihydro-1-naphthyl, 1,2-dihydro- 2-naphthyl, etc.), tetrahydronaphthyl (e.g., 5,6,7,8 -tetrahydro-1-naphthyl, 5,6,7, 8-tetrahydro-2-naphthyl, etc.), 5H-benzocycloheptenyl (e.g., 5H-5-benzocycloheptenyl, 5H-8-benzocycloheptenyl, etc.), dihydro-5H-benzocycloheptenyl (e.g., 6,7-dihydro-5H-8-benzocycloheptenyl, etc.), tetrahydrobenzocyclooctenyl (e.g., 5,6,7,8-tetrahydro-9-benzocyclooctenyl, etc.), etc.], tricyclic hydrocarbon residues in which a condensed ring is formed by two benzene rings and a 5 to 8 membered ring [e.g., acenaphthenyl (e.g., 1-acenaphthenyl, etc.), tetrahydroanthryl (e.g., 1,2,3,4 -tetrahydro-1-anthryl, etc.), etc.] and the like.

As the "lower alkyl group substituted with a halogen atom, an aryl or a heterocyclic group", there are lower alkyl groups having 1 to 6 carbon atoms substituted with 1 to 3 halogen atoms, aryl groups and heterocyclic groups as exemplified above.

As the "lower alkenyl group substituted with a halogen atom, an aryl or a heterocyclic group", there are lower alkenyl groups having 2 to 6 carbon atoms substituted with 1 to 3 halogen atoms, aryl groups and heterocyclic groups as exemplified above.

The compound (I) forms a salt-such as an acid addition salt as well as a solvate. Examples of the acid to be used to form the acid addition salt of the compound (I) include inorganic acids (e.g., hydrochloric acid, hydrobromic acid, sulfuric acid, phosphoric acid, etc.) and organic acids (e.g, acetic acid, oxalic acid, methanesulfonic acid, maleic acid, fumaric acid, citric acid, tartaric acid, lactic acid, etc.).

Examples of the solvent to be used to form the solvate include methanol, ethanol, propanol, isopropanol, acetone, tetrahydrofuran, dioxane and the like.

The compound of the formula (I) can have an asymmetric carbon atom. When two kinds of stereoisomers of R-configuration and S-configuration exist, each isomer and the mixture thereof are included in the scope of the present invention.

Among the compounds of the formula (I), the compounds of the formulas (II) to (V) are novel.

In the compound of the formula (II), preferably, $R_1$ and $R_2$ are the same or different and a hydrogen atom, amino group or an acylamino group. X is preferably an oxygen or sulfur atom. A is preferably a bivalent $C_{1-6}$ hydrocarbon residue, more preferably, methylene, ethylene, propylene or butylene. $R_3$ is preferably a hydrogen atom, an optionally substituted aralkyl group or an optionally substituted aryl. Preferably, $R_4'$ is a $C_{2-30}$ alkyl group, a halogenoalkyl group, an optionally substituted aryl or an optionally substituted monocyclic or bicyclic heterocyclic group. Y is preferably an oxygen atom.

In the compounds of the formula (III), preferably, $R_1$ and $R_2$ are the same or different and are a hydrogen atom, amino group or an acyl amino group. More preferably, $R_1$ and $R_2$ are each hydrogen atom. X is preferably an oxygen or sulfur atom. A is preferably a bivalent $C_{1-6}$ hydrocarbon residue, more preferably, methylene, ethylene, propylene or butylene. Y is preferably an oxygen atom. $R_5$ and $R_6$ are the same or different and are a hydrogen atom or a lower alkyl group, or $R_5$ and $R_6$ are joined to form the group of the formula:

wherein $R_7$ and $R_8$ are the same and different and preferably are a hydrogen atom, a lower alkyl group, an optionally substituted aralkyl group, an optionally substituted aryl or an optionally substituted monocyclic or bicyclic heterocyclic group. $B_1$ is preferably —C(=O)—O—, —C(=O)—S—, —C(=O)—CH$_2$ or —C(=O)—NR$_9$—, more preferably, —C(=O)—S— or —C(=O)—NR$_9$—, wherein $R_9$ is as defined above.

In the compounds of the formula (IV), preferably, $R_1$ and $R_2$ are the same or different and are a hydrogen atom, amino group or an acylamino group. More preferably, $R_1$ and $R_2$ are each hydrogen atom. X is preferably an oxygen or sulfur atom. A is preferably a bivalent $C_{1-6}$ hydrocarbon residue, more preferably, methylene, ethylene, propylene or butylene. Y is preferably an oxygen atom. $B_2$ is preferably —(CH$_2$)$_p$—, —(HO—)CH—, —C(=O)—O—, —C(=S)—O—, —SO$_2$—, —C(=O)— NR$_9$— or —C(=S)—NR$_9$—, more preferably —CH$_2$—, —C(=O)—O—, —C(=S)—O—, —SO$_2$—, —C(=O)—NR$_9$— or —C(=S)—NR$_9$—, wherein $R_9$ is as defined above. $R_9$ is preferably a hydrogen atom or an optionally substituted lower alkyl group. The substituent of the optionally substituted lower alkyl group is preferably a pyridylthio group.

In the compounds of the formula (V), preferably, $R_1$ and $R_2$ are the same or different and are a hydrogen atom, amino group or an acylamino group. More preferably, $R_1$ and $R_2$ are each hydrogen atom. X is an oxygen or sulfur atom.

The specific examples of the pyridine derivative of the present invention are as follows:

4-[3-(N-Benzyl-N-trifluoroacetylamino)propylthio]pyridine hydrochloride,

4-[2-(Thianaphthene-2-carbonylamino)ethylthio]pyridine,
1,2-bis[N-[4-(4-Pyridylthio)butyl]-N-propyonylamino]benzene dihydrochloride,
4-[4-(5-Benzylidene-2,4-thiazolidinedione)butylthio]pyridine,
4-[4-[5-(4-Chlorobenzylidene)-2,4-thiazolidinedione]butylthio]pyridine,
4-[4-[5-(2-Thienylmethylene)-2,4-thiazolidinedione]butylthio]pyridine,
4-[4-(5-Propylmethylene-2,4-thiazolidinedione)butylthio]pyridine,
4-(5,5-Dimethyloxazolidine-2,4-dione)methylthiopyridine,
4-[4-[5-(4-Pyridyl)methylene-2,4-thiazolidinedione]butylthio]pyridine,
4-[4-[5-(3-Pyridyl)methylene-2,4-thiazolidinedione]butylthio]pyridine,
4-[4-(5-Nonylmethylene-2,4-thiazolidinedione)butylthio]pyridine hydrochloride,
3-[3-(4-Pyridylthio)propyl]-2H-1,3-benzoxazine-2 -thion-4(3H)-one,
3-[4-(4-Pyridylthio)butyl]quinazoline-2,4-(1H,3H)dione,
1,3-bis[4-(4-Pyridylthio)butyl]quinazoline-2,4-( 1H,3H)-dione,
3-[4-(4-Pyridylthio)butyl]-2H-1,3-benzoxazine-2 -thion-4(3H)-one,
4-Saccharinmethylthiopyridine,
4-Saccharinmethylthiopyridine hydrochloride,
1,3-bis[4-(2-Pyridylthio)butyl]quinazoline- 2,4(1H,3H)-dione,
1-(4-Pyridylthio)methyl-3-[4-(4-pyridylthio)butyl]quinazoline-2,4(1H,3H)-dione dihydrochloride,
1,3-bis[4-(4-Pyridylthio)butyl]quinazoline-2(1H)-thion-4(3H)-one dihydrochloride,
4-(Phthalimidomethylthio)pyridine, and
4-(Phthalimidomethyloxy)pyridine.

The pyridine derivative of the present invention can be synthesized, for example, according to the following processes.

(A) When X is O or S in the formula (I), a compound of the formula (VIII):

 R-E (VIII)

wherein E is halogen such as chloro, bromo or iodo, and R is as defined above, is reacted with a compound of the formula (IX)

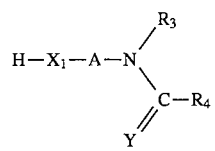 (IX)

wherein $X_1$ is O or S, and the other groups are as defined above.

(B) When X is O or S in the formula (I), a compound of the formula (X):

 R—$X_1$—H (X)

wherein each symbol is as defined above, is reacted with a compound of the formula (XI):

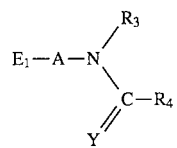 (XI)

wherein $E_1$ is halogen such as chloro, bromo, iodo or the like or a leaving group such as methanesulfonyloxy, p-toluenesulfonyloxy or the like, and the other symbols are as defined above.

(C) A compound of the formula (XII):

 R—X-A-$E_1$ (XII)

wherein each symbol is as defined above, is reacted with a compound of the formula (XIII):

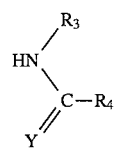 (XIII)

wherein each symbol is as defined above.

(D) When Y is O in the formula (I), a compound of the formula (XIV):

R—X-A-$NHR_3$ (XIV)

wherein each symbol is as defined above, is reacted with a compound of the formula (XV):

 (XV)

wherein $E_2$ is halogen such as chloro, bromo or the like, O—C(=O)—$R_4$ or OH, and the other symbol is as defined above.

(E) When Y is O and $R_3$ is an alkyl group or aralkyl group in the formula (I), a compound of the formula (XVI):

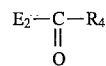 (XVI)

wherein each symbol is as defined above, is reacted with the compound of the formula (XVII):

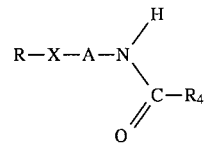 $R_3'$-$E_1$ (XVII)

wherein $R_3'$ is an alkyl group or aralkyl group, and the other group is as defined above.

(F) When X is S and A is $CH_2$ in the formula (I), a compound of the formula (XVIII):

 R—SH (XVIII)

wherein each symbol is as defined above, is reacted with the compound of the formula (XIX):

 $R_4CONHCH_2OH$ (XIX)

wherein each symbol is as defined above.

(G) When, in the formula (I), $R_3$ is H, Y is O, $R_4$ is a group of the formula:

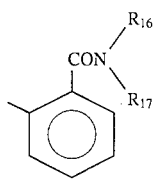

wherein $R_{16}$ and $R_{17}$ are the same or different and are a hydrogen atom or a lower alkyl group, or may be joined to form a ring, and the group of the formula:

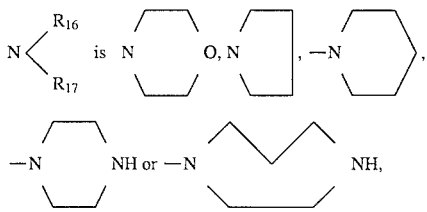

the compound of the formula (I) wherein the group of the formula:

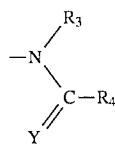

is phthalimido group, is a reacted with a compound of the formula:

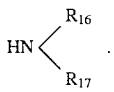

(H) When, in the formula (I), X is S(O), S(O)$_2$, the compound of the formula (I) wherein X is S is reacted with an oxidizing agent.

(I) When, in the formula (I), $R_3$ and $R_4$ are joined together with the carbamoyl group or the thiocarbamoyl group to which they are attached to form the group of the formula (VI), the compound of the formula (VIII) is reacted with a compound of the formula (XX):

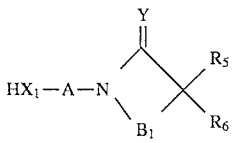

(XX)

wherein each symbol is as defined above.

(J) When, in the formula (I), $R_3$ and $R_4$ are joined together with the carbamoyl group or the thiocarbamoyl group to which they are attached to form the group of the formula (VI), the compound of the formula (X) is reacted with a compound of the formula (XXI):

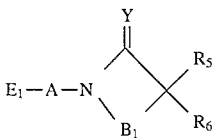

(XXI)

wherein each symbol is as defined above.

(K) When, in the formula (I), $R_3$ and $R_4$ are joined together with the carbamoyl group or the thiocarbamoyl group to which they are attached to form the group of the formula (VI), the compound of the formula (XII) is reacted with a compound of the formula (XXII):

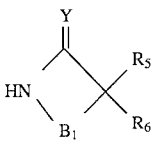

(XXII)

wherein each symbol is as defined above.

(L) When, in the formula (I), $R_3$ and $R_4$ are joined together with the carbamoyl group or the thiocarbamoyl group to which they are attached to form the group of the formula (VI) and $R_5$ and $R_6$ are joined to form the group of the formula:

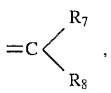

a compound of the formula (XXIII):

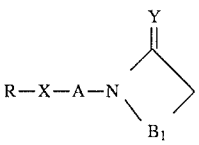

(XXIII)

wherein each symbol is as defined above, is reacted with a compound of the formula:

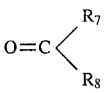

wherein each symbol is as defined above.

(M) When, in the formula (I), $R_3$ and $R_4$ are joined together with the carbamoyl group or the thiocarbamoyl group to which they are attached to form the group of the formula (VI) and $B_1$ is $-(CH_2)_p-$, a compound of the formula (XXIV):

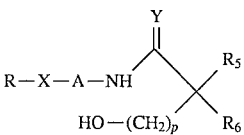

(XXIV)

wherein each group is as defined above, is subjected to cyclodehydration.

(N) When, in the formula (I), $R_3$ and $R_4$ are joined together with the carbamoyl group or the thiocarbamoyl group to which they are attached to form the group of the formula (VI) and $B_1$ is represented by the formula:

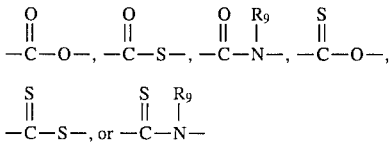

a compound of the formula (XXV):

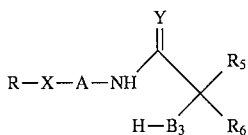   (XXV)

wherein $B_3$ is O, S or —$N(R_9)$—, and the other groups are as defined above, is reacted with the compound of the formula (XXVI):

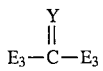   (XXVI)

wherein $E_3$ is an imidazolyl group, chloro or phenoxy group and the other group is as defined above.

(O) When, in the formula (I), $R_3$ and $R_4$ are joined together with the carbamoyl group or thiocarbamoyl group to which they are attached to form the group of the formula (VI) and Y is O and $B_1$ is —CH(OH)—$CH_2$—, a compound of the formula (XXVII):

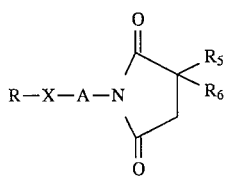   (XXVII)

wherein each symbol is as defined above, is reduced with a reducing agent, e.g., sodium borohydride.

(P) When, in the formula (I), $R_3$ and $R_4$ are joined together with the carbamoyl group or thiocarbamoyl group to which they are attached to form the group of the formula (VI) and X is S(O) or $S(O)_2$, the compound (I) whose X is S is reacted with an oxidizing agent.

(Q) When, in the formula (I), $R_3$ and $R_4$ are joined together with the carbamoyl group or the thiocarbamoyl group to which they are attached to form the group of the formula (VII), the compound of the formula (VIII) is reacted with a compound of the formula (XXVIII):

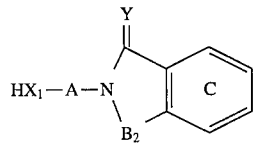   (XXVIII)

wherein each symbol is as defined above.

(R) When, in the formula (I), $R_3$ and $R_4$ are joined together with the carbamoyl group or the thiocarbamoyl group to which they are attached to form the group of the formula (VII), the compound of the formula (X) is reacted with a compound of the formula (XXIX):

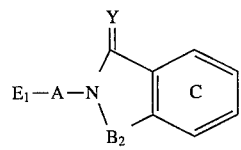   (XXIX)

wherein each symbol is as defined above.

(S) When, in the formula (I), $R_3$ and $R_4$ are joined together with the carbamoyl group or the thiocarbamoyl group to which they are attached to form the group of the formula (VII), the compound of the formula (XII) is reacted with a compound of the formula (XXX):

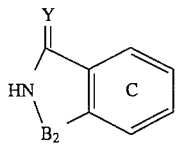   (XXX)

wherein each symbol is as defined above.

(T) When, in the formula (I), $R_3$ and $R_4$ are joined together with the carbamoyl group or the thiocarbamoyl group to which they are attached to form the group of the formula (VII) and $B_2$ is —$(CH_2)_p$—, a compound of the formula (XXXI):

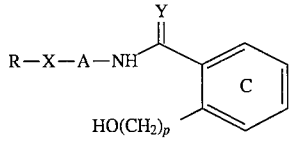   (XXXI)

is cyclized by dehydration.

(U) When, in the formula (I), $R_3$ and $R_4$ are joined together with the carbamoyl group or the thiocarbamoyl group to which they are attached to form the group of the formula (VII) and $B_2$ is a group of the formula:

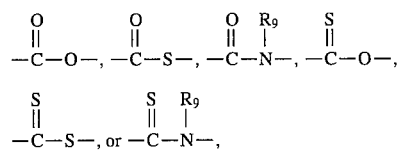

a compound of the formula (XXXII):

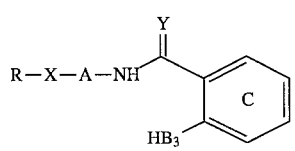   (XXXII)

wherein each symbol is as defined above, is reacted with the compound of the formula (XXVI).

(V) When, in the formula (I), $R_3$ and $R_4$ are joined together with the carbamoyl group or the thiocarbamoyl group to which they are attached to form the group of the formula (VII) and $B_2$ is —$CH_2CH_2X_1$—, a compound of the formula (XXXIII):

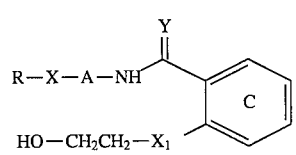   (XXXIII)

wherein each symbol is as defined above, is subjected to cyclodehydration.

(W) When, in the formula (I), $R_3$ and $R_4$ are joined together with the carbamoyl group or the thiocarbamoyl group to which they are attached to form the group of the formula (VII) and $B_2$ is a group of the formula:

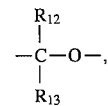

a compound of the formula (XXXIV):

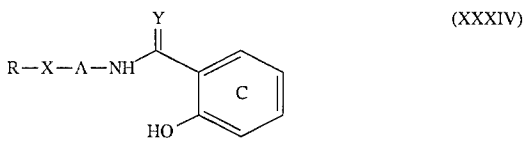

wherein each symbol is as defined above, is reacted with a compound of the formula:

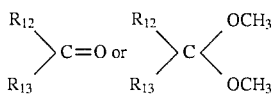

wherein each symbol is as defined above.

(X) When, in the formula (I), $R_3$ and $R_4$ are joined together with the carbamoyl group to which these are bonded to form the group of the formula (VII) and Y is O and $B_1$ is

a compound of the formula (XXXV):

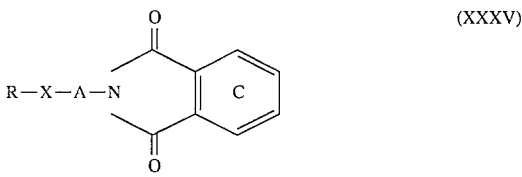

wherein each symbol is as defined above, is reduced with a reducing agent, e.g., sodium borohydride.

(Y) When, in the formula (I), $R_3$ and $R_4$ are joined together with the carbamoyl group to which they are attached to form the group of the formula (VII) and Y is O and $B_1$ is $CH_2$, a compound of the formula (XXXVI):

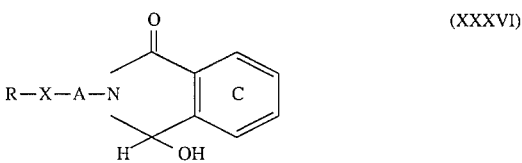

wherein each symbol is as defined above, is reduced with a reducing agent, e.g., sodium borohydride in a solvent, e.g., trifluoroacetic acid.

(Z) When, in the formula (I), $R_3$ and $R_4$ are joined together with the carbamoyl group to which they are attached to form the group of the formula (VII) and X is S(O) or S(O)$_2$, the compound (I) whose X is S is reacted with an oxidizing agent.

In the reaction of the compound (VIII) with the compound (IX) in the above process A, the compound (IX) is used in an amount of 1 equivalent to large excess based on the compound (VIII). The reaction can be carried out at −20° to +200° C. in a solvent in the presence of a basic compound such as sodium hydroxide, potassium hydroxide, sodium hydride, potassium carbonate, triethylamine, diisopropylethylamine, 1,8-diazabicyclo[5.4.0]-7-undecene or the like. Examples of the solvent to be used in the reaction include water, lower alcohols (e.g., methanol, ethanol, propanol, etc.), ketones (e.g., acetone, methyl ethyl ketone, etc.), ethers (e.g., tetrahydrofuran, etc.), aprotic polar solvents (e.g., N,N-dimethylformamide, dimethylsulfoxide, etc.) and the like.

The reaction of the compound (X) with the compound (XI) in the process B is carried out under the same conditions as those in the reaction of the compound (VIII) with the compound (IX) in the process A.

The reaction of the compound (XII) with the compound (XIII) in the process C is carried out under the same conditions as those in the reaction of the compound (VIII) with the compound (IX) in the process A.

In the reaction of the compound (XIV) with the compound (XV) whose $E_2$ is chloro, bromo or —C(=O)$R_4$ in the process D, the compound (XV) is used in an amount of 1 equivalent to large excess based on the compound (XIV). The reaction can be carried out at −30° to +200° C. in a solvent in the presence or absence of an inorganic base (e.g., potassium carbonate, sodium bicarbonate, etc.) or an organic base [e.g., triethylamine, pyridine, dimethylaniline, 1,4-diazabicyclo[2.2.2]octane (DABCO)]. As the solvent to be used in the reaction, there are, for example, halogenated hydrocarbons (e.g., methylene chloride, chloroform, dichloroethane, etc.), ethers (e.g., diethyl ether, tetrahydrofuran, dimethoxyethane, etc.), esters (e.g., methyl acetate, ethyl acetate, etc.), aprotic polar solvents (e.g., N,N-dimethylformamide, dimethyl sulfoxide, etc.) and the like.

The reaction of the compound (XIV) with the compound (XV) whose $E_2$ is OH in the process D is carried out by using the compound (XV) in an amount of 1 to 3 equivalents based on the compound (XIV) under conventional conditions for peptide syntheses. For example, the reaction is carried out in a solvent at −30° to +100° C. by using N,N-dicyclohexylcarbodiimide, 1-ethyl-3-(3-dimethylaminopropyl)carbidiimide hydrochloride, diethyl cyanophosphonate, 1,1'-carbonyldiimidazole or the like as a condensation agent. As the solvent to be used in the reaction, there are, for example, ketones (e.g., acetone, methyl ethyl ketone, etc.), ethers (e.g., tetrahydrofuran, etc.), halogenated hydrocarbons (e.g., methylene chloride, chloroform, etc.), aprotic polar solvents (e.g., N,N-dimethylformamide, etc.) and the like.

The reaction of the compound (XVI) with the compound (XVII) in the process E is carried out under the same conditions as those in the reaction of the compound (VIII) with the compound (IX) in the process A.

The reaction of the compound (XVIII) with the compound (XIX) in the process F is carried out at −30° to 100° C. in a solvent or without using any solvent in the presence of trifluoroacetic acid by using the compound (XIX) in an amount of 1 equivalent to large excess based on the compound (XVIII). As the solvent to be used in the reaction, there are, for example, methylene chloride, chloroform, dichloroethane and the like.

The reaction of the compound (I) with the compound of the formula:

wherein each symbol is as defined above, in the process G is carried out at −30° to +100° C. in a solvent. The amount of the compound of the formula:

wherein each symbol is as defined above, is 1 equivalent to large excess relative to the compound (I). As the solvent to be used in the reaction, there are, for example, water, lower alcohols (e.g., methanol, ethanol, propanol, etc.), ethers (e.g., tetrahydrofuran, etc.), halogenated hydrocarbons (e.g., methylene chloride, chloroform, dichloroethane, etc.) and the like.

The oxidation of the compound (I) whose X is S in the process H is carried out at −30° to +100° C. in the presence of a solvent by using an oxidizing agent in an amount of 1 equivalent to large excess based on the compound (I) whose X is S. As the solvent to be used in the reaction, there are, for example, water, methanol, ethanol, dichloromethane, chloroform and the like. Examples of the oxidizing agent include m-chloroperbenzoic acid, sodium metaperiodate, hydrogen peroxide and the like.

The reaction of the compound (VIII) with the compound (XX) in the process I is carried out under the same conditions as those in the reaction of the compound (VIII) with the compound (IX) in the process A.

The reaction of the compound (X) with the compound (XXI) in the process J is carried out under the same conditions as those in the reaction of the compound (VIII) with the compound (IX) in the process A.

The reaction of the compound (XII) with the compound (XXII) in the process K is carried out under the same conditions as those in the reaction of the compound (VIII) with the compound (IX) in the process A.

The reaction of the compound (XXIII) with the compound of the formula:

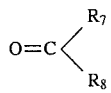

wherein each symbol is as defined above, is carried out at −30° to +200° C. in a solvent in the presence of an inorganic base (e.g., potassium bicarbonate, sodium bicarbonate, etc.), an organic base (e.g., piperidine, pyrrolidine, etc.) or sodium acetate. The amount of the compound of the formula:

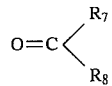

wherein each symbol is as defined above, is 1 equivalent to large excess relative to the compound (XXIII). As the solvent to be used in the reaction, there are, for example, water, lower alcohols (e.g., methanol, ethanol, propanol, etc.), ketones (e.g., acetone, methyl ethyl ketone, etc.), aprotic polar solvents (e.g., N,N-dimethylformamide, dimethyl sulfoxide, etc.), acetic acid, propionic acid and the like.

The cyclization by dehydration of the compound (XXIV) in the process M can be carried out at −80° to +100° C. in a solvent in the presence of a dehydrating agent. As the dehydrating agent to be used in the reaction, there are, for example, methanesulfonyl chloride or p-toluenesulfonyl chloride in combination with a base. Examples of the base include triethylamine, pyridine, diisopropyl ethyl amine and the like. As the solvent to be used in the reaction, there are, for example, ketones (e.g., acetone, methyl ethyl ketone. etc.), ethers (e.g., tetrahydrofuran, etc.), halogenated hydrocarbons (methylene chloride, chloroform, dichloroethane, etc.), aprotic polar solvents (e.g., N,N-dimethylformamide, dimethyl sulfoxide, etc.) and the like.

The reaction of the compound (XXV) with the compound (XXVI) in the process N is carried out at −30° to 100° C. in a solvent. The amount of the compound (XXVI) is 1 to 3 equivalents relative to the compound (XXV). As the solvent to be Used in the reaction, there are, for example, halogenated hydrocarbons (e.g., methylene chloride, chloroform, dichloroethane, etc.), ethers (e.g., diethyl ether, tetrahydrofuran, etc.), N,N-dimethylformamide and the like.

The reduction of the compound (XXVII) in the process O is carried out at −30° to +100° C. in a solvent. The amount of sodium borohydride is 1 equivalent to large excess relative to the compound (XXVII). As the solvent to be used in the reaction, there are, for example, water, methanol, ethanol and the like.

The oxidation of the compound (I) in the process P is carried out under the same conditions as those in the process H.

The reaction of the compound (VIII) with the compound (XXVIII) in the process Q is carried out under the same conditions as those in the reaction of the compound (VIII) with the compound (IX) in the process A.

The reaction of the compound (X) with the compound (XXIX) in the process R is carried out under the same conditions as those in the reaction of the compound (VIII) with the compound (IX) in the process A.

The reaction of the compound (XII) with the compound (XXX) in the process S is carried out under the same conditions as those in the reaction of the compound (VIII) with the compound (IX) in the process A.

The cyclization by dehydration of the compound (XXXI) in the process T is carried out under the same conditions as those in the reaction of the compound (XXIV) in the process M.

The reaction of the compound (XXXII) with the compound (XXVI) in the process U is carried out under the same conditions as those in the reaction of the compound (XXV) with the compound (XXVI) in the process N.

The cyclization by dehydration of the compound (XXXIII) in the process V is carried out under the same conditions as those in the reaction of the compound (XXIV) in the process M.

The reaction of the compound (XXXIV) with the compound of the formula:

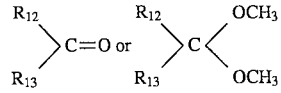

wherein each symbol is as defined above, in the process W is carried out under conventional conditions of acetanol syntheses. The reaction is carried out, for example, at −30° to +150° C. in a solvent in the presence of an acid. As the acid to be used in the reaction, there are, for example, BF3.Et$_2$O in which Et means ethyl, p-toluenesulfonic acid, camphorsulfonic acid and the like. Examples of the solvent include benzene, toluene, xylene, N,N-dimethylformamide and the like.

The reduction of the compound (XXXV) in the process X is carried out under the same conditions as those in the reduction of the compound (XXVII) with sodium borohydride in the process O.

The reduction of the compound (XXXVI) in the process Y is carried out at −10° to +100° C. in trifluoroacetic acid by using a reducing agent, e.g., sodium borohydride in an amount of 1 equivalent to large excess.

Oxidation of the compound (I) in the process Z is carried out under the same conditions as those in the process H.

The starting compounds for the production of the compounds (I) according to the invention can be produced by a known method or a per se known method, for example, in the following manner:

The compound (XII), when X is O or S, can be obtained, for example, according to the following process:

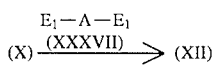

wherein each symbol is as defined above.

The reaction of the compound (X) with the compound (XXXVII) is carried out under the same conditions as those in the reaction of the compound (VIII) with the compound (IX) in the process A.

The compound (XIV), when X is O or S, can be obtained, for example, according to the following process:

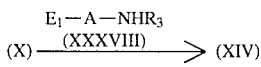

wherein each symbol is as defined above.

The reaction of the compound (X) with the compound (XXXVIII) is carried out under the same conditions as those in the reaction of the compound (VIII) with the compound (IX) in the process A.

The compound (XIX) can be obtained, for example, according to the following process:

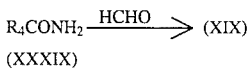

wherein each symbol is as defined above.

The reaction of the compound (XXXIX) with formaldehyde is carried out at 0° to +200° C. in a solvent in the presence or absence of a base by using formaldehyde in an amount of 1 equivalent to large excess based on the compound (XXXIX). As the base to be used in the reaction, there are, for example, potassium carbonate, potassium hydroxide, sodium hydroxide and the like. Examples of the solvent include water, methanol, ethanol, N,N-dimethylformamide and the like.

The compound (I) can be separated and purified from the reaction mixture according to conventional separation and purification techniques such as extraction, concentration, filtration, recrystallization, column chromatography, thin layer chromatography or the like.

The compound (I) of the present invention and a pharmaceutically acceptable salt or solvate thereof have cyclooxygenase inhibitory activity, 5-lipoxygenase inhibitory activity, antiinflammatory activity, antipyretic activity, analgesic activity, antiallergic activity, immunomodulatory activity and adhesion protein expression inhibitory activity. Examples of the adhesion proteins include ICAM-1, ICAM-2, ELAM-1 (endothelial leukocyte adhesion molecule-1) and VCAM-1 (vascular cell adhesion molecule-1) which participate infiltration of inflammatory cells and antigen or cell recognition by immunocytes as well as LFA-1 (lymphocyte function-associated antigen-1), Mac-1 (macrophage antigen-1) and the like. Therefore, these compounds are useful as an analgesic, antipyretic or antiinflammatory agent for acute and chronic inflammatory diseases (e.g., rheumatism, osteoarthritis, etc.), an immunotherapic agent (immunosuppressive agent and immunomodulator) against autoimmune diseases (e.g., rheumatism, etc.) and cancer, an antiallergic agent, an antiasthmatic agent, 5-lipoxygenase inhibitory agent. Further, they are useful as agents for treating thrombotic diseases (cardiac infarction, arterial embolism, venous embolism, etc.), nephritis, fulminant hepatitis, implantation immuno-rejection and the like.

When the compound (I) or a pharmaceutically acceptable salt or solvate thereof is used as the above medicament, the compound (I) or a pharmaceutically acceptable salt or solvate thereof is mixed with appropriate pharmaceutically acceptable carriers, excipients, diluents (e.g., starch, physiological saline, etc.) and the like, and can be administered orally or parenterally in the per se known form such as powders, granules, tablets, capsules, injection preparations or the like. The dosage is varied depending upon a particular administration route, conditions of a disease to be treated, age or weight of a patient to be treated and the like. However, for example, in the case of treatment of, e.g., thrombotic diseases by oral administration to an adult patient, it is preferred that the dosage is 0.2 to 50 mg/kg/day, preferably 0.5 to 30 mg/kg/day and can be administered 1 to several times daily.

The following Experiments, Examples and Reference Examples further illustrate the present invention in detail but are not to be construed to limit the scope thereof.

EXPERIMENT 1

Cyclooxygenase Inhibitory Activity

Test Method

A rat (Jcl:wistar, male, 12 to 15 weeks old) was subjected to peritoneotomy under anesthesia, and 8 ml of blood was taken from the abdominal aorta using a syringe [in which 0.72 ml of 3.2% sodium citrate was presucked]. The blood was centrifuged at room temperature (for 15 seconds at 2000 rpm and for 5 seconds at 3000 rpm, and thereafter centrifugation was stopped without using a brake), platelet-rich plasma (PRP) was taken, and the remaining blood was further centrifuged (at 3000 rpm for 10 minutes) to obtain platelet-poor plasma (PPP). The number of platelets in PPP was counted and PRP was diluted with PPP to, adjust the concentration of platelets to $10^6/\mu l$. Arachidonic acid (25 μl, 500 μg/100 μl) and 2.5 μl of a test compound were added to 0.225 ml of this PRP, which was allowed to stand at 37° C. for 15 minutes. Then, 1.1 ml of ethanol was added thereto and the mixture was shaken well, and centrifuged (at 2000 rpm, for 10 minutes). Water (1 ml) was added to 1 ml of the supernatant and the mixture was injected into a high performance liquid chromatography column (HPLC), and chromatographed under the following conditions to measure the peak height of 12 (S)-hydroxy-5,8,10-hepta-decatrienoic acid (HHT). As a control, the measurement was carried out according to the same manner except for using 2.5 μl of the solvent used for dissolving the test compound in place of the test compound.

The inhibitory percentage at respective concentrations was calculated using the following equation to obtain $IC_{50}$.

The inhibitory percentage (%)=(1-As/Ac)×100 wherein As is the peak height of HHT in the test compound and Ac is the peak height of HHT in the control.

Results

The results are shown in Table 1.

TABLE 1

| Cyclooxygenase inhibitory activity | |
|---|---|
| Compound (Example No.) | $IC_{50}$ (μM) |
| Indomethacin (control compound) | 14.0 |
| 1 | 1.6 |
| 7 | 4.4 |
| 8 | 1.1 |

TABLE 1-continued

| Cyclooxygenase inhibitory activity | |
|---|---|
| Compound (Example No.) | IC$_{50}$ (μM) |
| 9 | 2.2 |
| 10 | 2.2 |
| 14 | 13.2 |
| 15 | 5.1 |
| 16 | 12.9 |
| 17 | 1.5 |
| 18 | 7.0 |
| 25 | 3.4 |
| 26 | 3.5 |
| 27 | 5.4 |
| 28 | 5.6 |
| 30 | 6.6 |
| 31 | 4.6 |
| 32 | 6.5 |
| 33 | 2.8 |
| 34 | 2.9 |
| 35 | 2.3 |
| 36 | 6.0 |
| 39 | 4.4 |
| 40 | 7.6 |
| 41 | 11.3 |
| 42 | 13.1 |
| 43 | 13.0 |
| 44 | 3.3 |
| 45 | 6.6 |
| 46 | 7.9 |
| 51 | 8.9 |
| 53 | 8.6 |
| 54 | 9.0 |
| 55 | 8.7 |
| 57 | 3.6 |
| 58 | 7.9 |
| 59 | 3.5 |
| 60 | 4.2 |
| 61 | 11 |
| 73 | 2.8 |
| 76 | 13 |
| 78 | 5.2 |
| 81 | 6.8 |
| 83 | 10 |
| 84 | 4.5 |
| 85 | 1.4 |
| 88 | 1.2 |
| 90 | 4.9 |
| 93 | 6.3 |
| 96 | 13 |
| 99 | 12 |
| 100 | 8.0 |
| 101 | 3.2 |
| 104 | 7.7 |
| 105 | 5.1 |
| 106 | 3.7 |
| 107 | 4.3 |
| 109 | 6.2 |
| 110 | 11.0 |
| 111 | 7.0 |
| 112 | 13.0 |
| 119 | 4.6 |
| 122 | 3.8 |
| 123 | 3.3 |
| 124 | 5.5 |
| 129 | 2.5 |
| 146 | 5.1 |
| 147 | 1.8 |
| 148 | 3.1 |
| 154 | 6.0 |
| 156 | 2.9 |
| 166 | 12 |
| 168 | 3.6 |

EXPERIMENT 2

5-Lipoxygenase Inhibitory Activity

Test Method

A solution of a given concentration of a test compound (0.01 ml) was added to 0.9 ml of a rat basophilic leukemia cell suspension [$10^7$ cells/mast cell medium (150 mM NaCl/3.7 mM KCl/3.0 mM Na$_2$HPO$_4$/3.5 mM KH$_2$PO$_4$/0.9 mM CACl$_2$/5.6 mM dextrose, adjusted to pH 7.0 with 30% NaOH] and the mixture was allowed to stand at 37° C. for 5 minutes. Then, 0.1 ml of mast cell medium containing 50 μg of arachidonic acid and 1 μg of calcium ionophore (A-23187) were added and the mixture was allowed to stand at 37° C. for 15 minutes. Ethanol (1 ml) was added thereto and the mixture was shaken well, and filtered (Membrane filter, 0.45 μm). A part of the filtrate was injected into a HPLC column, and chromatographed under the following conditions to measure the peak height of 5-hydroxyeicosatetraenoic acid (5-HETE) and leukotriene B$_4$ (LTB$_4$). As a control, the measurement was carried out according to the same manner except that 0.01 ml of the solvent used for dissolving the test compound was used in place of the test compound.

The inhibitory percentage (%) was calculated from the following equation to obtain IC$_{50}$.

The inhibitory percentage (%)=(1-As/Ac)×100 wherein As is the peak height of 5-HETE or LTB$_4$ of the test compound and Ac is the peak height of 5-HETE or LTB$_4$ of a control.

Results

The results are shown in Table 2.

TABLE 2

| 5-Lipoxygenase inhibitory activity | | |
|---|---|---|
| Compound (Example No.) | 5-HETE IC$_{50}$ (μM) | LTB$_4$ IC$_{50}$ (μM) |
| 1 | 16.8 | 16.1 |
| 3 | 22.2 | 17.5 |
| 4 | 17.4 | 11.8 |
| 17 | 17.5 | 14.3 |
| 21 | 21.5 | 16.4 |
| 77 | 3.5 | 3.2 |
| 94 | 2.4 | 2.0 |
| 95 | 0.044 | 0.033 |
| 109 | 1.4 | 1.2 |
| 128 | 6.1 | 5.4 |
| 133 | 4.6 | 4.3 |
| 149 | 2.3 | 2.2 |
| 150 | 2.6 | 2.5 |
| 151 | 1.8 | 1.1 |
| 153 | 1.3 | 0.79 |
| 155 | 3.8 | 3.7 |

EXPERIMENT 3

In Vitro ART (Antigen-responding T-cell) Proliferation Test

Test Method

A male Lewis rat (7 weeks old) was sensitized with μg/rat of killed *M. tuberculosis* H 37 RA to induce adjuvant arthritis, and the inguen lymph node was removed after 14 days. This was suspended in a RPMI-1640 culture medium containing 5% fetal calf serum (FCS) to obtain a single cell suspension and incubated at 37° C. for 1 hour in a nylon wool column. The column was eluted with the same culture medium, and cells which did not adhere to the column were used as T cells.

On the other hand, spleen cells were prepared as antigen-presenting cells from a nonsensitized male Lewis rat (8 to 9 weeks old) and the cells were used after irradiation of 2500 R soft X-rays.

The above T cells ($5 \times 10^5$ cells/well) and spleen cells ($1 \times 10^5$ cells/well) were incubated in RPMI-1640 culture medium (total volume 200 μl) containing 2% of syngeneic rat serum (treated at 56° C. for 30 minutes) together with purified protein derivative (PPD) (final concentration 2 μg/ml) in 0.5% $CO_2$ at 37° C. for 72 hours. After addition of $^3$H-Tdr (0.5 μCi/well), the mixture was further incubated for 24 hours and cells were recovered to measure the radioactivity of Tdr which was taken in.

A solution of a test compound (20 μl) was added just before the addition of PPD and it was present throughout the incubation period. The effect of the test compound was indicated as an inhibitory percentage relative to the amount of $^3$H-Tdr which was taken in T cells by PPD.

Results

The results are shown in Table 3.

TABLE 3

| | In vitro ART proliferation test | |
|---|---|---|
| Compound | % Inhibition of ART growth Concentration of compound | |
| (Example No.) | 1 μM | 10 μM |
| 24 | 29 | 35* |
| 25 | 44** | −7 |
| 32 | 43** | 37** |
| 33 | 33 | 46** |
| 34 | 31** | 47** |
| 35 | 18 | 33** |
| 73 | 23 | 82*** |
| 74 | −3 | 52** |
| 75 | 5 | 45** |
| 76 | 3 | 38** |
| 77 | 28 | 85** |
| 90 | 34 | 49* |
| 91 | 44* | 42* |
| 93 | 42* | 11 |
| 94 | 33* | 70* |
| 95 | 20 | 32* |
| 97 | 30 | 31* |
| 100 | 19 | 32* |
| 101 | 39* | 12 |
| 105 | −4 | −49** |
| 109 | −11 | −33* |
| 110 | −21* | 1 |
| 111 | 30** | −12 |
| 115 | 18 | 53** |
| 116 | 10 | 31** |
| 117 | 3 | 39** |
| 118 | 8 | 38* |
| 119 | 13 | 43* |
| 120 | 16 | 74** |
| 123 | 15 | 66** |
| 140 | −9 | −25** |
| 141 | −21* | 64** |
| 145 | 17 | −42** |
| 146 | 22 | 20* |
| 147 | 9 | 72*** |
| 149 | −10 | 19* |
| 150 | −31 | 75*** |
| 151 | −1 | 74*** |
| 152 | −20 | 68*** |
| 153 | −20 | 75*** |
| 154 | 16* | 27* |
| 155 | 4 | 78*** |

TABLE 3-continued

| | In vitro ART proliferation test | |
|---|---|---|
| Compound | % Inhibition of ART growth Concentration of compound | |
| (Example No.) | 1 μM | 10 μM |
| 157 | −50 | 62** |
| 160 | −14 | 33* |
| 162 | −31 | −54* |
| 163 | −227*** | 99* |
| 164 | 3 | −54* |
| 171 | 96* | 41 |

*$p < 0.05$;
**$p < 0.01$;
***$p < 0.001$

EXPERIMENT 4

Rat Carrageenin Pedal Edema Inhibitory Activity

Test Method

A Jcl: SD male rat (6 weeks old, weight 160–220 g) was used. After the mesurement of the volume of the dexter hind limb foot pad, a test compound suspended in 5% gum arabic solution was administered orally. Immediately after the administration, water was further administered orally so that the total administration volume of liquid became 5 ml/rat. After one hour, 0.05 ml of 1% carrageenin suspension in physiological saline was injected subcutaneously in the foot pad to induce edema [Winter, C. A., Risley, E. A. and Nuss, G. W.: Proc. Soc. exp. Biol. Med. 111, 544 (1962)]. Three hours after injection of carrageenin, the volume of the dexter limb was measured, and the edema volume was calculated by the difference between the volume after injection and the volume prior to injection.

Results

The results are shown in Table 4.

TABLE 4

| Rat carrageenin pedal edema inhibitory activity | | |
|---|---|---|
| Compound (Example No.) | Dose (mg/kg) | Inhibitory percentage (%) |
| 28 | 50 | 25* |
| 29 | 50 | 25* |
| 31 | 50 | 32* |
| 33 | 50 | 37* |
| 42 | 50 | 34** |
| 43 | 50 | 24* |
| 46 | 50 | 39** |
| 47 | 50 | 25* |
| 54 | 50 | 45* |
| 55 | 50 | 41** |
| 57 | 50 | 35* |
| 58 | 50 | 48** |
| 59 | 50 | 35* |
| 62 | 50 | 36* |
| | 12.5 | 20* |
| 63 | 50 | 34** |
| 65 | 50 | 39** |
| 68 | 50 | 23* |
| 90 | 50 | 21* |
| 97 | 50 | 29* |
| 100 | 50 | 22* |
| 101 | 50 | 26* |
| 104 | 50 | 21* |
| 105 | 50 | 31* |
| 109 | 50 | 25* |
| 110 | 50 | 44** |

TABLE 4-continued

Rat carrageenin pedal edema inhibitory activity

| Compound (Example No.) | Dose (mg/kg) | Inhibitory percentage (%) |
|---|---|---|
| 112 | 50 | 42** |
| 113 | 50 | 35 |
| 114 | 50 | 28* |
| 116 | 50 | 45** |
| 118 | 50 | 31** |
| 124 | 50 | 51** |
| 126 | 50 | 30** |
| 127 | 50 | 32** |
| 129 | 50 | 34* |
| 132 | 50 | 45** |
| 133 | 50 | 27* |
| 136 | 50 | 33* |
| 138 | 50 | 25* |
| 141 | 50 | 36** |
| 143 | 50 | 27** |
| 145 | 50 | 22* |
| 156 | 50 | 32* |
| 159 | 50 | 25* |
| 162 | 50 | 34* |
| 163 | 50 | 29* |
| 169 | 50 | 44** |
| 172 | 50 | 19** |
| 173 | 50 | 23* |

*$p < 0.05$;
**$p < 0.01$

EXPERIMENT 5

Mouse Phenylquinone Writhing Inhibitory Activity

Test Method

A Slc: ICR male mouse (4 weeks, weight 17 to 24 g) was used. A test compound suspended in 5% gum arabic solution was administered orally. After 30 minutes, 0.1 ml/10 g body weight of 0.02% phenylquinone solution in water (dissolved by the aid of 5% ethanol) was injected intraperitoneally, and writhing and stretching responses of individual animals were measured for 20 minutes [Siegmund, E., Cadmus, R. and Lu, G.; Proc. Soc. exp. Biol. Med. 95, (1957)].

Results

The results are shown in Table 5.

TABLE 5

Mouse phenylquinone writhing inhibitory activity

| Compound (Example No.) | Dose (mg/kg) | Inhibitory percentage (%) |
|---|---|---|
| 1 | 100 | 61** |
| 23 | 50 | 58* |
| 24 | 50 | 56** |
| 25 | 50 | 60** |
| 26 | 50 | 67** |
| 32 | 50 | 63** |
| 35 | 50 | 60*** |
| 40 | 50 | 45** |
| 41 | 50 | 73** |
| 42 | 50 | 51* |
| 43 | 50 | 48* |
| 46 | 50 | 66*** |
| 47 | 50 | 47* |
| 48 | 50 | 31* |
| 51 | 50 | 72*** |
| 54 | 50 | 58** |
| 55 | 50 | 58** |
| 57 | 50 | 71** |
| 58 | 50 | 34* |
| 59 | 50 | 49** |

TABLE 5-continued

Mouse phenylquinone writhing inhibitory activity

| Compound (Example No.) | Dose (mg/kg) | Inhibitory percentage (%) |
|---|---|---|
| 60 | 50 | 41** |
| 62 | 50 | 55** |
| 63 | 50 | 56** |
| 64 | 50 | 56** |
| 65 | 50 | 80** |
| 67 | 50 | 49* |
| 68 | 50 | 50* |
| 71 | 50 | 55* |
| 73 | 50 | 75*** |
| 74 | 50 | 51* |
| 75 | 50 | 54** |
| 76 | 50 | 61** |
| 77 | 50 | 62** |
| 78 | 50 | 55*** |
| 79 | 50 | 48** |
| 81 | 50 | 75** |
| 82 | 50 | 47** |
| 83 | 50 | 59** |
| 84 | 50 | 84** |
| 85 | 50 | 70*** |
| 86 | 50 | 51* |
| 87 | 50 | 47* |
| 88 | 50 | 41* |
| 89 | 50 | 62* |
| 90 | 50 | 53** |
| 91 | 50 | 52** |
| 92 | 50 | 74** |
| 93 | 50 | 41** |
| 101 | 50 | 66*** |
| 105 | 50 | 59*** |
| 109 | 50 | 89*** |
| 111 | 50 | 64*** |

*$p < 0.05$;
**$p < 0.01$;
***$p < 0.001$;

EXPERIMENT 6

Mouse Acetic Acid Writhing Inhibitory Activity

Test Method

Ten male Slc: ICR mice, 4 weeks old, per 1 group were used. A test compound was administered orally, and after 30 minutes, 0.1 ml/10 g body weight of physiological saline containing 0.6% acetic acid was injected intraperitoneally. For 20 minutes, writhing (in agony condition) response by administration of acetic acid was counted regarding individual animals. The inhibitory percentage relative to the mean response counts of a control group was calculated regarding respective animals in a test compound administration group. The test compound was suspended in 5% gum arabic solution, and the administration volume was 0.2 ml/10 g.

Results

The results are shown in Table 6.

TABLE 6

Mouse acetic acid writhing inhibitory activity

| Compound (Example No.) | Dose (mg/kg) | Inhibitory percentage (%) |
|---|---|---|
| 124 | 50 | 69** |
| 147 | 50 | 46* |
| 150 | 50 | 54** |
| 153 | 50 | 49* |
| 167 | 50 | 62* |

TABLE 6-continued

Mouse acetic acid writhing inhibitory activity

| Compound (Example No.) | Dose (mg/kg) | Inhibitory percentage (%) |
|---|---|---|
| 169 | 50 | 96*** |
| 170 | 50 | 91*** |
| 173 | 50 | 75*** |
| 176 | 50 | 87*** |
| 179 | 50 | 66*** |

*p < 0.05;
**p < 0.01;
***p < 0.001;

EXPERIMENT 7

Pain Relief Test By Randall Celit Method

Seven to eight male Jcl: Winter rats, 5 weeks old, per one group were used. 0.1 ml of 10% brewer's yeast physiological saline suspension was injected subcutaneously in the rat dexter hind limb foot pad to induce inflammation. After three hours, the pain threshold was measured by pressure stimulating pain relief measuring apparatus manufactured by Ugo Basile Company (Cat. No. 7200) using an index of false pain reflex in the inflammatory limb (dexter hind limb), and this was taken as response threshold value in the inflammatory limb. A test compound was administered after additional 45 minutes orally, and the threshold was measured after one and two hours. The efficacy was determined by comparing threshold of a control group and that of the test compound group. The test compound was suspended in 5% gum arabic solution and the administration volume was 0.5 ml/100 g.

Results

The results are shown in Table 7.

TABLE 7

| Compound (Example No.) | Dose (mg/kg) | Randall Celit method % Of control | |
|---|---|---|---|
| | | 1 hour | 2 hours |
| 169 | 200 | 242 ± 21.9*** | 326.1 ± 80.1* |
| | 50 | 215.2 ± 16.1 | 158.4 ± 26.2 |
| 173 | 200 | 222.7 ± 26.4*** | 165.8 ± 24.9* |

*p < 0.05;
***p < 0.001

EXPERIMENT 8

Antipyretic Activity

Six male DS line rats, 7 weeks old, weighing 200 to 240 g (Nihon Clea) per one group were used. According to the method of Winder et al. (J. Pharmac. Exp. Ther. 138: 405 (1963)), a suspension of 15% brewer's yeast (Sigma) in physiological saline (1 ml/100 g, b.w.) was injected subcutaneously at 16 hours before measurement of the body temperature to induce pyrexia. After injection of yeast, only water was provided, and each rat was bred separately in a five duplicate cage. At 16, 17 and 18 hours after yeast injection, the rectal temperature was measured by a thermistor thermometer (Takara Kogyo K.K.), and this was taken as the basal body temperature. The rectal temperature was indicated by the temperature which was digitally displayed at 15 seconds after a thermistor thermometer sensor was inserted in the rectum to the extent of 4 cm. Animals having the body temperature of not lower than 38.5° C. at 18 hours after yeast injection were selected, and a test compound was administered orally (1 ml/100 g, b.w.). As a control, only the solvent was provided. Upon administration, the body temperature of the control group and that of the test compound-administered group were adjusted to the same temperature. The rectal temperature was measured every hour till five hours after administration.

Results

The results are shown in Table 8.

TABLE 8

| Antipyretic activity | | |
|---|---|---|
| Compound (Example No.) | Dose (mg/kg) | Δ°C. (peak time) |
| 24 | 50 | −1.33**(2 h) |
| 32 | 50 | −1.39**(1 h) |
| 40 | 50 | −2.00**(3 h) |
| 42 | 50 | −0.80**(1 h) |
| 46 | 50 | −4.08**(4 h) |
| 54 | 50 | −3.50**(5 h) |
| 57 | 50 | −1.28**(4 h) |
| 62 | 50 | −1.40**(4 h) |
| 64 | 50 | −2.58**(3 h) |
| 65 | 50 | −0.62* (4 h) |
| 71 | 50 | −0.52* (2 h) |
| 73 | 50 | −0.65* (2 h) |
| 83 | 50 | −0.82**(2 h) |
| 84 | 50 | −0.97**(3 h) |
| 85 | 50 | −1.00**(2 h) |
| 89 | 50 | −2.72**(3 h) |
| 111 | 50 | −0.68**(2 h) |
| 112 | 50 | −1.58**(3 h) |
| 113 | 50 | −0.82* (4 h) |
| 114 | 50 | −1.14* (4 h) |
| 116 | 50 | −0.63* (3 h) |
| 124 | 50 | −1.52**(2 h) |
| 126 | 50 | −1.21**(2 h) |
| 141 | 50 | −2.40**(3 h) |
| | 12.5 | −1.60**(3 h) |
| 169 | 50 | −2.43**(2 h) |
| | 12.5 | −2.13**(2 h) |
| 173 | 50 | −2.02**(2 h) |

*p < 0.05,
**p < 0.01

EXPERIMENT 9

Rat Reversed Passive Arthus Reaction (Skin) Inhibitory Activity

This reaction was induced by using-domestic rabbit anti-egg albumin (EA) antiserum according to the method of Chang and Otterness [Chang, Y. -H. and Otterness, I. G.: Eur. J. Pharmacol. 69, 155 (1981)]. Using six Jcl: SD male rats (7 weeks old, weight about 250 g) per one group, the hair was removed from the back under ether anesthesia, 1 ml of 0.5% EA physiological saline was injected intracutaneously into the tail vein, and further each 0.1 ml of diluted antiserum (6 mg protein antibody/ml) was injected in the back on both dexter and sinister sides. A test compound (50 mg/kg) was suspended in 5% gum arabic solution and the suspension was administered orally at one hour before EA administration. Acceleration of permeability through the vessel by the reaction was measured by injecting 1 ml of 1% Evans blue physiological saline intravenously at three hours after the induction of the reaction. Then, after 30 minutes, the rat was sacrificed by exsanguination. The skin was peeled off and the area of pigment spot (length×breadth, mm²) was measured.

Results

The results are shown in Table 9.

TABLE 9

| Rat reversed passive Arthus reaction inhibitory activity | |
|---|---|
| Compound (Example No.) | Inhibitory percentage (%) |
| 24 | 46** |
| 25 | 24** |
| 32 | 41** |
| 35 | 30** |
| 41 | 35** |
| 53 | 21* |
| 56 | 32* |
| 62 | 27* |

*: $p < 0.05$,
**: $p < 0.01$

EXPERIMENT 10

Activity to Rat Adjuvant Arthritis

Test Method

A male SD rat or Lewis rat (6 weeks oil, weight 190–230 g, Nihon Clea) was sensitized by intracutaneously injecting 0.05 ml of Freund's complete adjuvant (liquid paraffin suspension of 0.5% killed *M. tuberculosis*) in the dexter hind limb foot pad. The volume of dexter hind limb was measured just before the adjuvant sensitization and the 14th day after sensitization. A test compound was suspended in 5% gum arabic solution and it was administered through the entire period from the day 0 to the day 13.

Results

The results are shown in Table 10.

TABLE 10

| Adjuvant arthritis test | | |
|---|---|---|
| Compound (Example No.) | Dose (mg/kg) | Swelling inhibitory percentage (%) |
| 73 | 50 | 52** |

**: $p < 0.01$

EXPERIMENT 11

Adhesion Protein Expression Inhibitory Activity

Test Method

The various concentrations of test compounds were added to the human umbilical cord-derived vascular endothelial cells [sold by Klabo] which were seeded in the gelatin coat plate and the mixture were incubated at 37 °C. for 15 minutes. Then, the human tumor necrosis factor-α[TNF-α; sold by Genzyme] was added therein to the final concentration of 1 ng/ml and incubation was carried out at 37° C. for 3 hours for expression of ELAM-1 and for 6 hours for that of ICAM-I. After the reaction, the cells were fixed using glutaraldhyde and the expression amount of ELAM-1 and ICAM-1 was measured by the cell-ELISA method. That is, the expression was determined by fluorescence-labeling the adhesion-proteins-on the cells in the system using anti-ELAM-1 antibody BBA-2 and anti-ICAM-1 antibody BBA4 as the first antibody as well as horseradish peroxidase-labeled rabbit anti-mouse IgG antibody as the second antibody.

Results

The results are shown in Table 11.

TABLE 11

| Adhesion protein expression inhibition test | | | |
|---|---|---|---|
| Compound | Concentration | Expression Inhibitory Potency (%) | |
| (Example No.) | (μM) | ELAM-1 | ICAM-1 |
| 73 | 30 | — | 42 |
| 123 | 30 | — | 34 |
| 141 | 3 | — | 21 |
|  | 30 | — | 54 |
| 146 | 13 | 33 | — |
| 147 | 13 | 96 | 83 |
| 150 | 30 | — | 94 |
| 151 | 30 | — | 60 |
| 157 | 30 | — | 78 |
| 171 | 13 | 94 | 75 |
| 172 | 13 | 31 | 34 |
| 173 | 30 | — | 35 |
| 180 | 13 | 29 | 35 |
| 184 | 10 | 47 | — |
| 185 | 10 | 33 | — |
| 187 | 10 | 53 | 79 |
| 198 | 13 | — | 25 |
| 200 | 13 | 71 | 83 |

EXPERIMENT 12

Effect On Acute Renal Failure Induced By Renal Ischemia-Reperfusion

Male Sprague-Dawley rats (6 to 7 weeks old) were anesthetized using pentobarbital sodium (50 mg/kg, i.p.) and bilateral renal arteries were completely occluded for 45 minutes followed by reperfusion. After 20 hours of the reperfusion, the blood was collected from the abdominal aorta under anesthesia and the blood urea nitrogen (BUN) was determined. The test compounds were orally (5 ml/kg) administered 1 hour before-the ligation of the renal arteries.

Results

The results are shown in Table 12.

TABLE 12

| The effects on acute renal failure induced by the renal ischemia followed by reperfusion in rats | | |
|---|---|---|
| Compound (Exmaple No.) | Dose (mg/kg) | Blood urea nitrogen (mg/dl) |
| vehicle |  | 106 ± 5 |
| 73 | 50 | 68 ± 3 |
| vehicle |  | 100 ± 10 |
| 150 | 50 | 76.8 ± 16.9 |
| 157 | 50 | 62.4 ± 7.0 |
| vehicle |  | 93 ± 11 |
| 171 | 50 | 64 ± 11 |

As shown in Table 12, these invented compounds inhibited the increase in BUN in the model of acute renal failure induced by occlusion of the bilateral renal arteries of rats followed by reperfusion.

EXPERIMENT 13

PAF Induced Respiratory Tract Constriction Inhibitory Activity

Test Method

Male and female Hartley guinea pigs, weighing about g, were used. The guinea pigs were fixed at a dorsal position under urethane anethesia (1.5 g/kg, i.p.). One leg of a cannula (having four legs) was inserted in the trachea and two of the other three legs were bound to the respirator (Harvard apparatus rodent respirator). The remaining one leg (side branch) was bound to the bronchospasm transducer 7.020 (Ugobasile). Under the conditions of 5 to 7 ml of air supply/time, 70 times/min. of supply time and 10 cm $H_2O$ of pulmonary pressure load, the amount of over flow air was recorded on a Rectigraph (Rectigraph-8S Saneissoki) via the transducer. After Gallamine triethoxide treatment (1 mg/kg, i.v.), PAF was administered intravenously (1.0 µg/kg) and the maximum respiratory tract constriction response was observed after 30 seconds. Under these conditions, the inhibitory activity of the test compounds were examined. The test compounds were suspended in 5% gum arabic solution, respectively, and they were administered intravenously 2 minutes before PAF administration Results The results are shown in Table 13.

TABLE 13

PAF induced respiratory tract constriction inhibitory test

| Compound (Example No.) | Dose (mg/kg) | Inhibitory activity (%) |
| --- | --- | --- |
| 141 | 3 | 51.7** |
| 147 | 3 | 50.7 |
| 162 | 3 | 39.8 |
| 199 | 3 | 53.5** |
| 200 | 10 | 61.4** |
| 203 | 0.3 | 90.4** |

**:p < 0.01

EXAMPLE 1

Synthesis of 4-[3-(Caprylamino)propylthio]pyridine i) Synthesis of 4-(3-aminopropylthio)pyridine Dihydrochloride 4-Mercaptopyridine (50.0 g, 0.44 mol) was dissolved in 2N aqueous solution of sodium hydroxide. (500 ml, 1.00 mol) and 98.4 g (0.44 mol) of 3-bromopropylamine hydrobromide was added and the mixture was heated at 60° C. for 2 hours. After cooling, the reaction mixture was extracted with ethyl acetate. The extract was separated and dried, and the solvent was distilled off to obtain 67.0 g of a free base (90.5%, yellow oil).

The free base (57.0 g, 0.34 mol) was treated with 2N hydrogen chloride solution in methanol 350 ml, 0.70 mol) and the solvent was distilled off. The resulting crystals were washed with acetone and dried to obtain 82.0 g of the desired compound (quant., colorless powder), mp: 150.0°–152.0° C.

Anal. for $C_{18}H_{14}N_2OSCl_2 \cdot 0.5H_2O$, Calcd.: C; 38.41, H; 6.04, N; 11.20, Found: C; 38.48, H; 6.10, N; 11.11, NMR (200 MHz, $D_2O$) δ:2.18 (2H, quint., J=7 Hz), 3.22 (2H, t, J=7 Hz), 3.37 (2H, t, J=7 Hz), 7.83 (2H, dd, J=7, 2 Hz), 8.45 (2H, d, J=7 Hz), IR (KBr) $cm^{-1}$: 3370, 3320, 1620.

ii) Synthesis of 4-[3-(Caprylamino)propylthio]pyridine

To a solution of 2.50 g (10.4 mmol) of 4-(3aminopropylthio)pyridine dihydrochloride and 4.77 ml (34.2 mmol) of triethylamine in 200 ml of methylene chloride was added 2.37 ml (11.4 mmol) of capryl chloride under ice-cooling with stirring and the mixture was stirred at room temperature for 30 minutes. The reaction mixture was washed with an aqueous saturated sodium bicarbonate solution and water and dried and the solvent was distilled off. The residue was purified by column chromatography (eluent: methanol/ethyl acetate=1:10) to obtain the powder which was washed with ether and dried to obtain 2.80 µg of the desired compound (83.9% colorless powder), mp: 64.0°–65.0° C.

Anal. for $C_{18}H_{30}N_2OS$, Calcd.: C; 67.04, H; 9.38, N; 8.69, Found: C; 67.09, H; 9.55, N; 8.59, NMR (200 MHz, $CDCl_3$) δ:0.86 (3H, t, J=7 Hz), 1.24 (12H, m), 1.61 (2H, quint., J=7 Hz), 1.92 (2H, quint., J=7 Hz), 2.16 (2H, t, J=7 Hz), 2.99 (2H, t, J=7 Hz), 3.40 (2H, q, J=7 Hz), 5.80 (1H, m), 7.08 (2H, dd, J=5, 2 Hz), 8.37 (2H, dd, J=5, 2 Hz), IR $(KBr)cm^{-1}$: 3300, 3070, 1640.

EXAMPLE 2

Synthesis of 3-[3-(Caprylamino)propylthio]pyridine

A solution of 1.00 g (5.49 mmol) of 3-(dimethylaminocarbonylthio)pyridine in 1 ml of methanol was added to 2N aqueous solution of sodium hydroxide (20 ml, 50.0 mmol) and the mixture was heated with stirring for 30 minutes. After cooling, 1.20 g (5.49 mmol) of 3bromopropylamine hydrobromide was added and the mixture was stirred at room temperature for 30 minutes. The reaction mixture was extracted with ethyl acetate. The extract was separated and dried and the solvent was distilled off. To a solution of 900 mg of the residue and 0.92 ml (6.59 mmol) of triethylamine in 10 ml of methylene chloride was added 1.25 ml (6.04 mmol) of capryl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: ethyl acetate) to obtain the powder which was washed with hexane and dried to obtain 1.06 g of the desired compound (60.0%, colorless powder), mp: 41.0°–42.0° C.

Anal. for $C_{18}H_{30}N_2OS$, Calcd.: C; 67.04, H; 9.38, N; 8.69, Found: C; 66.82, H; 9.46, N; 8.79, NMR (200 MHz, $CDCl_3$) δ:0.88 (3H, t, J=7 Hz), 1.26 (12H, m), 1.61 (2H, quint., J=7 Hz), 1.85 (2H, quint., J=7 Hz), 2.16 (2H, t, J=7 Hz), 2.96 (2H, t, J=7 Hz), 3.38 (2H, q, J=7 Hz), 5.60 (1H, m), 7.23 (1H, dd, J=8, 5 Hz), 7.66 (1H, dt, J=8, 2 Hz), 8.44 (1H, dd, J=5, 2 Hz), 8.58 (1H, d, J=2 Hz), IR $(KBr)=cm^{-1}$: 3300, 3070, 1640.

EXAMPLE 3

Synthesis of 2-[3-(Caprylamino)propylthio]pyridine i) Synthesis of 2-(3-Aminopropylthio)pyridine Dihydrochloride 2-Mercaptopyridine (5.55 g, 50.0 mmol) was dissolved in 1N aqueous solution of sodium hydroxide (150ml, mmol) and 10.9 g (50.0 mmol) of 3-bromopropylamine hydrobromide was added and the mixture was heated at 60° C. for 1 hour. After cooling, the reaction mixture was extracted with ethyl acetate. The extract was separated and dried and the solvent was distilled off. The residue was treated with 10% hydrogen chloride solution in methanol, and the solvent was distilled off. The resulting crystals were washed with acetone, and dried to obtain 10.0 g of the desired compound (82.9%, colorless powder), mp: 167.0°–169.0° C.

Anal. for $C_8H_{14}N_2SCl_2.0.2H_2O$, Calcd.: C; 39.25, H; 5.93, N; 11.44, Found: C; 39.44, H; 5.78, N; 11.50.

ii) Synthesis of 2-[3-(Caprylamino)propylthio]pyridine

To a solution of 2.41 g (10.0 mmol) of 2-(3aminopropylthio)pyridine dihydrochloride and 5.02 ml (36.0 mmol) of triethylamine in 100 ml of methylene chloride was added 2.49 ml (12.0 mmol) of capryl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: ethyl acetate) to obtain the powder which was washed with hexane, and dried to obtain 2.60 g of the desired compound (80.6%, yellow powder).

Anal. for $C_{18}H_{30}N_2OS$, Calcd.: C; 67.04, H; 9.38, N; 8.69, Found: C; 67.04, H; 9.67, N; 8.42, NMR (200 MHz, $CDCl_3$) δ: 0.87 (3H, t, J=7 Hz), 1.26 (12H, m), 1.65 (2H, quint., J=7 Hz), 1.90 (2H, quint., J=7 Hz), 2.21 (2H, t, J=7 Hz), 3.25 (2H, t, J=7 Hz.), 3.38 (2H, q, J=7 Hz), 6.50 (1H, m), 7.01 (1H, dd, J=8, 5 Hz), 7.21 (1H, d, J=8 Hz), 7.50 (1H, td, J=8, 2 Hz), 8.41 (1Hi, dd, J=5, 2 Hz), IR (Neat) cm$^{-1}$: 3290, 3070, 1640.

EXAMPLE 4

Synthesis of 2-(2-Phthalimidoethylthio)pyridine

Triethylamine [12.54 ml (90 mmol)] was added to a suspension of 6.67 g (60 mmol) of 2-mercaptopyridine and 15.24 g (60 mmol) of N-(2-bromoethyl)phthalimide in 200 ml of ethanol and stirred at room temperature for 24 hours. The mixture was heated under reflux for 2 hours. The solvent was distilled off chloroform was added to the residue, and the mixture was washed with water and dried over anhydrous magnesium sulfate. The solvent was distilled off and the residue was purified by column chromatography (eluent: ethyl acetate/n-hexane=1:2) to obtain 8.00 g of the desired compound (46.9%, colorless crystals).

NMR (90 MHz, $CDCl_3$) δ: 3.50 (2H, t, J=6 Hz), 3.72 (2H, t, J=6 Hz), 6.90 (1H, m), 7.16 (1H, m), 7.43 (1H, m), 7.60–7.93 (4H, m), 8.35 (1H, m).

EXAMPLE 5

Synthesis of 4-[3-(Caprylamino)propylsulfinyl]pyridine

To a solution of 800 mg (2.81 mmol) of 4-[3-(t-butoxycarbonylamino)propylsulfinyl]pyridine in 2 ml of methanol was added 2N hydrogen chloride solution in methanol (5 ml, 10.0 mmol)and the mixture was stirred at room temperature for 2 hours. The solvent was distilled off. To a solution of 740 mg of the residue and 1.88 ml (13.5 mmol) of triethylamine in 30 ml of chloroform was added 0.70 ml (3.37 mmol) of capryl chloride under ice-cooling with stirring and the mixture was stirred at room temperature for minutes. The reaction mixture was washed with an aqueous saturated sodium bicarbonate solution and water and dried and the solvent was distilled off. The residue was purified by column-chromatography (eluent: methanol/ethyl acetate=1:10) to obtain 780 mg of the desired compound (81.9%, colorless powder), mp: 78.0°–79.0° C.

Anal. for $C_{18}H_{30}N_2O_2S$, Calcd.: C; 63.87, H; 8.93, N; 8.27, Found: C; 64.02, H; 9.14, N; 8.21, NMR (200 MHz, $CDCl_3$) δ:0.88 (3H, t, J=7 Hz), 1.26 (12H, m), 1.61 (2H, quint., J=7 Hz), 1.86 (1H, sextet, J=7 Hz), 2.06 (1H, sextet, J=7 Hz), 2.17 (2H, t, J=7 Hz), 2.81 (2H, dt, J=14, 7 Hz), 3,01 (1H, dt, J=14, 7 Hz), 3.40 (2H, q, J=7 Hz), 3.41 (2H, q, J=7 Hz), 5.99 (1H, m), 7.53 (2H, dd, J=5, 2 Hz), 8.79 (2H, dd, J=5, 2 Hz), IR (KBr)cm$^{-1}$: 3310, 3060, 1640, 1600.

EXAMPLE 6

Synthesis of 4-[3-(Caprylamino)propylsulfonyl]pyridine

To a solution of 800 mg (2.66 mmol) of 4-[3-(t-butoxycarbonylamino)propylsulfonyl]pyridine in 2 ml of methanol was added 2N hydrogen chloride solution in methanol (5 ml, 10.0 mmol) and the mixture was stirred at room temperature for 2 hours. The solvent was distilled off. To a solution of 670 mg of the residue and 1.92 ml (12.8 mmol) of triethylamine in 30 ml of chloroform was added 0.66 ml (3.19 mmol) of capryl chloride under ice-cooling with stirring and the mixture was stirred at room temperature for minutes. The reaction mixture was washed with an aqueous saturated sodium bicarbonate solution and water and dried. The solvent was distilled off. The residue was purified by column chromatography (eluent: methanol/ethyl acetate=1:10) to obtain 690 mg of the desired compound (73.2%, colorless powder), mp: 100.0°–101.0° C.

Anal. for $C_{18}H_{30}N_2O_3S$, Calcd.: C; 60.98, H; 8.53, N; 7.90, Found: C; 61.08, H; 8.68, N; 7.86, NMR (200 MHz, $CDCl_3$) δ: 0.88 (3H, t, J=7 Hz), 1.26 (12H, m), 1.59 (2H, quint., J7 Hz), 1.99 (2H, quint., J=7 Hz), 2.16 (2H, t, J=7 Hz), 3.17 (2H, t, J=7 Hz), 3.40 (2H, q, J=7 Hz), 5.75 (1H, m), 7.77 (2H, dd, J=5, 2 Hz), 8.93 (2H, dd, J=5, 2 Hz), IR (KBr)cm$^{-1}$: 3330, 1640.

EXAMPLE 7

Synthesis of 4-[2-(Caprylamino)ethylthio]pyridine

4-Mercaptopyridine (1.11 g, 10.0 mmol) was dissolved in 1N aqueous solution of sodium hydroxide (40 ml, 40.0 mmol) and 2.46 g (12.0 mmol) of 3-bromopropylamine hydrobromide was added. The mixture was heated with stirring at 60° C. for 1 hour. After cooling, the reaction mixture was extracted with ethyl acetate. The extract was washed with 1N aqueous solution of sodium hydroxide and water and dried. The solvent was distilled off to obtain 350 mg of yellow oil. To a solution of the free base thus obtained and 0.38 ml (2.72 mmol) of triethylamine in 30 ml of methylene chloride was added 0.57 ml (2.72 mmol) of capryl chloride under ice-cooling with stirring. The mixture was stirred at room temperature for 30 minutes. The reaction solution was washed with 1N aqueous solution of sodium hydroxide and water and dried. The solvent was distilled off. The residue was washed with ether to obtain 360 mg of the desired compound (11.7%, pale yellow powder), mp: 76.0°–77.0° C.

Anal. for $C_{17}H_{28}N_2OS$, Calcd.: C; 66.19, H; 9.15, N; 9.08, Found: C; 65.98, H; 9.29, N; 8.70, NMR (200 MHz, $CDCl_3$) δ: 0.88 (3H, t, J=7 Hz), 1.26 (12H, m), 1.62 (2H, quint., J=7 Hz), 2.17 (2H, t, J=7 Hz), 3.17 (2H, t, J=7 Hz), 3.54 (2H, q, J=7 Hz), 5.92 (1H, m), 7.21 (2H, dd, J=5, 2 Hz), 8.42 (2H, dd, J=5, 2 Hz) IR (KBr)cm$^{-1}$: 3270, 3090, 1630, 1570.

EXAMPLE 8

Synthesis of 4-[4-(Caprylamino)butylthio]pyridine i) Synthesis of N-(4-Hydroxybutyl)caprylamide To a solution of 2.00 g (22.4 mmol) of 4-amino-1-butanol and 3.75 ml (26.0 mmol) of triethylamine in 50 ml of methylene chloride was added 5.59 ml (26.9 mmol) of capryl chloride and the mixture was stirred at room temperature for minutes. The reaction mixture was washed successively with 1N aqueous solution of sodium hydroxide, water, 1N hydrochloric acid and water and dried. The solvent was distilled off. The residue was washed with hexane to obtain 4.27 g of the desired compound (78.2%, colorless powder), mp: 76.0°–77.0° C.

Anal. for $C_{14}H_{29}NO_2$, Calcd.: C; 69.09, H; N; 5.75, Found: C; 69.32, H; 12.31, N; 5.63, NMR (200 MHz, CDCl$_3$) δ:0.87 (3H, t, J=6 Hz), 1.26 (12H, m), 1.60 (6H, m), 2.16 (2H, t, J=7 Hz), 3.29 (2H, q, J=6 Hz), 3.68 (2H, t, J=6 Hz), 5.74 (1H, m), IR (KBr)cm$^{-1}$: 3380, 3300, 3060, 1640.

ii) Synthesis of N-(4-Methanesulfonyloxybutyl)caprylamide

To a solution of 2.00 g (8.22 mmol) of N-(4-hydroxybutyl)caprylamide and 1.37 ml (9.86 mmol) of triethylamine in 50 ml of methylene chloride was added 0.76 ml (9.86 mmol) of methanesulfonyl chloride: under ice-cooling with stirring. The mixture was stirred at room temperature for 30 minutes. The reaction mixture was washed with an aqueous saturated sodium bicarbonate solution and water and dried. The solvent was distilled off. The residue was washed with hexane to obtain 2.55 g of the desired compound (96.5%, colorless powder), mp: 59.0-60.0° C.

Anal. for $C_{15}H_{31}NO_4S \cdot 0.7H_2O$, Calcd.: C; 53.93, H; 9.77, N; 4.19, Found: C; 53.76 H; 9.64, N; 4.25, NMR (200 MHz, CDCl$_3$) δ:0.88 (3H, t, J=6 Hz), 1.26 (12H, m), 1.50–1.90 (6H, m), 2.21 (2H, t, J=7 Hz), 3.02 (3H, s), 3.31 (2H, q, J=6 Hz), 4.26 (2H, t, J=6 Hz), 6.00 (1H, m), IR (KBr)cm$^{-1}$: 3310, 2920, 1630.

iii) Synthesis of 4-[4-(Caprylamino)butylthio]pyridine

4-Mercaptopyridine (415 mg, 3.73 mmol) was dissolved in 30 ml of anhydrous methanol, 4.1M sodium methylate solution in methanol (0.91 ml, 3.71 mmol) was added and the mixture was stirred for 30 minutes. N-(4-Mesyloxybutyl)-caprylamide (1.00 g, 3.11 mmol) was added and the mixture was refluxed for 3 hours. After cooling, the solvent was distilled off and the residue was dissolved in chloroform. The solution was washed with 1N aqueous solution of sodium hydroxide and water and dried. The solvent was distilled off. The residue was purified by column chromatography (eluent: ethyl acetate) to obtain the powder which was washed with ether and dried to obtain 990 mg of the desired compound (94.6%, colorless powder), mp: 72.0°–73.0° C.

Anal. for $C_{19}H_{32}N_2OS$, Calcd.: C; 67.81, H; 9.58, N; 8.32, Found: C; 67.70, H; 9.73, N; 8.26, NMR (200 MHz, CDCl$_3$) δ:0.84 (3H, t, J=7 Hz), 1.23 (12H, m), 1.40–1.90 (6H, m), 2.12 (2H, t, J=7 Hz), 2.97 (2H, t, J=7 Hz), 3.27 (2H, q, J=7 Hz), 5.48 (1H, m), 7.07 (2H, dd, J=5, 2 Hz), 8.35 (2H, dd, J=5, 2 Hz), IR (KBr)cm$^{-1}$ : 3290, 3100, 1630, 1570.

EXAMPLE 9

Synthesis of 4-[5-(Caprylamino)pentylthio]pyridine i) Synthesis of N-(5-hydroxypentyl)caprylamide To a solution of 2.00 g (19.4 mmol) of 5-amino-1-pentanol and 3.24 ml (23.3 mmol) of triethylamine in 50 ml of methylene chloride was added 4.83 ml (23.3 mmol) of capryl chloride under ice-cooling with stirring and the mixture was stirred at room temperature for 30 minutes. The reaction mixture was washed successively with 1N aqueous solution of sodium hydroxide, water, 1N hydrochloric acid and water and dried. The solvent was distilled off. The residue was washed with hexane to obtain 4.38 g of the desired compound (87.8%, colorless powder), mp: 62.0°–63.0° C.

Anal. for $C_{15}H_{30}NO_2$, Calcd.: C; 69.99, H; 12.14, N; 5.44, Found: C; 70.53, H; 12.36, N; 5.05, NMR (200 MHz, CDCl$_3$) δ:0.88 (3H, t, J=6 Hz), 1.26 (12H, m), 1.30–1.85 (8H, m), 2.15 (2H, t, J=7 Hz), 3.26 (2H, q, J=6 Hz), 3.65 (2H, t, J=6 Hz), 5.55 (1H, m), IR (KBr)cm$^{-1}$: 3400, 3310, 3060, 1630.

ii) Synthesis of N-(5-methanesulfonyloxypentyl)caprylamide

To a solution of 2.00 g (7.77 mmol) of N-(5-hydroxypentyl)caprylamide and 1.30 ml (9.32 mmol) of triethylamine in50 ml of methylene chloride was added 0.72 ml (9.32 mmol) of methanesulfonyl chloride under ice-cooling with stirring and the mixture was stirred at room temperature for 30 minutes. The reaction mixture was washed with an aqueous saturated sodium bicarbonate solution and water and dried. The solvent was distilled off. The residue was washed with hexane to obtain 1.95 g of the desired compound (74.8%, colorless powder), mp: 67.0°–68.0° C.

Anal. for $C_{16}H_{33}NO_4S$, Calcd.: C; 57.28, H; 9.91, N; 4.17, Found: C; 57.13, H; 10.18, N; 4.23, NMR (200 MHz, CDCl$_3$) δ:0.88 (3H, t, J=6 Hz), 1.26 (12H, m), 1.30–1.90 (8H, m), 2.16 (2H, t, J=7 Hz), 3.02 (3H, s), 3.31 (2H, q, J=6 Hz), 4.26 (2H, t, J=6 Hz), 6.00 (1H, m), IR (KBr)cm$^{-1}$: 3330, 3040, 2920, 1640.

iii) Synthesis of 4-[5-(Caprylamino)pentylthio]pyridine

4-Mercaptopyridine (397 mg, 3.58 mmol) was dissolved in 30 ml of anhydrous methanol and 4.1M sodium methylate solution in methanol (0.87 ml, 3.58 mmol) was added. The mixture was stirred for 30 minutes. N-(5-Methanesulfonyloxypentyl)caprylamide (1.00 g, 2.98 mmol) was added and refluxed for 3 hours. After cooling, the solvent was distilled off and the residue was dissolved in chloroform. The solution was washed with 1N aqueous solution of sodium hydroxide and water and dried. The solvent was distilled off. The residue was purified by column chromatography (eluent: ethyl acetate) to obtain the powder which was washed with ether and dried to obtain 860 mg of the desired compound (82.3%, colorless powder), mp: 60.0°–61.0° C.

Anal. for $C_{20}H_{34}N_2OS$, Calcd.: C; 68.52, H; 9.78, N; 7.99, Found: C; 68.49, H; 9.94, N; 7.95, NMR (200 MHz, CDCl$_3$) δ:0.88 (3H, t, J=7 Hz), 1.26 (12H, m), 1.40–1.90 (8H, m), 2.16 (2H, t, J=7 Hz), 2.97 (2H, t, J=7 Hz), 3.27 (2H, q, J=7 Hz), 5.51 (1H, m), 7.10 (2H, dd, J=5, 2 Hz), 8.39 (2H, dd, J=5, 2 Hz), IR (KBr)cm$^{-1}$: 3310, 3050, 1630, 1580.

PREPARATION 10

Synthesis of 4-[6-(Caprylamino)hexylthio]pyridine i) Synthesis of N-(6-hydroxyhexyl)caprylamide To a solution of 2.00 g (17.1 mmol) of 6-amino-1-hexanol and 2.85 ml (20.5 mmol) of triethylamine in 50 ml of methylene chloride was added 4.83 ml (23.3 mmol) of capryl chloride under ice-cooling with stirring and the mixture was stirred at room temperature for 30 minutes. The reaction mixture was washed successively with 1N aqueous solution of sodium hydroxide, water, 1N hydrochloric acid and water and dried. The solvent was distilled off. The residue was washed with hexane to obtain 4.56 g of the desired compound (98.4%, colorless powder), mp: 77.0°–78.00° C.

Anal. for $C_{16}H_{33}NO_2$, Calcd.: C; 70.80, H; 12.25, N; 5.16, Found: C; 70.94, H; 12.55, N; 5.02, NMR (200 MHz, CDCl$_3$) δ:0.88 (3H, t, J=6 Hz), 1.26 (12H, m), 1.20–1.85 (10H, m), 2.15 (2H, t, J=7 Hz), 3.25 (2H, q, J=6 Hz), 3.64 (2H, t, J=6 Hz), 5.49 (1H, m), IR (KBr)cm$^{-1}$: 3390, 3310, 3060, 1640.

ii) Synthesis of N-(6-mesyloxyhexyl)caprylamide

To a solution of 2.00 g (7.37 mmol) of N-(6-hydroxyhexyl)caprylamide and 1.23 ml of triethylamine in 50 ml of methylene chloride was added 0.68 ml (8.84 mmol) of methanesulfonyl chloride under ice-cooling with stirring and the mixture was stirred at room temperature for 30 minutes. The reaction mixture was washed with an aqueous saturated sodium bicarbonate solution and water and dried. The solvent was distilled off. The residue was washed with hexane to obtain 2.54 g of the desired compound (98.6%, colorless powder), mp: 62.0°–63.0° C.

Anal. for $C_{17}H_{35}NO_4S \cdot 0.7H_2O$, Calcd.: C; 56.38, H; 10.13, N; 3.87, Found: C; 56.28, H; 10.03, N; 3.94, NMR (200 MHz, CDCl$_3$) δ:0.,88 (3H, t, J=6 Hz), 1.27 (12H, m), 1.05–1.92 (10H, m), 2.20 (2H, t, J=7 Hz), 3.01 (3H, s), 3.26 (2H, q, J=6 Hz), 4.23 (2H, t, J=6 Hz), 5.72 (1H, m), IR (KBr)cm$^{-1}$: 3320, 3040, 2920, 1630.

iii) Synthesis of 4-[6-(Caprylamino)hexylthio]pyridine

4-Mercaptopyridine (381 mg, 3.43 mmol) was dissolved in 30 ml of anhydrous methanol and 4.1M sodium methylate solution in methanol (0.84 ml, 3.43 mmol) was added thereto. The mixture was stirred for 30 minutes. N-(6-Methanesulfonyloxyhexyl)caprylamide (1.00 g, 2.86 mmol) was added and refluxed for 3 hours. After cooling, the solvent was distilled off, the residue was dissolved in chloroform. The solution was washed with 1N aqueous solution of sodium hydroxide and water and dried. The solvent was distilled off. The residue was purified by column chromatography (eluent: ethyl acetate) to obtain the powder which was washed with ether, and dried to obtain 870 mg of the desired compound (87.4%, colorless powder), mp: 72.0°–73.0° C.

Anal. for $C_{21}H_{36}N_2OS$, Calcd.: C; 69.18, H; 9.95, N; 7.68, Found: C; 69.14, H; 10.13, N; 7.61, NMR (200 MHz, CDCl$_3$) δ:0.88 (3H, t, J=7 Hz), 1.26 (12H, m), 1.00–2.00 (10H, m), 2.15 (2H, t, J=7 Hz), 2.97 (2H, t, J=7 Hz), 3.25 (2H, q, J=7 Hz), 5.48 (1H, m), 7.10 (2H, dd, J=5, 2 Hz), 8.38 (2H, dd, J=5, 2 Hz), IR (KBr)cm$^{-1}$: 3290, 3100, 2920, 2850, 1630, 1570.

EXAMPLE 11

Synthesis of 4-[4-(Caprylpiperidyl)thio]pyridine i) Synthesis of N-t-butoxycarbonyl-4-methanesulfonyloxypiperidine To a solution of 1.00 g (4.97 mmol) of N-t-butoxycarbonyl-4-hydroxypiperidine and 0.83 ml (5.96 mmol) of triethylamine in 50 ml of methylene chloride was added 0.46 ml (5.96 mmol) of methanesulfonylchloride under ice-cooling and stirring and the mixture was stirred at room temperature for 30 minutes. The reaction mixture was washed with an aqueous saturated sodium bicarbonate solution and water and dried. The solvent was distilled off. The residue was washed with hexane to obtain 1.37 g of the desired compound (98.6%, colorless powder), mp: 87.0°–88.0° C.

Anal. for $C_{11}H_{21}NO_5S$, Calcd.: C; 47.29, H; 7.58, N; 5.01, Found: C; 47.04, H; 7.76, N; 5.06, NMR (200 MHz, CDCl$_3$) δ:1.46 (9H, s), 1.70–2.08 (4H, m), 3.04 (3H, s), 3.30 (2H, ddd, J=14, 8, 4 Hz), 3.71 (2H, ddd, J=14, 7, 4 Hz), 4.88 (1H, septet, J=4 Hz), IR (KBr)cm$^{-1}$: 2960, 2850, 1690, 1680.

ii) Synthesis of 4-[4-(t-Butoxycarbonyl)piperidylthio]pyridine

4-Mercaptopyridine (362 mg, 3.26 mmol) was dissolved in 30 ml of anhydrous methanol and 4.1M sodium methylate solution in methanol (0.80 ml, 3.26 mmol) was added. The mixture was stirred for 30 minutes. N-t-Butoxycarbonyl-4-methanesulfonyloxypiperidine (760 mg, 2.72 mmol) was added and the mixture was refluxed for 18 hours. After cooling, the solvent was distilled off. The residue was dissolved in ethyl acetate and was washed with 1N aqueous solution of sodium hydroxide and water and dried. The solvent was distilled off. The residue was purified by column chromatography (eluent: hexane/ethyl acetate=1:1) to obtain 660 mg of the desired compound (82.4%, colorless powder), mp: 71.0°–72.0° C.

Anal. for $C_{15}H_{22}N_2O_2S$, Calcd.: C; 61.19, H; 7.53, N; 9.51, Found: C; 61.28, H; 7.64, N; 9.39, NMR (200 MHz, CDCl$_3$) δ:1.46 (9H, s), 1.50–1.80 (2H, m), 2.03 (2H, ddd, J=14, 9, 4 Hz), 3.61 (2H, ddd, J=14, 10, 4 Hz), 3.56 (1H, tt, J=10, 4 Hz), 3.96 (2H, dt, J=14, 4 Hz), 7.14 (2H, dd, J=5, 2 Hz), 8.42 (2H, dd, J=5, 2 Hz), IR (KBr)cm$^{-1}$: 2960, 2930, 2850, 1690, 1580.

iii) Synthesis of 4-[4-(Caprylpiperidyl)thio]pyridine

To a solution of 250 mg (0.85 mmol) of 4-[4-(N-t-butoxycarbonyl)piperidylthio]pyridine in 5 ml of methanol was added of 2N hydrogen chloride solution in methanol (5 ml, 10 mmol) and the mixture was stirred at room temperature for 1 hour. The solvent was distilled off. To a solution of 225 mg of the residue and 0.42 ml (3.03 mmol) of triethylamine in 5 ml of methylene chloride was added 0.21 ml (1.01 mmol) of capryl chloride under ice-cooling with stirring and the mixture was stirred at room temperature for minutes. The reaction mixture was washed with an aqueous saturated sodium bicarbonate solution and water and dried. The solvent was distilled off. The residue was purified by column chromatography (eluent: ethyl acetate) to obtain 210 mg of the desired compound (71.7%, colorless oil).

Anal. for $C_{20}H_{32}N_2OS \cdot 0.5H_2O$, Calcd.: C; 67.18, H; 9.30, N; 7.83, Found: C; 67.33, H; 9.19, N; 7.71, NMR (200 MHz, CDCl$_3$) δ:0.88 (3H, t, J=7 Hz), 1.27 (12H, m), 1.50–1.90 (4H, m), 2.00–2.20 (2H, m), 2.33 (2H, t, J=7 Hz), 3.10 (1H, td, J=12, 3 Hz), 3.27 (1H, td, J=12, 3 Hz, 3.59 (1H, m), 3.83 (1H, dt, J=14, 3 Hz), 4.32 (1H, dt, J=14, 3 Hz), 7.16 (2H, dd, J=5, 2 Hz), 8.44 (2H, brd, J=5 Hz), IR (Neat) cm$^{-1}$: 3270, 3100, 1630, 1570.

EXAMPLE 12

Synthesis of 3-(4-Phthalimidobutylthio)pyridine

To a solution of 3.64 g (20 mmol) of 3-dimethylaminocarbamoylthiopyridine in 100 ml of methanol was added 1.6 g (40 mmol) of sodium hydroxide. The mixture was heated and refluxed for 3 hours under nitrogen atmosphere. After cooling, 5.64 g (20 mmol) of N-(4-bromobutyl)phthalimide was added. The mixture was heated and refluxed for 2.5 hours. The solvent was distilled off and chloroform was added to the residue. The mixture was washed with water and dried over anhydrous magnesium sulfate. The solvent was distilled off and the residue was purified by column chromatography (eluent: ethyl acetate/n-hexane=1:1) to obtain 280 mg of the desired compound (4.5%, colorless oil).

NMR (90 MHz, CDCl$_3$) δ:1.47–2.05 (4H, m), 2.95 (2H, t, J=7 Hz), 3.68 (2H, t, J=7 Hz), 7.16 (1H, dd, J=7, 4 Hz), 7.54–7.95 (5H, m), 8.38 (1H, dd, J=5, 2 Hz), 8.54 (1H, d).

EXAMPLE 13

Synthesis of 4-[3-(Propionylamino)propylthio]pyridine

To a solution of 700 mg (2.90 mmol) of 4-(3-aminopropylthio)pyridine dihydrochloride and 1.62 ml (11.6 mmol) of triethylamine in 30 ml of methylene chloride was added 0.30 ml (3.48 mmol) of propionyl chloride and the mixture was stirred at room temperature for 30 minutes. The reaction solution was washed with an aqueous saturated sodium bicarbonate solution and water and dried. The solvent was distilled off. The residue was purified by column chromatography (eluent: methanol/ethyl acetate=1:10) to obtain the powder which was washed with ether and dried to obtain 483 mg of the desired compound (74.2%, yellow prisms), mp: 50.0°–51.0° C.

Anal. for $C_{11}H_{16}N_2OS$, Calcd.: C; 58.90, H; 7.19, N; 12.49, Found: C; 58.59, H; 7.25, N; 12.33, NMR (200 MHz, CDCl$_3$) δ:1.16 (3H, t, J=7 Hz), 1.94 (2H, quint., J=7 Hz), 2.22 (2H, q, J=7 Hz), 3.01 (2H, t, J=7 Hz), 3.42 (2H, q, J=7 Hz), 5.80 (1H,m), 7.11 (2H, dd, J=5, 2 Hz), 8.39 (2H, dd, J=5, 2 Hz), IR (KBr)cm$^{-1}$: 3310, 3080, 1640, 1580.

EXAMPLE 14

Synthesis of 4-[3-(Butyrylamino)propylthio]pyridine

To a solution of 700 mg (2.90 mmol) of 4-(3-aminopropylthio)pyridine dihydrochloride and 1.62 ml (11.6 mmol) of triethylamine in 30 ml of methylene chloride was added 0.36 ml (3.48 mmol) of butyryl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: methanol/ethyl acetate=1:1) to obtain 630 mg of the desired compound (91.1%, pale yellow oil).

Anal. for $C_{12}H_{18}N_2OS \cdot 0.1H_2O$, Calcd.: C; 60.02, H; 7.64, N; 11.66, Found: C; 60.01, H; 7.86, N; 11.39, NMR (200 MHz, CDCl$_3$) δ:0.95 (3H, t, J=7 Hz), 1.67 (2H, sextet., J=7 Hz), 1.93 (2H, quint., J=7 Hz), 2.16 (2H, t, J=7 Hz), 3.01 (2H, t, J=7 Hz), 3.42 (2H, q, J=7 Hz), 5.70 (1H, m), 7.11 (2H, dd, J=5, 2 Hz), 8.40 (2H, dd, J=5, 2 Hz), IR (KBr)cm$^{-1}$: 3310, 3080, 1640, 1570.

EXAMPLE 15

Synthesis of 4-[3-(Hexanoylamino)propylthio]pyridine

To a solution of 600 mg (2.49 mmol) of 4-(3-aminopropylthio)pyridine dihydrochloride and 1.39 ml (9.96 mmol) of triethylamine in 25 ml of methylene chloride was added 0.42 ml (2.99 mmol) of hexanoyl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: methanol/ethyl acetate=1:10) to obtain 542 mg of the desired compound (81.7%, pale yellow oil).

Anal. for $C_{14}H_{22}N_2OS \cdot 0.7H_2O$, Calcd.: C; 60.27, H; 8.45, N; 10.04, Found: C; 60.45, H; 8.19, N; 9.95, NMR (200 MHz, CDCl$_3$) δ:0.89 (3H, t, J=7 Hz), 1.10–1.50 (4H, m), 1.63 (2H, quint., J=7 Hz), 1.93 (2H, quint., J=7 Hz), 2.18 (2H, t, J=7 Hz), 3.01 (2H, t, J=7 Hz), 3.41 (2H, q, J=7 Hz), 5.78 (1H, m), 7.10 (2H, dd, J=5, 2 Hz), 8.39 (2H, dd, J=5, 2 Hz), IR (Neat) cm$^{-1}$: 3280, 3070, 1650, 1570.

EXAMPLE 16

Synthesis of 4-[3-(Caproylamino)propylthio]pyridine

To a solution of 1.21 g (5.00 mmol) of 4-(3-aminopropylthio)pyridine dihydrochloride and 2.79 ml (20.0 mmol) of triethylamine in 50 ml of methylene chloride was added 1.02 ml (6.00 mmol) of caproyl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: ethyl acetate) to obtain the powder which was washed with hexane and dried to obtain 1.24 g of the desired compound (84.2%, colorless powder), mp: 48.0°–49.0° C.

Anal. for $C_{16}H_{26}N_2OS$, Calcd.: C; 65.26, H; 8.90, N; 9.51, Found: C; 65.35, H; 9.07, N; 9.42, NMR (200 MHz, CDCl$_3$) δ:0.87 (3H, t, J=7 Hz), 1.27 (8H, m), 1.62 (2H, quint., J=7 Hz), 1.93 (2H, quint., J=7 Hz), 2.18 (2H, t, J=7 Hz), 3.01 (2H, t, J=7 Hz), 3.41 (2H, q, J=7 Hz), 5.70 (1H, m), 7.10 (2H, dd, J=5, 2 Hz), 8.40 (2H, dd, J=5, 2 Hz), IR (KBr)cm$^{-1}$: 3300, 3070, 1640, 1580.

EXAMPLE 17

Synthesis of 4-[3-(Lauroylamino)propylthio]pyridine

To a solution of 1.00 g (4.15 mmol) of 4-(3-aminopropylthio)pyridine dihydrochloride and 2.77 ml (19.8 mmol) of triethylamine in 40 ml of methylene chloride was added 1.15 ml (4.96 mmol) of lauroyl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: ethyl acetate) to obtain the powder which was washed with hexane and dried to obtain 1.05 g of the desired compound (72.2%, colorless powder), mp: 71.0°–72.0° C.

Anal. for $C_{20}H_{34}N_2OS$, Calcd.: C; 68.52, H; 9.78, N; 7.99, Found: C; 68.62, H; 10.00, N; 7.91, NMR (200 MHz, $CDCl_3$) δ:0.88 (3H, t, J=7 Hz), 1.25 (16H, m), 1.62 (2H, quint., J=7 Hz), 1.93 (2H, quint., J=7 Hz), 2.17 (2H, t, J=7 Hz), 3.01 (2H, t, J=7 Hz), 3.41 (2H, q, J=7 Hz), 5.71 (1H, m), 7.10 (2H, dd, J=5, 2 Hz), 8.39 (2H, dd, J=5, 2 Hz), IR $(KBr)cm^{-1}$: 3290, 3070, 1640, 1580.

EXAMPLE 18

Synthesis of 4-[3-(Myristoylamino)propylthio]pyridine

To a solution of 1.00 g (4.15 mmol) of 4-(3-aminopropylthio)pyridine dihydrochloride and 2.77 ml (19.8 mmol) of triethylamine in 40 ml of methylene chloride was added 1.22 ml (4.96 mmol) of myristoyl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: ethyl acetate) to obtain the powder which was washed with hexane and dried to obtain 1.17 g of the desired compound (74.5%, colorless powder), mp: 80.0°–81.0° C.

Anal. for $C_{22}H_{38}N_2OS$, Calcd.: C; 69.79, H; 10.12, N; 7.40, Found: C; 69.79, H; 10.32, N; 7.32, NMR (200 MHz, $CDCl_3$) δ:0.88 (3H, t, J=7 Hz), 1.25 (20H, m), 1.62 (2H, quint., J=7 Hz), 1.93 (2H, quint., J=7 Hz), 2.17 (2H, t, J=7 Hz), 3.01 (2H, t, J=7 Hz), 3.41 (2H, q, J=7 Hz), 5.67 (1H, m), 7.10 (2H, dd, J=5, 2 Hz), 8.39 (2H, dd, J=5, 2 Hz), IR $(KBr)cm^{1-}$: 3300, 3080, 1640, 1570.

EXAMPLE 19

Synthesis of 4-[3-(Palmitoylamino)propylthio]pyridine

To a solution of 1.21 g (5.00 mmol) of 4-(3-aminopropylthio)pyridine dihydrochloride and 2.79 ml (20.0 mmol) of triethylamine in 50 ml of methylene chloride was added 1.65 ml (6.00 mmol)of palmitoyl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: ethyl acetate) to obtain the powder which was washed with hexane and dried to obtain 1.50 g of the desired compound (73.8%, colorless powder), mp: 84.0°–85.0° C.

Anal. for $C_{24}H_{42}N_2OS$, Calcd.: C; 70.88, H; 10.41, N; 6.89, Found: C; 70.89, H; 10.64, N; 6.81, NMR (200 MHz, $CDCl_3$) δ:0.88 (3H, t, J=7 Hz), 1.25 (20H, m), 1.62 (2H, quint., J=7 Hz), 1.93 (2H, quint., J=7 Hz), 2.17 (2H, t, J=7 Hz), 3.00 (2H, t, J=7 Hz), 3.40 (2H, q, J=7 Hz), 5.69 (1H, m), 7.09 (2H, dd, J=5, 2 Hz), 8.40 (2H, dd, J=5, 2 Hz), IR $(KBr)cm^{-1}$: 3300, 3070, 1640, 1570.

EXAMPLE 20

Synthesis of 4-[3-(Stearoylamino)propylthio]pyridine

To a solution of 700 mg (2.90 mmol) of 4-(3-aminopropylthio)pyridine dihydrochloride and 1.62 ml (11.6 mmol) of triethylamine in 30 ml of methylene chloride was added 1.18 ml (3.48 mmol) of stearoyl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: ethyl acetate) to obtain the powder which was washed with hexane and dried to obtain 1.20 g of the desired compound (95.2%, colorless powder), mp: 88.0°–89.0° C.

Anal. for $C_{26}H_{46}N_2OS$, Calcd.: C; 70.88, H; 10.41, N; 6.89, Found: C; 70.89, H; 10.64, N; 6.81, NMR (200 MHz, $CDCl_3$) δ:0.88 (3H, t, J=7 Hz), 1.25 (20H, m), 1.62 (2H, quint., J=7 Hz), 1.93 (2H, quint., J=7 Hz), 2.17 (2H, t, J=7 Hz), 3.03 (2H, t, J=7 Hz), 3.41 (2H, q, J=7 Hz), 5.63 (1H, m), 7.10 (2H, dd, J=5, 2 Hz), 8.40 (2H, dd, J=5, 2 Hz), IR $(KBr)cm^{-1}$: 3290, 3070, 1640, 1570.

EXAMPLE 21

Synthesis of 4-[3-(Oleoylamino)propylthio]pyridine

To a solution of 700 mg (2.90 mmol) of 4-(3-aminopropylthio)pyridine dihydrochloride and 1.62 ml (11.6 mmol) of triethylamine in 30 ml of methylene chloride was added 1.55 ml (3.48 mmol) of oleoyl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: ethyl acetate) to obtain the powder which was washed with hexane and dried to obtain 1.05 g of the desired compound (83.7%, colorless powder), mp: 50.0°–50.5° C.

Anal. for $C_{26}H_{44}N_2OS$, Calcd.: C; 70.70, H; 10.27, N; 6.38, Found: C; 70.83, H; 10.35, N; 6.42, NMR (200 MHz, $CDCl_3$) δ:0.88 (3H, t, J=7 Hz), 1.26 (20H, m), 1.66 (2H, quint., J=7 Hz), 1.70–2.10 (6H, m), 2.17 (2H, t, J=7 Hz), 3.00 (2H, t, J=7 Hz), 3.41 (2H, q, J=7 Hz), 5.34 (2H, t, J=6 Hz), 5.63 (1H, m), 7.10 (2H, dd, J=5, 2 Hz), 8.39 (2H, dd, J=5, 2 Hz), IR $(KBr)cm^{-1}$: 3300, 3070, 1640, 1570.

EXAMPLE 22

Synthesis of 4-[3-(2-Ethylhexanoylamino)propylthio]pyridine Hydrochloride

To a solution of 800 mg (3.32 mmol) of 4-(3-aminopropylthio)pyridine dihydrochloride and 2.22 ml (15.9 mmol) of triethylamine in 30 ml of methylene chloride was added 0.69 ml (3.98 mmol) of 2-ethylhexanoyl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: ethyl acetate) to obtain 1.02 g of the desired compound (free base) (quant., pale yellow oil).

Anal. for $C_{16}H_{26}N_2OS \cdot 0.4H_2O$, Calcd.: C; 63.71, H; 8.96, N; 9.29, Found: C; 64.06, H; 9.16, N; 8.74, NMR (200 MHz, $CDCl_3$) δ:0.87 (3H, t, J=7 Hz), 0.88 (3H, t, J=7 Hz), 1.00–1.75 (8H, m), 1.91 (1H, quint., J=7 Hz), 1.94 (2H, quint., J=7 Hz), 3.02 (2H, t, J=7 Hz), 3.43 (2H, q, J=7 Hz), 5.70 (1H, m), 7.11 (2H, dd, J=5, 2 Hz), 8.39 (2H, dd, J=5, 2 Hz), IR (neat) $cm^{-1}$: 3290, 3050, 2960, 1640.

The above free base (250 mg, 0.81 mmol) was treated with 2N hydrogen chloride solution in methanol (5 ml, 10.0 mmol). The solvent was distilled off. The powder was washed with acetone and dried to obtain 280 mg of the desired compound (quant., colorless powder), mp: 163.0°–165.0° C.

Anal. for $C_{16}H_{27}N_2OSCl \cdot 0.2H_2O$, Calcd.: C; 57.45, H; 8.26, N; 8.37, Found: C; 57.78, H; 8.32, N; 8.31,

EXAMPLE 23

Synthesis of 4-[3-(Cyclohexanoylamino)propylthio]pyridine Hydrochloride

To a solution of 1.00 g (4.15 mmol) of 4-(3-aminopropylthio)pyridine dihydrochloride and 2.77 ml (19.8 mmol) of triethylamine in 40 ml of methylene chloride was added 0.66 ml (4.96 mmol) of cyclohexanoyl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: ethyl acetate) to obtain 890 mg of the desired compound (free base) (77.0%, colorless prisms), mp: 93.0°–94.0° C.

Anal. for $C_{15}H_{22}N_2OS$, Calcd.: C; 64.71, H; 7.96, N; 10.06, Found: C; 64.88, H; 8.02, N; 10.07 NMR (200 MHz, $CDCl_3$) δ:1.10–2.15 (13H, m), 3.00 (2H, t, J=7 Hz), 3.40 (2H, q, J=7 Hz), 5.68 (1H, m), 7.10 (2H, dd, J=5, 2 Hz), 8.40 (2H, d, J=5 Hz), IR (KBr)$cm^{-1}$: 3290, 3050, 2930, 1630.

The above free base (650 mg, 2.33 mmol) was treated with 2N hydrogen chloride solution in methanol (5 ml, 10.0 mmol). The solvent was distilled off. The powder was washed with acetone and dried to obtain 670 mg of the desired compound (91.1%, colorless powder).

Anal. for $C_{15}H_{23}N_2OSCl \cdot 1.5H_2O$, Calcd.: C; 52.69, H; 7.66, N; 8.19, Found: C; 52.58, H; 6.95, N; 8.14.

EXAMPLE 24

Synthesis of 4-[3-(Pivaloylamino)propylthio]pyridine Hydrochloride

To a solution of 1.00 g (4.15 mmol) of 4-(3-aminopropylthio)pyridine dihydrochloride and 2.77 ml (19.8 mmol) of triethylamine in 40 ml of methylene chloride was added 0.61 ml (4.96 mmol) of pivaloyl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: ethyl acetate) to obtain 1.01 g of the desired compound (free base) (96.4%, yellow oil).

Anal. for $C_{13}H_{20}N_2OS$, Calcd.: C; 60.15, H; 8.08, N; 10.79, Found: C; 60.44, H; 7.93, N; 10.66, NMR (200 MHz, $CDCl_3$) δ:1.20 (9H, s), 1.94 (2H, quint., J=7 Hz), 3.00 (2H, t, J=7 Hz), 3.40 (2H, q, J=7 Hz), 5.85 (1H, m), 7.11 (2H, dd, J=5, 2 Hz), 8.40 (2H, dd, J=5, 2 Hz), IR (KBr)$cm^{-1}$: 3270, 3030, 2980, 1650.

The above free base (1.01 g, 4.00 mmol) was treated with 2N hydrogen chloride solution in methanol (5 ml, 10.0 mmol). The solvent was distilled off. The powder was washed with acetone and dried to obtain 1.16 g of the desired compound (quant., colorless powder), mp: 87.0°–90.0° C.

Anal. for $C_{13}H_{21}N_2OSCl \cdot 2.0H_2O$, Calcd.: C; 48.06, H; 7.76, N; 8.62, Found: C; 47.93, H; 7.57, N; 8.53.

EXAMPLE 25

Synthesis of 4-[3-(Trifluoroacetylamino)propylthio]pyridine Hydrochloride

To a solution of 1.00 g (4.15 mmol) of 4-(3-aminopropylthio)pyridine dihydrochloride and 2.77 ml (19.8 mmol) of triethylamine in 40 ml of methylene chloride was added 0.70 ml (4.96 mmol) of anhydrous trifluoroacetic acid under ice-cooling with stirring and the mixture was stirred for at room temperature for 30 minutes. The reaction mixture was washed with an aqueous saturated sodium bicarbonate solution and water and dried. The solvent was distilled off. The residue was purified by column chromatography (eluent: ethyl acetate) to, obtain the powder which was washed with hexane and dried to obtain 750 mg of the desired compound (free base) (68.4%, pale yellow prisms).

Anal. for $C_{10}H_{11}N_2OSF_3$, Calcd.: C; 45.45, H; 4.20, N; 10.60, Found: C; 45.26, H; 4.17, N; 10.52, NMR (200 MHz, $CDCl_3$) δ:2.02 (2H, quint., J=7 Hz), 3.03 (2H, t, J=7 Hz), 3.55 (2H, q, J=7 Hz), 7.08 (2H, dd, J=5, 2 Hz), 7.34 (1H, m), 8.37 (2H, dd, J=5, 2 Hz), IR (KBr)$cm^{-1}$: 3160, 3030, 2850, 1720, 1590.

The above free base (340 mg, 1.29 mmol) was treated with 2N hydrogen chloride solution in methanol (5 ml, 10.0 mmol). The solvent was distilled off. The powder was washed with acetone and dried to obtain 367 mg of the desired compound (94.9%, colorless powder), mp: 184.0°–186.0° C.

Anal. for $C_{10}H_{12}N_2OSClF_3 \cdot 0.3H_2O$, Calcd.: C; 39.23, H; 4.15, N; 9.15, Found: C; 39.45, H; 3.99, N; 9.14.

EXAMPLE 26

Synthesis of 4-[3-(4-Phenylbenzoylamino)propylthio]pyridine Hydrochloride

To a solution of 1.00 g (4.15 mmol) of 4-(3-aminopropylthio)prydine dihydrochloride and 2.89 ml (19.9 mmol) of triethylamine in 40 ml of methylene chloride was added 1.08 ml (4.98 mmol) of 4-phenylbenzoyl chloride under ice-cooling with stirring and the mixture was stirred at room temperature for 30 minutes. The reaction solution was washed with an aqueous saturated sodium bicarbonate solution and water and dried. The solvent was distilled off. The residue was purified by column chromatography (eluent: methanol/ethyl acetate=1:10) to obtain the powder which was washed with ether and dried to obtain 980 mg of the desired compound (free base) (67.8%, pale yellow powder), mp: 169.0°–170.0° C.

Anal. for $C_{21}H_{20}N_2OS$, Calcd.: C; 72.38, H; 5.78, N; 8.04, Found: C; 72.15, H; 5.84, N; 7.95, NMR (200 MHz, $CDCl_3$) δ:2.07 (2H, quint., J=7 Hz), 3.09 (2H, t, J=7 Hz), 3.65 (2H, q, J=7 Hz), 6.50 (1H, m), 7.12 (2H, dd, J=5, 2 Hz), 7.30–7.90 (9H, m), 8.39 (2H, dd, J=5, 2 Hz), IR (KBr)cm$^{-1}$: 3340, 3030, 2930, 1640, 1600.

The above free base (500 mg, 1.43 mmol) was treated with 2N hydrogen chloride solution in methanol (5 ml, 10.0 mmol). The solvent was distilled off. The powder was washed with acetone and dried to obtain 545 mg of the desired compound (98.7%, colorless powder), mp: 198.0°–200.0° C.

Anal. for $C_{21}H_{21}N_2OSCl$, Calcd.: C; 65.53, H; 5.50, N; 7.28, Found: C; 65.36, H; 5.52, N; 7.20.

EXAMPLE 27

Synthesis of 4-[3-(1-Naphthoylamino)propylthio]pyridine Hydrochloride

To a solution of 1.00 g (4.15 mmol) of 4-(3-aminopropylthio)pyridine dihydrochloride and 2.78 ml (19.9 mmol) of trietylamine in 40 ml of methylene chloride was added 0.75 ml (4.98 mmol) of 1-naphthoyl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: methanol/ethyl acetate=1:10) to obtain the powder which was washed with ether and dried to obtain 1.00 g of the desired compound (free base) (74.8%, yellow powder), mp: 113.0°–114.0° C.

Anal. for $C_{19}H_{18}N_2OS$, Calcd.: C; 70.78, H; 5.63, N; 8.69, Found: C; 70.55, H; 5.70, N; 8.46, NMR (200 MHz, CDCl$_3$) δ:2.09 (2H, quint., J=7 Hz), 3.11 (2H, t, J=7 Hz), 3.68 (2H, q, J=7 Hz), 6.31 (1H, m), 7.11 (2H, dd, J=5, 2 Hz), 7.35–7.70 (4H, m), 7.80–8.00 (2H, m), 8.20–8.35 (1H, m), 8.39 (2H, dd, J=5, 2 Hz), IR (KBr)cm$^{-1}$: 3280, 3050, 2960, 1640, 1610.

The above free base (850 mg, 2.64 mmol) was treated with 2N hydrogen chloride solution in methanol (5 ml, 10.0 mmol). The solvent was distilled off. The powder was washed with acetone and dried to obtain 930 mg of the desired compound (98.3%, pale yellow powder) mp: 190.0°–192.0° C.

Anal. for $C_{19}H_{19}N_2OSCl$, Calcd.: C; 63.59, H; 5.34, N; 7.81, Found: C; 63.45, H; 5.32, N; 7.74.

EXAMPLE 28

Synthesis of 4-[3-(Cinnamoylamino)propylthio]pyridine Hydrochloride

To a solution of 1.00 g (4.15 mmol) of 4-(3-aminopropylthio)pyridine dihydrochloride and 2.78 ml (19.9 mmol) of triethylamine in 40 ml of methylene chloride was added 830 mg (4.98 mmol) of cinnamoyl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: methanol/ethyl acetate=1:10) to obtain the powder which was washed with ether and dried to obtain 1.10 g of the desired compound (free base) (88.8%, colorless powder), mp: 116.0°–11.7.0° C.

Anal. for $C_{17}H_{18}N_2OS$, Calcd.: C; 68.43, H; 6.08, N; 9.39, Found: C; 68.26, H; 6.18, N; 9.19, NMR (200 MHz, CDCl$_3$) δ:2.01 (2H, quint., J=7 Hz), 3.05 (2H, t, J=7 Hz), 3.56 (2H, q, J=7 Hz), 6.05 (1H, m), 6.41 (1H, d, J=16 Hz), 7.10 (2H, dd, J=5, 2 Hz), 7.30–7.55 (5H, m), 7.65 (1H, d, J=16 Hz), 8.39 (2H, dd, J=5, 2 Hz), IR (KBr)cm$^{-1}$: 3350, 3300, 3030, 1650, 1620, 1570.

The above free base (830 mg, 2.78 mmol) was treated with 2N hydrogen chloride solution in methanol (5 ml, 10.0 mmol). The solvent was distilled off. The powder was washed with acetone and dried to obtain 950 mg of the desired compound (quant., colorless powder), mp: 105.0°–108.0° C.

Anal. for $C_{17}H_{19}N_2OSCl.2.0H_2O$, Calcd.: C; 55.05, H; 6.25, N; 7.55, Found: C; 54.95, H; 5.83, N; 7.74.

EXAMPLE 29

Synthesis of 4-[3-(4-Chlorobenzoylamino)propylthio]pyridine Hydrochloride

To a solution of 1.00 g (4.15 mmol) of 4-(3-aminopropylthio)pyridine dihydrochloride and 2.77 ml (19.8 mmol) of triethylamine in 40 ml of methylene chloride was added 0.63 ml (4.96 mmol) of 4-chlorobenzoyl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: ethyl acetate) to obtain the powder which was washed with ether and dried to obtain 1.01 g of the desired compound (free base) (79.3%, pale yellow powder), mp: 95.0°–96.0° C.

Anal. for $C_{15}H_{15}N_2OSCl$, Calcd.: C; 58.72, H; 4.93, N; 9.13, Found: C; 58.64, H; 4.95, N; 9.00, NMR (200 MHz, CDCl$_3$) δ:2.05 (2H, quint., J=7 Hz), 3.07 (2H, t, J=7 Hz), 3.61 (2H, q, J=7 Hz), 6.50 (1H, m), 7.10 (2H, dd, J=5, 2 Hz), 7.41 (2H, d, J=9 Hz), 7.71 (2H, d, J=9 Hz), 8.38 (2H, dd, J=5, 2 Hz), IR (KBr)cm$^{-1}$: 3280, 3030, 2930, 1630, 1600.

The above free base (700 mg, 2.28 mmol) was treated with 2N hydrogen chloride solution in methanol (5 ml, 10.0 mmol). The solvent was distilled off. The powder was washed with acetone and dried to obtain 750 mg of the desired compound (95.8%, pale yellow powder), mp: 195.0°–197.0° C.

Anal. for $C_{15}H_{16}OSCl_2.0.3H_2O$, Calcd.: C; 51.67, H; 4.80, N; 8.03, Found: C; 51.73, H; 4.80, N; 7.88.

EXAMPLE 30

Synthesis of 4-[3-(4-Methoxybenzoylamino)propylthio]pyridine

To a solution of 1.00 g (4.15 mmol) of 4-(3-aminopropylthio)pyridine dihydrochloride and 2.77 ml (19.8 mmol) of triethylamine in 40 ml of methylene chloride was added 846 mg (4.96 mmol) of 4-anisoyl chloride under ice-cooling with stirring and the mixture was stirred for at room temperature for 30 minutes. The reaction mixture was washed with an aqueous saturated sodium bicarbonate solution and water and dried. The solvent was distilled off. The residue was purified by column chromatography (eluent: ethyl acetate) to obtain the powder which was washed with ether and dried to obtain 990 mg of the desired compound (78.9%, colorless powder), mp: 121.0°–122.0° C.

Anal. for $C_{16}H_{18}O_2S$, Calcd.: C; 63.55, H; 6.00, N; 9.26, Found: C; 63.50, H; 6.10, N; 9.14, NMR (200 MHz, CDCl$_3$) δ: 2.04 (2H, quint., J=7 Hz), 3.07 (2H, t, J=7 Hz), 3.60 (2H, q, J=7 Hz), 3.85 (3H, s), 6.38 (1H, m), 6.92 (2H, dd, J=7, 2 Hz), 7.11 (2H, dd, J=5, 2 Hz), 7.74 (2H, dd, J=7, 2 Hz), 8.38 (2H, dd, J=5, 2 Hz), IR (KBr)cm$^{-1}$: 3340, 3030, 2930, 1640, 1600.

EXAMPLE 31

Synthesis of
4-[3-(4-Methylbenzoylamino)propylthio]pyridine

To a solution of 1.00 g (4.15 mmol) of 4-(3-aminopropylthio)pyridine dihydrochloride and 2.77 ml (19.8 mmol) of triethylamine in 40 ml of methylene chloride was added 0.65 ml (4.96 mmol) of 4-toluoyl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: ethyl acetate) to obtain the powder which was washed with ether and dried to obtain 910 mg of the desired compound (76.6%, colorless powder), mp: 110.0°–111.0° C.

Anal. for $C_{16}H_{18}N_2OS$, Calcd.: C; 67.10, H; 6.33, N; 9.78, Found: C; 67.25, H; 6.41, N; 9.67, NMR (200 MHz, CDCl$_3$) δ:2.04 (2H, quint., J=7 Hz), 2.39 (3H, s), 3.06 (2H, t, J=7 Hz), 3.61 (2H, q, J=7 Hz), 6.47 (1H, m), 7.11 (2H, dd, J=5, 2 Hz), 7.23 (2H, d, J=8Hz), 7.67 (2H, d, J=8 Hz), 8.39 (2H, d, J=5, 2 Hz), IR (KBr)cm$^{-1}$: 3330, 3040, 2930, 1630.

EXAMPLE 32

Synthesis of
4-[3-(4-t-Butylbenzoylamino)propylthio]pyridine
Hydrochloride

To a solution of 1.00 g (4.15 mmol) of 4-(3-aminopropylthio)pyridine dihydrochloride and 2.77 ml (19.8 mmol) of triethylamine in 40 ml of methylene chloride was added 0.48 ml (4.96 mmol) of 4-t-butylbenzoyl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: ethyl acetate) to obtain 1.20 g of the desired compound (free base) (88.0%, yellow powder).

NMR (200 MHz, CDCl$_3$) δ:1.33 (9H, s), 2.05 (2H, quint., J=7 Hz), 3.07 (2H, t, J=7 Hz), 3.62 (2H, q, J=7 Hz), 6.38 (1H, m), 7.11 (2H, dd, J=5, 2 Hz), 7.45 (2H, dd, J=7, 2 Hz), 7.71 (2H, dd, J=7, 2 Hz), 8.39 (2H, dd, J=5, 2 Hz), IR (Neat) cm$^{-1}$: 3390, 3270, 2960, 1650, 1600.

The above free base (1.20 g, 3.65 mmol) was treated with 2N hydrogen chloride solution in methanol (5 ml, 10.0 mmol). The solvent was distilled off. The powder was washed with acetone and dried to obtain 1.33 g of the desired compound (quant., yellow powder)

Anal. for $C_{19}H_{25}N_2OSCl.3.5H_2O$, Calcd.: C; 53.32, H; 7.54, N; 6.55, Found: C; 53.45, H; 7.24, N; 6.57.

EXAMPLE 33

Synthesis of
4-[3-(3,5-Dimethoxybenzoylamino)propylthio]pyridine

To a solution of 1.00 g (4.15 mmol) of 4-(3-aminopropylthio)pyridine dihydrochloride and 2.77 ml (19.8 mmol) of triethylamine in 40 ml of methylene chloride was added 995 mg (4.96 mmol) of 3,5-dimethoxybenzoyl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: ethyl acetate) to obtain 1.21 g of the desired compound (87.7%, pale yellow powder), mp: 110.0°–111.0° C.

Anal. for $C_{17}H_{20}N_2O_3S$, Calcd.: C; 61.42, H; 6.06, N; 8.43, Found: C; 61.32, H; 6.11, N; 8.24, NMR (200 MHz, CDCl$_3$) δ:2.04 (2H, quint., J=7 Hz), 3.06 (2H, t, J=7 Hz), 3.60 (2H, q, J=7 Hz), 3.82 (6H, s), 6.47 (1H, m), 6.58 (1H, t, J=2 Hz), 6.89 (2H,.d, J=2 Hz), 7.11 (2H, dd, J=5, 2 Hz), 8.38 (2H, dd, J=5, 2 Hz), IR (Neat) cm$^{-1}$: 3250, 3060, 2930, 1650, 1590.

EXAMPLE 34

Synthesis of
4-[3-(4-n-Butylbenzoylamino)propylthio]pyridine
Hydrochloride

To a solution of 1.00 g (4.15 mmol) of 4-(3-aminopropylthio)pyridine dihydrochloride and 2.78 ml (19.9 mmol) of triethylamine in 40 ml of methylene chloride was added 0.93 ml (4.96 mmol) of 4-n-butylbenzoyl chloride under ice-cooling with stirring and the mixture was stirred at room temperature for 30 minute. The reaction mixture was washed with an aqueous saturated sodium bicarbonate solution and water and dried. The solvent was distilled off. The residue was purified by column chromatography (eluent: ethyl acetate) to obtain 1.10 g of the desired compound (free base) (80.7%, colorless wax), mp: 46.0°–47.0° C.

Anal. for $C_{19}H_{24}N_2OS.0.3H_2O$, Calcd.: C; 68.35, H; 7.43, N; 8.39, Found: C; 68.36, H; 7.26, N; 8.49, NMR (200 MHz, CDCl$_3$) δ:0.92 (3H, t, J=7 Hz), 1.35 (2H, sextet., J=7 Hz), 1.60 (2H, quint., J=7 Hz), 2.05 (4H, quint., J=7 Hz), 2.65 (2H, t, J=7 Hz), 3.07 (2H, t, J=7 Hz), 3.61 (2H, q, J=7 Hz), 6.43 (1H, m), 7.12 (2H, dd, J=5, 2 Hz), 7.24 (2H, d, J=8 Hz), 7.68 (2H, dd, J=5, 2 Hz), 8.38 (2H, d, J=8 Hz), IR (KBr)cm$^{-1}$: 3360, 3030, 2920, 1630.

The above free base (1.10 g, 3.35 mmol) was treated with 2N hydrogen chloride solution in methanol (5 ml, 10.0 mmol). The solvent was distilled off. The powder was washed with acetone and dried to obtain 1.33 g of the desired compound (quant., colorless powder), mp: 77.0°–80.0° C.

Anal. for $C_{19}H_{25}N_2OSCl.1.0H_2O$, Calcd.: C; 57.20, H; 6.82, N; 7.02, Found: C; 57.16, H; 6.87, N; 6.91.

EXAMPLE 35

Synthesis of
4-[3-(4-n-Butoxybenzoylamino)propylthio]pyridine
Hydrochloride

To a solution of 1.00 g (4.15 mmol) of 4-(3-aminopropylthio)pyridine dihydrochloride and 2.78 ml (19.9 mmol) of triethylamine in 40 ml of methylene chloride was added 0.94 ml (4.96 mmol) of 4-n-butoxybenzoyl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: ethyl acetate) to obtain 1.10 g of the desired compound (free base) (76.9%, colorless powder), mp: 98.0°–99.0° C.

Anal. for $C_{19}H_{24}N_2O_2OS$, Calcd.: C; 66.25, H; 7.02, N; 8.13, Found: C; 66.52, H; 6.99, N; 8.11, NMR (200 MHz, $CDCl_3$) δ:0.98 (3H, t, J=7 Hz), 1.49 (2H, sextet., J=7 Hz), 1.79 (2H, quint., J=7 Hz), 2.04 (2H, quint., J=7 Hz), 3.06 (2H, t, J=7 Hz), 3.60 (2H, q, J=7 Hz), 4.00 (2H, t, J=7 Hz), 6.36 (1H, m), 6.91 (2H, dd, J=9, 2 Hz), 7.11 (2H, dd, J=5, 2 Hz), 7.72 (2H, dd, J=9, 2 Hz), 8.38 (2H, dd, J=5, 2 Hz), IR $(KBr)cm^{-1}$: 3360, 3030, 2920, 1630.

The above free base (800 mg, 2.32 mmol) was treated with 2N hydrogen chloride solution in methanol (5 ml, 10.0 mmol). The solvent was distilled off. The powder was washed With acetone and dried to obtain 880 mg of the desired compound (99.5%, colorless powder), mp: 140.0°–142.0° C.

Anal. for $C_{19}H_{25}N_2O_2SCl.1.0H_2O$, Calcd.: C; 52.55, H; 5.59, N; 8.17, Found: C; 52.45, H; 5.57, N; 8.02.

EXAMPLE 36

Synthesis of 4-[3-(Salicyloylamino)propylthio]pyridine Hydrochloride

To a solution of 1.00 g (4.15 mmol) of 4-(3-aminopropylthio)pyridine dihydrochloride and 2.77 ml (19.8 mmol) of triethylamine in 40 ml of methylene chloride was added 985 mg (4.96 mmol) under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: ethyl acetate) to obtain 960 mg of the desired compound (free base) (70.0%, colorless powder), mp: 124.0°–125.0° C.

Anal. for $C_{15}H_{16}N_2O_2S$, Calcd.: C; 62.48, H; 5.59, N; 9.71, Found: C; 62.59, H; 5.77, N; 9.41, NMR (200 MHz, $CDCl_3$) δ:2.06 (2H, quint., J=7 Hz), 3.07 (2H, t, J=7 Hz), 3.63 (2H, q, J=7 Hz), 6.84 (1H, td, J=8, 1 Hz), 6.88 (1H, m), 6.99 (1H, dd, J=8,. 1 Hz), 7.10 (2H, dd, J=5, 2 Hz), 7.39 (1H, td, J=9, 1 Hz), 7.41 (1H, dd, J=8, 1 Hz), 8.38 (2H, d, J=5 Hz), IR $(KBr)cm^{-1}$: 3250, 3050, 1640, 1590.

The above free base (400 mg, 1.39 mmol) was treated with 2N hydrogen chloride solution in methanol (5 ml, 10.0 mmol). The solvent was distilled off. The powder was washed with acetone and dried to obtain 420 mg of the desired compound (93.2%, colorless powder), mp:74.0°–76.0° C.

Anal. for $C_{15}H_{17}N_2O_2SCl..1.0H_2O$, Calcd.: C; 52.55, H; 5.59, N; 8.17, Found: C; 52.42, H; 5.58, N; 8.05.

EXAMPLE 37

Synthesis of 4-[3-(3,5-di-t-Butyl-4-hydroxybenzoylamino)propylthio]pyridine

To a solution of 1.49 g (5.94 mmol) of 3,5-di-t-butyl-4-hydroxybenzoic acid and 889 mg (7.73 mmol) of N-hydroxysuccinimide in 60 ml of methylene chloride was added 1.38 g (7.13 mmol) of 1-ethyl-3-(3-dimethylaminopropyl)carbodiimide hydrochloride under ice-cooling with stirring and the mixture was stirred at room temperature for 30 minutes. Further 1.00 g (5.94 mmol) of 4-(3-aminopropylthio)pyridine was added and the mixture was stirred at room temperature for 8 hours. The reaction mixture was washed with water and dried. The solvent was distilled off. The residue was purified by column chromatography (eluent: ethyl acetate) to obtain 650 mg of the desired compound (27.3%, colorless powder) mp: 203.0°–204.0° C.

Anal. for $C_{23}H_{32}N_2O_2S$, Calcd.: C; 68.96, H; 8.05, N; 6.99, Found: C; 68.70, H; 8.09, N; 6.80, NMR (200 MHz, $CDCl_3$) δ:1.46 (18H s), 2.04 (2H, quint., J=7 Hz), 3.08 (2H, t, J=7 Hz), 3.57 (2H, q, J=7 Hz), 7.12 (2H, dd, J=5, 2 Hz), 7.65 (2H, s), 8.37 (2H, dd, J=5, 2 Hz), IR $(KBr)cm^{-1}$: 3270, 3070, 2950, 1620, 1590.

EXAMPLE 38

Synthesis of 4-[3-(2-Carboxybenzoylamino)propylthio]pyridine

A solution of 340 mg (2.02 mmol) of 4-(3-aminopropylthio)pyridine and 738 mg (4.98 mmol) of anhydrous phthalic acid in 5 ml of methylene chloride was stirred at room temperature for 30 minutes. The resulting crystals were filtered and dried to obtain 590 mg of the desired compound (92.3%, colorless powder), mp: 151.0°–153.3° C.

Anal. for $C_{16}H_{16}N_2O_3S.0.5H_2O$, Calcd.: C; 59.06, H; 5.27, N; 8.85, Found: C; 58.77, H; 5.09, N; 8.45, NMR (200 MHz, $CDCl_3$) δ:1.87 (2H, quint., J=7 Hz), 3.15 (2H, t, J=7 Hz), 3.35 (2H, q, J=7 Hz), 7.29 (2H, dd, J=5, 2 Hz), 7.42 (1H, dd, J=7, 1 Hz), 7.54 (2H, td, J=7, 1 Hz), 7.78 (1H, dd, J=7, 1 Hz), 8.37 (2H, d, J=5 Hz), IR (Neat) $cm^{-1}$: 3250, 3080, 2950, 1700, 1640, 1590.

EXAMPLE 39

Synthesis of 4-[3-(4-Phenyl-n-butyrylamino)propylthio]pyridine

To a suspension of 3.28 g (20.0 mmol) of 4-phenylbutyric acid in 100 ml of benzene was added 6.98 ml (80.0 mmol) of oxalyl chloride and the mixture was refluxed for 1 hour. After cooling, the solvent was distilled off to obtain 3.60 g of the desired compound (98.5%). To a solution of 2.00 g (8.29 mmol) of 4-(3-aminopropylthio)pyridine dihydrochloride and 4.16 ml (29.8 mmol) of triethylamine in 90 ml of methylene chloride was added 1.80 g (10.0 mmol) of 4-phenyl-n-butyryl chloride under ice-cooling with stirring and the mixture was stirred at room temperature for 30 minutes. The reaction mixture was washed with an aqueous saturated sodium bicarbonate solution and water and dried. The solvent was distilled off. The residue was purified by column chromatography (eluent: methanol/ethyl acetate= 1:10) to obtain 2.25 g of the desired compound (86.3%, colorless powder), mp: 58.0°–59.0° C.

Anal. for $C_{18}H_{22}N_2OS$, Calcd.: C; 68.75, H; 7.05, N; 8.91, S; 10.20, Found: C; 68.95, H; 7.13, N; 8.89, S; 10.17, NMR (200 MHz, $CDCl_3$) δ:1.91 (2H, quint., J=7 Hz), 1.97 (2H, quint., J=7 Hz), 2.18 (2H, t, J=7 Hz), 2.66 (2H, t, J=7 Hz), 2.99 (2H, t, J=7 Hz), 3.40 (2H, q, J=7 Hz), 5.66 (1H, m), 7.08 (2H, dd, J=5, 2 Hz), 7.10–7.35 (5H, m), 8.37 (2H, dd, J=5, 2 Hz), IR (KBr) $cm^{-1}$: 3320, 2940, 1640, 1580.

EXAMPLE 40

Synthesis of 4-[3-(Benzoylamino)propylthio]pyridine

To a solution of 1.00 g (4.15 mmol) of 4-(3 -aminopropylthio)pyridine dihydrochloride and 2.77 ml (19.8 mmol) of triethylamine in 40 ml of methylene chloride was added 0.58 ml (4.96 mmol) of benzoyl chloride under ice-cooling with stirring and the mixture stirred at room temperature for 30 minutes. The reaction mixture was washed with an aqueous saturated sodium bicarbonate solution and water and dried. The solvent was distilled off. The residue was purified by column chromatography (eluent: ethyl acetate) to obtain 960 mg of the desired compound (84.9%, colorless needles), mp: 120.0°–121.0° C.

Anal. for $C_{15}H_{16}N_2OS$, Calcd.: C; 66.15, H; 5.92, N; 10.29, Found: C; 66.12, H; 5.95, N; 10.18, NMR (200 MHz, CDCl$_3$) δ:2.05 (2H, quint., J=7 Hz), 3.07 (2H, t, J=7 Hz), 3.62 (2H, q, J=7 Hz), 6.65 (1H, m), 7.10 (2H, dd, J=5, 2 Hz), 7.35–7.60 (3H, m), 7.70–7.85 (2H, m), 8.37 (2H, dd, J=5, 2 Hz), IR (KBr)cm$^{-1}$: 3300, 1620, 1580.

EXAMPLE 41

Synthesis of
4-[3-(Nicotinoylamino)propylthio]pyridine

To a solution of 10.0 g (41.5 mmol) of 4-(3-aminopropylthio)pyridine dihydrochloride and 27.7 ml (200 mmol) of triethylamine in methylene chloride (100 ml), 8.86 g (49.8 mmol) of nicotinoyl chloride hydrochloride was added under ice-cooling with stirring. The mixture was stirred at room temperature for 30 minutes. The reaction mixture was washed with a saturated aqueous solution of sodium bicarbonate and water and dried, and then the solvent was distilled off. The residue was purified by column chromatography (eluent: methanol/ethyl acetate=1:10) to obtain powder. The powder was washed with ether and dried to obtain the desired compound (8.50 g, yield: 75.8%, pale yellow powder).

mp: 90.0°–91.0° C., Anal. for $C_{14}H_{15}N_3OS$, Calcd.: C; 61.51, H; 5.53, N; 15.37, Found: C; 61.31, H; 5.61, N; 15.27, NMR (200 MHz, CDCl$_3$) δ:2.08 (2H, quint., J=7 Hz), 3.08 (2H, t, J=7 Hz), 3.65 (2H, q, J=7 Hz), 6.84 (1H, m), 7.10, (2H, dd, J=5,2 Hz), 7.40 (1H, dd, J=8,5 Hz), 8.13 (1H, dt, J=8,2 Hz), 8.37 (2H, dd, J=5,2 Hz), 8.73 (1H, dd, J=5,2 Hz), 8.99 (1H, d, J=2 Hz). IR (KBr) cm$^{-1}$: 3320, 3030, 1630.

EXAMPLE 42

Synthesis of
4-[3-(2-Picolynoylamino)propylthio]pyridine

To a solution of 20.0 g (82.9 mmol) of 4-(3-aminopropylthio)pyridine dihydrochloride and 55.5 ml (400 mmol) of triethylamine in 200 ml of methylene chloride, 17.8 g (100 mmol) of 2-picolynoyl chloride was added under ice-cooling with stirring. The mixture was stirred at room temperature for 30 minutes. The reaction mixture was washed with a saturated aqueous solution of sodium bicarbonate and water and dried, and then the solvent was distilled off. The residue was purified by column chromatography (eluent: methanol/ethyl acetate=1:10) to obtain powder. The powder was recrystallized from hexane/ethyl acetate (=1:1) to obtain the desired compound (18.8 g, yield: 82.9%, pale yellow needles).

mp: 52.0°–53.0° C., Anal. for $C_{14}H_{15}N_3OS$, Calcd.: C; 61.51, H; 5.53, N; 15.37, S; 11.73, Found: C; 61.46, H; 5.48, N; 15.30, S; 11.83, NMR (200 MHz, CDCl$_3$) δ:2.07 (2H, quint., J=7 Hz), 3.08 (2H, t, J=7 Hz), 3.65 (2H, q, J=7 Hz), 7.12 (2H, dd, J=5,2 Hz), 7.45 (1H, ddd, J=8,5,1 Hz), 7.87 (1H, td, J=8,2 Hz), 8.20 (2H, dr, J=8,1 Hz) , 8.38 (2H, dd, J=5,2 Hz) , 8.55 (1H, ddd, J=5, 2, 1 Hz). IR (KBr)cm$^{-1}$: 3350, 3050, 2940, 1660.

EXAMPLE 43

Synthesis of
4-[3-(4-Picolynoylamino)propylthio]pyridine

To a solution of 20.0 g (82.9 mmol) of 4-(3-aminopropylthio)pyridine dihydrochloride and 55.5 ml (400 mmol) of triethylamine in 200 ml of methylene chloride, 17.7 g (9.95 mmol) of 4-picolynoyl chloride hydrochlride was added under ice-cooling with stirring. The mixture was stirred at room temperature for 30 minutes. The reaction mixture was washed with a saturated aqueous solution of sodium bicarbonate and water and dried, and then the solvent was distilled off. The residue was purified by column chromatography (eluent: methanol/ethyl acetate=1:5) to obtain powder. The powder was washed with ether and dried to obtain the desired compound (1.63 g, yield: 71.9%, pale brown powder).

mp: 115.0°–117.0° C., Anal. for $C_{14}H_{15}N_3OS \cdot 0.3H_2O$, Calcd.: C; 60.32, H; 5.64, N 15.07, Found: C; 60.62, H; 5.58, N 14.81. NMR (200 MHz, CDCl$_3$) δ:2.07 (2H, quint., J=7 Hz), 3.07 (2H, t, J=7 Hz), 3.64 (2H, q, J=7 Hz), 6.92 (1H, m), 7.09 (2H, dd, J=5,2 Hz), 7.62 (1H, dd, J=5,2 Hz), 8.36 (1H, dd, J=5,2 Hz), 8.73 (2H, dd, J=5,2 Hz). IR (KBr)cm$^{-1}$: 3250, 3030, 2950, 1670.

EXAMPLE 44

Synthesis of
4-[3-(3-Quinolineacryloylamino)propylthio]pyridine

To a solution of 396 mg (1.64 mmol) of 4-(3-aminopropylthio)pyridine dihydrochloride and 0.27 ml (1.97 mmol) of triethylamine in 20 ml of methylene chloride, 500 mg (1.96 mmol) of 3-quinolineacryloyl chloride hydrochlride was added under ice-cooling with stirring. The mixture was stirred at room temperature for 30 minutes. The reaction mixture was washed with a saturated aqueous solution of sodium bicarbonate and water and dried, and then the solvent was distilled off. The residue was purified by column chromatography (eluent: methanol/ethyl acetate=1:10) to obtain powder. The powder was washed with ether and dried to obtain the desired compound (480 mg, yield: 83.8%, pale yellow powder).

mp: 154.0°–155.0° C., Anal. for $C_{20}H_{19}N_3OS$, Calcd.: C; 68.74, H; 5.48, N; 12.02, Found: C; 68.50, H; 5.48, N; 11.84. NMR (200 MHz, CDCl$_3$ ) δ:2.04 (2H, quint., J=7 Hz), 3.07 (2H, t, J=7 Hz), 3.60 (2H, q, J=7 Hz), 6.50 (1H, t, J=6 Hz), 6.66 (1H, d, J=16 Hz), 7.10 (2H, dd, J=5,2 Hz), 7.56 (1H, td, J=8,1 Hz), 7.73 (1H, td, J=8,1 Hz),7.80 (1H, d, J=16 Hz), 7.81 (1H, d, J=8Hz), 8.07 (1H, d, J=8 Hz), 8.16 (1H, d, J=2 Hz), 8.38 (2H, dd, J=5,2 Hz), 9.06 (1H, d, J=2 Hz). IR (KBr)cm$^{-1}$: 3300, 3030, 1650, 1620.

EXAMPLE 45

Synthesis of
4-[3-(1-Methyl-2-pyrrolecarbonylamino)-
propylthio]pyridine

Oxalyl chloride [3.49 ml (40 mmol)] was added to a suspension of 1.25 g (10.0 mmol) of 1-methyl-2-pyrrolecarboxylic acid in 50 ml of benzene, and the mixture was refluxed for 1 hour. After cooling, the solvent was distilled off to obtain the-desired compound (1.80 g, yield: 98.5%). To a solution of 2.00 g (8.29 mmol) of 4-(3 -aminopropylthio)pyridine dihydrochloride and 4.16 ml (29.8 mmol) of triethylamine in 90 ml of methylene chloride, 1.45 g (10.0 mmol) or, the above acid chloride was added under ice-cooling with stirring. The mixture was stirred at room temperature for 30 minutes. The reaction mixture was washed with a saturated aqueous solution of sodium bicarbonate and water and dried, and then the solvent was distilled off. The residue was purified by column chromatography (eluent: methanol/ethyl acetate=1:10) to obtain 1.97 g of the desired compound (yield: 86.3%, colorless powder).

mp: 74.0°–75.0° C., Anal. for $C_{14}H_{17}N_3OS$, Calcd.: C; 61.06, H; 6.22, N; 15.26, Found: C; 60.99, H; 6.30, N; 15.14. NMR (200 MHz, $CDCl_3$) δ:2.01 (2H, quint., J=7 Hz), 3.06 (2H, t, J=7 Hz), 3.53 (2H q, J=7 Hz), 3.94 (3H, s), 6.08, (1H, dd, J=4,2 Hz), 6.55 (1H, m), 6.53 (1H, dd, J=4,2 Hz), 6.73 (1H, t, J=2 Hz), 7.11 (2H, dd, J=5,2 Hz), 8.39 (2H, dd, J=5,2 Hz). IR (KBr)$cm^{-1}$: 3270, 2940, 1650.

EXAMPLE 46

Synthesis of
4-[3-(2-Thenoylamino)propylthio]pyridine

To a solution of 10.0 g (41.5 mmol) of 4-(3-aminopropylthio)pyridine dihydrochloride and 27.7 ml (200 mmol) of triethylamine in 10.0 ml of methylene chloride, 5.35 ml (50.0 mmol) of 2-thenoyl chloride was added under ice-cooling with stirring. The mixture was stirred at room temperature for 30 minutes. The reaction mixture was washed with a saturated aqueous solution of sodium bicarbonate and water and dried, and then the solvent was distilled off. The residue was purified by column chromatography (eluent: methanol/ethyl acetate=1:20) to obtain powder. The powder was recrystallized from methanol/ethyl acetate (=1:20) to obtain 8.05 g of the desired compound (yield: 70.5%, yellow prisms).

mp: 112.0°–113.0° C., Anal. for $C_{13}H_{14}N_2OS_2$, Calcd.: C; 56.09, H; 5.07, N; 10.06, S; 23.04, Found: C; 56.17, H; 5.10, N; 10.00, S; 23.22. NMR (200 MHz, $CDCl_3$) δ:2.04 (2H, quint., J=7 Hz), 3.07 (2H, t, J=7 Hz), 3.59 (2H, q, J=7 Hz), 6.44 (1H, m), 7.08 (1H, dd, J=5,4 Hz), 7.11 (2H, dd, J=5,2 Hz), 7.48 (1H, dd, J=5,1 Hz), 7.52 (1H, dd, J=4,1 Hz), 8.38 (2H, dd, J=5,2 Hz). IR (KBr) $cm^{-1}$: 3210, 3040, 1640.

EXAMPLE 47

Synthesis of
2-[3-(Thenoylamino)propylthio]pyridine

To a solution of 1.50 g (6.22 mmol) of 2-(3 -aminopropylthio)pyridine dihydrochloride and 3.19 ml (22.9 mmol) of triethylamine in 60 ml of methylene chloride, 1.09 ml (7.46 mmol) of 2-thenoyl chloride was added under ice-cooling with stirring. The mixture was stirred at room temperature for 30 minutes. The reaction mixture was washed with a saturated aqueous solution of sodium bicarbonate and water and dried, and then the solvent was distilled off. The residue was purified by column chromatography (eluent: ethyl acetate) to obtain powder. The powder was washed with ether and dried to obtain 1.48 g of the desired compound (yield: 85.5%, colorless powder).

mp: 81.0°–82.0° C., Anal. for $C_{13}H_{14}N_2OS_2$, Calcd.: C; 56.09, H; 5.07, N; 10.06, Found: C; 55.51, H; 5.00, N; 9.61. NMR (200 MHz, $CDCl_3$) δ:2.00 (2H, quint., J=7 Hz), 3.33 (2H, t, J=7 Hz), 3.56 (2H, q, J=7 Hz), 7.01 (1H, dd, J=7,5,1 Hz), 7.11(1H, dd, J=5,4 Hz), 7.23 (1H, dt, J=8,1 Hz), 7.35–7.55 (3H, m), 7.61 (1H, dd, J=4,1 Hz), 8.45 (1H, ddd, J=5,2,1 Hz), IR (KBr)$cm^{-1}$: 3350, 3070, 2920, 1620.

EXAMPLE 48

Synthesis of
3-[3-(Thenoylamino)propylthio]pyridine i) 3-(3-Aminopropylthio)pyridine Dihydrochloride A solution of 2.00 g (11.0 mmol) of 3-(dimethylaminocarbonylthio)pyridine in 2 ml of methanol was added to 40 ml (80.0 mmol) of an 2N aqueous solution of sodium hydroxide, and the mixture was heated with stirring at 60° C. for 30 minutes. After cooling, 2.40 g (11.0 mmol) of 3-bromopropylamine hydrobromide was added and the resulting mixture was further stirred for 30 minutes. After cooling, the reaction mixture was extracted with ethyl acetate. The extract was separated and dried, and then the solvent was distilled off. The residue was treated with 15 ml (30.0 mmol) of a 2N solution of hydrogen chloride in methanol. The solvent was distilled off to obtain powder. The powder was washed with acetone and dried to obtain the desired compounds (2.62 g, yield: 98.8%).

mp: 169.0°–71.0° C., Anal. for $C_8H_{14}N_2SCl_2$, Calcd.: C; 37.07, H; 6.22, N; 10.81, Found: C; 38.88, H; 5.62, N; 10.66. NMR (200 MHz, $CDCl_3$) δ:2.08 (2H, quint., J=7 Hz), 3.17 (2H, t, J=7 Hz), 3.28 (2H, t, J=7 Hz), 7.98 (1H, dd, J=8,6 Hz), 8.55 (1H, d, J=8Hz), 8.59 (1H, d, J=6 Hz), 8.73 (1H, s). IR (KBr)$cm^{-1}$: 2930, 1610, 1520.

ii) Synthesis of
3-[3-(Thenoylamino)propylthio]pyridine

To a solution of 2.00 g (8.29 mmol) of 3-(3-aminopropylthio)pyridine dihydrochloride and 4.16 ml (29.9 mmol) of triethylamine in 80 ml of methylene chloride, 1.06 ml (9.95 mmol) of 2-thenoyl chloride was-added under ice-cooling with stirring. The-mixture was stirred at room temperature for 30 minutes. The reaction mixture was washed with a saturated aqueous solution of sodium bicarbonate and water and dried, and then the solvent was distilled off. The residue was purified by column chromatography (eluent: ethyl acetate) to obtain powder. The powder was washed with ether and dried to obtain 1.97 g of the desired compound (yield: 85.3%, yellow powder).

mp: 66.0°–67.0° C., Anal. for $C_{13}H_{14}N_2OS_2$, Calcd.: C; 56.09 H; 5.07, N; 10.06, Found: C; 55.90 H; 5.06, N; 9.94. NMR (200 MHz, $CDCl_3$) δ:1.95 (2H, quint., J=7 Hz), 3.01 (2H, t, J=7 Hz), 3.57 (1H, q, J=7 Hz), 6.36 (1H, m), 6.67 (1H, dd, J=5,4 Hz), 7.22 (1H, ddd, J=8,5,0.6 Hz), 7.47 (1H, dd, J=5,1 Hz), 7.50 (1H, dd, J=4,1 Hz), 7.67 (1H, ddd, J=8,2,1 Hz), 8.43 (1H, dd, J=5,1 Hz), 8.58 (1H, dd, J=2,0.6 Hz). IR (KBr)$cm^{-1}$: 3340, 3060, 2930, 1620.

EXAMPLE 49

Synthesis of
4-[3-(Thenoylamino)propylsulfinyl]pyridine

To a solution of 1.00 g (3.52 mmol) of 4-[3-(t-butoxycarbonylamino)propylsulfinyl]pyridine in 2 ml of methanol, 20 ml (40.0 mmol) of a 2N solution of hydrogen chloride in methanol was added. The mixture was stirred for 1 hour at room temperature. The solvent was distilled off. To 900 mg of the residue (Anal. calcd. for $C_8H_{14}N_2OSCl_2.0.5H_2O$ C; 36.10, H; 5.68, N; 10.52. Found C; 35.92, H; 5.95, N; 10.44.) thus obtained and 1.59 ml (11.4 mmol) of triethylamine in 30 ml of methylene chloride, 0.41 ml (3.79 mmol) of 2-thenoyl chloride was added under ice-cooling with stirring. The mixture was stirred at room temperature for 30 minutes. The reaction mixture was washed with a saturated aqueous solution of sodium bicarbonate and water and dried, and then the solvent was distilled off. The residue was purified by column chromatography (eluent: ethyl acetate) to obtain powder. The powder was washed with ether and dried to obtain 740 mg of the desired compound (yield: 71.5%, colorless powder).

mp: 101.0°–102.0° C., Anal. for $C_{13}H_{14}N_2O_2S_2$, Calcd.: C; 53.04, H; 4.79, N; 9.52, Found: C; 52.96, H; 4.76, N; 9.49. NMR (200 MHz, CDCl$_3$) δ:1.99 (1H, dquint., J=14,7 Hz), 2.15 (1H, dquint., J=14,7 Hz), 2.90 (1H, dt, J=14,7 Hz), 3.13 (1H, dt, J=14,7 Hz), 3.58 (1H, q, J=7 Hz), 3.59 (1H, q, J=7 Hz), 6.20 (1H, m), 7.04 (1H, dd, J=5,4 Hz), 7.49 (1H, dd, J=5,1 Hz), 7.54 (2H, dd, J=5,2 Hz), 7.58 (1H, dd, J=4,1 Hz), 8.78 (1H, dd, J=5,2 Hz). IR (KBr)cm$^{-1}$: 3370, 3320, 1630.

EXAMPLE 50

Synthesis of
4-[3-(Thenoylamino)propylsulfonyl]pyridine

To a solution of 1.00 g (3.33 mmol) of 4-[3-(t-butoxycarbonylamino)propylsulfonyl]pyridine in 2 ml of methanol, 20 ml (20.0 mmol) of a 2N solution of hydrogen chloride in methanol was added. The mixture was stirred for 1 hour at room temperature. The solvent was distilled off. To 920 mg of the residue (Anal. calcd. for $C_8H_{14}N_2O_2SCl_2 \cdot 0.3H_2O$ C; 34.48, H; 5.28, N; 10.06. Found C; 34.58, H; 5.46, N; 9.92.) thus obtained and 1.47 ml (10.5 mmol) of triethylamine in 30 ml of methylene chloride, 0.38 ml (3.51 mmol) of 2-thenoyl chloride was added under ice-cooling with stirring. The mixture was stirred at room temperature for 30 minutes. The reaction mixture was washed with a saturated aqueous solution of sodium bicarbonate and water and dried, and then the solvent was distilled off. The residue was purified by column chromatography (eluent: ethyl acetate) to obtain powder. The powder was washed with ether and dried to obtain 757 mg of the desired compound (yield: 72.6%, colorless powder).

mp: 124.0–125.0° C., Anal. for $C_{13}H_{14}N_2O_3S_2$, Calcd.: C; 50.30, H; 4.55, N; 9.03, Found: C; 50.31, H; 4.55, N; 8.99. NMR (200 MHz, CDCl$_3$) δ:2.12 (2H, quint., J=7 Hz), 3.25 (2H, t, J=7 Hz), 3.60 (2H, q, J=7 Hz), 6.54 (1H, m), 7.08 (1H, dd, J=5,4 Hz), 7.49 (1H, dd, J=5,1 Hz), 7.52 (1H, dd, J=4,1 Hz), 7.77 (1H, dd, J=5,2 Hz), 8.92 (1H, dd, J=5,2 Hz). IR (KBr)cm$^{-1}$: 3380, 3080, 1630.

EXAMPLE 51

Synthesis of
4-3-(N-methyl-2-thenoylamino)propylthio]pyridine i) Synthesis of 4-(3-Hydroxypropylthio)pyridine In 100 ml of methylene chloride were dissolved 11.1 g (100 mmol) of 4-mercaptopyridine and 13.9 ml (100 mmol) of triethylamine, and 9.04 ml (100 mmol) of 3-bromo-1-propanol was added. The mixture was stirred at room temperature for hours. The reaction mixture was washed with a 1N aqueous solution of sodium hydroxide and water and dried. Then the solvent was distilled off. The residue was purified by column chromatography (eluent: ethyl acetate) to obtain 14.2 g of the desired compound (yield: 83.9%, yellow oil).

NMR (200 MHz, CDCl$_3$) δ:1.97 (2H, quint., J=7 Hz), 3.12 (2H, t, J=7 Hz), 3.81 (2H, t, J=7 Hz), 7.14 (2H, dd, J=5,2 Hz), 8.37 (2H, dd, J=5,2 Hz). IR (neat)cm$^{-1}$: 3350, 2940, 1580.

ii) Synthesis of
4-[3-(N-methyl-2-thenoylamino)propylthio]pyridine

To a solution of 3.46 g (20.4 mmol) of 4-(3-hydroxypropylthio)pyridine and 3.42 ml (24.5 mmol) of triethylamine in 100 ml of methylene chloride, 1.90 ml (24.5 mmol) of methanesulfonyl chloride was added. The mixture was stirred at room temperature for 30 minutes. The reaction mixture was washed with a saturated aqueous solution of sodium bicarbonate and water and dried. Then the solvent was distilled off.

To 10 ml of a solution of 2.00 g of the obtained residue (4.00 g) in methanol, 3.14 g (40.5 mmol) of a 40% solution of methylamine in methanol was added. The resulting mixture was heated at 80° C. for 1 hour in a sealed tube. After cooling, the solvent was distilled off. To a solution of 1.52 g of the residue thus obtained and 1.35 ml (9.71 mmol) in triethylamine in 80 ml of methylene chloride, 1.34 ml (9.71 mmol) of 2-thenoyl chloride was added under ice-cooling with stirring. The mixture was stirred at room temperature for 30 minutes. The reaction mixture was washed with a saturated aqueous solution of sodium bicarbonate and water and dried. Then the solvent was distilled off. The residue was purified by column chromatography (eluent: ethyl acetate) to obtain powder. The powder was washed with ether and dried to obtain 1.62 g of the desired compound (yield: 68.5%, pale yellow powder).

mp: 72.0°–72.5° C. Anal. for $C_{14}H_{16}N_2OS_2$, Calcd.: C; 57.50, H; 5.51, N; 9.58, Found: C; 57.44, H; 5.56, N; 9.60. NMR (200 MHz, CDCl$_3$) δ:2.07 (2H, quint., J=7 Hz), 3.02 (2H, t, J=7 Hz), 3.21 (3H, s), 3.69 (2H,.t, J=7 Hz), 7.05 (1H, dd, J=5,4 Hz), 7.10 (2H, dd, J=5,2 Hz), 7.36 (1H, d, J=4 Hz), 7.46 (1H, dd, J=5,1 Hz), 8.40 (2H, dd, J=5,2 Hz). IR (KBr)cm$^{-1}$: 3100, 2930, 1590.

EXAMPLE 52

Synthesis of
4-[3-(N-phenyl-2-thenoylamino)propylthio]pyridine

To a solution of 1.50 g (8.86 mmol) of 4-(3-hydroxypropylthio)pyridine and 1.48 ml (10.6 mmol) of triethylamine in 90 ml of methylene chloride, 0.82 ml (10.6 mmol) of methanesulfonyl chloride was added. The mixture was stirred at room temperature for 30 minutes. The reaction mixture was washed with a saturated aqueous solution of sodium bicarbonate and water and dried, and then the solvent was distilled off. 1.94 g (17.7 mmol) of aniline was added to 1.70 g of the residue and the mixture was heated at 80° C. for 1 hour. After cooling, the mixture was purified by column chromatography (eluent: ethyl acetate) to obtain yellow oil (680 mg, yield: 31.4%). To a solution of 350 mg (1.43 mmol) of the oil and 0.24 ml (1.72 mmol) of triethylamine in 15 ml of methylene chloride, 0.18 ml (1.72 mmol) of 2-thenoyl chloride was added under ice-cooling with stirring. The mixture was stirred at room temperature for 30 minutes. The reaction mixture was washed with a saturated aqueous solution of sodium bicarbonate and water and dried, and then the solvent was distilled off. The residue was purified by column chromatography (eluent: ethyl acetate) to obtain powder. The powder was washed with ether and dried to obtain 413 mg of the desired compound (yield: 81.5%, pale yellow powder).

mp: 66.0°–67.0° C., Anal. for $C_{19}H_{18}N_2OS_2 \cdot 0.2H_2O$ Calcd.: C; 63.73, H; 5.18, N; 7.82, Found: C; 63.82, H; 5.11, N; 7.77. NMR (200 MHz, CDCl$_3$) δ:2.07 (2H, quint., J=7 Hz), 3.05 (2H, t, J=7 Hz), 4.02 (2H, t, J=7 Hz), 6.69 (1H, dd, J=4,1 Hz), 6.78 (1H, dd, J=5,4 Hz), 7.07 (2H, dd, J=5,2 Hz), 7.15–7.30 (2H, m), 7.31 (1H, dd, J=5,1 Hz), 7.35–7.50 (3H, m), 8.36 (2H, dd, J=5,2 Hz). IR (KBr)cm$^{-1}$: 3430, 3090, 3020, 1580.

EXAMPLE 53

Synthesis of 4-[3-(2-Furoylamino)propylthio]pyridine

To a solution of 1.00 g (4.15 mmol) of 4-(3-aminopropylthio)pyridine dihydrochloride and 2.78 ml (19.9 mmol) of triethylamine in 40 ml of methylene chloride, 0.49 ml (4.98 mmol) of 2-furoyl chloride was added under ice-cooling with stirring. The mixture was stirred at room temperature for 30 minutes. The reaction mixture was washed with a saturated aqueous solution of sodium bicarbonate and water and dried, and then the solvent was distilled off. The residue was purified by column chromatography (eluent: ethyl acetate) to obtain powder. The powder was washed with ether and dried to obtain 960 mg of the desired compound (yield: 87.3%, colorless powder).

mp: 98.0°–99.0° C., Anal. for $C_{13}H_{14}N_2O_2S$, Calcd.: C; 59.52, H; 5.38, N; 10.68, Found: C; 59.30, H; 5.39, N; 10.45. NMR (200 MHz, CDCl$_3$) δ:2.03 (2H, quint., J=7 Hz), 3.07 (2H, t, J=7 Hz), 3.59 (2H, q, J=7 Hz), 6.51 (1H, dd, J=4,2 Hz), 6.55 (1H, m), 7.00–7.20 (3H, m), 7.44 (1H, d, J=2 Hz), 8.40 (2H, dd, J=5,2 Hz). IR (KBr)cm$^{-1}$: 3360, 3030, 2920, 1630.

EXAMPLE 54

Synthesis of 4-[3-(3-Thiophenecarbonylamino)propylthio]pyridine

To a solution of 1.00 g (7.80mmol) of thiophene-3-carboxylic acid and 1.08 g (10.1 mmol) of N-hydroxysuccinimide in 70 ml of methylene chloride, 1.80 g (9.36 mmol) of 1-ethyl-3-(3-dimethylaminopropyl)carbodiimide hydrochloride was added under ice-cooling with stirring. The mixture was stirred at room temperature for 1 hour. Further, 1.31 g (7.80 mmol) of 4-(3-aminopropylthio)pyridine was added, and the mixture was stirred at room temperature for 2 hours. The reaction mixture was washed with water and dried, and then the solvent was distilled off. The residue was purified by column chromatography (eluent: methanol/ethyl acetate=1:10) to obtain 1.65 g of the desired compound (yield: 76.1%, colorless powder).

mp: 121.0°–122.0° C., Anal. for $C_{13}H_{14}N_2OS_2$, Calcd.: C; 56.09, H; 5.07, N; 10.06, Found: C; 56.07, H; 4.99, N; 10.23. NMR (200 MHz, CDCl$_3$) δ:2.04 (2H, quint., J=7 Hz), 3.06 (2H, t, J=7 Hz), 3.58 (2H, q, J=7 Hz), 6.45 (1H, m), 7.10 (2H, dd, J=5,2 Hz), 7.34 (1H, ddd, J=5,3,0.8 Hz), 7.39 (1H, dd, J=5,1 Hz), 7.88 (1H, dd, J=3,1 Hz), 8.37 (2H, dd, J=5,2 Hz). IR (KBr)cm$^{-1}$: 3340, 1630.

EXAMPLE 55

Synthesis of 4-[3-(2-Thienylacetylamino)propylthio]pyridine

To a solution of 913 mg (6.42 mmol) of 2-thienylacetic acid and 961 mg (8.35 mmol) of N-hydroxysuccinimide in 65 ml of methylene chloride, 1.48 g (7.70 mmol) of 1-ethyl-3-(3-dimethylaminopropyl)carbodiimide hydrochloride was added under ice-cooling with stirring. The mixture was stirred at room temperature for 1 hour. Further, 1.08 g (6.42 mmol) of 4-(3-aminopropylthio)pyridine was added, and the mixture was stirred at room temperature for 2 hours. The reaction mixture was washed with water and dried, and then the solvent was distilled off. The residue was purified by column chromatography (eluent: methanol/ethyl acetate= 1:10) to obtain powder. The powder thus obtained was washed with ether and dried to obtain 1.62 g of the desired compound (yield: 86.3%, pale yellow powder).

mp: 62.0°–63.0° C., Anal. for $C_{14}H_{16}N_2OS_2 \cdot 0.1H_2O$, Calcd.: C; 57.15, H; 5.55, N; 9.52, Found: C; 57.06, H; 5.53, N; 9.44. NMR (200 MHz, CDCl$_3$) δ:1.89 (2H, quint., J=7 Hz), 2.94 (2H, t, J=7 Hz), 3.39 (2H, q, J=7 Hz), 3.79 (2H, s), 5.84 (1H, m), 6.94 (1H, bd, J=3 Hz), 7.00 (1H, dd, J=5,3 Hz), 7.05 (2H, dd, J=5,2 Hz), 7.26 (1H, dd, J=5,1 Hz), 7.88 (1H, dd, J=3,1 Hz), 8.38 (2H, dd, J=5,2 Hz). IR (KBr)cm$^{-1}$: 3230, 3040, 1660, 1590.

EXAMPLE 56

Synthesis of 4-[3-(2-Thiopheneacrylamino)propylthio]pyridine

To a solution of 1.37 g (8.91 mmol) of 2-thiopheneacrylic acid and 1.33 g (11.6 mmol) of N-hydroxysuccinimide in 90 ml of methylene chloride, 2.05 g (10.7 mmol) of 1-ethyl-3-(3-dimethylaminopropyl)carbodiimide hydrochloride was added under ice-cooling with stirring. The mixture was stirred at room temperature for 1 hour. Further, 1.50 g (8.91 mmol) of 4-(3-aminopropylthio)pyridine was added, and the mixture was stirred at room temperature for 2 hours. The reaction mixture was washed and dried, and then the solvent was distilled off. The residue was purified by column chromatography (eluent: ethyl acetate) to obtain powder. The powder thus obtained was washed with ether and dried to obtain 1.95 g of the desired compound (yield: 71.9%, colorless powder).

mp: 111.0°–112.0° C., Anal. for $C_{15}H_{16}N_2OS_2$, Calcd.: C; 59.18, H; 5.30, N; 9.20, Found: C; 59.26, H; 5.36, N; 9.15. NMR (200 MHz, CDCl$_3$) δ:2.00 (2H, quint., J=7 Hz), 3.04 (2H, t, J=7 Hz), 3.54 (2H, q, J=7 Hz), 6.05 (1H, m), 6.21 (1H, d, J=15 Hz), 7.03 (1H, dd, J=5,3 Hz), 7.10 (2H, dd, J=5,2 Hz), 7.21 (1H, d, J=3 Hz), 7.31 (1H, d, J=5 Hz), 7.76 (1H, d, J=15 Hz), 8.38 (2H, dd, J=5,2 Hz). IR (KBr)cm$^{-1}$: 3290, 3070, 1640, 1600.

EXAMPLE 57

Synthesis of 4-[3-(Thianaphtene-2-carbonylamino)-propylthio]pyridine

To a solution of 2.00 g (8.29 mmol) of 4-(3-aminopropylthio)pyridine dihydrochloride and 4.17 ml (29.9 mmol) of triethylamine in 80 ml of methylene chloride, 1.96 ml (9.95 mmol) of thianaphtene-2-carbonyl chloride was added under ice-cooling with stirring. The mixture was stirred at room temperature for 30 minutes. The reaction mixture was washed with a saturated aqueous solution of sodium bicarbonate and water and dried, and then the solvent was distilled off. The residue was purified by column chromatography (eluent: ethyl acetate) to obtain powder. The powder thus obtained was washed with ether and dried to obtain 2.40 g of the desired compound (yield: 97.6%, pale yellow powder).

mp: 123.0°–124.0° C., Anal. for $C_{17}H_{16}N_2OS_2$, Calcd.: C; 62.17, H; 4.91, N; 8.53, Found: C; 61.97, H; 4.89, N; 8.42. NMR (200 MHz, CDCl$_3$) δ:2.07 (2H, quint., J=7 Hz), 3.07 (2H, t, J=7 Hz), 3.63 (2H, q, J=7 Hz), 6.66 (1H, m), 7.10 (1H, dd, J=5,2 Hz), 7.30–7.50 (2H, m), 7.75–7.90 (3H, m), 8.37 (2H, dd, J=5,2 Hz). IR (KBr)cm$^{-1}$: 3330, 3030, 2930, 1620.

EXAMPLE 58

Synthesis of 4-[3-(4,5-dibromothenoylamino)propylthio]pyridine

To a solution of 2.55 g (8.91 mmol) of 4,5-dibromothiophene- 2-carboxylic acid and 1.33 g (11.6 mmol) of N-hydroxysuccinimide in 90 ml of methylene chloride, 2.05 g (10.7 mmol) of 1-ethyl-3-(3-dimethylaminopropyl)carbodiimide hydrochloride was added under ice-cooling with stirring. The mixture was stirred at room temperature for 1 hour. Further, 1.50 g (8.91 mmol) of 4-(3-aminopropylthio)pyridine was added, and the mixture was stirred at room temperature for 2 hours. The reaction mixture was washed with water and dried, and then the solvent was distilled off. The residue was purified by column chromatography (eluent: ethyl acetate) to obtain powder. The powder thus obtained was washed with ether and dried to obtain 2.79 g of the desired compound (yield: 71.8%, colorless powder).

mp: 129.0°–130.0° C., Anal. for $C_{13}H_{12}N_2OBr_2S_2$, Calcd.: C; 35.80, H; 2.77, N; 6.42, Found: C; 35.52, H; 2.70, N; 6.23. NMR (200 MHz, CDCl$_3$) δ:2.02 (2H, quint., J=7 Hz), 3.04 (2H, t, J=7 Hz), 3.57 (2H, q, J=7 Hz), 6.64 (1H, t, J=6 Hz), 7.08 (2H, dd, J=5,2 Hz), 7.29 (1H, s), 8.37 (2H, dd, J=5,2 Hz). IR (KBr)cm$^{-1}$: 3200, 3080, 3020, 1640, 1580.

EXAMPLE 59

Synthesis of 4-[3-(5-Methylthenoylamino)propylthio]pyridine

To a solution of 1.27 g (8.91 mmol) of 5-methyl-2-thiophenecarboxylic acid and 1.33 g (11.6 mmol) of N-hydroxysuccinimide in 90 ml of methylene chloride, 2.05 g (10.7 mmol) of t-ethyl-3-(3-dimethylaminopropyl)carbodiimide hydrochloride was added under ice-cooling with stirring. The mixture was stirred at room temperature for 1 hour. Further, 1.50 g (8.91 mmol) of 4-(3-aminopropylthio)pyridine was added, and the mixture was stirred at room temperature for 2 hours. The reaction mixture was washed with water and dried, and then the solvent was distilled off. The residue was purified by column chromatography (eluent: ethyl acetate) to obtain powder. The powder thus obtained was washed with ether and dried to obtain 1.68 g of the desired compound (yield: 64.5%, colorless powder).

mp: 86.0°–87.0° C., Anal. for $C_{14}H_{16}N_2OS_2$, Calcd.: C; 57.50, H; 5.51, N; 9.58, Found: C; 57.35, H; 5.51, N; 9.49. NMR (200 MHz, CDCl$_3$) δ:2.02 (2H, quint., J=7 Hz), 2.51 (3H, d, J=1 Hz), 3.05 (2H, t, J=7 Hz), 3.57 (2H, q, J=7 Hz), 6.25 (1H, t, J=5 Hz), 6.73 (1H, dd, J=4,1 Hz), 7.10 (2H, dd, J=5,2 Hz), 7.32 (1H, d, J=4 Hz), 8.38 (2H, dd, J=5,2 Hz). IR (KBr)cm$^{-1}$: 3320, 3030, 2940, 1610.

EXAMPLE 60

Synthesis of 4-[3-(3-Methylthenoylamino)propylthio]pyridine

In 100 ml of benzene was suspended 3.00 g (21.1 mmol) of 3-methyl-2-thiophenecarboxylic acid, oxalyl chloride [7.36 ml (84.4 mmol)] was added and the mixture was refluxed for 2 hours. After cooling, the solvent was distilled off to obtain 3.40 g of 3-methylthenoyl chloride (yield: quant.). To a solution of 1.50 g (6.23 mmol) of 4-( 3-aminopropylthio)pyridine dihydrochloride and 2.61 ml (18.7 mmol) of triethylamine in 60 ml of methylene chloride, 1.20 ml (7.48 mmol) of the 3-methylthenoyl chloride was added under ice-cooling with stirring. The mixture was stirred at room temperature for 30 minutes. The reaction mixture was washed with a saturated aqueous solution of sodium bicarbonate and water and dried, and then the solvent was distilled off. The residue was purified by column chromatography (eluent: ethyl acetate) to obtain powder. The powder was washed with ether and dried to obtain 1.54 g of the desired compound (yield: 84.5%, pale yellow powder).

mp: 104.0°–105.0° C., Anal. for $C_{14}H_{16}N_2OS_2$, Calcd.: C; 57.50, H; 5.51, N; 9.58, Found: C; 57.23, H; 5.50, N; 9.52. NMR (200 MHz, CDCl$_3$) δ:2.04 (2H, quint., J=7 Hz), 2.52 (3H, s), 3.07 (2H, t, J=7 Hz), 3.57 (2H, q, J=7 Hz), 6.60 (1H, m), 6.89 (1H, d, J=5 Hz), 7.11 (1H, dd, J=5,2 Hz), 7.26 (1H, d, J=5 Hz), 8.38 (2H, dd, J=5,2 Hz). IR (KBr)cm$^{-1}$: 3220, 3090, 3040, 1630.

EXAMPLE 61

Synthesis of 2-[3-(2-Thenoylamino)propyloxy]pyridine

In 50 ml of DMF was suspended 3.04 g (76 mmol) of 60% oily sodium hydride, a mixture of 10.0 g (63.5 mmol) of 2-bromopyridine and 4.47 mmol (63.5 mmol) of 3-amino-1-propanol was added dropwise under ice-cooling with stirring. The mixture was stirred at room temperature for 18 hours. The reaction mixture was diluted with chloroform, washed with water and dried. Then the solvent was distilled off. The residue was purified by column chromatography (eluent: conc. ammonia water/methanol=1:50) to obtain 2.00 g of pale yellow oil (yield: 20.7%). To a solution of the above oil and 2.20 ml (15.8 mmol) of triethylamine in 50 ml of methylene chloride, 1.69 ml (15.8 mmol) of 2-thenoyl chloride was added under ice-cooling with stirring. The mixture was stirred at room temperature for 30 minutes. The reaction mixture was washed with a saturated aqueous solution of sodium bicarbonate and water and dried, and then the solvent was distilled off. The residue was purified by column chromatography (eluent: hexane/ethyl acetate= 1:1) to obtain powder. The powder was washed with ether and dried to obtain 2.20 g of the desired compound (yield: 63.8%, colorless powder).

mp: 91.0°–92.0° C.

Anal. for $C_{13}H_{14}N_2O_2S$, Calcd.: C; 59.52, H; 5.38, N; 10.68, Found: C; 59.14, H; 5.14, N; 10.45. NMR (200 MHz, CDCl$_3$) δ:2.07 (2H, quint., J=7 Hz), 3.59 (2H, q, J=7 Hz), 4.50 (2H, t, J=7 Hz), 6.77 (1H, d, J=8 Hz), 6.90 (1H, td, J=5,1 Hz), 7.03 (1H, m), 7.10 (1H, dd, J=5,4 Hz), 7.47 (1H, td, J=5,1 Hz), 7.56 (1H, dd, J=4,1 Hz), 7.61 (1H, ddd, J=8,5,2 Hz), 8.18 (1H, dd, J=5,2 Hz). IR (KBr)cm$^{-1}$: 3280, 3050, 2940, 1620.

EXAMPLE 62

Synthesis of 4-(Phthalimidomethylthio)pyridine

In 250 ml of ethanol were suspended 6.95 g (62.5 mmol) of 4-mercaptopyridine and 15.0 g (62:5 mmol) of (N-bromomethyl)phthalimide, triethylamine [10.5 ml (74.8 mmol)] was added and the mixture was stirred at room temperature for 18 hours. The solvent was distilled off. The residue was dissolved in chloroform, washed with a saturated aqueous solution of sodium bicarbonate and water and dried. Then the solvent was distilled off. The residue was purified by column chromatography (eluent: chloroform/ethyl acetate= 3:2) to obtain powder. The powder thus obtained was recrystallized from ethyl acetate to obtain 12.0 g of the desired compound: (yield: 71.6%, colorless needles).

mp: 133.0°–134.0° C., Anal. for $C_{14}H_{10}N_2O_2S$, Calcd.: C; 62.21, H; 3.73, N;: 10.36, S; 11.86, Found: C; 62.21, H; 3.73, N 10.32, S; 11.86. NMR (200 MHz, $CDCl_3$) δ:5.19 (2H s), 7.41 (2H, dd, J=5,2 Hz), 7.70–7.80 (2H, m), 7.80–7.95 (2H, m), 8.45 (2H, dd, J=5,2 Hz). IR (KBr)cm$^{-1}$: 1770, 1710.

EXAMPLE 63

Synthesis of 3-(Phthalimidomethylthio)pyridine

To a solution of 1.00 g (5.49 mmol) of 3-(dimethylaminocarbonylthio)pyridine in 50 ml of methanol, 5.49 ml (5.49 mmol) of a 1N aqueous solution of sodium hydroxide was added. The mixture was heated at 60° C. for 1 hour with stirring. After cooling, the solvent was distilled off. The residue was dissolved in ethanol and dried. The solvent was distilled off. The residue thus obtained and 1.58 g of (6.59 mmol) of (N-bromomethyl)phthalimide were suspended in 50 ml of ethanol, and 0.92 ml (6.59 mmol) of triethylamine was added. The mixture was stirred at room temperature for 4 hours. The solvent was distilled off, and the residue was dissolved in chloroform, washed with water and dried. Then the solvent was distilled off. The residue was purified by column chromatography (eluent: hexane/ethyl acetate=1:1) to obtain powder. The powder thus obtained was washed with ether and dried to obtain 1.20 g of the desired compound (yield: 80.9%, colorless powder).

mp: 123.0°–124.0° C., Anal. for $C_{14}H_{10}N_2O_2S$, Calcd.: C; 62.21, H; 3.73, N; 10.36, Found: C; 62.62, H; 3.70, N; 9.98. NMR (200 MHz, $CDCl_3$) δ:5.04 (2H, s), 7.27 (1H, t, J=5 Hz), 7.70–8.00 (5H, m), 8.52 (1H, dd, J=5,1 Hz), 8.64 (1H, d, J=1 Hz). IR (KBr)cm$^{-1}$: 1770, 1720.

EXAMPLE 64

Synthesis of 2-(Phthalimidomethylthio)pyridine

In 50 ml of ethanol were suspended 1.11 g (10 mmol) of 2-mercaptopyridine and 2.40 g (10.0 mmol) of (N-bromomethyl)phthalimide, triethylamine [1.54 ml (11.0 mmol)] was added and the mixture was stirred at room temperature for 4 hours. The solvent was distilled off. The residue was dissolved in chloroform, washed with water and dried. Then the solvent was distilled off. The residue was purified by column chromatography (eluent: hexane/ethyl acetate=1:1) to obtain powder. The powder thus obtained was washed with ether and dried to obtain 2.16 g of the desired compound (yield: 80.0%, colorless powder).

mp: 93.0°–94.0° C., Anal. for $C_{14}H_{10}N_2O_2S$, Calcd.: C; 62.21, H; 3.73, N; 10.36, Found: C; 62.07, H; 3.69, N; 10.27. NMR (200 MHz, $CDCl_3$) δ:5.54 (2H,s), 7.06 (1H, ddd, J=8,5,1 Hz), 7.26 (1H, dd, J=8,1 Hz), 7 53 (1H, td, J=8,1 Hz), 7.65–7.75 (2H, m), 7.75–7.90 (2H, m), 8.53 (1H, dd, J=5,1 Hz). IR (KBr)cm$^{-1}$: 1780, 1720.

EXAMPLE 65

Synthesis of 4-(Phthalimidomethyloxy)pyridine

To a solution of 4.76 g (50 mmol) of 4-hydroxypyridine and 10.76 g (55 mmol) of N-chloromethylphthalimide in 80 ml of DME, 8.23 ml (55 mmol) of 1,8-diazabicyclo[5,4,0] -2-undecene was added. The mixture was stirred at room temperature for 2 hours. After the solvent was distilled off, the reaction mixture was poured into water and extracted with ethyl acetate. The precipitate was filtered off. The aqueous layer was further extracted with ethyl acetate. The organic layer was washed with water and dried over anhydrous magnesium sulfate, and the solvent was distilled off under reduced pressure. The residue was purified by column chromatography (eluent: ethyl acetate) to obtain 2.67 g of the desired compound (yield: 21%, colorless crystals).

mp: 129.0°–131.0° C., Anal. for $C_{14}H_{10}N_2O_3 \cdot 0.2H_2O$, Calcd.: C; 65.21, H; 4.07, N; 10.86, Found: C; 65.33, H; 3.93, N; 10.66. NMR (200 MHz, $CDCl_3$) δ:5.72 (2H, s), 7.03 (1H, dd, J=5,2 Hz), 7.70–7.86 (2H, m), 7.86–8.00 (2H, m), 8.47 (2H, dd, J=5,2 Hz). IR (KBr)cm$^{-1}$: 1780, 1720, 1590.

EXAMPLE 66

Synthesis of 3-(Phthalimidomethyloxy)pyridine

In 100 ml of acetone were suspended 2.43 g (25.6 mmol) of 3-hydroxypyridine and 5.00 g (25.6 mmol) of (N-chloromethyl)phthalimide, potassium carbonate [3.52 g (25.6 mmol)] was added and the mixture was stirred at 60° C. for 7 hours under heating. After cooling, the solvent was distilled off. The residue was dissolved in dichloromethane, washed with a saturated aqueous solution of sodium bicarbonate and water and dried. Then the solvent was distilled off. The residue was purified by column chromatography (eluent: dichloromethane to ethyl acetate/hexane=1:1) to obtain 2.60 g of the desired compound (yield: 40.0%, colorless columns).

Anal. for $C_{14}H_{10}N_2O_3$, Calcd.: C; 66.14, H; 3.96, N; 11.02, Found: C; 65.91, H; 4.17, N; 10.99. NMR (200 MHz, $CDCl_3$) δ:5.71 (2H, s), 7.27 (1H, dd, J=4.0,8.6 Hz), 7.51 (1H, ddd, J=1.4,3.0,8.6 Hz), 7.80 (2H dd, J=3.0,5.4 Hz), 7.94 (2H, dd, J=3.0,5.4 Hz), 8.31 (1H, dd, J=1.4,4.0 Hz), 8.44 (1H, d, J=3.0 Hz). IR (KBr) cm$^{-1}$: 3060, 1780, 1730, 715.

EXAMPLE 67

Synthesis of 2-(Phthalimidomethyloxy)pyridine a) Method Wherein a Silver Salt Is Generated In Situ In 4 ml of benzene were suspended 0.095 g (1.0 mmol) of 2-hydroxypyridine and 0.14 g (0.5 mmol) of silver carbonate, N-bromomethylphthalimide [0.29 g (1.2 mmol)] was added at room temperature, and the mixture was stirred at 80° C. for 14 hours under heating. After cooling, the residue was filtered and the solvent was distilled off. The residue was purified by column chromatography (eluent: ethyl acetate/hexane=10:1) to obtain powder. The powder was recrystallized from ethyl acetate to obtain 0.10 g of the desired compound (yield: 39.0%, colorless columns).

b) Method Wherein a Silver Salt Is Isolated i) Synthesis of 2-Hydroxypyridine Silver Salt A solution of 20.40 g (120 mmol) of silver nitrate in 200 ml of water was added to a solution of 11.42 g (120 mmol) of 2-hydroxypyridine in 300 ml of water at room temperature. The reaction mixture was neutralized with 8.0 ml of an aqueous ammonium solution. The resulting precipitate was collected, washed successively with water, ethanol and ether and dried to obtain 25.01 g of the desired compound (yield: quant., colorless columns).

ii) Synthesis of 2-(Phthalimidemethyloxy)pyridine

In 4 ml of benzene was suspended 0.20 g (1.0 mmol) of 2-hydroxypyridine silver salt, N-bromomethylphthalimide [0.29 g (1.2 mmol)] was added at room temperature, and the mixture was stirred at room temperature for 16 hours. The residue was filtered and the solvent was distilled off. The residue was purified by column chromatography (eluent: ethyl acetate/hexane=10:1) to obtain powder. The powder was recrystallized from ethyl acetate to obtain 0.21 g of the desired compound (yield: 82.5%, colorless columns).

Anal. for $C_{14}H_{10}N_2O_3$, Calcd.: C; 66.14, H; 3.96, N; 11.02, Found: C; 65.93, H; 4.12, N; 10.96. NMR (200 MHz, $CDCl_3$) δ:6.00 (2H, s), 6.75 (1H, dt, J=1.0,8.3 Hz), 6.94 (1H, ddd, J=1.0,5.2,7.1 Hz), 7.60 (1H, ddd, J=2.2,7.0,8.3 Hz), 7.74–7.79 (4H, m), 8.21 (1H, ddd, J=1.0,2.0,5.2 Hz). IR $(KBr)cm^{-1}$: 3100, 3050, 1780, 1730, 1600, 1570.

EXAMPLE 68

Synthesis of
4-[3-[N-(2-Thienylmethyl)-N-trifluoroacetylamino]-propylthio]pyridine Hydrochloride i) Synthesis of
4-[3-[N-(2-Thienylmethyl)amino]propylthio]pyridine In 200 ml of methylene chloride were dissolved 10.34 g (61.1 mmol) of 4-(3-hydroxypropylthio)pyridine and 10.2 ml (73.3 mmol) of triethylamine, methanesulfonyl chloride [5.7 ml (73.3 mmol)] was added, and the mixture was stirred at room temperature for 30 minutes. The reaction mixture was washed with a saturated aqueous solution of sodium bicarbonate and water and dried. Then the solvent was distilled off. To 8.05 g of the residue was added 3.3 ml (32.5 mmol) of 2-thiophenemethylamine. The mixture was heated at 80° C. for 3 hours. After cooling, the mixture was purified by column chromatography (eluent: chloroform/methanol= 25:1) to obtain 2.5 g of the desired compound (yield: 29.1%, yellow oil).

ii) Synthesis of
4-[3-[N-(2-Thienylmethyl)-N-trifluoroacetylamino]-propylthio]pyridine Hydrochloride According to the same manner as that described in Example 25, the title compound was synthesized.

NMR (200 MHz, DMSO-$d_6$) δ:1.75–2.13 (2H, m), 3.13–3.34 (2H, m), 3.42–3.61 (2H, m), 4.80 and 4.86 (2H, each s), 6.94–7.03 (1H, m), 7.12–7.19 (1H, m), 7.50 (1H, m), 7.78–7.93 (2H, m), 8.58–8.69 (2H, m).

EXAMPLE 69

Synthesis of
3-[2-(Phthalimido)ethyl]-2-(pivaloylamino)pyridine

In 100 ml of ethanol was suspended 6.28 g (29.8 mmol) of 3-mercapt-2-(pivaloylamino)pyridine and 11.4 g (44.8 mmol) of N-(2-bromoethyl)phthalimide, triethylamine [8.32 ml (59.7 mmol)] was added and the mixture was heated under reflux form 1 hour. The reaction mixture was poured into water and extracted with chloroform. The combined chloroform solution was dried and then the solvent was distilled off. The residue was purified by column chromatography (eluent: hexane/ethyl acetate 1:1 to ethyl acetate) to obtain 11.0 g of the desired compound (yield: 96.3%, white solid).

NMR (200 MHz, $CDCl_3$) δ:1.34 (9H, s), 3.18 (2H, t, J=6.6 Hz), 3.87 (2H, t, J=6.4 Hz), 7.06 (1H, dd J=4.8,7.6 Hz), 7.71–7.85 (4H, m), 7.93 (1H, dd, J=1.6,7.8 Hz), 8.30 (1H, dd, J=1.8,4.8 Hz), 8.39 (1H, br.s). IR $(KBr)cm^{-1}$: 3380, 1760, 1700.

EXAMPLE 70

Synthesis of
2-Amino-3-[2-(phthalimido)ethyl]pyridine

Hydrochloric acid (5N) was added to 8.84 g (23.1 mmol) of 3-[2-(phthalimide)ethyl]-2-(pivaloylamino)pyridine, and the mixture was stirred at 100° C. for 4 hours. After cooling, 25% ammonia water was added to the mixture to make it basic. The resulting mixture was extracted with methylene chloride. The combined methylene chloride solution was dried and then the solvent was distilled off. The residue was purified by column chromatography (eluent: hexane/ethyl acetate 1:1 to ethyl acetate) to obtain liquid. The liquid was precipitated by adding ether to obtain 2.75 g of the desired compound (yield: 39.8%, pale yellow powder).

NMR (200 MHz, $CDCl_3$) δ:3.11 (2H, t, J=6.5 Hz), 3.88 (2H, t, J=6.5 Hz), 5.14 (2H, br.s), 6.62 (1H, dd, J=4.9,7.5 Hz), 7.71–7.87 (5H, m), 7.98 (1H, dd, J=1.8,4.8 Hz). IR $(KBr)cm^{-1}$: 3450, 3400, 3300, 1770, 1700.

EXAMPLE 71

Synthesis of
3-[2-(Phthalimido)ethyl]-2(pivaloylamino)pyridine Hydrochloride

In 5 ml of methanol was dissolved 248 mg (0.647 mmol) of 3-[2-(phthalimide)ethyl]-2-(pivaloylamino)piridine. The solution was treated with 5 ml (10 mmol) of a 2N solution of hydrogen chloride in methanol. The solvent was distilled off to obtain 272 mg of the desired compound (yield: 100%, white powder).

NMR (200 MHz, $D_2O$) δ:1.27 (9H, s), 3.51 (2H, br.t, J=5.5 Hz), 3.92 (2H, br.t, J=5.0 Hz), 7.49 (1H, br.t, J=7.0 Hz), 7.68–7.77 (4H, m), 8.07 (1H, br.d, J=6.0 Hz), 8.53 (1H, br.d, J=8.2 Hz). IR $(KBr)cm^{-1}$: 3350, 1770, 1710.

EXAMPLE 72

Synthesis of
2-Amino-3-[2-(phthalimido)ethyl]pyridine Hydrochloride

In 5 ml of methanol was dissolved 237 mg (0.792 mmol) of 2-amino-3-[2-(phthalimido)ethyl]pyridine. The solution was treated with 5 ml (10 mmol) of a 2N solution of hydrogen chloride in methanol. The solvent was distilled off to obtain the desired powder. The powder thus obtained was washed with ether to obtain 233 mg of the desired compound (yield: 79.0%, pale yellow powder).

NMR (200 MHz, D$_2$O) δ:3.33 (2H, t, J=5.9 Hz), 3.88 (2H, t, J=5.9 Hz), 6.70 (1H, dd, J=6.4,7.6 Hz), 7.46 (1H, dd, J=1.5,6.3 Hz), 7.71–7.78 (4H, m), 8.05 (1H, dd, J=1.5,7.5 Hz). IR (KBr)cm$^{-1}$: 3280, 3210, 1765, 1710.

EXAMPLE 73

Synthesis of
4-[3-(N-benzyl-N-trifluoroacetylamino)-propylthiio]pyridine Hydrochloride i) Synthesis of 4-(3-Hydroxypropylthio)pyridine In 250 ml of methylene chloride was dissolved 22.2 g (200 mmol) of 4-mercaptopyridine and 27.9 ml (200 mmol) of triethylamine. Thereto was added 18.1 g (200 mmol) of 3-bromo- 1-propanol. The mixture was stirred at room temperature for 3 hours. The reaction mixture was washed with a 1N aqueous solution of sodium hydroxide and water and dried. Then the solvent was distilled off. The residue was purified by column chromatography (eluent: ethyl acetate) to obtain 21.3 g of the desired compound (yield: 62.9%, yellow oil).

NMR (200 MHz, CDCl$_3$) δ:1.97 (2H, quint., J=7 Hz), 3.12 (2H, t, J=7 Hz), 3.81 (2H, t, J=7 Hz), 7.14 (2H, dd, J=5,2 Hz), 8.37 (2H, dd, J=5,2 Hz). IR (neat) cm$^{-1}$: 3350, 2940, 1580.

ii) Synthesis of
4-[3-(N-benzylamino)propylthio]pyridine

In 150 ml of methylene chloride were dissolved 5.22 g (30.8 mmol) of 4-(3-hydroxypropylthio)pyridine and 5.16 ml (37.0 mmol) of triethylamine, methanesulfonyl chloride [2.86 ml (37.0 mmol)] was added, and the mixture was stirred at room temperature for 30 minutes. The reaction mixture was washed with a saturated aqueous solution of sodium bicarbonate and water and dried. Then the solvent was distilled off. 2.62 ml (24.0 mmol) of benzylamine was added to the residue, and the mixture was heated at 80° C. for 3 hours. After cooling, the mixture was purified by column chromatography (eluent: chloroform/methanol= 25:1) to obtain 10 g of the desired compound (yield: 16.1%, yellow oil).

NMR (200 MHz, CDCl$_3$) δ:1.57 (1H, br.s), 1.90 (2H, quint., J=7.0 Hz), 2.79 (2H, t, J=6.8 Hz), 3.07 (2H, t, J=7.2 Hz), 3.84 (2H, d, J=15.2 Hz), 7.11 (2H, dd, J=1.6,4.8 Hz), 7.29–7.33 (5H, m), 8.37 (2H, dd, J=1.6,4.8 Hz).

iii) Synthesis of
4-[3-(N-benzyl-N-trifluoroacetylamino)-propylthio]pyridine

To a solution of 7.27 g (28.1 mmol) 4-[3-(N-benzylamino)propylthio)-pyridine and 4.70 ml (33.7 mmol) of triethylamine in 150 ml of methylene chloride, 4.76 ml (33.7 mmol) of trifluoroacetic anhydride was added under ice-cooling with stirring. The mixture was stirred at room temperature for 30 minutes. The reaction mixture was washed with a saturated aqueous solution of sodium bicarbonate and water and dried, and then the solvent was distilled off . The residue was purified by column chromatography (eluent: ethyl acetate/hexane=2:1 to 1:1) to obtain 6.04 g of 4-[3 -(N-benzyl-N-trifluoroacetylamino)-propylthio]pyridine (yield: 60.7%, yellow oil).

NMR (200 MHz, CDCl$_3$) δ:1.80–2.11 (2H, m), 2.91 and 2.93 (2H, t, J=7.4,7.0 Hz)‡, 3.46 and 3.50 (2H, t, J=7.4,7.0 Hz), 4.62 and 4.64 (2H, s)‡, 7.02–7.08 (2H, m), 7.19–7.38 (5H, m), 8.41 (2H, m).

‡: The peak is split due to the rotational isomers.

iv) Synthesis of
4-[3-(N-benzyl-N-trifluoroacetylamino)-propylthio]pyridine Hydrochloride The above free base [1.20 g (3.39 mmol)] was treated with 150ml of a 10% solution of hydrogen chloride in methanol. The solvent was distilled off to obtain 1.26 g of the desired compound (yield: 95.1%, yellow oil).

NMR (200 MHz, D$_2$O) δ:1.78–2.21 (2H, m), 3.18–3.28 (2H, m), 3.49–3.73 (2H, m), 4.71 and 4.74 (2H, s)‡, 7,27–7.34 (5H, m), 7.63–7.82 (2H, m), 8.35–8.41 (2H, m).

‡: The peak is split due to the rotational isomers.

EXAMPLE 74

Synthesis of
3-(Phthalimidomethylthio)-2-pivaloylaminopyridine

In 3 ml of ethanol were suspended 0.21 g (1.0 mmol) of 3-mercapto-2-(pivaloylamino)pyridine and 0.29 g (1.2 mmol) of (N-bromomethyl)phthalimide, triethylamine [0.14 ml (1.2 mmol)] was added and the mixture was stirred for 4 hours. The solvent was distilled off. The residue was dissolved in chloroform, washed with a saturated aqueous solution of sodium bicarbonate and water and dried. Then the solvent was distilled off. The residue was purified by column chromatography (eluent: ethyl acetate/hexane=2:1) to obtain powder. The powder thus obtained was recrystallized from ethyl acetate to obtain 0.29 g of the desired compound (yield: 78.0%, colorless columns).

Anal. for C$_{19}$H$_{19}$N$_3$O$_3$S, Calcd.: C; 61.77, H; 5.18, N; 11.37, Found: C; 61.78, H; 5.46, N; 11.20. NMR (200 MHz, CDCl$_3$) δ:1.27 (9H, s), 4.97 (2H, s), 7.08 (1H, dd, J=4.8,7.8 Hz), 7.70–7.86 (4H, m), 8.01 (1H, dd, J=1.8,7.8 Hz), 8.41 (1H, dd, J=1.8,7.8Hz), 8.55 (1H, bs). IR (KBr)cm$^{-1}$: 3200, 2960, 1730, 1720, 1680, 1420, 910, 710.

EXAMPLE 75

Synthesis of
4-[3-(N-benzyl-N-acetylamino)propylthio]pyridine

To a solution of 1.0 g (3.87 mmol) of 4-[3-(N-benzylamino)propylthio)-pyridine and 0.65 ml (4.64 mmol) of triethylamine in 25 ml of methylene chloride, 0.49 ml (4.64 mmol) of acetyl chloride was added under ice-cooling with stirring. The mixture was stirred at room temperature for 30 minutes. The reaction mixture was washed with a saturated aqueous solution of sodium bicarbonate and water and dried, and then the solvent was distilled off. The residue was purified by column chromatography (eluent: chloroform/methanol= 25:1) to obtain 980 mg of the desired compound (yield: 84.2%, yellow oil).

NMR (200 MHz, CDCl$_3$) δ:1.94 (2H, quint., J=7 Hz), 2.15 and 2.19 (2H, s)‡, 2.92 and 2.96 (2H, t, J=7 Hz)‡, 3.39 and 3.51 (2H, t, J=7 Hz)‡, 4.53 and 4.61 (2H, s)‡, 7.02–7.13 (2H, m), 7.13–7.42 (5H, m), 8,41 (2H, m).

‡: The peak is split due to the rotational isomers.

IR (neat)cm$^{-1}$: 3050, 1645, 1580, 800.

EXAMPLE 76

Synthesis of
4-[3-(N-benzyl-N-acetylamino)propylthio]pyridine
Hydrochloride

The above free base [800 mg (2.66 mmol)] was treated with 50 ml of a 10% solution of hydrogen chloride in methanol. The solvent was distilled off to obtain 794 mg of the desired compound (yield: 90.2%, yellow oil).

NMR (200 MHz, $D_2O$) δ:1.85–2.03 (2H, m), 2.19 and 2.24 (2H, s)‡, 3.12–3.19 (2H, m), 3.47–3.61 (2H, m), 4.60 and 4.67 (2H, s)‡, 7.25–7.38 (5H, m), 7.69 (2H, bd, J=6.0 Hz), 8.37 (2H, br.d, J=6.0 Hz).

‡: The peak is split due to the rotational isomers.

EXAMPLE 77

Synthesis of
4-[3-(N-benzyl-N-benzoylamino)-propylthio]pyridine
Hydrochloride i) Synthesis of
4-[3-(N-benzyl-N-benzoylamino)propylthio]pyridine To a solution of 400 mg (1.21 mmol) of 4-[3-(N-benzylamino)propylthio] pyridine dihydrochloride and 0.55 ml (4.00 mmol) of triethylamine in 5 ml of methylene chloride, 0.17 ml (1.45 mmol) of benzoyl chloride was added under ice-cooling with stirring. The mixture was stirred at room temperature for 30 minutes. The reaction mixture was washed with a saturated aqueous solution of sodium bicarbonate and water and dried, and then the solvent was distilled off. The residue was purified by column chromatography (eluent: ethyl acetate) to obtain 0.22 g of the desired compound (yield: 50.4%, yellow oil).

NMR (200 MHz, $CDCl_3$) δ:2.06 (2H ,m), 2.72 and 3.01 (2H, m)‡, 3.35 and 3,59 (2H ,m)‡, 4.54 and 4.79 (2H m)‡, 6.92–7.42 (7H, m), 8.38 (2H, bd, J=3 Hz).

‡: The peak is split due to the rotational isomers.

ii) Synthesis of
4-[3-(N-benzyl-N-benzoylamino)propylthio]pyridine
Hydrochloride The above free base [0.22 g (0.61 mmol)] was treated with 50 ml of a 10% solution of hydrogen chloride in methanol. The solvent was distilled off to obtain 0.29 g of the desired compound (yield: quant., yellow oil).

NMR (200 MHz, $D_2O$) δ:1.80–2.08 (2H,m), 2.94 and 3.21 (2H, J=6.5 Hz)‡, 3.39–3.47 and 3.56–3.64 (2H, m)‡, 4.52 and 4.77 (2H, s), 7.15–7.71 (12H, m), 8.34–8.39 (2H,m).

‡: The peak is split due to the rotational isomers.

EXAMPLE 78

Synthesis of
4-[3-(N-2-pyridylmethyl-N-trifluoroacetylamino)-
propylthio] pyridine Dihydrochloride i) Synthesis of
4-[3-(N-2-pyridylmethylamino)propylthio]pyridine To a solution of 5.26 g (31.1 mmol) of 4-(3-hydroxypropylthio)pyridine and 5.20 ml (37.3 mmol) of triethylamine in150 ml of methylene chloride, 2.90 ml (37.3 mmol) of methanesulfonyl chloride was added under ice-cooling with stirring. The mixture was stirred at room temperature for 30 minutes. The reaction mixture was washed with a saturated aqueous solution of sodium bicarbonate and water and dried, and then the solvent was distilled off. To 6.33 g of the residue was added 2.64 ml (25.6 mmol) of 2-aminomethylpyridine. The resulting mixture was heated at 80° C. for 3 hours. After cooling, the mixture was purified by column chromatography (eluent: chloroform/methanol=25:1) to obtain 1.62 g of the desired compound (yield: 25.4%, yellow oil).

NMR (200 MHz, $CDCl_3$) δ:1.94 (2H, quant., J=7.0 Hz), 2.13 (1H, br.s), 2.83 (2H, t, J=6.8 Hz), 3.09 (2H, t, J=7.4 Hz), 3.92 (2H, s), 7.12 (2H, dd, J=1.6,4.8 Hz), 7.28 (1H, dd, J=1.0,5.1 Hz), 7.30 (1H, d, J=7.6 Hz), 7.66 (1H, dt, J=1.8,7.6 Hz), 8.38 (2H, dd, J=1.6,4.8 Hz), 8.56 (1H, dd, J=1.0,5.0 Hz).

ii) Synthesis of
4-[3-(N-2-pyridylmethyl-N-trifluoroacetylamino)-
propylthio]pyridine Dihydrochloride To a solution of 1.40 g (5.40 mmol) of 4-[3-(N-2-pyridylmethylamino)propylthio]pyridine and 0.91 ml (6.48 mmol) of triethylamine in 10 ml of methylene chloride, 0.51 ml (6.48 mmol) of trifluoroacetic anhydride was added under ice-cooling with stirring. The mixture was stirred at room temperature for 30 minutes. The reaction mixture was washed with a saturated aqueous solution of sodium bicarbonate and water and dried, and then the solvent was distilled off. The residue was purified by column chromatography (eluent: ethyl acetate/acetone=10:1) to obtain 390 mg of 4-[3-(N-2 -pyridylmethyl-N-trifluoroacetylamino)-propylthio]pyridine (yield: 20.4%, yellow oil).

NMR (200 MHz, $CDCl_3$): 1.96 and 2.08 (2H, quant., J=7 Hz)‡, 2.95 and 2.97 (2H, t, J=8 Hz)‡, 3.59 and 3.68 (2H, t, J=8 Hz)‡, 4.72 and 4.74 (2H, s)‡, 7.07 (2H, m), 7.17–7.31 (2H, m), 7.60–7.74 (1H, m), 8.40 (2H, br.s , 8.53 (1H, m).

‡: The peak is split due to the rotational isomers.

The above free base [390 mg (1.10 mmol)] was treated with 70 ml of a 10% solution of hydrogen chloride in methanol. The solvent was distilled off to obtain 418 mg of the desired compound (yield: 89.1%, yellow oil).

NMR (200 MHz, $D_2O$) −δ:2.18–2.34 (2H, m), 3.24–3.44 (4H, m), 4.55 (2H, s), 7.74–8.04 (4H, m), 8.20–8.29 (1H, m), 8.44 (2H, br.d, J=6.0 Hz), 8.70–8.79 (1H, m).

EXAMPLE 79

Synthesis of
4-[3-(N-2-pyridylmethyl-N-acetylamino)-
propylthio]pyridine

To a solution of 1.62 g (6.24 mmol) of 4-[3-(N-2-pyridylmethylamino)propylthio]pyridine and 1.10 ml (7.80 mmol) of triethylamine in 10 ml of methylene chloride, 0.51 ml (7.80 mmol) of acetyl chloride was added under ice-cooling with stinting. The mixture was stirred at room temperature for 30 minutes. The reaction mixture was washed with a saturated aqueous solution of sodium bicarbonate and water and dried, and the solvent was distilled off. The residue was purified by column chromatography (eluent: ethyl acetate/methanol=10:1) to obtain 1.61 g of the desired compound (yield: 85.6%, yellow oil).

NMR (200 MHz, $CDCl_3$) δ:1.87–2.03 (2H, m), 2.15 and 2.18 (3H, s)‡, 2.97 and 2.98 (2H, t, J=7 Hz)‡, 3.53 and 3.57 (2H, t, J=6 Hz)‡, 4.62 and 4.70 (2H, s), 7.06–7.09 (2H, m), 7.14–7.34 (2H, m), 7.60–7.73 (1H, m), 8.43–8.43 (2H, m), 8.49–8.59 (1H, m).

‡: The peak is split due to the rotational isomers.

IR (neat)cm$^{-1}$: 3000, 2940, 1650, 1580.

EXAMPLE 80

Synthesis of
4-[3-(N-2-pyridylmethyl-N-acetylamino) propylthio]pyridine Dihydrochloride The above free base [1.25 g (4.15 mmol)] was treated with 250 ml of a 10% solution of hydrogen chloride in methanol. The solvent was distilled of to obtain 1.49 g of the desired compound (yield: 95.6%, yellow oil).

NMR (200 MHz, D$_2$O) δ:2.04–2.27 (2H, m), 2.17 and 2.28 (3H, s)‡, 3.21–3.38 (2H, m), 3.61 and 3.81 (2H, br.t, J=7.6 Hz)‡, 4.97 and 5.18 (2H, s)‡, 7.79–7.86 (2H, m), 7.93–8.02 (2H, m), 8.42–8.47 (2H, m), 8.52–8.72 (2H, m).

‡: The peak is split due to the rotational isomers.

EXAMPLE 81

Synthesis of
4-[3-(N-2-pyridylmethyl-N-benzoylamino)-propylthio]pyridine

To a solution of 1.60 g (6.17 mmol) of 4-[3-(N-2-pyridyl-methylamino)propylthio)pyridine and 1.05 ml (7.40 mmol) of triethylamine in 10 ml of methylene chloride, 0.86 ml (7.40 mmol) of benzoyl chloride was added under ice-cooling with stirring. The mixture was stirred at room temperature for 30 minutes. The reaction mixture was washed with a saturated aqueous solution of sodium bicarbonate and water and dried, and then the solvent was distilled off. The residue was purified by column chromatography (eluent: ethyl acetate/methanol=10:1) to obtain 1.32 g of the desired compound (yield: 58.9%, yellow oil).

NMR (200 MHz, CDCl$_3$) δ:2.02 (2H, m), 2.78 and 3.06 (2H, m)‡, 3.49 and 3.76 (2H, m)‡, 4.64 and 4.87 (2H, m)‡, 6.95–7.23 (4H, m), 7.39 (5H, br.s), 7.69 (5H, br.s), 8.38 (2H, d, J=6 Hz), 8.56 (1H, d, J=4 Hz).

‡: The peak is split due to the rotational isomers.

IR (neat)cm$^{-1}$: 3055, 2940, 1640, 1580.

EXAMPLE 82

Synthesis of
4-[3-(N-2-Pyridylmethyl-N-benzoylamino)-propylthio]pyridine Dihydrochloride The above free base [1.00 g (2.75 mmol)] was treated with 300 ml of a 10% solution of hydrogen chloride in methanol. The solvent was distilled off to obtain 1.15 g of the desired compound (yield: 95.6%, yellow oil).

NMR (200 MHz, D$_2$O) δ:2.00–2.15 (2H, m), 3.11 (2H, br.t, J=6.0 Hz), 3.72–3.84 (2H, m), 5.12 (2H, s), 7.35–7.64 (7H, m), 7.94–8.33 (2H, m), 8.40 (2H, br.d, J=6.2 Hz), 8.58–8.79 (2H, m).

EXAMPLE 83

Synthesis of 4-(3-Phthalimidopropyloxy)pyridine

To a solution of 4.76 g (50 mmol) of 4-hydroxypyridine and 14.75 g (55 mmol) of N-(3-bromopropyl)phthalimide in 80 ml of DMF was added 8.23 ml (55 mmol) of 1,8-diazabicyclo[5.4.0]-7-undecene. The mixture was stirred at room temperature for 6 hours. After the solvent was distilled off, the mixture was poured into water and extracted with ethyl acetate. The mixture was washed with water and dried over anhydrous magnesium sulfate, and the solvent was distilled off. The residue was purified by column chromatography (eluent: ethyl acetate) to obtain 2.32 g of the desired compound (yield: 16.4% colorless crystals).

mp: 81.0°–82.0° C., Anal. for C$_{16}$H$_{14}$N$_2$O$_3$, Calcd.: C; 68.08, H; 5.00, N; 9.92, Found: C; 68.23, H; 5.06, N; 10.00. NMR (200 MHz, CDCl$_3$) δ:2.22 (2H, m), 3.92 (2H, t, J=6.8 Hz), 4.08 (2H, t, J=6.2 Hz), 6.70 (2H, dd, J=5,1.4 Hz), 7.67–7.92 (4H, m), 8.39 (2H, dd, J=5,1.4 Hz). IR (KBr)cm$^{-1}$: 1775, 1710, 1595, 1565, 1505.

EXAMPLE 84

Synthesis of 4-(4-Phthalimidobutyloxy)pyridine

To a solution of 4.76 g (50 mmol) of 4-hydroxypyridine and 15.52 g (55 mmol) of N-(4-bromobutyl)phthalimide in 80 ml of DMF was added 8.23 ml (5 mmol) of 1,8-diazabicyclo[5.4.0]-7-undecene. The mixture was stirred at room temperature for 7 hours. After the solvent was distilled off, the mixture was poured into water and extracted with ethyl acetate. The mixture was washed with water and dried over anhydrous magnesium sulfate, and the solvent was distilled off. The residue was purified by column chromatography (eluent: ethyl acetate) to obtain 2.63 g of the desired compound (yield: 17.2%, colorless crystals).

mp: 126°–127° C., Anal. for C$_{17}$H$_{16}$N$_2$O$_3$.0.5H$_2$O, Calcd.: C; 66.87, H; 5.61, N; 9.17, Found: C; 67.05, H; 5.43, N; 9.20. NMR (200 MHz, CDCl$_3$) δ: 1.75–1.97 (4H, m), 3.78 (2H, m), 4.05 (2H, m), 6.78 (2H, dd, J=4.8,1.6 Hz), 7.88–7.91 (4H, m), 8.41 (2H, dd, J=4.8,1.6 Hz). IR (KBr)cm$^{-1}$: 1770, 1710, 1595, 1570.

EXAMPLE 85

Synthesis of 4-[3-(Thianaphtene-2-carbonylamino)-propyloxy]pyridine i) Synthesis of 4-(3-Aminopropyloxy)pyridine Hydrazine monohydrate [2.99 ml (61.6 mmol)] was added to a suspension of 5.80 g (20.5 mol) of 4-(3-phthalimidopropyloxy)pyridine in 50 ml of ethanol, and the mixture was stirred at room temperature for 3 hours. 100 ml of ethyl acetate was added and insoluble materials were filtered off. The volatile component in the filtrate was distilled off and then chloroform was added to the residue. The mixture was washed with brine and dried over potassium carbonate. The solvent was distilled off to obtain 2.99 g of the desired compound (yield: 99.5%, pale yellow oil).

NMR (200 MHz, CDCl$_3$) δ:1.42 (2H, br.), 1.94 (2H, m), 2.91 (2H, t, J=6.6 Hz), 4.11 (2H, t, J=6.2 Hz), 6.80 (2H, J=4.8,1.6 Hz), 8.41 (2H, dd, J=4.8,1.6 Hz).

ii) Synthesis of
4-[3-(thianaphthene-2-carbonylamino)-propylthio]pyridine

To a solution of 1.15 g (7.56 mmol) of 4-(3-aminopropyloxy)pyridine and 1.27 ml (9.11 mmol) of triethylamine in 50 ml of methylene chloride, 1.49 ml (7.58 mmol) of thianaphthene-2-carbonyl chloride was added under ice-cooling with stirring. The mixture was stirred at room temperature for 1.5 hours. The reaction mixture was washed successively with a saturated aqueous solution of sodium bicarbonate and brine and dried over anhydrous magnesium sulfate, and the solvent was distilled off. The residue was purified by column chromatography (eluent: ethyl acetate) to obtain 1.65 g of the desired compound (yield: 69.1%, pale yellow crystals).

mp: 127°–128.5° C., Anal. for $C_{17}H_{16}N_2O_2S.0.2H_2O$, Calcd.: C; 64.62, H; 5.23, N; 8.87, Found: C; 64.54, H; 5.20, N; 8.93. NMR (200 MHz, CDCl$_3$) δ:2.18 (2H ,m) , 3.70 (2H, m), 4.15 (2H, t, J=5.8 Hz), 6.66 (1H, br.), 6.81 (2H, dd, J=4.8,1.6 Hz), 7.34–7.48 (2H, m), 7.75–7.91 (3H, m), 8.43 (2H, dd, J=4.8,1.6 Hz). IR (KBr)cm$^{-1}$: 3370, 1635, 1590, 1570, 1535, 1505, 1280, 1210, 1195.

EXAMPLE 86

Synthesis of 4-(3-Pivaloylaminopropyloxy) Pyridine

To a solution of 700 mg (4.60 mmol) of 4-(3-aminopropyloxy)pyridine and 0.77 ml (5.52 mmol) of triethylamine in 30 ml of methylene chloride, 0.57 ml (4.63 mmol) of pivaloyl chloride was added under ice-cooling with stirring. The mixture was stirred at room temperature for 1.5 hours. The reaction mixture was washed successively with a saturated aqueous solution of sodium bicarbonate and brine and dried over anhydrous magnesium sulfate, and then the solvent was distilled off. The residue was purified by column chromatography (eluent: ethyl acetate) to obtain 840 mg of the desired compound (yield: 77.3%, colorless crystals).

mp: 71.5°–72.5° C., Anal. for $C_{13}H_{20}N_2O_2$, Calcd.: C; 66.07, H; 8.53, N; 11.85, Found: C; 65.91, H; 8.88, N; 11.71. NMR (200 MHz, CDCl$_3$) δ:1.20 (9H, s), 2.04 (2H, m), 3.46 (2H, m), 4.09 (2H, t, J=6 Hz), 5.98 (1H, br.), 6.80 (2H, dd, J=4.8,1.6 Hz), 8.44 (2H, dd, J=4.8,1.6 Hz). IR (KBr)cm$^{-1}$: 3345, 2970, 1640, 1595, 1570, 1530, 1505, 1285.

EXAMPLE 87

Synthesis of 4-(3-Nicotinoylaminopropyloxy)pyridine

To a solution of 700 mg (4.60 mmol) of 4-(3-aminopropyloxy)pyridine and 1.54 ml (11.0 mmol) of triethylamine in 30 ml of methylene chloride, 830 mg (4.66 mmol) of nicotinoyl chloride hydrochloride was added under ice-cooling within stirring. The mixture was stirred at room temperature for 1.5 hours. The reaction mixture was washed successively with a saturated aqueous solution of sodium bicarbonate and brine and dried over anhydrous magnesium sulfate, and then the solvent was distilled off. The residue was purified by column chromatography (eluent: ethanol/ethyl acetate=1:10 to 1:5) to obtain 1.05 g of the desired compound (yield: 85.8%, colorless crystals).

mp: 117°–119° C., Anal. for $C_{14}H_{15}N_3O_2.0.2H_2O$, Calcd.: C; 64.45, H; 5.95, N; 16.11, Found: C; 64.55, H; 5.84, N; 16.03. NMR (200 MHz, CDCl$_3$) δ:2.17 (2H, m), 3.71 (2H, m), 4.13 (2H, t, J=5.8 Hz), 6.77 (2H, dd, J=4.8,1.6 Hz) , 7.03 (1H, br.), 7.39 (1H, m), 8,15 (1H, dt, J=7.8,2.2 Hz), 8.40 (2H, m), 8.73 (1H, dd, J=4.8,1.6 Hz), 9.01 (1H, d, J=2.2 Hz). IR (KBr)cm$^{-1}$: 3315, 1640, 1590, 1555, 1505, 1475, 1420, 1285, 1215.

EXAMPLE 88

Synthesis of 4-(3-Caprylaminopropyloxy)pyridine

To a solution of 700 mg (4.60 mmol) of 4-(3-aminopropyloxy)pyridine and 0.77 ml (5.52 mmol) of triethylamine in 30 ml of methylene chloride, 0.96 ml (4.63 mmol) of capryl chloride was added under ice-cooling with stirring. The mixture was stirred at room temperature for 1.5 hours. The reaction mixture was washed successively with a saturated aqueous solution of sodium bicarbonate and brine and dried over anhydrous magnesium sulfate, and then the solvent was distilled off. The residue was purified by column chromatography (eluent: ethyl acetate) to obtain 1.05 g of the desired compound (yield: 74.5%, colorless crystals).

mp: 44°–46° C., Anal. for $C_{18}H_{30}N_2O_2$, Calcd.: C; 70.55, H; 9.87, N; 9.14, Found: C; 70.55, H; 9.78, N; 8.82. NMR (200 MHz, CDCl$_3$) δ:0.88 (3H, m), 1.26 (12H, m), 1.62 (2H, m), 2.03 (2H, m), 2.18 (2H, m), 3.46 (2H, m), 4.07 (2H, t, J=6.0 Hz), 5.79 (1H, br.), 6.79 (2H, dd, J=4.8,1.6 Hz), 8.43 (2H, dd, J=4.8,1.6 Hz). IR (KBr)cm$^{-1}$: 3290, 2925, 2850, 1640, 1595, 1565, 1555, 1505, 1290, 1210.

EXAMPLE 89

Synthesis of 4-[3-(2-Thenoylamino)propyloxy]pyridine

To a solution of 700 mg (4.60 mmol) of 4-(3-aminopropyloxy)pyridine and 0.77 ml (5.52 mmol) of triethylamine in 30 ml of methylene chloride, 0.50 ml (4.68 mmol) of thenoyl chloride was added under ice-cooling with stirring. The mixture was stirred at room temperature for 1.5 hours. The reaction mixture was washed successively with a saturated aqueous solution of sodium bicarbonate and brine and dried over anhydrous magnesium sulfate, and the solvent was distilled off. The residue was purified by column chromatography (eluent: ethyl acetate) to obtain 850 mg of the desired compound (yield: 70.0%, colorless crystals).

mp: 123°–125° C. Anal. for $C_{13}H_{14}N_2O_2S.0.1H_2O$, Calcd.: C; 59.12, H; 5.42, N; 10.61, Found: C; 59.01, H; 5.45, N; 10.59. NMR (200 MHz, CDCl$_3$) δ:2.14 (2H, m), 3.65 (2H, m), 4.13 (2H, t, J=6 Hz), 6.64 (1H, br.), 6.79 (2H, dd, J=4.8,1.6 Hz), 7.08 (1H, dd, J=4.8,3.6 Hz), 7.48 (2H, dd, J=4.8,1 Hz), 7.54 (1H, dd, J=3.6,1 Hz), 8.42(2H, dd, J=4.8, 1.6 Hz). IR (KBr)cm$^{-1}$: 3205, 1635, 1595, 1560, 1505, 1425, 1290, 1210.

EXAMPLE 90

Synthesis of 4-[3-(N-2-thienylmethyl)-N-acetylamino)-propylthio]pyridine

To a solution of 2.5 g (9.45 mmol) of 4-[3-(N-(2-thienylmethyl)amino)propylthio]pyridine and 1.32 ml (9.45 mmol) of triethylamine in 50 ml of methylene chloride, 0.67 ml (9.45 mmol) of acetyl chloride was added under ice-cooling with stirring. The mixture was stirred at room temperature for 30 minutes. The reaction mixture was washed with a saturated aqueous solution of sodium bicarbonate and water and dried, and the solvent was distilled off. The residue was purified by column chromatography (eluent: ethyl acetate) to obtain 1.10 g of the desired compound (yield: 37.9%, yellow oil).

NMR (200 MHz, CDCl$_3$) δ: 1.84–2.04 (2H, m), 2.14 and 2.22 (3H, s)‡, 2.95 and 2.96 (2H, t, J=6.6,7.2 Hz)‡, 3.45 and 3.54 (2H, t, J=7.6,7.0 Hz)‡, 4.64 and 4.71 (2H, s)‡, 6.89–6.99 (2H, m), 7.08 (2H, dd, J=1.6,4.6 Hz), 7.20–7.27 (1H, m), 8.37–8.43 (2H, m).

‡: The peak is split due to the rotational isomers.

IR (neat)cm$^{-1}$: 3040, 1640, 1580, 8100, 710.

EXAMPLE 91

Synthesis of 4-[3-[N-(2-thienylmethyl)-N-acetylamino)-propylthio]pyridine Hydrochloride The above free base [1.01 g (3.3 mmol)] was treated with 80 ml of a 10% solution of hydrogen chloride in methanol. The solvent was distilled off to obtain 1.13 g of the desired compound (yield: quant., yellow oil).

NMR (200 MHz, D$_2$O) δ:1.86–2.08 (2H, m), 2.18 and 2.24 (3H,s)‡, 3.12–3.23 (2H, m), 3.48–3.65 (2H, m), 4.79 and 4.71 (2H, s)‡, 6.89–7.14 (2H, m), 7.30–7.39 (1H, m), 7.72 (2H, d, J=7.2 Hz), 8.40 (2H, d, J=7.0 Hz).

‡: The peak is split due to the rotational isomers.

EXAMPLE 92

Synthesis of 4-[3-(N-(2-thienylmethyl)-N-benzoylamino)-propylthio]pyridine

To a solution of 2..5 g (9.45 mmol) of 4-[3-(N-(2-thienylmethyl)amino)propylthio]pyridine and 1.32 ml (9.45 mmol) of triethylamine in 50 ml of methylene chloride, 1.1 ml (9.45 mmol) of benzoyl chloride was added under ice-cooling with stirring. The mixture was stirred at room temperature for 30 minutes. The reaction mixture was washed with a saturated aqueous solution of sodium bicarbonate and water and dried, and the solvent was distilled off. The residue was purified by column chromatography (eluent: ethyl acetate) to obtain 1.25 g of the desired compound (yield: 35.9%, yellow oil).

NMR (200 MHz, CDCl$_3$) δ:1.83–2.31 (2H, br.m), 2.82–3.22 (2H, br.m), 3.35–3.68 (2H, br.m), 4.64–4.85 (2H, br.s), 6.90–7.09 (3H, m), 7.27 (2H, m), 7,42 (5H, s), 8.40 (2H, m). IR (neat)cm$^{-1}$: 3060, 1630, 1580, 800, 700.

EXAMPLE 93

Synthesis of 4-[3-(N-(2-thienylmethyl)benzoylamino)-propylthio]pyridine Hydrochloride The above free base [0.99 g (2.69 mmol)] was treated with 80 ml of a 10% solution of hydrogen chloride in methanol. The solvent was distilled off to obtain 1.09 g of the desired compound (yield: quant., yellow oil).

NMR (200 MHz, D$_2$O) δ:1.86–2.09 (2H, m), 3.18–3.69 (4H, m), 4.92 (2H, s), 6.92–7.17 (2H, m), 7.29–7.82 (6H, m), 8.38–8.43 (2H, m).

EXAMPLE 94

Synthesis of 4-[3-(N-dodecyl-N-trifluoroacetylamino)-propylthio]pyridine i) Synthesis of 4-[3-(N-dodecylamino)propylthio]pyridine

In 120 ml of methylene chloride was dissolved 5.60 g (33.1 mmol) of 4-(3-hydroxypropylthio)pyridine and 5.53 ml (39.7 mmol) of triethylamine. 3.07 ml (39.7 mmol) of methanesulfonyl chloride was added, and the mixture was stirred at room temperature for 30 minutes. The reaction mixture was washed with a saturated aqueous solution of sodium bicarbonate and water and dried, and then the solvent was distilled off, 5.34 g (28.8 mmol) of dodecylamine was added to 7.12.g of the residue, and the mixture was heated at 80° C. for 3 hours. After cooling, the mixture was purified by column chromatography (eluent: chloroform/methanol=25:1) to obtain 2.86 g of the desired compound (yield: 29.5%, yellow oil).

NMR (200 MHz, CDCl$_3$) δ:0.88 (3H, br.t, J=6.8 Hz), 1.22–1.40 (18H, m), 1.42–1.58 (2H, m), 1.93 (2H, quint., J=7.4 Hz), 2.21 (1H, br.s), 2.63 (2H, t, J=7.4 Hz), 2.80 (2H, t, J=6.8 Hz), 3.06 (2H, t, J=7.4 Hz), 7.12 (2H, dd, J=1.6,4.6 Hz), 8,38 (2H, dd, J=1.6,4.6 Hz). IR (neat) cm$^{-1}$: 3300, 3035, 2930, 2860, 1580, 805, 715.

ii) Synthesis of 4-[3-(N-dodecyl-N-trifluoroacetylamino)-propylthio]pyridine To a solution of 2.86 g (8.5 mmol) of 4-[3-(N-dodecylamino)propylthio]pyridine and 1.2 ml (8.5 mmol) of triethylamine in 30 ml of methylene chloride, 1.2 ml (8.5 mmol) of trifluoroacetic anhydride was added under ice-cooling with stirring. The mixture was stirred at room temperature for 30 minutes. The reaction mixture was washed with a saturated aqueous solution of sodium bicarbonate and water and dried, and then the solvent was distilled off. The residue was purified by column chromatography (eluent: ethyl acetate/hexane=1:1) to obtain 1.72 g of the desired compound (yield: 48.6%, yellow oil).

NMR (200 MHz, CDCl$_3$) δ:0.88 (3H, t, J=7.6 Hz), 1.21–1.33 (16H, m), 1.53–1.65 (2H, m), 2.02 (2H, quint., J=7.8 Hz), 3.00 (2H, dt, J=1.8,7.0 Hz), 3.35 (2H, bt, J=7.6 Hz), 3.53 (2H, bt, J=7.6 Hz), 7.14 (2H, dd, J=1.6,4.6 Hz), 8.41 (2H, dd, J=1.6,4.6 Hz). IR (neat)cm$^{-1}$: 2930, 1690, 1580, 800, 710.

EXAMPLE 95

Synthesis of 4-[(4-Nitrophthalimido)methylthio]pyridine

N-Chloromethyl-4-nitrophthalimide [2.89 g (12 mmol)] was added under ice-cooling with stirring to a suspension of 1.11 g (10 mmol) of 4-mercaptopyridine and 1.4 ml (12 mmol) of triethylamine in 50 ml of ethanol. The mixture was stirred at room temperature for 16 hours. The solvent was distilled off and the residue was purified by column chromatography (eluent: ethyl acetate) to obtain 1.99 g of the desired compound (yield: 63.1%, yellow crystals).

NMR (200 MHz, CDCl$_3$) δ:5.25 (2H ,m), 7,40 (2H, dd, J=1.8,4.6 Hz), 8.08 (1H, d, J=8.0 Hz), 8.48 (2H, dd, J=1.8, 4.6 Hz), 8.63 (1H, dd, J=1.8,8.0 Hz). IR (KBr)cm$^{-1}$: 3100, 1725, 1535, 1345.

EXAMPLE 96

Synthesis of 4-[cis-(1,2,3,6-Tetrahydrophthalimido)-methylthio]pyridine i) Synthesis of cis-(N-hydroxymethyl)-1,2,3,6-tetrahydrophthalimide

Formalin [8.1 ml (100 mmol)] was added to a suspension of 15.12 g (100 mmol) of cis-1,2,3,6-tetrahydrophthalimide in 150 ml of water. The mixture was stirred for about 1 hour under heating at 110° C. until the precipitate was dissolved and the mixture became a clear solution. The reaction mixture was filtered while it was hot, and then was allowed to stand overnight in a refrigerator. The resulting precipitate was filtered off, washed with ice water and then dried to obtain 17.48 g of the desired compound (yield: 96.5%, pale yellow solid).

Anal. for $C_9H_{11}NO_3$, Calcd.: C; 59.66, H; 6.12, N; 7.73, Found: C; 59.96, H; 6.27, N; 7.76. NMR (200 MHz, DMSO-$d_6$) δ:5.00 (2H, d, J=6.8 Hz), 6.50 (1H, t, J=6.8 Hz), 7.95 (1H, dd, J=1.0,4.8 Hz), 9.14 (1H, d, J=4.8 Hz), 9.19 (1H, d, J=1.0 Hz). IR (KBr)cm$^{-1}$: 3480, 3045, 2950, 1700.

ii) Synthesis of cis-(N-bromomethyl)-1,2,3,6-tetrahydrophthalimide

Triphenylphosphine [3.15 g (12 mmol)] was added to solution of 1.81 g (10 mmol) of cis-(N-hydroxymethyl)-1,2,3,6-tetrahydrophthalimide and 3.98 g (12 mmol) of carbon tetrachloride in 100 ml of methylene chloride. The mixture was stirred at room temperature for 16 hours. The solvent was distilled off and then the residue was purified by column chromatography (eluent: ethyl acetate/hexane=1:2) to obtain 1.25 g of the desired compound (yield: 51.2%, brown oil).

NMR (200 MHz, CDCl$_3$) δ:2.27 (2H, m), 2.63 (2H, m), 3.16 (2H, m), 5.17 (2H, s), 5.91 (2H, m). IR (neat)cm$^{-1}$: 3050, 2950, 1730, 1710, 655, 600.

iii) Synthesis of 4-[cis-(1,2,3,6-tetrahydrophthalimido)-methylthio]pyridine To a suspension of 110 mg (1.0 mmol) of 4-mercaptopyridine and 0.14 ml (1.2 mmol) of triethylamine in 5 ml of ethanol, 2.93 mg (1.2 ml) of cis- (N-bromomethyl) 1,2,3,6-tetrahydrophthalimide was added under ice-cooling with stirring. The mixture was stirred at room temperature for 16 hours. The solvent as distilled off and then the residue was purified by column chromatography (eluent: ethyl acetate) to obtain 250 mg of the desired compound (yield: 91.0%, yellow oil).

NMR (200 MHz, CDCl$_3$) δ:2.17–2.27 (2H, m), 2.53–2.64 (2H, m), 3.11 (2H, m), 4.93 (2H, m), 5.80 (2H, m), 7.34 (2H, dd, J=1.2,4.2 Hz), 8.44 (2H, bd, J=4.2 Hz). IR (neat)cm$^{-1}$: 3040, 2950, 1710, 1570.

EXAMPLE 97

Synthesis of 4-(3-Hydroxyisoindolin-1-on-2-ylmethylthio)pyridine

To a solution of 4.01 g (14.8 mmol) of 4-(phthalimidomethylthio)pyridine in 25 ml of methanol, a solution of 1.08 g (29.7 mmol) of sodium borohydride in 20 ml of methanol was added. The mixture was stirred at room temperature for 4 hours. Glacial acetic acid (0.5 ml) was added to quench the reaction, and then the solvent was distilled off. The residue was dissolved in chloroform, washed with water and dried, and the solvent was distilled off. The residue was purified by recrystallization (recrystallization solvent: ethanol) to obtain 2.35 g of the desired compound (yield: 58.3%, yellow crystals).

Anal. for $C_{14}H_{12}N_2O_2S$, Calcd.: C; 61.75, H; 4.44, N; 10.29, Found: C; 61.51, H; 4.39, N; 10.40. NMR (200 MHz, CDCl$_3$) δ: 4.77 (1H, d, J=14.2 Hz), 4.78 (1H, bs), 5.49 (1H, d, J=14.2 Hz), 6.01 (1H, bs), 7.30–7.33 (2H, m), 7.46–7.77 (4H, m), 8.17–8.12 (2H, m). IR (KBr)cm$^{-1}$: 3420, 3140, 3050, 1700.

EXAMPLE 98

Synthesis of 4-(2-Phthalimidoethyloxy)pyridine

To a solution of 4.76 g (50 mmol) of 4-hydroxypyridine and 13.97 g (55 mmol) of N-(2-bromoethyl)phthalimide in 80 ml of DMF, 80 ml (55 mmol) of 1,8-diazabicyclo[5.4.0] -7-undecene was added. The mixture was stirred at room temperature for 32 hours. After the solvent was distilled off, the mixture was poured into water and extracted with ethyl acetate. The mixture was washed with water and dried over anhydrous magnesium sulfate, and then the solvent was distilled off. The residue was purified by column chromatography (eluent: ethyl acetate) to obtain 0.41 g of the desired compound (yield: 3.1%, colorless crystal).

mp: 157°–158° C., NMR (200 MHz, CDCl$_3$) δ:4.14 (2H, m), 4.29 (2H,m), 6.80 (2H, dd, J=4.8,1.6 Hz), 7.69–7.93 (4H, m), 8.41 (2H, dd, J=4.8,1.6 Hz). IR (KBr) cm$^{-1}$: 1775, 1705, 1595, 1570, 1510, 1290.

EXAMPLE 99

Synthesis of 4-[3-(3-hydroxyisoindolin-1-on-2-yl)propyloxy]pyridine

Sodium borohydride [1.89 g (50 mmol)] was added to a solution of 2.82 g (10.0 mmol) of 4-(3-phthalimidopropyloxy)pyridine in 150 ml of ethanol. The mixture was stirred at room temperature for 15 minutes. After the solvent was distilled off, brine was added to the residue. The mixture was extracted with chloroform and dried over anhydrous magnesium sulfate, and then the solvent was distilled off. The residue was purified by column chromatography (eluent: ethanol/ethyl acetate=1:10), and then recrystallized from ethyl acetate to obtain 1.54 g of the desired compound (yield: 54.2%, colroless crystals).

mp: 124°–125° C., Anal. for $C_{16}H_{16}N_2O_3$, Calcd.: C; 67.59, H; 5.67, N; 9.85, Found: C; 62.74, H; 5.74, N; 9.84. NMR (200 MHz), CDCl$_3$) δ:2.04–2.36 (2H, m), 3.60–4.05 (4H, m), 5.22 (1H, br.), 5.85 (1H, s), 6.55 (1H, dd, J=4.8,1.6 Hz), 7.47–7.67 (3H, m), 7.79 (1H, m), 7.97 (2H, dd, J=4.8,1.6 Hz). IR (KBr)cm$^{-1}$: 3115, 1685, 1605, 1570, 1505, 1470, 1445, 1420, 1290, 1215.

EXAMPLE 100

Synthesis of 4-[3-(2-Hydroxymethylbenzoyl)-aminopropyloxy]pyridine

Sodium borohydride [3.78 g (100 mmol)] was added to a solution of 2.82 g (10.0 mmol) of 4-(3-phthalimidopropyloxy)pyridine in 150 ml of ethanol. The mixture was stirred at room temperature for 3 hours. After the solvent was distiled off, brine was added to the residue. The mixture was extracted with chloroform and dried over anhydrous magnesium sulfate. The solvent was distilled off and then the residue was purified by column chromatography (eluent: ethanol/ethyl acetate=1:10) to obtain 1.488 g of the desired compound (yield: 52.0%, colorless crystals).

mp: 108°–109° C., Anal. for $C_{13}H_{18}N_2O_3$, Calcd.: C; 67.12, H; 6.34, N; 9.78, Found C; 67.20, H; 6.40, N; 9.68. NMR (200 MHz, CDCl$_3$) δ:2.16 (2H, m), 3.67 (2H, m), 4.13 (2H, t, J=6 Hz), 4.61 (2H, s), 4.75 (1H,br.), 6.76 J=4.8,1.6 Hz), (2H, dd, 7.28 (1H, hr.), 7.30–7.50 (3H, m), 7.59 (1H, m), 8.33 (2H, dd, J=4.8,1.6 Hz). IR (KBr) cm$^{-1}$: 3400, 3205, 1635, 1600, 1585, 1565, 1510, 1440.

EXAMPLE 101

Synthesis of 4-[3-(isoindolin-1-on-2-yl)propyloxy]pyridine

To a solution of 1.25 ml (9.0 mmol) of 4-[3-(2-hydroxymethylbenzoyl)-aminopropyloxy]pyridine and 1.25 ml (9.0 mmol) of triethylamine in 50 ml of methylene chloride, 0.47 ml (6.1 mmol) of methanesulfonyl chloride was added under ice-cooling with stirring. The mixture was stirred at room temperature for 15 minutes. The reaction mixture was washed successively with a saturated aqueous solution of sodium bicarbonate, water and brine and dried over anhydrous magnesium sulfate, and then the solvent was distilled off. The residue was purified by column chromatography (eluent: ethanol/ethyl acetate=1:10) to obtain 537 mg of the desired compound (yield: 66.6%, pale brown crystals).

mp: 70°–71° C. Anal. for $C_{16}H_{16}N_2O_2$, Calcd.: C; 71.62, H; 6.01, N; 10.44, Found: C; 71.47, H; 6.07, N; 10.33. NMR (200 MHz, $CDCl_3$) δ:2.17 (2H, m), 3.69 (2H, t, J=6.6 Hz), 4.18 (2H, t, J=6.4 Hz), 5.29 (2H, 6.82 (2H, dd, J=4.8,1.6 Hz), 7.33–7.56 (3H, m), .7.83 (1H, 8.40 (2H, dd, J=4.8,1.6 Hz). IR (KBr)cm$^{-1}$: 1685, 1590, 1565, 1505, 1465, 1290, 1215.

EXAMPLE 102

Synthesis of 4-(3,4-Pyridinedicarboxyimidomethylthio)pyridine i) Synthesis of (N-hydroxymethyl)-3,4-pyridinedicarboxyimide Formalin [0.81 ml (10.0 mmol)] was added to a suspension of 1.48 g (10.0 mmol) of 3,4-pyridinecarboxyimide in 17.5 ml of water. The mixture was stirred for about 1 hour under heating at 110° C. until the precipitate was dissolved and the mixture became a clear solution. The reaction mixture was filtered while it was hot, and then was allowed to stand overnight in a refrigerator. The resulting precipitate was filtered off, washed with ice water and then dried to obtain 0.34 g of the desired compound (yield: 19.0%, pale red yellow solid).

Anal. for $C_8H_6N_2O_3 \cdot 0.1H_2O$, Calcd.: C; 53.40, H; 3.47, N; 15.57, Found: C; 53.28, H; 3.37, N; 15.57. NMR (200 MHz, DMSO-$d_6$) δ:5.00 (2H, d, J=6.8 Hz), 6.50 (1H, t, J=6.8 Hz), 7.95 (1H, dd, J=1.0,4.8 Hz), 9.14 (1H, d, J=4.8 Hz), 9.19 (1H, d, J=1.0 Hz). IR (KBr)cm$^{-1}$: 3170, 1785, 1710.

ii) Synthesis of 4-(3,4-Pyridinedicarboxyimidomethylthio)pyridine

Thionyl chloride [0.22 ml (3.0 mmol)] was added to a suspension of 180 mg (1.0 mmol) of (N-hydroxymethyl)-3,4-pyridinedicarboxyimide in 5 ml of carbon tetrachloride. The mixture was stirred under heating at 80° C. for 3 hours. After cooling, the solvent was distilled off. 0.42 ml (3.0 mmol) of triethylamine and 110 mg (1.0 mmol) of 4-mercaptopyridine were added to a suspension of the residue in 5 ml of ethanol. The mixture was stirred at room temperature for 16 hours. The solvent was distilled off. Then the residue was dissolved in chloroform, washed with water and dried. The solvent was distilled off and then the residue was purified by column chromatography (eluent: ethyl acetate) to obtain 70 mg of the desired compound (yield: 27%, yellow crystals).

NMR (200 MHz, $CDCl_3$) δ:5.22 (2H, s), 7.40 (2H, dd, J=1.6,4.6 Hz)‡, 7.78 (1H, dd, J=1.0,4.8 Hz), 8.47 (2H, dd, J=1.6,4.6 Hz), 9.11 (1H, d, J=4.8 Hz), 9.20 (1H, d, J=1.0 Hz). IR (KBr)cm$^{-1}$: 1720, 1580, 920, 810, 740.

EXAMPLE 103

Synthesis of 4-[2-(2-Hydroxymethylbenzoyl)aminoethylthio]pyridine

To a solution of 2.84 g (10.0 mmol) of 4-(2-phthalimidoethylthio)pyridine in 150 ml of ethanol, 3.78 g (100 mmol) of sodium borohydride was added, and the mixture was stirred at room temperature for 3 hours. The solvent was distilled off and saturated saline was added to the residue. The mixture was extracted with chloroform and the extract was dried over anhydrous magnesium sulfate. The solvent was distilled off and the residue was purified by column chromatography (eluent: ethanol/ethyl acetate=1:10) to give 2.24 g of the desired compound (77.8% yield, colorless crystals), mp. 132°–133° C.

Anal. for $C_{15}H_{16}N_2O_2S$, Calcd.: C; 62.48, H; 5.59, N; 9.71. Found: C; 62.20, H; 5.65, N; 9.53. NMR (200 MHz, $CDCl_3$) δ: 3.30 (2H, t, J=6.6 Hz), 3.76 (2H, m), 4.20 (1H, br), 4.64 (2H, ABq), 6.99 (1H, br), 7.23 (2H, dd, J=4.8, 1.6 Hz), 7.31–7.58 (4H, m), 8.42 (2H, dd, J=4.8, 1.6 Hz). IR (KBr) cm$^{-1}$: 3260, 1655, 1590, 1555.

EXAMPLE 104

Synthesis of 4-[2-(3-Hydroxyisoindolin-1-on-2-yl)ethylthio]pyridine

To a solution of 5.69 g (20.0 mmol) of 4-(2-phthalimidoethylthio)pyridine in 150 ml of ethanol, 2.27 g (60 mmol) of sodium borohydride was added, and the mixture was stirred at room temperature for 15 minutes. The solvent was distilled off and saturated saline was added to the residue. The mixture was extracted with chloroform and the extract was dried over anhydrous magnesium sulfate. The solvent was distilled off and the residue was purified by column chromatography (eluent: ethanol/ethyl acetate=1:10), after which subsequent recrystallization from ethyl acetate gave 3.63 g of the desired compound (63.4% yield, colorless crystals), mp. 111.5°–112.5° C.

NMR (200 MHz, $CDCl_3$) δ:3.31 (2H, t, J=7.2 Hz), 3.79 (2H, m), 5.89 (1H, s), 7.23 (2H, dd, J=6.4, 1.6 Hz), 7.42–7.65 (3H, m), 7.50 (1H, dd, J=6.8, 1.2 Hz), 8.21 (2H, m). IR (KBr) cm$^{-1}$: 3510, 3435, 1700, 1680, 1585.

EXAMPLE 105

Synthesis-of 4-[2-(Isoindolin-1-on-2-yl)ethylthio]pyridine

To a solution of 1.153 g (4.0 mmol) of 4-[2-(2-hydroxymethylbenzoyl)aminoethylthio]pyridine and 1.68 ml (12.1 mmol) of triethylamine in 50 ml of methylene chloride, 0.62 ml (8.0 mmol) of methanesulfonyl chloride was added with stirring at room temperature, and the mixture was stirred for 30 minutes. The mixture was washed with saturated aqueous sodium bicarbonate, water and saturated saline, and dried over anhydrous magnesium sulfate. The solvent was distilled off and the residue was purified by column chromatography (eluent: ethyl acetate) to give 623 mg of the desired compound (57.6% yield, colorless crystals), mp. 86°–87° C.

Anal. for $C_{15}H_{14}N_2OS$, Calcd.: C; 66.64, H; 5.22, N; 10.36. Found:. C; 66.49, H; 5.25, N; 10.26. NMR (200 MHz, CDCl$_3$) δ:3.29 (2H, m), 3.84 (2H, m), 5.34 (2H, s), 7.22 (2H, dd, J=4.6, 1.6 Hz), 7.34–7.58 (3H, m), 7.83 (1H, d, J=7.6 Hz), 8.38. (2H, dd, J=4.6, 1.6 Hz). IR (KBr) cm$^{-1}$: 1705, 1695, 1575.

EXAMPLE 106

Synthesis of 4-[4-(2-Hydroxymethylbenzoyl)aminobutylthio]pyridine

To a solution of 6.25 g of (20.0 mmol) of 4-(4-phthalimidobutylthio)pyridine in 300 ml of ethanol, 7.57 g (200 mmol) of sodium borohydride was added, and the mixture was stirred at room temperature for 14 hours. The solvent was distilled off and saturated saline was added to the residue. The mixture was extracted with chloroform and the extract was dried over anhydrous magnesium sulfate. The solvent was distilled off and the residue was purified by column chromatography (eluent: ethanol/ethyl acetate= 1:10) to give 4.63 g of the desired compound (73.1% yield, colorless crystals), mp. 87°–88° C.

NMR (200 MHz, CDCl$_3$) δ:1.83 (4H, m), 3.06 (2H, m), 3.52 (2H, m), 4.60 (2H, s), 6.63 (1H, br), 7.13 (2H, dd, J=6.4, 1.6 Hz), 7.25–7.58 (4H, m), 8.37 (2H, m). IR (KBr) cm$^{-1}$: 3300, 1655, 1590, 1560.

EXAMPLE 107

Synthesis of 4-[4-(3-Hydroxyisoindolin-1-on-2-yl)butylthio]pyridine

To a solution of 6.25 g (20.0 mmol) of 4-(4-phthalimidobutylthio)pyridine in 300 ml of ethanol, 1.51 g (40 mmol) of sodium borohydride was added, and the mixture was stirred at room temperature for 2.5 hours. The solvent was distilled off and saturated saline was added to the residue. The mixture was extracted with chloroform and the extract was dried over anhydrous magnesium sulfate. The solvent was distilled off and the residue was purified by column chromatography (eluent: ethyl acetate) to give 1.73 g of the desired compound (27.5% yield, colorless crystals), mp. 144°–145° C.

NMR (200 MHz, CDCl$_3$) δ:1.82 (4H, m), 3.04 (2H, t, J=7.2 Hz), 3.45–3.75 (2H, m), 5.80 (1H, s), 7.13 (2H, dd, J=4.8, 1.6 Hz), 7.45–7.65 (3H, m), 7.74 (1H, m), 8.25 (2H, m). IR (KBr) cm$^{-1}$: 1700, 1585.

EXAMPLE 108

Synthesis of 4-[3-(2-Hydroxymethylbenzoyl)-aminopropylthio]pyridine

To a solution of 5.97 g (20.0 mmol) of 4-(3-phthalimidopropylthio)pyridine in 300 ml of ethanol, 7.57 g (200 mmol) of sodium borohydride was added, and stirred at room temperature for 24 hours. The solvent was distilled off and saturated saline was added to the residue. The mixture was extracted with chloroform and the extract was dried over anhydrous magnesium sulfate. The solvent was distilled off and the residue was purified by column chromatography (eluent:ethanol/ethyl acetate=1:10) to give 4.73 g of the desired compound (78.2% yield, colorless crystals), mp. 110°–111° C.

NMR (200 MHz, CDCl$_3$) δ:2.08 (2H, m), 3.11 (2H, t, J=7.2 Hz), 3.64 (2H, m), 4.62 (2H, s), 6.81 (1H, br), 7.16 (2H, dd, J=4.8, 1.6 Hz), 7.32–7.52 (3H, m), 7.57 (1H, d, J=7.6 Hz), 8.38 (2H, dd, J=4.8, 1.6 Hz).

IR (KBr) cm$^{-1}$: 3280, 1655, 1585, 1555.

EXAMPLE 109

Synthesis of 4-[4-(isoindolin-1-on-2-yl)butylthio]pyridine

To a solution of 1.58 g (5.0 mmol) of 4-[4-(2-hydroxymethylbenzoyl)aminobutylthio]pyridine and 2.09 ml (15.0 mmol) of triethylamine in 50 ml of methylene chloride, 0.77 ml (10.0 mmol) of methanesulfonyl chloride was added with stirring at room temperature, and the mixture was stirred at room temperature for 30 minutes. The mixture was washed with saturated aqueous sodium bicarbonate, water and saturated saline, and dried over anhydrous magnesium sulfate. The solvent was distilled off and the residue was purified by column chromatography (eluent:ethyl acetate) to give 1.075 g of the desired compound (72.1% yield, pale brown crystals), top. 57°–58° C.

NMR (200 MHz, CDCl$_3$) δ:1.87 (4H, m), 3.05 (2H, m), 3.59 (2H, m), 5.36 (2H, s), 7.11 (2H, dd, J=4.8, 1.6 Hz), 7.34–7.59 (3H, m), 7.97 (1H, d, J=7.2 Hz), 8.35 (2H, dd, J=4.8, 1.6 Hz).

IR (KBr) cm$^{-1}$: 1685, 1580, 1535, 1485, 1470, 1460, 1415, 1375, 1350.

EXAMPLE 110

Synthesis of 4-[3-(3-hydroxyisoindolin-1-on-2-yl)propylthio]pyridine

To a solution of 5.97 g (20.0 mmol) of 4-(3-phthalimidopropylthio)pyridine in 300 ml of ethanol, 1.51 g (40 mmol) of sodium borohydride was added, and the mixture was stirred at room temperature for 5 hours. The solvent was distilled off and saturated saline was added to the residue. The mixture was extracted with chloroform and the extract was dried over anhydrous magnesium sulfate. The solvent was distilled off and the residue was purified by column chromatography (eluent:ethanol/ethyl acetate=1:10 ) to give 3.27 g of the desired compound (54.4% yield, colorless crystals), mp. 132°–134° C.

NMR (200 MHz, CDCl$_3$) δ:2.11 (2H, m), 2.97 (2H, m), 3.72 (2H, m), 5.83 (1H, s), 6.98 (2H, d, J=5.4 Hz), 7.47–7.67 (3H, m), 7.77 (1H, dd, J=7.6, 1.2 Hz), 8.02 (2H, m).

IR (KBr) cm$^{-1}$: 3430, 1690, 1585, 1470, 1415, 1350.

EXAMPLE 111

Synthesis of 4-[3-(isoindolin-1-on-2-yl)propylthio]pyridine

To a solution of 1.51 g (5.0 mmol) of 4-[3-(2-hydroxymethylbenzoyl)aminopropylthio]pyridine and 2.09 ml (15.0 mmol) of triethylamine in 50 ml of methylene chloride, 0.77 ml (10.0 mmol) of methanesulfonyl chloride was added with stirring at room temperature, and the mixture was stirred at room temperature for 30 minutes. The mixture was washed with saturated aqueous sodium bicarbonate, water and saturated saline, and dried over anhydrous magnesium sulfate. The solvent was distilled off and the residue was purified by column chromatography (eluent:ethyl acetate) to give 1.12 g of the desired compound (78.9% yield, pale brown crystals), mp. 73°–74.5° C.

NMR (200 MHz, CDCl$_3$) δ:2.11 (2H, m), 3.16 (2H, m), 3.68 (2H, t, J=6.6 Hz), 5.37 (2H, s), 7.17 (2H, dd, J=6.6, 1.6 Hz), 7.36–7.61 (3H, m), 8.01 (1H, d, J=7.6 Hz), 8.35 (2H, dd, J=6.6, 1.6 Hz).

IR (KBr) cm$^{-1}$: 1690, 1580.

EXAMPLE 112

Synthesis of 4-[(2-methylcarbamoylbenzoyl)-aminomethylthio]pyridine

To a solution of 6.76 g (25.0 mmol) of 4-phthalimidomethylthiopyridine in 100 ml of chloroform, 5 ml of 40% methylamine-methanol solution was added, and the mixture was stirred at room temperature for 3 hours. Additional 5 ml of 40% methylamine-methanol solution was added, and the mixture was stirred at room temperature for 3 hours. The solvent was distilled off and the residue was purified by column chromatography (eluent:ethanol/ethyl acetate= 1:10), and the resulting crude product-was crystallized from methylene chloride-diethyl ether to give 2.645 g of the desired compound (35.1% yield, yellow crystals), mp. 118°–121° C.

NMR (200 MHz, CDCl$_3$) δ:2.81 (3H, d, J=5.0 Hz), 4.97 (2H, d, J=6.2 Hz), 6.46 (1H, br), 7.32 (2H, dd, J=4.8, 1.6 Hz), 7.36–7.71 (4H, m), 8.24 (1H, br), 8.39 (2H, dd, J=4.8, 1.6 Hz).

IR (KBr) cm$^{-1}$:3550, 3295, 1645, 1620, 1585, 1540.

EXAMPLE 113

Synthesis of 4-(3-phthalimidopropyloxy)pyridine hydrochloride

To a solution of 1.41 g (5.0 mmol) of 4-(3-phthalimidopropyloxy)pyridine in 20 ml of methanol, 10 ml of hydrogen chloride-methanol was added. The solvent was distilled off and acetone was added to the residue. The resulting crystals were collected by filtration and washed with acetone to give 1.03 g of the desired compound (64.8% yield, colorless crystals), mp. 167°–169° C.

NMR (200 MHz, DMSO-d$_6$) δ:2.15 (2H, m), 3.78 (2H, t, J=6.6 Hz), 4.39 (2H, t, J=6.2 Hz), 7.45 (2H, d, J=7.2 Hz), 7.86 (4H, m), 8.73 (2H, d, J=7.2 Hz).

IR (KBr) cm$^{-1}$: 1780, 1715, 1640, 1595, 1510.

EXAMPLE 114

Synthesis of 4-(4-phthalimidobutyloxy)pyridine hydrochloride

To a suspension of 1.48 g (5.0 mmol) of 4-(4-phthalimidobutyloxy)pyridine in 20 ml of methanol, 15 ml of hydrogen chloride-methanol was added and dissolve. The solvent was distilled off and the residue was crystallized from acetone-ether. The resulting crystals were collected by filtration and washed with ether to give 1.51 g of the desired compound (86.3% yield, colorless crystals), mp. 154°–156° C.

Anal. for C$_{17}$H$_{16}$N$_2$O$_3$S·HCl·H$_2$O,

Calcd.: C; 58.21, H; 5.46, N; 7.99.

Found: C; 58.29, H; 5.38, N; 8.02.

NMR (200 MHz, DMSO-d$_6$) δ:1.81 (4H, m), 3.66 (2H, m), 4.37 (2H, m), 7.54 (2H, d, J=7.4 Hz), 7.87 (4H, m), 8.74 (2H, d, J=7.4 Hz).

IR (KBr) cm$^{-1}$: 1770, 1715, 1640, 1595, 1510.

EXAMPLE 115

Synthesis of 4-[3-(thianaphthene-2-carbonyl)-aminopropyloxy]pyridine hydrochloride To a solution of 625 mg (2.0 mmol) of 4-[3-(thianaphthene- 2-carbonyl)aminopropyloxy]pyridine in 20 ml of methanol, 10 ml of hydrogen chloride-methanol was added. The solvent was distilled off and the residue was crystallized from acetone-ether. The resulting crystals were collected by filtration and washed with ether to give 650 mg of the desired compound (93.1% yield, colorless crystals), mp. 163°–165° C.

NMR (200 MHz, DMSO-d$_6$) δ:2.10 (2H, m), 3.47 (2H, m), 4.43 (2H, t, J=6.2 Hz), 7.37–7.60 (2H, m), 7.87–8.06 (2H, m), 8.11 (1H, s), 8.75 (2H, d, J=7.2 Hz), 8.94 (1H, br).

IR (KBr) cm$^{-1}$: 3430, 1645, 1545, 1510.

EXAMPLE 116

Synthesis of 4-phthalimidomethyloxypyridine hydrochloride

To a solution of 1.27 g (5.0 mmol) of 4-phthalimidomethyloxypyridine in 20 ml of methylene chloride, 10 ml of hydrogen chloride-methanol was added. The solvent was distilled off and acetone was added to the residue. The resulting crystals were collected by filtration and washed with acetone to give 1.35 g (93.1% yield, colorless crystals), mp. 157°–159° C.

Anal. for C$_{14}$H$_{10}$N$_2$O$_3$·HCl,

Calcd.: C; 57.84, H; 3.81, N; 9.64.

Found: C; 57.74, H; 3.82, N; 9.69.

NMR (200 MHz, DMSO-d$_6$) δ:5.96 (2H, s), 7.73 (2H, t, J=6 Hz), 7.88–8.06 (4H, m), 8.83 (2H, d, J=6.2 Hz).

IR (KBr) cm$^{-1}$: 1785, 1725, 1640, 1505.

EXAMPLE 117

Synthesis of 4-[2-(N-benzyl-N-benzoyl)aminoethyloxy]pyridine

To a solution of 2.55 g (10 mmol) of N-benzyl-N-benzoylethanolamine in 30 ml of DMF, 800 mg (20 mmol) of 60% sodium hydride (oily) was added with stirring under ice-cooling, and the mixture was stirred for 5 minutes. Then, 1.94 g (10 mmol) of 4-bromopyridine hydrochloride was added, and the mixture was stirred at room temperature for 7 hours. The reaction mixture was poured into water, and extracted with ethyl acetate. The extract was washed two times with water and dried over anhydrous magnesium sulfate. The solvent was distilled off and the residue was purified by column chromatography (eluent:ethyl acetate) to give 1.97 g of the desired compound (59.3% yield, pale yellow oil).

NMR (200 MHz, CDCl$_3$) δ:3.68–4.98 (6H, m), 6.55–7.55 (12H, m), 8.44 (2H, m).

IR (neat) cm$^{-1}$: 1635, 1500, 1460, 1420, 1285.

EXAMPLE 118

Synthesis of 4-[2-(N-benzyl-N-benzoyl)aminoethyloxy]pyridine hydrochloride.

To a solution of 0.71 g (2.78 mmol) of 4-[2-(N-benzyl-N-benzoyl)aminoethyloxy]pyridine in 20 ml of methanol, 15 ml of hydrogen chloride-methanol was added. The solvent was distilled off and acetone was added to the residue. The solvent was distilled off and toluene was further added to the residue. The solvent was distilled off and the residue was crystallized from acetone. The resulting crystals were collected by filtration and washed with acetone to give 585 mg of the desired compound (74.2% yield, colorless crystals), mp. 150°–152° C.

NMR (200 MHz, DMSO-d$_6$) δ:3.70 (2H, m), 4.30–4.90 (4H, m), 7.17–7.65 (12H, m) 8.74 (2H, m).

IR (KBr) cm$^{-1}$: 1640, 1625, 1605, 1505.

EXAMPLE 19

Synthesis of 4-[2-(N-benzyl-N-trifluoroacetylamino)-ethylthio]pyridine i) Synthesis of N-benzyl-N-trifluoroacetylaminoethanol To a solution of 14.2 ml (100 mmol) of N-benzylaminoethanol and 14.3 ml (205 mmol) of triethylamine in 200 ml of methylene chloride, 14.5 ml (205 mmol) of anhydrous trifluoroacetic anhydride was added with stirring under ice-cooling, and the mixture was stirred at room temperature for 16 hours. The reaction mixture was washed with saturated aqueous sodium bicarbonate and water, and dried. The solvent was distilled off and the residue was purified by column chromatography (eluent:ethyl acetate/hexane=1:1) to give 20.12 g of the desired compound (81.4% yield, yellow oil).

NMR (200 MHz, CDCl$_3$) δ:1.70 (1H, bs), 3.51 and 3.54 (2H, t, J=5.2, 5.6 Hz)‡, 3.77 and 3.80 (2H, t, J=5.4 Hz)‡, 4.76 and 4.81 (2H, s)‡, 7.21–7.40 (5H, m). ‡: The peak is split due to the rotational isomers.

IR (neat) cm$^{-1}$: 3450, 3025, 1680, 1450, 760, 700.

ii) Synthesis of 4-[2-(N-benzyl-N-trifluoroacetylamino)ethylthio]pyridine a) Process by Way of Mesylate N-Benzyl-N-trifluoroacetylaminoethanol [2.0 g (8.1 mmol)] and 1.35 ml (9.7 mmol) of triethylamine were dissolved in 50 ml of methylene chloride, and 0.75 ml (9.7 mmol) of methanesulfonyl chloride was added to this solution, and the mixture was stirred at room temperature for 5 hours. The reaction mixture was washed with saturated aqueous sodium bicarbonate and water, and dried. The solvent was distilled off.

To a solution of 2.2 g of the residue and 0.75 g (6.8 mmol) of 4-mercapto pyridine in 30 ml of methylene chloride, 1.14 ml (8.2 mmol) of triethylamine was added with stirring under ice-cooling, and the mixture was stirred at room temperature for 16 hours. The reaction mixture was washed with saturated aqueous sodium bicarbonate and water, and dried. The solvent was distilled off and the residue was purified by column chromatography (eluent:ethyl acetate/hexane=1:1) to give 0.17 g of the desired compound (6.17% yield, yellow oil).

NMR (200 MHz, CDCl$_3$) δ:3.02–3.15 (2H, m), 3.50–3.68 (2H, m), 4.68 and 4.74 (2H, s)‡, 7.08 (2H, dd, J=1.6, 4.8 Hz), 7.19–7.24 (2H, m), 7.35–7.42 (3H, m), 8.38 (2H, bd, J=5.6 Hz). ‡: The peak is split due to the rotational isomers.

IR (neat) cm$^{-1}$: 3040, 2950, 1690, 1580, 805, 705.

b) Process by Way of Bromide

To a solution of 2.47 g (10.0 mmol) of N-benzyl-N-trifluoroacetylaminoethanol and 3.65 g (11.0 mmol) of carbon tetrabromide in 80 ml of methylene chloride, 2.89 g (11.0 mmol) of triphenylphosphine was added, and the mixture was stirred at room temperature for 16 hours. The solvent was distilled off and the residue was purified by column chromatography (eluent:ethyl acetate/hexane=1:1) to give 2.69 g of the desired compound (86.7% yield, colorless oil).

NMR (200 MHz, CDCl$_3$) δ:3.35 and 3.45 (2H, t, J=7.8, 6.6 Hz)‡, 3.69 and 3.47 (2H, t, J=6.4 Hz)‡, 4.73 and 4.76 (2H, s)‡, 7.19–7.25 (2H, m), 7.35–7.42 (3H, m). ‡: The peak is split due to the rotational isomers.

IR (neat) cm$^{-1}$: 3040, 2950, 1685, 1205, 750, 700.

To a solution of 0.11 g (1.0 mmol) of 4-mercaptopyridine and 0.15 ml (1.1 mmol) of DBU in 5 ml of DMF, 0.34 g (1.1 mmol) of the above bromide was added with stirring under ice-cooling, and the mixture was stirred at room temperature for 16 hours. The reaction mixture was washed with water, and dried. The solvent was distilled off and the residue was purified by column chromatography (eluent:ethyl acetate/hexane=1:1) to give 0.12 g of the desired compound (35.0% yield, yellow oil).

EXAMPLE 120

Synthesis of 4-[2-(N-benzyl-N-benzoylamino)ethylthio]pyridine a) Process by Way of Chloride N-Benzyl-N-benzoylaminoethanol [2.0 g (8.1 mmol)] and 1.35 ml (9.7 mmol) of triethylamine were dissolved in 50 ml of methylene chloride, and 0.75 ml (9.7 mmol) of methanesulfonyl chloride was added to this solution, and the mixture was stirred at room temperature for 5 hours. The reaction mixture was washed with saturated aqueous sodium bicarbonate and water, and dried. The solvent was distilled off.

To a solution of 2.42 g of the residue and 0.90 g (8.1 mmol) of 4-mercaptopyridine in 20 ml of ethanol, 1.36 ml (9.7 mmol) of triethylamine was added with stirring under ice-cooling, and the mixture was stirred at room temperature for 64 hours. The solvent was distilled off and the residue was dissolved in chloroform. The solution was washed with water and dried. The solvent was distilled off and the residue was purified by column chromatography (eluent:ethyl acetate/hexane=1:1) to give 1.04 g of the desired compound (36.8% yield, yellow oil).

Anal. for C$_{21}$H$_{20}$N$_2$OS,

Calcd.: C; 72.38, H; 5.78, N; 8.04.

Found: C; 72.10, H; 5.99, N; 7.74.

NMR (200 MHz, CDCl$_3$) δ:3.27 (2H, bm), 3.69 (2H, bm), 4.56–4.83 (2H, bm), 7.16–5.46 (7H, bm), 8.32–8.44 (2H, bm).

IR (neat) cm$^{-1}$: 3030, 1640, 1580, 815, 700.

b) Process by Way of Bromide

To a solution of 2.55 g (10.0 mmol) of N-benzyl-N-benzoylaminoethanol and 3.65 g (11.0 mmol) of carbon tetrabromide in 80 ml of methylene chloride, 2.89 g (11.0 mmol) of triphenylphosphine was added, and the mixture was stirred at room temperature for 16 hours. The solvent was distilled off and the residue was purified by column chromatography (eluent:ethyl acetate/hexane=1:1) to give 0.50 g of the desired compound (15.7% yield, colorless oil).

EXAMPLE 121

Synthesis of 4-(2-picolinylaminoethylthio)pyridine

To a solution of 1.42 g (5.0 mmol) of 4-(2-phthalimidoethylthio)pyridine in 50 ml of ethanol, 0.73 ml (15.0 mmol) of hydrazine monohydrate was added, and the mixture was stirred at room temperature for 3 hours. The solvent was distilled off and the residue was dissolved in chloroform. The precipitate was filtered and the filtrate was concentrated. The resulting residue was used for the subsequent reaction.

To a solution of the above residue and 3.14 ml (22.5 mmol) of triethylamine in 50 ml of methylene chloride, 1.78 g (10.0 mmol) of picolinyl chloride hydrochloride was added with stirring under ice-cooling, and the mixture was stirred at room temperature for 16 hours. The reaction mixture was washed with saturated aqueous sodium bicarbonate and water, and dried. The solvent was distilled off and the residue was purified by column chromatography (eluent:ethyl acetate/hexane=1:1 to ethyl acetate) to give 0.67 g of the desired compound (51.6% yield, yellow crystals).

NMR (200 MHz, CDCl$_3$) δ:3.28 (2H, t, J=6.6 Hz), 3.76 and 3.79 (2H, t, J=7.2 Hz)‡, 7.27 (2H, dd, J=1.6, 4.6 Hz), 7.45 (1H, ddd, J=1.4, 4.8, 7.8 Hz), 7.87 (1H, ddd, J=1.8, 7.6, 7.6 Hz), 8.20 (1H, ddd, J=1.2, 1.4, 7.8 Hz), 8.41 (2H, dd, J=1.6, 4.6 Hz), 8.43 (1H, bs), 8.51–8.62 (1H, m). ‡: The peak is split due to the rotational isomers.

IR (KBr) cm$^{-1}$: 3300, 3050, 2950, 1670.

EXAMPLE 122

Synthesis of 4-(2-thenoylaminoethylthio)pyridine

To a solution of 1.42 g (5.0 mmol) of 4-(2-phthalimidoethylthio)pyridine in 50 ml of ethanol, 0.73 ml (15.0 mmol) of hydrazine monohydrate was added, and the mixture was stirred at room temperature for 3 hours. The solvent was distilled of and the residue was dissolved in chloroform. The precipitate was filtered and the filtrate was concentrated. The resulting residue was used for the subsequent reaction.

To a solution of the above residue and 3.14 ml (22.5 mmol) of triethylamine in 50 ml of methylene chloride, 1.07 ml (10.0 mmol) of thenoyl chloride was added with stirring under ice-cooling, and the mixture was stirred at room temperature for 16 hours. The reaction mixture was washed with saturated aqueous sodium bicarbonate and water, and dried. The solvent was distilled off and the residue was purified by column chromatography (eluent:ethyl acetate/hexane=1:1 to ethyl acetate) to give 0.79 g of the desired compound (60.0% yield, yellow crystals).

NMR (200 MHz, CDCl$_3$) δ:3.27 (2H, t, J=6.6 Hz), 3.70 and 3.74 (2H, t, J=6.8, 6.4 Hz)‡, 6.46 (1H, bs), 7.08 (1H, dd, J=3.9, 5.0 Hz), 7,24 (2H, dd, J=1.8, 4.6 Hz), 7.47–7.52 (2H, m), 8.41 (2H, dd, J=1.8, 4.6 Hz). ‡: The peak is split due to the rotational isomers.

IR (KBr) cm$^{-1}$: 3180, 3005, 1640, 1580, 810, 700.

EXAMPLE 123

Synthesis of 4-[2-(thianaphthene-2-carbonylamino)ethylthio]pyridine

To a solution of 2.82 g (10.0 mmol) of 4-(2-phthalimidoethylthio)pyridine in 50 ml of ethanol, 1.46 ml (30.0 mmol) of hydrazine monohydrate was added,land the mixture was stirred at room temperature for 3 hours. The solvent was distilled off and the residue was dissolved in chloroform. The precipitate was filtered and the filtrate was concentrated. The resulting residue was used for the subsequent reaction.

To a solution of the above residue and 2.79 ml (20.0 mmol) of triethylamine in 50 ml of methylene chloride, 1.96 g (10.0 mmol) of thianaphthene-2-carbonyl chloride was added with stirring under ice-cooling, and the mixture was stirred at room temperature for 16 hours. The reaction mixture was washed with saturated aqueous sodium bicarbonate and water, and dried. The solvent was distilled off and the residue was purified by column chromatography (eluent:ethyl acetate/hexane=1:1) to give 0.419 g of the desired compound (13.3% yield, yellow crystals).

NMR (200 MHz, CDCl$_3$) δ:3.29 (2H, t, J=6.8 Hz), 3.27 and 3.77 (2H, t, J=7.0, 6.4 Hz)‡, 6.78 (1H, bs), 7.24 (1H, dd, J=1.6, 4.6 Hz), 7.39–7.45 (2H, m), 7.77 (1H, s), 7.81–7.88 (2H, m), 8.41 (2H, dd, J=1.8, 4.6 Hz). ‡: The peak is split due to the rotational isomers.

IR (KBr) cm$^{-1}$: 3220, 3050, 1650, 1630, 805.

EXAMPLE 124

Synthesis of 4-[3-(2-pyrazinecarbonylamino)propylthio]pyridine

To a solution of 1.00 g (8.06 mmol) of 2-pyrazinecarboxylic acid and 1.21 g (10.5 mmol) of N-hydroxysuccinimide in 70 ml of methylene chloride, 1.85 g (9.67 mmol) of 1-ethyl-3-(3-dimethylaminopropyl)carbodiimide hydrochloride (WSC) was added with stirring under ice-cooling, and the mixture was stirred at room temperature for 1 hour. Further, 1.94 g (8.06 mmol) of 4-(3-aminopropylthio)pyridine dihydrochloride was added, and the mixture was stirred at room temperature for 3 hours. The reaction mixture was washed with saturated aqueous sodium bicarbonate and water, and dried. The solvent was distilled off and the residue was purified by column chromatography (eluent:ethyl acetate) to give 0.751 g of the desired compound (34.0% yield, colorless powder).

Anal. for $C_{13}H_{14}N_4OS$,

Calcd.: C; 56.91, H; 5.14, N; 20.42.

Found: C; 56.84, H; 5.25, N; 20.22.

NMR (200 MHz, CDCl$_3$) δ:2.08 (2H, quint., J=6.8 Hz), 3.09 (2H, t, J=7.2 Hz), 3.65 and 3.68 (2H, t, J=6.6 Hz)‡, 7.13 (2H, dd, J=1.6, 4.6 Hz), 7.94 (1H, bs), 8.40 (2H, bd, J=6.0 Hz), 8.53 (1H, dd, J=1.4, 2.4 Hz), 8.78 (1H, d, J=2.4 Hz), 9.42 (1H, d, J=1.4 Hz). ‡: The peak is split due to the rotational isomers.

IR (KBr) cm$^{-1}$: 3380, 3030, 1660, 1580, 800, 710.

EXAMPLE 125

Synthesis of 4-[3-(2-picolinoylamino)propyloxy]pyridine

The desired compound was synthesized in the same manner as described in Example 86.

NMR (200 MHz, CDCl$_3$) δ:2.18 (2H,: m), 3.70 (2H, m), 4.16 (2H, t, J=6 Hz), 6.85 (2H, dd, J=4.8, 1.6 Hz), 7.44 (1H, m), 7.86 (1H, m), 8.20 (1H, m), 8.34 (1H, br), 8.43 (2H, dd, J=4.8, 1.6 Hz), 8.56 (1H, m).

IR (neat) cm$^{-1}$: 1670, 1595, 1570, 1530.

EXAMPLE 126

Synthesis of 4-[3-(2-picolinoylamino)propyloxy]pyridine dihydrochloride

The desired compound was synthesized in the same manner as described in Example 113, mp. 156°–168° C.

Anal. for C$_{14}$H$_{15}$N$_3$O$_2$·2HCl·0.5H$_2$O,

Calcd.:C; 49.57, H; 5.35, N; 12.39, Cl; 20.90.

Found: C; 49.86, H; 5.28, N; 12.62, Cl; 21.06.

NMR (200 MHz, DMSO-d$_6$) δ:2.09 (2H, m), 3.49 (2H, m), 4.40 (2H, m), 7.55 (2H, d, J=7.2 Hz), 7.62 (1H, m), 7.98–8.08 (2H, m), 8.66 (1H, m), 8.76 (2H, d, J=7.2 Hz), 9.03 (1H, br).

IR (KBr) cm$^{-1}$: 3420, 1685, 1640, 1605, 1510.

EXAMPLE 127

Synthesis of 4-[4-(benzoylamino)butylthio]pyridine i) Synthesis of 4-(4-aminobutylthio)pyridine To a suspension of 12.50 g (40 mmol) of 4-(4-phthalimidobutylthio)pyridine in 200 ml of ethanol, 5.82 ml (120 mmol) of hydrazine monohydrate was added, and the mixture was stirred at room temperature for 4 hours. Then, ml of ethyl acetate was added, and the insoluble material was filtered off. The volatile components were distilled off and chloroform was added to the residue. The mixture was washed with saturated saline and dried over potassium carbonate. The solvent was distilled off and 7.30 g of the desired compound were obtained (quantitative yield, yellow oil).

NMR (200 MHz, CDCl$_3$) δ: 1.54–1.90 (4H, m), 2.55 (2H, br), 2.76 (2H, t, J=6.8 Hz), 3.00 (2H, m), 7.08 (2H, dd, J=4.8, 1.6 Hz), 8.35 (2H, dd, J=4.8, 1.6 Hz).

ii) Synthesis of 4-[4-(benzoylamino)butylthio)]pyridine

To a solution of 1.00 g (5.49 mmol) of 4-(4-aminobutylthio)pyridine and 0.92 ml (6.60 mmol) of triethylamine in 30 ml of methylene chloride, 0.67 ml (5.77 mmol) of benzoylchloride was added with stirring under ice-cooling and the mixture was stirred at room temperature for 13 hours. The mixture was washed with saturated aqueous sodium bicarbonate and saturated saline, and dried over anhydrous magnesium sulfate. The solvent was distilled off and the residue was purified by column chromatography (eluent:ethyl acetate) to give 0.54 g of the desired compound (34.4% yield, colorless crystals), mp. 75°–77° C.

Anal. for C$_{16}$H$_{18}$N$_2$OS,

Calcd.: C; 67.10, H; 6.33, N; 9.78.

Found: C; 67.36, H; 6.19, N; 9.80.

NMR (200 MHz, CDCl$_3$) δ:1.82 (4H, m), 3.05 (2H, m), 3.52 (2H, m), 6.19 (1H, br), 7.12 (2H, m), 7.36–7.56 (3H, m), 7.70–7.80 (2H, m), 8.38 (2H, m).

IR (KBr) cm$^{-1}$: 1640, 1575, 1530.

EXAMPLE 128

Synthesis of 4-[4-(thianaphthene-2-carbonylamino)butylthio]pyridine

The desired compound was synthesized in the same manner as described in Example 86, mp. 90°–92° C.

Anal. for C$_{18}$H$_{18}$N$_2$OS,

Calcd.: C; 63.13, H; 5.30, N; 8.18.

Found: C; 63.27, H; 5.30, N; 8.21.

NMR (200 MHz, CDCl$_3$) δ:1.82 (4H, m), 3.02 (2H, m), 3.52 (2H, m), 6.48 (1H, br), 7.10 (2H, dd, J=4.8, 1.6 Hz), 7.32–7.46 (2H, m), 7.73–7.86 (3H, m), 8.36 (2H, m).

IR (KBr)cm$^{-1}$: 1635, 1575, 1540.

EXAMPLE 129

Synthesis of 4-[4-(2-thenonylamino)butylthio]pyridine

The desired compound was synthesized in the same manner as described in Example 86, mp. 89°–91° C.

Anal. for C$_{14}$H$_{16}$N$_2$OS$_2$,

Calcd.: C; 57.50, H; 5.51, N; 9.58.

Found: C; 57.61, H; 5.30, N; 9.62.

NMR (200 MHz, CDCl$_3$) δ:1.80 (4H, m), 3.03 (2H, m), 3.48 (2H, m), 6.23 (1H, br), 7.07 (1H, dd, J=5, 1.8 Hz), 7.11 (2H, dd, J=4.8, 1.6 Hz), 7.44–7.52 (2H, m), 8.37 (2H), m).

IR (KBr) cm$^{-1}$:1630, 1580, 1540.

EXAMPLE 130

Synthesis of 4-[4-(2-picolinoylamino)butylthio]pyridine

The desired compound was synthesized in the same manner as described in Example 86.

NMR (200 MHz, CDCl$_3$) δ:1.83 (4H, m), 3.04 (2H, 3.55 (2H, m), 7.11 (2H, dd, J=4.6, 1.8 Hz), 7.44 (1H, m), 7.87 (1H, m), 8.13 (1H, br), 8.21 (1H, m), 8.36 (2H, dd, J=4.6, 1.6 Hz), 8.54 (1H, m).

IR (neat) cm$^{-1}$: 1670, 1575, 1530.

EXAMPLE 131

Synthesis of 4-(4-benzoylpiperidylthio)pyridine

The desired compound was synthesized in the same manner as described in Example 13, mp. 123°–124° C.

Anal. for C$_{17}$H$_{18}$N$_2$OS,

Calcd.: C; 68.43, H; 6.08, N; 9.39.

Found: C; 68.71, H; 6.10, N; 9.42.

NMR (200 MHz, CDCl$_3$) δ:1.72 (2H, m), 2.10 (2H, m), 3.28 (2H, m), 3.64 (1H, m), 7.19 (2H, dd, J=4.6, 1.6 Hz), 7.41 (5H, m), 8.43 (2H, dd, J=4.6, 1.6 Hz).

IR (KBr) cm$^{-1}$: 1625, 1575.

EXAMPLE 132

Synthesis of 4-[4-(2-thenoyl)piperidylthio]pyridine

The desired compound was synthesized in the same manner as described in Example 13.

NMR (200 MHz, CDCl$_3$) δ:1.76 (2H, m), 2.15 (2H, m), 3.40 (2H, m), 3.67 (1H, m), 4.27 (2H, m), 7.05 (1H, dd, J=5, 3.6 Hz), 7.20 (2H, dd, J=4.6, 1.6 Hz), 7.29 (1H, dd, J=3.6, 1.2 Hz), 7.46 (1H, dd, J=5, 1.2 Hz), 8.44 (2H, dd, J=4.6, 1.6 Hz).

IR (KBr) cm$^{-1}$: 1600, 1575.

EXAMPLE 133

Synthesis of 4-[4-(thianaphthene-2-carbonyl)piperidylthio]pyridine

The desired compound was synthesized in the same manner as described in Example 13, mp. 146°–147° C.

Anal. for C$_{19}$H$_{18}$N$_2$OS$_2$,

Calcd.: C; 64.38, H; 5.12, N; 7.90.

Found: C; 64.34, H; 4.89, N; 7.94.

NMR (200 MHz, CDCl₃) δ:1.80 (2H, m), 2.17 (2H, m), 3.44 (2H, m), 3.69 (1H, m), 4.29 (1H, m), 7.22 (2H, dd, J=4.6, 1.6 Hz), 7.25–7.51 (3H, m), 7.75–7.92 (2H, m), 8.45 (2H, dd, J=4.6, 1.6 Hz).

IR (KBr) cm⁻¹: 1615, 1575, 1520.

EXAMPLE 134

Synthesis of 4-[4-(2-picolinyl)piperidylthio]pyridine

The desired compound was synthesized in the same manner as described in Example 13.

NMR (200 MHz, CDCl₃) δ:1.68–2.31 (4H, m), 3.36 (2H, m), 3.68 (1H, m), 3.98 (1H, m), 4.46 (1H, m), 7.21 (2H, dd, J=4.8, 1.6 Hz), 7.37 (1H, m), 7.66 (1H, m), 7.82 (1H, m), 8.44 (2H, dd, J=4.8, 1.6 Hz), 8.59 (1H, m).

IR (KBr) cm⁻¹: 1625, 1585, 1575, 1565.

EXAMPLE 135

Synthesis of 4-(4-pivaloylpiperidylthio)pyridine

The desired compound was synthesized in the same manner as described in Example 13.

NMR (200 MHz, CDCl₃) δ:1.29 (9H, s), 1.60 (2H, m), 2.11 (2H, m), 3.22 (2H, m), 3.61 (1H, m), 4.23 (2H, m), 7.17 (2H, dd, J=4.6, 1.6 Hz), 8.14 (2H, dd, J=4.6, 1.6 Hz).

IR (neat) cm⁻¹: 1630, 1575.

EXAMPLE 136

Synthesis of 4-(4-isobutyrylpiperidylthio)pyridine

The desired compound was synthesized in the same manner as described in Example 13.

NMR (200 MHz, CDCl₃) δ:1.13 (6H, d, J=6.8 Hz), 1.65 (2H, m), 2.10 (2H, m), 2.80 (1H, heptet, J=6.8 Hz), 3.10 (1H, m), 3.30 (1H, m), 3.60 (1H, m), 3.90 (1H, m), 4.33 (1H, m), 7.17 (2H, dd, J=4.6, 1.6 Hz), 8.44 (2H, dd, J=4.6, 1.6 Hz).

IR (neat) cm⁻¹: 1640, 1575.

EXAMPLE 137

Synthesis of 2-[3-(2-hydroxybenzoylamino)propylthio]pyridine

To a solution of 5.97 g (20 mmol) of 2-(3-phthalimido)propylthiopyridine in 100 ml of ethanol, 2.91 ml (60 mmol) of hydrazine monohydrate was added, and the mixture was heated under reflux for 1 hour. After cooling, 100 ml of methylene chloride was added and the insoluble material was filtered off. The solvent was distilled off from the filtrate. To the residue, 100 ml of methylene chloride and 4.18 ml (30 mmol) of triethylamine were added, and 4.77 g (24 mmol) of O-acetylsalicyloyl chloride was added with stirring under ice-cooling and the mixture was stirred at room temperature for 2 hours. The solvent was distilled off, and 60 ml of ethanol and 40 ml of 1N-NaOH was added to the residue. The mixture was stirred for 1 hour. Then, 40 ml of 1N-HCl was added and ethanol was distilled off. The residue was extracted with chloroform and the extract was dried over anhydrous magnesium sulfate. The solvent was distilled off and the residue was purified column chromatography (eluent:ethyl acetate/n-hexane=1:1) to give 4.86 g (84.2% yield, colorless oil).

NMR (200 MHz, CDCl₃) δ:2.00 (2H, m), 3.35 (2H, m), 3.59 (2H, m), 6.85–7.08 (3H, m), 7.25 (1H, d, J=8 Hz), 7.35–7.66 (3H, m), 8.02 (1H, br), 8.42 (1H, m).

IR (neat) cm⁻¹: 3355, 1640, 1595, 1580, 1545, 1530.

EXAMPLE 138

Synthesis of 4-(3-picolinoylaminomethylthio)pyridine

To a mixture of 1.11 g (10 mmol) of 4-mercaptopyridine and 1.52 g (10 mmol) of N-(hydroxymethyl)nicotinamide, 30 ml of trifluoroacetic acid was added, and the mixture was stirred at room temperature for 1 hour. The solvent was distilled off and 30 ml of ethanol was added to the residue. The solvent was distilled off and water was added to the residue. The mixture was neutralized with saturated aqueous sodium bicarbonate, followed by extraction with chloroform. After washing with saturated saline, the extract was dried over anhydrous magnesium sulfate. The solvent was distilled off and the residue was purified by column chromatography (eluent:ethyl acetate/ethanol=5:1 ) to give 390 mg of the desired compound (15.9% yield, yellow solid).

NMR (200 MHz, CDCl₃) δ:5.06 (2H, d, J=6 Hz), 7.27 (2H, dd, J=4.6, 1.6 Hz), 7.37 (1H, m), 7.71 (1H, br), 8.14 (1H, m), 8.36 (2H, dd, J=4.6, 1.6 Hz), 8.70 (1H, dd, J=4.8, 1.6 Hz), 8.97 (1H, m).

IR (KBr) cm⁻¹: 1655, 1620, 1585, 1540.

EXAMPLE 139

Synthesis of 3-[3-(4-pyridylthio)propyl]-2H-1,3-benzoxadine-2,4(3H)-dione

To a solution of 1.153 g (4.0 mmol) of 4-[3-(2-hydroxybenzoylamino)]propylthiopyridine in 30 ml of dry tetrahydrofuran, 1.30 g (10.0 mmol) of 1,1'-carbonyldiimidazol was added, and the mixture was stirred at room temperature for 3 hours. The solvent was distilled off and chloroform was added to the residue. The mixture was washed with water and dried over anhydrous magnesium sulfate. The solvent was distilled off and the residue was purified by column chromatography (eluent:ethyl acetate) to give 1.14 g of the desired compound (90.7% yield, colorless crystals), mp. 101.5°–102° C.

Anal. for $C_{16}H_{14}N_2O_3S$,

Calcd.: C; 61.13, H; 4.49, N; 8.91.

Found: C; 61.20, H; 4.25, N; 8.98.

NMR (200 MHz, CDCl₃) δ:2.16 (2H, m), 3.08 (2H, t, J=7.4 Hz), 4.22 (2H, t, J=7 Hz), 7.15 (2H, dd, J=4.8, 1.6 Hz), 7.25–7.44 (2H, m), 7.7.3 (1H, m), 8.09 (1H, dd, J=8, 1.8 Hz), 8.40 (2H, dd, J=4.8, 1.6 Hz).

IR (KBr) cm⁻¹: 1760, 1695, 1620, 1580.

EXAMPLE 140

Synthesis of 5,5-dimethyl-3-[4-(4-pyridylthio)butyl]hydantoin

To a solution of 2.56 g (20 mmol) of 5,5-dimethylhydantoin and 4.03 g (20 mmol) of 4-(4-chlorobutylthio)pyridine in 20 ml of N,N-dimethylformamide, 3.00 ml (20 mmol) of 1,8-diazabicyclo[5.4.0]-7-undecene was added, and the mixture was stirred at room temperature for 43 hours, followed by further stirring at 70° C. for 10 hours. Ethyl acetate was added to the reaction mixture, and the mixture was washed three times with water and dried over anhydrous magnesium sulfate. The soluent was distilled off and the residue was purified by column chromatography (eluent:ethyl acetate/ethanol=10:1) to give 3.33 g of the desired compound (56.8% yield, colorless crystals).

NMR (200 MHz, CDCl$_3$) δ:1.42 (6H, s), 1.77 (4H, m), 3.02 (2H, t, J=7 Hz), 3.54 (2H, t, J=6.6 Hz), 6.93 (1H, br), 7.11 (2H, dd, J=4.8, 1.6 Hz), 8.37 (2H, dd, J=4.8, 1.6 Hz).

IR (neat) cm$^{-1}$: 3300, 1775, 1710, 1580.

EXAMPLE 141

Synthesis of 3-[3-(4-pyridylthio)propyl]-2H-1,3-benzoxadine-2-thion-4(3H)-one

To a solution of 1.442 g (5.0 mmol) of 4-[3-(2-hydroxybenzoylamino)]propylthio]pyridine in 30 ml of dry tetrahydrofuran, 1.78 g (10.0 mmol) of 1,1'-thiocarbonyldiimidazole was added, and the mixture was stirred at room temperature for 6 hours. The solvent was distilled off and chloroform was added to the residue. The mixture was washed with water and dried over anhydrous magnesium sulfate. The solvent was distilled off and the residue was purified by column chromatography (eluent:ethyl acetate/n-hexane=2:1 ) to give 1.57 g of the desired compound (95.0% yield, colorless crystals), mp. 118.5°–119° C.

Anal. for C$_{16}$H$_{14}$N$_2$O$_2$S$_2$,

Calcd.: C; 58.16, H; 4.27, N; 8.48.

Found: C; 58.00, H; 4.28, N; 8.41.

NMR (200 MHz, CDCl$_3$) δ:2.26 (2H, m), 3.11 (2H, t, J=7.4 Hz), 4.62 (2H, m), 7.15 (2H, dd, J=4.8, 1.6 Hz), 7.32–7.46 (2H, m), 7.75 (1H, m), 8.07 (1H, dd, J=7.8, 1.8 Hz), 8.40 (2H, dd, J=4.8, 1.6 Hz).

IR (KBr) cm$^{-1}$: 1710, 1620, 1595, 1580.

EXAMPLE 142

Synthesis of 1-methyl-3-[4-(4-pyridylthio)butyl]hydantoin

The desired compound was synthesized in the same manner as described in Example 140.

NMR (200 MHz, CDCl$_3$) δ:1.77 (4H, m), 3.00 (3H, s), 3.02 (2H, t, J=7 Hz), 3.55 (2H, t, J=6.6 Hz), 3.85 (2H, s), 7.12 (2H, dd, J=4.8, 1.6 Hz), 8.39 (2H, dd, J=4.8, 1.6 Hz).

IR (neat) cm$^{-1}$: 1770, 1710, 1575.

EXAMPLE 143

Synthesis of 4-(4-succinimidobutylthio)pyridine

The desired compound was synthesized in the same manner as described in Example 140, mp. 80°–81° C.

Anal. for C$_{13}$H$_{16}$N$_2$O$_2$S,

Calcd.: C; 59.07, H; 6.10, N; 10.60.

Found: C; 59.36, H; 6.04, N; 10.63.

NMR (200 MHz, CDCl$_3$) δ:1.73 (4H, m), 2.70 (4H, s) 3.00 (2H, t, J=6.8 Hz), 3.55 (2H, t, J=6.8 Hz), 7.09 (2H, dd, J=4.6, 1.6 Hz), 8.39 (2H, dd, J=4.6, 1.6 Hz).

IR (KBr) cm$^{-1}$: 1770, 1710, 1580.

EXAMPLE 144

Synthesis of 4-(2-benzoylaminoethylthio)pyridine

To a solution of 1.99 g (7.0 mmol) of 4-(2-phthalimidoethylthio)pyridine in 70 ml of ethanol, 1.02 ml (21.0 mmol) of hydrazine monohydrate was added, and the mixture was stirred at room temperature for 4 hours. The solvent was distilled off and the residue was dissolved in chloroform. The precipitate was filtered and the filtrate was concentrated. The resulting residue was used for the subsequent reaction.

To a solution of the above residue and 1.25 ml (9.0 mmol) of triethylamine in 50 ml of methylene chloride, 0.89 ml (7.7 mmol) of benzoyl chloride was added with stirring under ice-cooling, and the mixture was stirred at room temperature for 30 minutes. The reaction mixture was washed with saturated aqueous sodium bicarbonate and water, and dried. The solvent was distilled off and the residue was purified by column chromatography (eluent:ethyl acetate/hexane=1:3) to give 0.50 g of the desired compound (27.7% yield, yellow oil).

NMR (200 MHz, CDCl$_3$) δ:3.29 (2H, t, J=6.6 Hz), 3.73 and 3.76 (2H, t, J=6.2, 6.6 Hz)‡, 6.67 (1H, bs), 7.25 (2H, dd, J=1.6, 4.6 Hz), 7.43–7.52 (3H, m), 7.72–7.77 (2H, m), 8.42 (2H, bd, J=6.0 Hz). ‡: The peak is split due to the rotational isomers.

IR (neat) cm$^{-1}$: 3300, 3055, 2930, 1640, 1580, 1310, 800, 710.

EXAMPLE 145

Synthesis of 4-(2,2-dimethyl-3-phthalimidopropylthio)pyridine

To a solution of 0.56 g (5.0 mmol) of 4-mercaptopyridine and 1.48 g (5.0 mmol) of (N-3-bromo-2,2-dimethylpropyl)phthalimide in 20 ml of dimethylformamide, 0.75 ml (5.0 mmol) of 1,8-diazabicyclo[5.4.0]-7-undecene was added, and the mixture was stirred at 80° C. for 8 hours. Water was added, and the mixture was extracted with ethyl acetate. The extract was dried and the solvent was distilled off. The residue was purified by column chromatography (eluent:ethyl acetate) to give 12.0 g of the desired compound (71.6% yield, colorless columns).

NMR (200 MHz, CDCl$_3$) δ:1.13 (6H, s), 3.03 (2H, s), 3.70 (2H, s), 7.17 (2H, dd, J=1.6, 4.6 Hz), 7.72–7.92 (4H, m), 8.38 (2H, dd, J=1.6, 4.6 Hz).

IR (KBr) cm$^{-1}$: 3030, 2960, 1715, 1580, 800, 720.

EXAMPLE 146

Synthesis of 3-[4-(4-pyridylthio)butyl]quinazolin-2,4(1H,3H)-dione

The desired compound was synthesized in the same manner as described in Example 140.

NMR (200 MHz, CDCl$_3$) δ:1.66–2.03 (4H, m), 3.07 (2H, t, J=7 Hz), 4.15 (2H, t, J=7 Hz), 7.06–7.16 (3H, m), 7.25 (1H, m), 7.61 (1H, m), 8.14 (1H, m), 8.38 (2H, m), 10.02 (1H, br).

IR (KBr) cm$^{-1}$: 1710, 1660.

EXAMPLE 147

Synthesis of 1,3-bis[4-(4-pyridylthio)butyl]-quinazolin-2,4(1H,3H)-dione

The desired compound was synthesized in the same manner as described in Example 140.

NMR (200 MHz, CDCl$_3$) δ: 1.70–2.07 (8H, m), 2.97–3.14 (4H, m), 4.07–4.25 (4H, m), 7.05–7.14 (4H, m), 7.17 (1H, d, J=8.4 Hz), 7.27 (1H, m), 7.69 (1H, m), 8.25 (1H, dd, J=7.8, 1.6 Hz), 8.31–8.45 (4H, m).

IR (neat) cm$^{-1}$: 1700, 1660, 1610, 1575.

EXAMPLE 148

Synthesis of 4-[4-[2-hydroxymethylbenzoyl)aminobutyloxy]pyridine

The desired compound was synthesized in the same manner as described in Example 100.

NMR (200 MHz, CDCl$_3$) δ:1.71–2.03 (4H, m), 3.56 (2H, m), 4.09 (2H, t, J=5.8 Hz), 4.62 (2H, s), 6.54 (1H, br), 6.80 (2H, dd, J=4.8, 1.6 Hz), 7.37–7.58 (4H, m), 8.42 (2H, dd, J=4.8, 1.6 Hz).

IR (KBr) cm$^{-1}$: 3290, 3090, 3070, 1650, 1605, 1570.

EXAMPLE 149

Synthesis of 3-[4-(4-pyridylthio)butyl]-1-benzylquinazolin-2,4-(1H,3H)-dione

The desired compound was synthesized in the same manner as described in Example 140.

NMR (200 MHz, CDCl$_3$) δ:1.72–2.05 (4H, m), 3.06 (2H, t, J=7.2 Hz), 4.21 (2H, t, J=7 Hz), 5.38 (2H, s), 7.05–7.40 (9H, m), 7.55 (1H, m), 8.24 (1H, dd, J=7.8, 1.6 Hz), 8.36 (2H, dd, J=6.8, 1.6 Hz).

IR (KBr) cm$^{-1}$: 1700, 1660, 1610, 1575, 1485.

EXAMPLE 150

Synthesis of 4-[4-(5-benzylidene-2,4-thiazolidinedione)-butylthio]pyridine i) Synthesis of 5-benzylidene-2,4-thiazolidinedione To a solution of 20 g (171 mmol) of 2,4-thiazolidinedione and 17.4 ml (171 mmol) of benzaldehyde in 350 ml of ethanol, 1.68 ml (17.1 mmol) of piperidine was added, and the mixture was heated under reflux for 5 hours. After cooling, the precipitated crystals were filtered and washed with cooled ethanol to give 31.67 g of the desired compound (90.4% yield, pale yellow crystals).

Anal. for C$_{10}$H$_7$NO$_2$S,

Calcd.: C; 58.52, H; 3.44, N; 6.82.

Found: C; 58.74, H; 3.42, N; 6.82.

NMR (200 MHz, DMSO-d$_6$) δ: 7.48–7.63 (5H, m), 7.81 (1H, s), 12.40 (1H, bs).

IR (KBr) cm$^{-1}$: 3140, 3020, 2780, 1740, 1690, 1605.

ii) Synthesis of 4-[4-(5-benzylidene-2,4-thiazolidinedione)butylthio]pyridine

To a solution of 2.0 g (9.74 mmol) of 5-benzylidene-2,4-thiazolidinedione and 1.96 g (9.74 mmol) of 4-(4-chlorobutylthio)pyridine in 80 ml of dimethylformamide, 1.46 ml (9.74 mmol) of 1,8-diazabicyclo[5.4.0]-7-undecene was added, and the mixture was stirred at 80° C. for 16 hours. After cooling, waiter was added to the react ion mixture, and the mixture was extracted with ethyl acetate. The extract was dried and the solvent was distilled off. The residue was purified by column chromatography (eluent:ethyl acetate/hexane=2:1) to give 2.40 g of the desired compound (66.6% yield, pale yellow crystals).

Anal. for C$_{19}$H$_{18}$N$_2$O$_2$S$_2$,

Calcd.: C; 61.60, H; 4.90, N; 7.56.

Found: C; 61.74, H;.5.04, N; 7.41.

NMR (200 MHz, CDCl$_3$) δ:1.68–1.96 (4H, m), 3.03 (2H, t, J=7.0 Hz), 3.81 (2H, t, J=6.8 Hz), 7.11 (2H, dd, J=1.6, 4.8 Hz), 7.45–7.54 (5H, m), 7.81 (1H, s), 8.39 (2H, dd, J=1.6, 4.8 Hz).

IR (KBr) cm$^{-1}$: 3040, 2950, 1745, 1680, 1615, 1580, 1130, 800, 770, 695.

EXAMPLE 151

Synthesis of 4-[4-[5-(4-chlorobenzylidene)-2,4-thiazolidinedione]butylthio]pyridine i) Synthesis of 5-(4-chlorobenzylidene)-2,4-thiazolidinedione To a solution of 20 g (171 mmol) of 2,4-thiazolidinedione and 17.4 ml (171 mmol) of 4-chlorobenzaldehyde in 350 ml of ethanol, 1.68 ml (17.1 mmol) of piperidine was added, and the mixture was heated under reflux for 5 hours. After cooling, the precipitated crystals were filtered and washed with cooled ethanol to give 17.75 g of the desired compound (43.4% yield, pale yellow crystals).

Anal. for C$_{10}$H$_6$NO$_2$SCl,

Calcd.: C; 50.11, H; 2.52, N; 5.84.

Found: C; 50.02, H; 2.52, N; 5.91.

NMR (200 MHz, DMSO-d$_6$) δ:7.61 (4H, s), 7.79 (1H, s).

IR (KBr) cm$^{-1}$: 3150, 3050, 2760, 1750, 1720, 1610.

ii) 4-[4-[5-(4-chlorobenzylidene)-2,4-thiazolidinedione] butylthio]pyridine

To a solution of 2.0 g (8.34 mmol) of 5-(4-chlorobenzylidene)- 2,4-thiazolidinedione and 1.68 g (8.34 mmol) of 4-(4-chlorobutylthio)pyridine in 80 ml of dimethylformamide, 1.24 ml (8.34 mmol) of 1,8-diazabicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent-:ethyl acetate/hexane=2:1) to give 2.08 g of the desired compound (61.5% yield, pale yellow crystals).

Anal. for C$_{19}$H$_{17}$N$_2$O$_2$S$_2$Cl,

Calcd.: C; 56.36, H; 4.23, N; 6.92.

Found: C; 56.27, H; 4.23, N; 6.77.

NMR (200 MHz, CDCl$_3$) δ:1.64–1.95 (4H, m), 3.02 (2H, t, J=7.2 Hz), 3.80 (2H, t, J=6.8 Hz), 7.10 (2H, dd, J=1.8, 4.8 Hz), 7.45 (4H, s), 7.84 (1H, s), 8.38 (2H, dd, J=1.6, 4.8 Hz).

IR (KBr) cm$^{-1}$: 3040, 2950, 1740, 1685, 1610, 1580, 1345, 810, 710.

EXAMPLE 152

Synthesis of 4-[4-[5-(41methoxybenzylidene)-2,4-thiazolidinedione]butylthio]pyridine To a solution of 20 g (171 mmol) of 2,4-thiazolidinedione and 20.6 ml (171 mmol) of an aldehyde in 350 ml of ethanol, 1.68 ml (17.1 mmol) of piperidine was added, and the mixture was heated under reflux for 5 hours. After cooling, the precipitated crystals were filtered and washed with cooled ethanol to give 30.75 g of the desired compound (76.5% yield, pale yellow crystals).

Anal. for C$_{11}$H$_9$NO$_3$S,

Calcd.: C; 56.16, H; 3.86, N; 5.95.

Found: C; 56.43, H; 4.04, N; 6.18.

NMR (200 MHz, DMSO-d$_6$) δ:3.83 (3H, s), 7.11 (2H, d, J=8.3 Hz), 7.55 (2H, d, J=7.4 Hz), 7.79 (1H, s).

IR (KBr) cm$^{-1}$: 3230, 1745, 1690, 1590, 1285, 695.

ii) Synthesis of 4-[4-[5-(4-methoxybenzylidene)-2,4-thiazolidinedione]butylthio]pyridine To a solution of 2.0 g (8.50 mmol) of 5-(4-methoxybenzylidene)-2,4-thiazolidinedione and 1.71 g (8.50 mmol) of 4-(4-chlorobutylthio)pyridine in 80 ml of dimethylformamide, 1.27 ml (8.50 mmol) of 1,8-diazabicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:-ethyl acetate/hexane=2:1) to give 2.35 g of the desired compound (69.0% yield, pale yellow crystals).

Anal. for $C_{20}H_{20}N_2O_3S_2$,

Calcd.: C; 59.98, H; 5.03, N; 6.99.

Found: C; 66.06, H; 5.19, N; 6.92.

NMR (200 MHz, CDCl$_3$) δ:1.68–1.94 (4H, m), 3.02 (2H, t, J=7.0 Hz), 3.79 (2H, t, J=6.8 Hz), 3.87 (3H, s), 6.99 (2H, d, J=8.8 Hz), 7.09 (2H, dd, J=1.8, 4.8 Hz), 7.47 (2H, d, J=9.0 Hz), 7.85 (1H, s), 8.38 (2H, dd, J=1.4, 4.4 Hz).

IR (KBr) cm$^{-1}$: 3040, 2950, 1750, 1690, 1600, 1580, 825, 805, 740, 715.

EXAMPLE 153

Synthesis of 4-[4-(5-benzylidenerhodanine)butylthio]pyridine i) Synthesis of 5-benzylidenerhodanine To a solution of 10 g (75.1 mmol) of rhodanine and 7.63 ml (75.1 mmol) of benzaldehyde in 150 ml of ethanol, 0.74 ml (7.5 mmol) of piperidine was added, and the mixture was heated under reflux for 5 hours. After cooling, the precipitated crystals were filtered and washed with cooled ethanol to give 1.07 g of the desired compound (66.6% yield, pale yellow crystals).

Anal. for $C_{10}H_7NOS_2$,

Calcd.: C; 54.27, H; 3.19, N; 6.33.

Found: C; 54.33, H; 3.31, N; 6.25.

NMR (200 MHz, DMSO-d$_6$) δ:7.51–7.64 (5H, m), 7.66 (1H, s).

IR (KBr) cm$^{-1}$: 3170, 3070, 2850, 1705, 1680, 1590, 1440, 680, 530.

ii) Synthesis of 4-[4-(5-benzylidenerhodanine)butylthio]pyridine

To a solution of 2.0 g (9.04 mmol) of 5-benzylidenrhodanine and 1.83 g (9.04 mmol) of 4-(4-chlorobutylthio)pyridine in 80 ml of dimethylformamide, 1.35 ml (9.04 mmol) of 1,8-diazabicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:ethyl acetate/hexane=2:1) to give 1.47 g of the desired compound (39.2% yield, pale yellow crystals).

NMR (200 MHz, CDCl$_3$) δ:1.72–1.98 (4H, m), 3.04 (2H, t, J=7.2 Hz), 4.18 (2H, t, J=6.8 Hz), 7.11 (2H, dd, J=1.6, 4.6 Hz), 7.45–7.58 (5H, m), 7.75 (1H, s), 8.39 (2H, dd, J=1.6, 4.6 Hz).

IR (KBr) cm$^{-1}$: 3020, 2940, 1710, 1580, 1340, 800, 760, 690.

EXAMPLE 154

Synthesis of 4-[3-(5-benzylidene-2,4-thiazolidinedione)-propylthio]pyridine

To a solution of 2.0 g (9.74 mmol) of 5-benzylidene-2,4-thiazolidinedione and 1.83 g (9.74 mmol) of 4-(3-chloropropylthio)pyridine in 80 ml of dimethylformamide, 1.46 ml (9.74 mmol) of 1,8-diazabicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:ethyl acetate/hexane=2:1) to give 1.92 g of the desired compound (55.4% yield, pale yellow crystals).

NMR (200 MHz, CDCl$_3$) δ:2.10 (2H, quint., J=7.4 Hz), 3.02 (2H, t, J=7.2 Hz), 3.93 (2H, t, J=7.0 Hz), 7.11 (2H, dd, J=1.8, 4.6 Hz), 7.45–7.54 (5H, m), 7.91 (1H, s), 8.40 (2H, dd, J=1.4, 4.4 Hz).

IR (KBr) cm$^{-1}$: 3030, 2950, 1755, 1685, 1605, 1580, 1380, 800, 760, 710, 685.

EXAMPLE 155

Synthesis of 4-[2-(5-benzylidene-2,4-thiazolidinedione)-ethylthio]pyridine

To a solution of 2.0 g (9.74 mmol) of 5-benzylidene-2,4-thiazolidinedione and 1.69 g (9.74 mmol) of 4-(2-chloroethylthio)pyridine in 80 ml of dimethylformamide, 1.46 ml (9.74 mmol) of 1,8-diazabicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:ethyl acetate/hexane=2:1) to give 1.33 g of the desired compound (39.8% yield, pale yellow crystals).

Anal. for $C_{17}H_{14}N_2O_2S_2$,

Calcd.: C; 59.63, H; 4.12, N; 8.18.

Found: C; 59.54, H; 3.99, N; 8.04.

NMR (200 MHz, CDCl$_3$) δ:3.27 (2H, t, J=7.8 Hz), 4.05 (2H, t, J=7.4 Hz), 7.27 (2H, dd, J=1.6, 4.2 Hz), 7.46–7.54 (5H, m), 7.93 (1H, s), 8.46 (2H, dd, J=1.4, 4.4 Hz).

IR (KBr) cm$^{-1}$: 3030, 1754, 1680, 1605, 1580, 800, 770, 710, 690.

EXAMPLE 156

Synthesis of 4-[4-(isoindolin-1-on-2-yl)butyloxy]pyridine

The desired compound was synthesized in the same manner as described in Example 101.

NMR (200 MHz, CDCl$_3$) δ:1.72–2.05 (4H, m), 3.60 (2H, t, J=6.6 Hz), 4.09 (2H, t, J=6.2 Hz), 5.34 (2H, s), 6.80 (2H, dd, J=4.8, 1.6 Hz), 7.31–7.57 (3H, m), 7.85 (1H, d, J=6.6 Hz), 8.40 (2H, dd, J=4.8, 1.6 Hz).

IR (KBr) cm$^{-1}$: 1700, 1685, 1595, 1585, 1570, 1505.

EXAMPLE 157

Synthesis of 4-[4-[5-(2-thienylmethylene)-2,4-thiazolidinedione]-butylthio]pyridine i) Synthesis of 5-(2-thienylmethylene)-2,4-thiazolidinedione To a solution of 20 g (171 mmol) of 2,4-thiazolidinedione and 16.0 ml (171 mmol) of 2-thiophenecarboxaldehyde in 350 ml of ethanol, 1.68 ml (17.1 mmol) of piperidine was added, and the mixture was heated under reflux for 5 hours. After cooling, the precipitated crystals were filtered and washed with cooled ethanol to give 24.03 g of the desired compound (66.6% yield, pale yellow crystals).

Anal. for $C_8H_5NO_2S_2$,

Calcd.: C; 45.48, H; 2.39, N; 6.63.

Found: C; 45.41, H; 2.41, N; 6.52.

NMR (200 MHz, DMSO-$d_6$) δ:7.29 (1H, dd, J=3.6, 4.4 Hz), 7.67 (1H, bd, J=3.6 Hz), 8.01 (1H, bd, J=4.4 Hz), 8.07 (1H, s).

IR (KBr) cm$^{-1}$: 3450, 3130, 3040, 2800, 1740, 1690, 1600, 1330, 640, 540.

ii) Synthesis of 4-[4-[5-(2-thienylmethylene)-2,4-thiazolidinedione]butylthio]pyridine To a solution of 2.5 g (11.8 mmol) of 5-(2-thienylmethylene)-2,4-thiazolidinedione and 1.9.9 g (9.86 mmol) of 4-(4-chlorobutylthio)pyridine in 100 ml of dimethylformamide, 1.76 ml (11.8 mmol) of 1,8-diazabicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:-ethyl acetate/hexane=2:1) to give 2.35 g of the desired compound (52.8% yield, pale yellow crystals).

NMR (200 MHz, CDCl$_3$) δ:1.68–1.95 (4H, m), 3.02 (2H, t, J=7.0 Hz), 3.79 (2H, t, J=7.0 Hz), 7.10 (2H, dd, J=1.6, 4.6 Hz), 7.20 (1H, dd, J=3.8, 5.0 Hz), 7.41 (1H, bd, J=4.2 Hz), 7.67 (1H, bd, J=5.0 Hz), 8.06 (1H, s), 8.38 (2H, dd, J=1.6, 4.8 Hz).

IR (KBr)cm$^{-1}$: 3040, 2950, 1740, 1680, 1600, 1580, 1350, 800, 740, 700.

EXAMPLE 158

Synthesis of 4-[4-[5-(4-dimethylaminobenzylidene)rhodanine]-butylthio]pyridine To a solution of 3.0 g (11.35 mmol) of 5-(4-dimethylaminobenzylidene)rhodanine and 1.91 g (9.46 mmol) of 4-(4-chlorobutylthio)pyridine in 100 ml of dimethylformamide, 1.41 ml (9.46 mmol) of 1,8-diazebicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:- ethyl acetate/hexane=2:1) to give 1.89 g of the desired compound (38.8% yield, pale yellow crystals).

NMR (200 MHz, CDCl$_3$) δ:1.71–2.01 (4H, m), 3.03 (2H, t, J=7.2 Hz), 3.09 (6H, s), 4.17 (2H, t, J=7.0 Hz), 6.73 (2H, d, J=9.0 Hz), 7.10 (2H, dd, J=1.8, 4.8 Hz), 7.40 (2H, d, J=9.0 Hz), 7.67 (1H, s), 8.38 (2H, dd, J=1.8, 4.8 Hz).

IR (KBr) cm$^{-1}$: 3030, 2950, 1700, 1620, 1580, 820, 800.

EXAMPLE 159

Synthesis of 4-(5-benzylidene-2,4-thiazolidinedione)-methylthiopyridine i) Synthesis of 4-chloromethylthiopyridine To a solution of 5.56 g (50.0 mmol) of 4-mercaptopyridine and 8.97 ml (60.0 mmol) of 1,8-diazabicyclo[5.4.0]-7-undecene in 50 ml of dimethylformaldehyde, 3.90 ml (60.0 mmol) of bromochloromethane was added with stirring under ice-cooling, and the mixture was stirred at room temperature for 16 hours.

Water was added to the reaction mixture, and the mixture was extracted with ethyl acetate. The extract was dried and the solvent was distilled off. The residue was purified by column chromatography (eluent:chloroform) to give 2.34 g of the desired compound (27.2% yield, pale yellow crystals).

NMR (200 MHz, CDCl$_3$) δ:5.05 (2H, s), 7.30 (2H, dd, J=1.8, 4.6 Hz), 8.51 (2H, dd, J=1.6, 4.6 Hz).

IR (KBr) cm$^{-1}$: 3020, 2950, 1570, 1480, 1405, 800, 735, 700, 645.

ii) Synthesis of 4-(5-benzylidene-2,4-thiazolidinedione)methylthiopyridine

To a solution of 0.308 g (1.50 mmol) of 5-benzylidene-2,4-thiazolidinedione and 0.127 g (0.80 mmol) of 4-chloromethylthiopyridine in 8 ml of dimethylformamide, 0.12 ml (0.80 mmol) of 1,8-diazabicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:ethyl acetate/hexane=1:1) to give 0.13 g of the desired compound (50.0% yield, pale yellow crystals).

Anal. for $C_{16}H_{12}N_2O_2S_2 \cdot 0.4H_2O$,

Calcd.: C; 57.26, H; 3.84, N; 8.35.

Found: C; 57.56, H; 3.53, N; 8.43.

NMR (200 MHz, CDCl$_3$) δ:5.23 (2H, s), 7.41 (2H, bd, J=6.0 Hz), 7.46–7.52 (5H, m), 7.95 (1H, s), 8.49 (2H, bs).

IR (KBr) cm$^{-1}$: 3030, 2920, 1740, 1690, 1575, 1370, 810, 760, 685.

EXAMPLE 160

Synthesis of 4-[4-(2,4-thiazolidinedione)butylthio]pyridine

To a solution of 2.34 g (20.0 mmol) of 2,4-thiazolidinedione and 4.03 g (20.0 mmol) of 4-(4-chlorobutylthio)pyridine in 120 ml of dimethylformamide, 3.0 ml (20 mmol) of 1,8-diazabicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:ethyl acetate/hexane=2:1 to ethyl acetate) to give 3.50 g of the desired compound (62.0% yield, pale yellow crystals).

Anal. for $C_{12}H_{14}N_2O_2S_2$,

Calcd.: C; 51.04, H; 5.00, N; 9.92.

Found: C; 50.73, H; 4.92, N; 9.94.

NMR (200 MHz, CDCl$_3$) δ:1.63–1.88 (4H, m), 3.00 (2H, t, J=7.0 Hz), 3.67 (2H, t, J=6.8 Hz), 3.95 (2H, s), 7.10 (2H, dd, J=1.6, 4.6 Hz), 8.40 (2H, dd, J=1.6, 4.6 Hz).

IR (KBr) cm$^{-1}$: 3040, 2950, 2930, 1750, 1685, 1580, 1380, 1355, 900, 800, 710.

EXAMPLE 161

Synthesis of 4-[4-(2-hydroxybenzoylamino)butylthio]pyridine

To a solution of 12.50 g (40 mmol) of 4-(phthalimidobuthylthio)pyridine in 200 ml of ethanol, 5.82 ml (120 mmol) of hydrazine monohydrate was added, and the mixture was stirred at room temperature for 4 hours. Then, 200 ml of ethyl acetate was added, and the precipitated materials were filtered off. The solvent was distilled off from the filtrate and chloroform was added to the residue. The mixture was washed with saturated saline and dried over anhydrous magnesium sulfate. The solvent was distilled off, and 400 ml of methylene chloride and 8.36 ml (60 mmol) of triethylamine were added to the residue. Then, 9.53 g (48 mmol) of O-acetylsalicyloyl chloride was added with stirring under ice-cooling, and the mixture was stirred at room temperature for 1 hour. The mixture was washed with saturated saline and the solvent was distilled off from the mixture, after which 62.4 ml of ethanol and 62.4 ml of 1N-NaOH were added to the residue and the mixture was stirred for 15 minutes. Then, 62.4 ml of 1N-HCl was added, and ethanol was distilled off, after which the residue was extracted with chloroform and the extract was dried over anhydrous magnesium sulfate. The solvent was distilled off and the residue was purified by column chromatography (eluent:ethyl acetate) to give 5.48 g of the desired compound (45.3% yield, colorless solid), mp. 83°–85° C.

Anal. for $C_{16}H_{18}N_2O_2S$,

Calcd.: C; 63.55, H; 6.00, N; 9.26.

Found: C; 63.27, H; 5.87, N; 8.96.

NMR (200 MHz, CDCl$_3$) δ:1.72–1.93 (4H, m), 3.04 (2H, m), 3.51 (2H, m), 6.50 (1H, br), 6.83 (1H, m), 6.99 (1H, dd, J=8.4, 1.0 Hz), 7.12 (2H, m), 7.29–7.44 (2H, m), 8.38 (2H, m).

IR (KBr) cm$^{-1}$: 3240, 1640, 1595, 1585, 1545, 1490.

EXAMPLE 162

Synthesis of 3-[4-(4-pyridylthio)butyl]-2H-1,3-benzoxadine-2-thion-4(3H)-on

To a solution of 2.43 g (8.04 mmol) of 4-[4-(2-hydroxybenzoylamino)butylthio]pyridine in 80 ml of dry tetrahydrofuran, 2.86 g (16.05 mmol) of 1,1'-thiocarbonyldiimidazole was added, and the mixture was stirred at room temperature for 70 hours. The solvent was distilled off and chloroform was added to the residue. The mixture was washed with water and dried over anhydrous magnesium sulfate. The solvent was distilled off and the residue was purified by column chromatography (eluent:ethyl acetate/n-hexane=2:1) to give 2.28 g of the desired compound (82.3% yield, colorless crystals), mp. 93°–94° C.

Anal. for $C_{17}H_{16}N_2O_2S_2$,

Calcd.: C; 59.28, H; 4.68, N; 8.13.

Found: C; 59.27, H; 4.72, N; 8.17.

NMR (200 MHz, CDCl$_3$) δ:1.83 (2H, m), 2.01 (2H, m), 3.06 (2H, t, J=7.2 Hz), 4.49 (2H, m), 7.11i (2H, m), 7.32–7.46 (2H, m), 7.75 (1H, m), 8.07 (1H, m), 8.39 (2H, m).

IR (KBr) cm$^{-1}$: 171.5, 1620, 1600, 1575.

EXAMPLE 163

Synthesis of 4-(4-rhodaninebutylthio)pyridine

To a solution of 4.0 g (30.0 mmol) of rhodanine and 6.05 g (30.0 mmol of 4-(4-chlorobutylthio)pyridine in 150 ml of dimethylformamide, 4.49 ml (30.0 mmol) of 1,8-diazabicyclo[5.4.0]-7-undecene was added, the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:ethyl acetate/hexane=2:1 to ethyl acetate) to give 1.75 g of the desired compound (19.6% yield, pale brown crystals).

NMR (200 MHz, CDCl$_3$) δ:1.66–1.93 (4H, m), 3.01 (2H, t, J=7.0 Hz), 3.97 (2H, s), 4.02 (2H, t, J=7.0 Hz), 7.10 (2H, dd, J=1.6, 4.6 Hz), 8.39 (2H, dd, J=1.6, 4.6 Hz).

IR (KBr) cm$^{-1}$: 3040, 2950, 1730, 1710, 1580, 1360, 1280, 1225, 1140, 810, 715.

EXAMPLE 164

Synthesis of 2-[4-(5-benzylidene-2,4-thiazolidinedione)-butylthio]pyridine i) Synthesis of 2-(4-chlorobutylthio)pyridine To a solution of 25.0 g (225 mmol) of 2-mercaptopyridine and 34.5 ml (247 mmol) of triethylamine in 300 ml of ethanol, 28.5 ml (247 mmol) of 1-bromo-4-chlorobutane was added with stirring under ice-cooling, and the mixture was stirred at room temperature for 16 hours. The solvent was distilled off and the residue was dissolved in chloroform. The solution was washed with saturated aqueous sodium bicarbonate and water, and dried. The solvent was distilled off and the residue was purified by column chromatography (eluent:ethyl acetate/hexane=1:3) to give 29.73 g of the desired compound (65.5% yield, pale yellow oil).

NMR (200 MHz, CDCl$_3$) δ:1.70–2.05 (4H, m), 3.21 (2H, t, J=6.8 Hz), 3.58 (2H, t, J=6.2 Hz), 6.98 (1H, ddd, J=1.2, 5.0, 7.4 Hz), 7.17 (1H, d, J=8.0Hz), 7.48 (1H, ddd, J=1.8, 7.2, 7.8 Hz), 8.40–8.45 (1H, m).

ii) Synthesis of 2-[4-(5-benzylidene-2,4-thiazolidinedione)butylthio]pyridine

To a solution of 4.10 g (20.0 mmol) of 5-benzylidene-2,4-thiazolidinedione and 4.03 g (20.0 mmol) of 2-(4-chlorobutylthio)pyridine in 80 ml of dimethylformamide, 3.0 ml (20.0 mmol) of 1,8-diazabicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:ethyl acetate/hexane=1:3) to give 3.89 g of the desired compound (52.5% yield, pale yellow crystals).

Anal. for $C_{19}H_{18}N_2O_2S_2$,

Calcd.: C; 61.60, H; 4.90, N; 7.56.

Found: C; 61.62, H; 4.86, N; 7.56.

NMR (200 MHz, CDCl$_3$) δ:1.67–1.93 (4H, m), 3.21 (2H, t, J=6.8 Hz), 3.79 (2H, t, J=7.0 Hz), 6.95 (1H, ddd, J=1.0, 5.0, 7.4 Hz), 7.15 (1H, ddd, J=1.0, 1.2, 8.2 Hz), 7.41–7.51 (6H, m), 7.26 (1H, s), 8.41 (1H, m).

IR (KBr) cm$^{-1}$: 3060, 3040, 2950, 2930, 1675, 1605, 1580, 1365, 1130, 755, 690.

EXAMPLE 165

Synthesis of 4-[5-(2-thienylmethylene)-2,4-thiazolidinedione)-methylthio]pyridine To a solution of 1.72 g (8.14 mmol) of 5-(2-thienylmethylene)- 2,4-thiazolidinedione and 1.30 g (8.14 mmol) of 4-chloromethylthiopyridine in 80 ml of dimethylformamide, 1.22 ml (8.14 mmol) of 1,8-diazabicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:- ethyl acetate/hexane=1:2 to 1:4) to give 1.88 g of the desired compound (69.0% yield, pale yellow crystals).

Anal. for $C_{14}H_{10}N_2O_2S_3$,

Calcd.: C; 50.28, H; 3.01, N; 8.38.

Found: C; 49.95, H; 3.00, N; 8.25.

NMR (200 MHz, CDCl$_3$) δ:5.21 (2H, s), 7.20 (1H, dd, J=3.8, 5.0 Hz), 7.39–7.43 (3H, m), 7.67–7.71 (1H, m), 8.10 (1H, s), 8.48 (2H, bd, J=5.4 Hz).

IR (KBr) cm$^{-1}$: 3040, 1740, 1680, 1600, 1580, 730.

EXAMPLE 166

Synthesis of 4-(4-saccharinbutylthio)pyridine

To a solution of 2.75 g (15.0 mmol) of saccharin and 3.03 g (15.0 mmol) of 4-(4-chlorobutylthio)pyridine in ml of dimethylformamide, 2.24 ml (15.0 mmol) of 1,8-diazabicyclo[5.4.0]-7-undecene was added, and the mixture was stirred at 80 ° C. for 16 hours. After cooling, water was added to the reaction mixture, and the mixture was extracted with ethyl acetate. The extract was dried and the solvent was distilled off. The residue was purified by column chromatography (eluent:ethyl acetate/hexane=1:2 to 4:1 ) to give 1.16 g of the desired compound (22.2% yield, white crystals).

Anal. for $C_{16}H_{16}N_2O_3S_2$,

Calcd.: C; 55.15, H; 4.63, N; 8.04.

Found: C; 55.00, H; 4.33, N; 8.00.

NMR (200 MHz, CDCl$_3$) δ:1.80–2.12 (4H, m), 3.04 (2H, t, J=7.2 Hz), 3.83 (1H, t, J=7.0 Hz), 7.10 (2H, dd, J=1.4, 4.6 Hz), 7.79–7.96 (3H, m), 8.04–8.08 (1H, m), 8.37 (2H, bd, J=6.0 Hz

IR (KBr) cm$^{-1}$: 3080, 2960, 1740, 1580, 1325, 1305, 1185, 760, 680.

EXAMPLE 167

Synthesis of 4-(4-(5,5-dimethyloxazolidine-2,4-dione)-butylthio]pyridine

To a solution of 1.29 g (10.0 mmol) of 5,5-dimethyloxazolidine- 2,4-dine and 2.02 g (10.0 mmol) 4-(4-chlorobutylthio)pyridine in 80 ml of dimethylformamide, 1.50 ml (10.0 mmol) of 1,8-diazabicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:ethyl acetate/ hexane=1:1→2:1) to give 2.44 g of the desired compound (82.9% yield, colorless oil).

NMR (200 MHz, CDCl$_3$) δ:1.55 (6H, s), 1.66–1.93 (4H, m), 3.02 (2H, t, J=7.0 Hz), 3.57 (2H, t, J=6.8 Hz), 7.09 (2H, dd, J=1.6, 4.6 Hz), 8.39 (2H, dd, J=1.6, 4.6 Hz).

IR (KBr) cm$^{-1}$: 3040, 2950, 1820, 1740, 1580, 1450, 1420, 1100, 805, 780, 710.

EXAMPLE 168

Synthesis of 4-[2-(2-hydroxybenzoyl)aminoethylthio]pyridine

To a solution of 5.69 g (20.0 mmol) of 4-(2-phthalimidoethylthio)pyridine in 100 ml of ethanol, 2.91 ml (60.0 mmol) of hydrazine monohydrate was added, and the mixture was stirred at room temperature for 5 hours. The solvent was distilled off and the residue was dissolved in chloroform. The precipitate was filtered and the filtrate was concentrated. The resulting residue was used for the subsequent reaction.

To a solution of the above residue and 4.18 ml (30.0 mmol) of triethylamine in 100 ml of methylene chloride, 4.97 g (25.0 mmol) of O-acetylsalicyloyl chloride was added with stirring under ice-cooling, and the mixture was stirred at room temperature for 2 hours. The reaction mixture was washed with saturated aqueous sodium bicarbonate and water, and dried. The solvent was distilled off and the residue was purified by-column chromatography (eluent:methylene chloride/acetone=8:1 to 2:1) to give 2.21 g of the desired compound (40.3% yield, white crystals).

NMR (200 MHz, CDCl$_3$) δ:1.79 (1H, bs), 3.28 (2H, t, J=6.8 Hz), 1.56–1.67 (2H, m), 3.74 (2H, q, J=6.4 Hz), 6.84 (1H, ddd, J=1.2, 7.1, 7.2 Hz), 7.00 (2H, bd, J=7.8 Hz), 7.08 (1H, bs), 7.23 (2H, bd, J=6.2 Hz), 7.36–7.4:5 (2H, m), 8.42 (2H, bd, J=4.0 Hz).

IR (KBr) cm$^{-1}$: 3440, 3250, 3080, 2930, 1640, 1595, 1580, 1495, 1340, 805, 760.

EXAMPLE 169

Synthesis of 4-(2,4-thiazolidinedonemethylthio)pyridine

To a solution of 1.76 g (15.0 mmol) of 2,4-thiazolidinedione and 2.39 g (15.0 mmol) of 4-chloromethylthiopyridine in 100 ml of dimethylformamide, 2.24 ml (15.0 mmol) of 1,8-diazabicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:ethyl acetate/hexane=2:1 to ethyl acetate) to give 1.49 g of the desired compound (41.5% yield, pale yellow crystals).

Anal. for $C_9H_3N_2O_2S_2$,

Calcd.: C; 44.98, H; 3.36, N; 11.66.

Found: C; 44.94, H; 3.41, N; 11.61.

NMR (200 MHz, CDCl$_3$) δ:3.99 (2H, s), 5.10 (2H, s), 7.37 (2H, dd, J=1.6, 4.6 Hz), 8.48 (2H, bd, J=6.0 Hz).

IR (KBr) cm$^{-1}$: 3080, 3010, 2940, 1755, 1680, 1570, 895, 805.

EXAMPLE 170

Synthesis of 4-[2-[2H-1,3-benzoxadine-2-thion-4(3H)-on]ethylthio]pyridine i) Synthesis of 4-[2-(2-hydroxybenzoyl)aminoethylthio]pyridine To a solution of 3.50 g (12.3 mmol) of 4-(2-phthalimidoethylthio)pyridine in 80 ml of ethanol, 1.80 ml (37.0 mmol) of hydrazine monohydrate was added, and the mixture was stirred at room temperature for 5 hours. The solvent was distilled off and the residue was dissolved in chloroform. The precipitate was filtered and the filtrate was concentrated. The resulting residue was used for the subsequent reaction.

To a solution of the above residue and 4.18 ml (30.0 mmol) of triethylamine in 100 ml of methylene chloride, 4.97 g (25.0 mmol) of O-acetylsalicyloyl chloride was added with stirring under ice-cooling, and the mixture was stirred at room temperature for 2 hours. The reaction mixture was washed with saturated aqueous sodium bicarbonate and water, and dried. The solvent was distilled off and the residue was purified by column chromatography (eluent:methylene chloride/acetone=8:1 to 2:1) to give 1.73 g of the desired compound (51.3% yield, white crystals).

ii) Synthesis of 4-[2-[2H-1,3-benzoxadine-2-thion-4(3H)-on]ethylthio]pyridine

To a solution of 4-[2-(2-hydroxybenzoyl)aminoethylthio]pyridine in 70 ml of tetrahydrofuran, 1.13 g (6.31 mmol) of 1,1'-thiocarbonyldiimidazole was added under nitrogen atmosphere, and the mixture was stirred at room temperature for 64 hours. The solvent was distilled off and the residue was dissolved in chloroform. The solution was washed with water and dried. The solvent was distilled off and the residue was purified by column chromatography (eluent:ethyl acetate) to give 1.40 g of the desired compound (70.0% yield, white crystals).

NMR (200 MHz, CDCl$_3$) δ:3.41 (2H, dd, J=7.8, 8.0 Hz), 4.74 (2H, dd, J=7.8, 8.0 Hz), 7.34–7.49 (4H, m), 7.77 (1H, ddd, J=1.8,7.4, 9.0 Hz), 8.10 (1H, dd, J=1.8, 8.0 Hz), 8.45 (2H, bs).

IR (KBr) cm$^{-1}$: 3020, 2350, 1705, 1620, 1475, 1320, 800, 755, 700.

EXAMPLE 171

Synthesis of 4-[4-(5-propylmethylene-2,4-thiazolidinedione)-butylthio]pyridine

To a solution of 0.5 g (1.77 mmol) of 4-[4-(2,4-thiazolidinedione)butylthio]pyridine and 0.16 ml (1.77 mmol) of butylaldehyde in 25 ml of ethanol, 0.02 ml (0.18 mmol) of piperidine was added, and the mixture was heated under reflux for 2 hours. After cooling, the solvent was distilled off and the residue was dissolved in ethyl acetate. The solution was washed with water and dried. The solvent was distilled off and the residue was purified by column chromatography (eluent:hexane/ethylacetate=2:1 to 1:1) to give 0.42 g of the desired compound (70.6% yield, yellow oil).

NMR (200 MHz, CDCl$_3$) δ:0.98 (3H, t, J=7.2 Hz), 1.50–1.68 (2H, m), 1.69–1.88 (4H, m), 2.22 (2H, q, J=7.4 Hz), 3.01 (2H, t, J=7.0 Hz), 3.73 (2H, t, J=6.8 Hz), 7.08 (1H, t, J=7.8 Hz), 7.09 (2H, dd, J=1.8, 4.6 Hz), 8.38 (2H, dd, J=1.6, 4.6 Hz).

IR (neat) cm$^{-1}$: 3030, 2955, 2930, 1740, 1680, 1580, 1480, 800, 705.

EXAMPLE 172

Synthesis of 4-saccharinmethylthiopyridine

To a solution of 2.75 g (15.0 mmol) of saccharin and 3.03 g (15.0 mmol) of 4-chloromethylthiopyridine in 100 ml of dimethylformamide, 2.24 ml (15.0 mmol) of 1,8-diazabicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:ethyl acetate/hexane=1:2 to 4:1) to give 1.73 g of the desired compound (37.7% yield, pale yellow crystals).

Anal. for $C_{13}H_{10}N_2O_3S_2$,

Calcd.: C; 50.97, H; 3.29, N; 9.14.

Found: C; 50.66, H; 3.27, N; 9.11.

NMR (200 MHz, CDCl$_3$) δ:5.32 (2H, s), 7.42 (2H, dd, J=1.6, 4.6 Hz), 7.81–7.96 (3H, m), 8.08–8.11 (1H, m), 8.50 (2H, dd, J=1.6, 4.6 Hz).

IR (KBr) cm$^{-1}$: 3090, 3030, 1740, 1570, 1400, 1340, 1180, 800, 750, 670.

EXAMPLE 173

Synthesis of 4-(5,5-dimethyloxazolidine-2,4-dione)-methylthiopyridine

To a solution of 1.93 g (15.0 mmol) of 5,5-dimethyloxazolidine-2,4-dione and 2.40 g (15.0 mmol) of 4-chloromethylthiopyridine in 100 ml of dimethylformamide, 2.24 ml (15.0 mmol) of 1,8-diazabicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:ethyl acetate/hexane=1:2 to 2:1) to give 2.32 g of the desired compound (61.3% yield, yellow crystals).

Anal. for $C_{11}H_{12}N_2O_3S$,

Calcd.: C; 52.37, H; 4.79, N; 11.10.

Found: C; 52.08, H; 4.94, N; 11.06.

NMR (200 MHz, CDCl$_3$) δ:1.54 (6H, s), 5.01 (2H, s), 7.38 (2H, dd, J=1.6, 4.6 Hz), 8.49 (2H, dd, J=1.6, 4.6 Hz).

IR (KBr) cm$^{-1}$: 3030, 2980, 1810, 1740, 1580, 800, 770, 700.

EXAMPLE 174

Synthesis of 4-[3-(2-quinoxaloylamino)propylthio]pyridine

To a solution of 4.30 g (17.8 mmol) of 4-(3-aminopropylthio)pyridine dihydrochloride and 8.68 ml (62.3 mmol) of triethylamine in 200 ml of methylene chloride, 3.43 g (17.8 mmol) of 2-quinoxaloyl chloride was added with stirring under ice-cooling, and the mixture was stirred at room temperature for 4 hours. The reaction mixture was washed with saturated aqueous sodium bicarbonate and water, and dried. The solvent was distilled off and the residue was purified by column chromatography (eluent:ethyl acetate) and recrystallization (solvent:ethyl acetate-ether) to give 2.82 g of the desired compound (48.9% yield, white crystals).

Anal. for $C_{17}H_{16}N_4OS$,

Calcd.: C; 62.94, H; 4.97, N; 17.27.

Found: C; 62.97, H; 5.06, N; 17.25.

NMR (200 MHz, CDCl$_3$) δ:2.14 (2H, quint., J=7.0 Hz), 3.13 (2H, t, J=7.4 Hz), 3.73 (2H, q, J=6.7 Hz), 7.14 (2H, dd, J=1.4, 4.6 Hz), 7.82–7.94 (2H, m), 8.09–8.24 (3H, m), 8.40 (2H, dd, J=1.4, 4.6 Hz), 9.69 (1H, s).

IR (KBr) cm$^{-1}$: 1680, 1580, 800, 760.

EXAMPLE 175

Synthesis of
4-[4-[5-(3,5-di-tert-butyl-4-hydroxyphenyl)methylene-2,4-thiazolidinedione]butylthio]pyridine i) Synthesis of 5-(3,5-di-tert-butyl-4-hydroxyphenyl)methylene- 2,4-thiazolidinedione To a solution of 12.5 g (107 mmol) of 2,4-thiazolidinedione and 25.0 g (107 mmol) of 3,5-di-tert-butyl-4-hydroxybenzaldehyde in 300 ml of ethanol, 1.05 ml (10.7 mmol) of piperidine was added, and the mixture was heated under reflux for 5 hours. After cooling, the precipitated crystals were filtered and washed with cooled ethanol to give 15.23 g of the desired compound (42.8% yield, pale yellow crystals).

NMR (200 MHz, DMSO-d$_6$) δ:1.41 (1H, s), 7.37 (2H, s), 7.76 (2H, s), 12.44 (1H, bs).

IR (KBr) cm$^{-1}$: 3620, 3440, 2960, 1740, 1690, 700, 650.

ii) Synthesis of 4-[4-[5-(3,5-di-tert-butyl-4-hydroxyphenyl)methylene- 2,4-thiazolidinedione]butylthio]pyridine To a solution of 5.0 g (15.0 mmol) of 5-(3,5-di-tert-butyl-4-hydroxyphenyl)methylene-2,4-thiazolidinedione and 3.02 g (15.0mmol) of 4-(4-chlorobutylthio)pyridine in 100 ml of dimethylformamide, 2.24 ml (15.0 mmol) of 1,8-diazabicyclo[5.4.0]-7-undecene was added, and the mixture was stirred at 80° C. for 16 hours. After-cooling, water was added to the reaction mixture, and the mixture was extracted with ethyl acetate. The extract was dried and the solvent was distilled off. The residue was purified by column chromatography (eluent:ethyl acetate/hexane=2:1) and recrystallization (solvent:ethyl acetate-ether) to give 3.83 g of the desired compound (51.3% yield, pale yellow crystals).

Anal. for $C_{27}H_{34}N_2O_3S_2$,

Calcd.: C; 65.03, H; 6.87, N; 5.62.

Found: C; 64.92, H; 6.78, N; 5.48.

NMR (200 MHz, CDCl$_3$) δ:1.47 (18H, s), 1.67–1.95 (4H, m), 3.03 (2H, t, J=7.0 Hz), 3.80 (2H, t, J=7.0 Hz), 5.73 (1H, s), 7.11 (2H, dd, J=1.8, 4.8 Hz), 7.37 (2H, s), 7.87 (1H, s), 8.39 (2H, dd, J=1.8, 4.8 Hz).

IR (KBr) cm$^{-1}$: 2950, 1740, 1680, 1580, 1130, 800, 740.

EXAMPLE 176

Synthesis of
4-(2,4-thiazolidinedionemethylthio)pyridine hydrochloride

To a solution of 702.9 mg (2.92 mmol) of 4-(2,4-thiazolidinedionemethylthio)pyridine in 30 ml of methanol, 70 ml of 10% hydrochloric acid-methanol was added, and the mixture was stirred at room temperature for 2 hours. The solvent was distilled off and the residue was purified by recrystallization(solvent:ethanol-ether) to give 689.9 mg of the desired compound (84.9% yield, pale yellow crystals).

Anal. for $C_9H_8N_2O_2S_2 \cdot HCl$,

Calcd.: C; 39.06, H; 3.28, N; 10.12.

Found: C; 38.85, H; 2.99, N; 10.10.

NMR (200 MHz, D$_2$O, ref=4.80 ppm of HDO) δ:4.18 (2H, s), 5.38 (2H; s), 8.05 (2H, bd, J=7.2 Hz), 8.50 (2H, bd, J=7.2 Hz).

IR (KBr) cm$^{-1}$: 1670, 1625, 1370, 1140, 800.

EXAMPLE 177

Synthesis of
4-[4-[5-(3,5-di-tert-butyl-4-hydroxyphenyl)-methylenerhodanine]butylthio]pyridine i) Synthesis of 5-(3,5-di-tert-butyl-4-hydroxyphenyl)methylenerhodanine To a solution of 14.6 g (110 mmol) of rhodanine and 25.7 g (110 mmol) of 3,5-di-tert-butyl-4-hydroxybenzaldehyde in 150 ml of ethanol, 1.08 ml (11.0 mmol) of piperidine was added, and the mixture was heated under reflux for 5 hours. After cooling, the precipitated crystals were filtered and washed with cooled ethanol to give 26.71 g of the desired compound (69.7% yield, pale yellow crystals).

Anal. for $C_{18}H_{23}NO_2S_2$,

Calcd.: C; 61.86, H; 6.63, N; 4.01.

Found: C; 61.95, H; 6.50, N; 3.96.

NMR (200 MHz, DMSO-d$_6$) δ:1.42 (18H, s), 7.37 (2H, s), 7.69 (1H, s), 7.76 (1H, s), 12.44 (1H, s).

IR (KBr) cm$^{-1}$: 3620, 2960, 1700, 1580, 1420, 1180, 690, 660.

ii) Synthesis of 4-[4-[5-(3,5-di-tert-butyl-4-hydroxyphenyl)methylenerhodanine]butylthio]pyridine To a solution of 5.24 g (15.0 mmol) of 5-(3,5-di-tert-butyl- 4-hydroxyphenyl)methylenerhodanine and 3.02 g (15.0 mmol) of 4-(4-chlorobutylthio)pyridine in 100 ml of dimethylformamide, 2.24 ml (15.0 mmol) of 1,8-diazabicyclo-[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:ethyl acetate/hexane=1:1) and recrystallization (solvent:ethyl acetate-ether) to give 2.21 g of the desired compound (28.6% yield, pale yellow crystals).

Anal. for $C_{27}H_{34}N_2O_2S_3$,

Calcd.: C; 63.00, H; 6.66, N; 5.44.

Found: C; 62.89, H; 6.79, N; 5.35.

NMR (200 MHz, CDCl$_3$) δ:1.48 (18H, s), 1.71–2.03 (4H, m), 3.04 (2H, t, J=7.0 Hz), 4.18 (2H, t, J=7.0 Hz), 5.79 (1H, s), 7.11 (2H, bd. J=6.4 Hz), 7.36 (2H, s), 7.72 (1H, s), 8.40 (2H, bd, J=6.4 Hz).

IR (KBr) cm$^{-1}$: 2950, 1705, 1580, 1160, 800.

EXAMPLE 178

Synthesis of
4-[3-(2-pyrazinecarbonylamino)propylthio]pyridine dihydrochloride

To a solution of 704.5 mg (2.57 mmol) of 4-[3-(2-pyrazinecarbonylamino)propylthio]pyridine in 30 ml of methanol, 70 ml of 10% hydrochloric acid-methanol was added, and the mixture was stirred at room temperature for 2 hours. The solvent was distilled off and the residue was purified by recrystallization (solvent:ethanol-ether) to give 842.4 mg of the desired compound (85.6% yield, pale yellow crystals).

Anal. for $C_{13}H_{14}N_4OS\cdot 2HCl$,

Calcd.: C; 44.96, H; 4.64, N; 16.13, S; 9.23, Cl; 20.42.

Found: C; 44.96, H; 4.55, N; 16.00, S; 9.23, Cl; 20.19.

NMR (200 MHz, $D_2O$, ref=4.80 ppm of HDO) δ:2.09 (2H, quint., J=6.6 Hz), 3.27 (2H, t, J=7.4 Hz), 3.59 (2H, t, J=6.6 Hz), 7.73 (2H, bd, J=6.8 Hz), 8.72 (2H, bd, J=7.6 Hz), 9.08 (1H, s).

IR (KBr) $cm^{-1}$: 3450, 3230, 3050, 1680, 1620, 1480, 800, 620.

EXAMPLE 179

Synthesis of
4-(5,5-dimethyloxazolidine-2,4-dionemethylthio)-pyridine hydrochloride To a solution of 627.2 mg (2.49 mmol) of 4-(5,5-dimethyloxazolidine- 2,4-dionemethylthio)pyridine in 30 ml of methanol, 70 ml of 10% hydrochloric acid-methanol was added, and the mixture was stirred at room temperature for 2 hours. The solvent was distilled off and the residue was purified by recrystallization (solvent:ethanol-ether) to give 631.5 mg of the desired compound (88.0% yield, white crystals).

Anal. for $C_{11}H_{12}N_2O_3S\cdot HCl$,

Calcd.: C; 45.76, H; 4.54, N; 9.70.

Found: C; 45.62, H; 4.60, N; 9.66.

NMR (200 MHz, $D_2O$, ref=4.80 ppm of HDO) δ: 1.57 (6H, s), 5.38 (2H, s), 8.07 (2H, d, J=7.2 Hz), 8.54 (2H, d, J=7.2 Hz).

IR (KBr) $cm^{-1}$: 1745, 1620, 1595, 1480, 815, 780.

EXAMPLE 180

Synthesis of 4-(saccharinmethylthio)pyridine hydrochloride

To a solution of 589.9 mg (1.93 mmol) of 4-(saccharinmethylthio)pyridine in 30 ml of methanol, 70 ml of 10% hydrochloric acid-methanol was added, and the mixture was stirred at room temperature for 2 hours. The solvent was distilled off and the residue was purified by recrystallization (solvent:ethanol-ether) to give 607.6 mg of the desired compound (91.7% yield, pale yellow crystals).

Anal. for $C_{13}H_{10}N_2O_3S\cdot HCl$,

Calcd.: C; 45.55, H; 3.23, N; 8.17.

Found: C; 45.45, H; 3.33, N; 8.17.

NMR (200 MHz, $D_2O$, ref=4.80 ppm of HDO) δ:5.67 (2H, s), 7.90–8.07 (6H, m), 8.55 (2H, bd, J=7.0 Hz).

IR (KBr) $cm^{-1}$: 3040, 2980, 1735, 1630, 1595, 1355, 1285, 1250, 1180, 800, 760.

EXAMPLE 181

Synthesis of
3-[3-(2-pyridylthio)propyl]-2H-1,3-benzoxadine-2-thion-4(3H)-one

To a solution of 1.153 g (4.00 mmol) of 2-[3-(2-hydroxybenzoylamino)propylthio]pyridine in 60 ml of dry tetrahydrofuran, 1.426 g (8.00 mmol) of 1,1'-thiocarbonyldiimidazole was added, and the mixture was stirred at room temperature for 64 hours. The solvent was distilled off and chloroform was added to the residue. The mixture was washed with water and dried over anhydrous magnesium sulfate. The solvent was distilled off and the residue was purified by column chromatography (eluent:ethyl acetate/n-hexane=1:4 ) to give 0.72 g of the desired compound 54.5% yield, colorless crystals), mp. 83°–84° C.

Anal. for $C_{16}H_{14}N_2O_2S_2$,

Calcd.: C; 58.16, H; 4.27, N; 8.48.

Found: C; 58.05, H; 4.21, N; 8.33.

NMR (200 MHz, $CDCl_3$) δ:2.25 (2H, m), 3.30 (2H, t, J=7.2 Hz), 4.62 (2H, m), 6.97 (1H, m), 7.19 (1H, d, J=8 Hz), 7.32–7.53 (3H, m), 7.74 (1H, m), 8.08 (1H, m), 8.38 (1H, m).

EXAMPLE 182

Synthesis of
3-[3-(2-pyridylthio)propyl]-2H-1,3-benzoxadine-2,4(3H)-dione

To a solution of 1.153 g (4.0 mmol) of 2-[3-(2-hydroxybenzoylamino)propylthio]pyridine in 60 ml of dry tetrahydrofuran, 1.30 g (10.0 mmol) of 1,1'-carbonyldiimidazole was added, and the mixture was stirred at room temperature for 16 hours. The solvent was distilled off and chloroform was added to the residue. The mixture was washed with water and dried over anhydrous magnesium sulfate. The solvent was distilled off and the residue was purified by column chromatography (eluent:ethyl acetate/n-hexane=1:3) to give 1.07 g of the desired compound (85.1% yield, colorless viscous liquid).

NMR (200 MHz, $CDCl_3$) δ:2.16 (2H, 3.26 (2H, t, J=7.2 Hz), 4.21 (2H, t, J=7 Hz), 6.95 (1H, 7.16 (1H, m), 7.24–7.50 (3H, m), 7.71 (1H, m), 8.09 (1H, dd, J=8, 1.6 Hz), 8.34 (1H, m).

IR (neat) $cm^{-1}$: 1760, 1700, 1685, 1620, 1585.

EXAMPLE 183

Synthesis of
4-[4-[5-(3-thienyl)methylene-2,4-thiazolidinedione]-butylthio]pyridine To a solution of 1.41 g (5.0 mmol) of 4-[4-(2,4-thiazolidinedione)butylthio]pyridine and 0.44 ml (5.0 mmol) of 3-thiophenecarbaldehyde in 50 ml of ethanol, 0.05 ml (0.5 mmol) of piperidine was added, and the mixture was heated under reflux for 8 hours. After cooling, the solvent was distilled off. The residue was dissolved in chloroform, and the solution was washed with saturated aqueous sodium bicarbonate, and dried. The solvent was distilled off and the residue was purified by column chromatography (eluent:ethyl acetate) to give 1.43 g of the desired compound (76.0% yield, pale yellow crystals).

NMR (200 MHz, $CDCl_3$) δ:1.68–1.94 (4H, m), 3.03 (2H, t, J=7.0 Hz), 3.79 (2H, t, J=6.8 Hz), 7.11 (2H, d, J=5.8 Hz), 7.29 (1H, dd, J=1.2, 5.2 Hz), 7.45 (1H, dd, J=3.0, 5.2 Hz), 7.63 (1H, dd, J=1.4, 3.0 Hz), 7.90 (1H, s), 8.39 (2H, s).

IR (KBr) $cm^{-1}$: 3100, 2950, 1730, 1680, 1610, 1360, 1120, 780, 710, 620, 545.

EXAMPLE 184

Synthesis of 4-[4-[5-(4-pyridyl)methylene-2,4-thiazolidinedione]-butylthio]pyridine To a solution of 1.41 g (5.0 mmol) of 4-[4-(2,4-thiazolidinedione)butylthio]pyridine and 0.48 ml (5.0 mmol) of 4-pyridinecarbaldehyde in 50 ml of ethanol, 0.05 ml (0.5 mmol) of piperidine was added, and the mixture was heated under reflux for 16 hours. After cooling, the solvent was distilled off. The residue was dissolved in chloroform, and the solution was washed with water, and dried. The solvent was distilled off and the residue was purified by column chromatography (eluent:ethyl acetate to ethyl acetate/ethanol=20:1 to 10:1) to give 0.666 g of the desired compound (35.9% yield, pale yellow crystals).

NMR (200 MHz, CDCl$_3$) δ:1.68–1.98 (4H, m), 3.03 (2H, t, J=7.0 Hz), 3.82 (2H, t, J=6.7 Hz), 7.11 (2H, d, J=5.3 Hz), 7.35 (2H, d, J=6.0 Hz), 7.79 (1H, s), 8.39 (2H, s), 8.75 (2H, d, J=4.5 Hz).

IR (KBr) cm$^{-1}$: 3030, 2950, 1745, 680, 1575, 1350, 1130, 805, 710, 650, 540.

EXAMPLE 185

Synthesis of 4-[4-[5-(3-pyridyl)methylene-2,4-thiazolidinedione]-butylthio]pyridine To a solution of 1.41 g (5.0 mmol) of 4-[4-(2,4-thiazolidinedione)butylthio]pyridine and 0.47 ml (5.0 mmol) of 3-pyridylcarboxaldehyde in 50 ml of ethanol, 0.05 ml (0.5 mmol) of piperidine was added, and the mixture was heated under reflux for 16 hours. After cooling, the solvent was distilled off. The residue was dissolved In chloroform, and the solution was washed with water, and dried. The solvent was distilled off and the residue was purified by column chromatography (eluent:ethyl acetate) to give 0.932 g of the desired compound (50.2% yield, pale yellow crystals).

NMR (200 MHz, CDCl$_3$) δ:1.70–1.98 (4H, m), 3.04 (2H, t, J=7.0 Hz), 3.82 (2H, t, J=6.8 Hz), 7.12 (2H, dd, J=1.6, 4.6 Hz), 7.44 (1H, dd, J=4.6, 8.0 Hz), 7.81 (1H, ddd, J=1.8, 2.0, 8.0 Hz), 7.88 (1H, s), 8.40 (2H, d, J=4.8 Hz), 8.66 (1H, dd, J=1.6, 4.8 Hz), 8.79 (1H, d, J=2.2 Hz).

IR (KBr) cm$^{-1}$: 3030, 2840, 1740, 1675, 1610, 1365, 1130, 800, 705.

EXAMPLE 186

Synthesis of 4-[4-[5-(2-pyridyl)methylene-2,4-thiazolidinedione]-butylthio]pyridine To a solution of 1.41 g (5.0 mmol of 4-[4-(2,4-thiazolidinedione)butylthio]pyridine and 0.48 ml (5.0 mmol) of 2-pyridinecarbaldehyde in 50 ml of ethanol, 0.05 ml (0.5 mmol) of piperidine was added, and the mixture was heated under reflux for 16 hours. After cooling, the solvent was distilled off. The residue was dissolved in chloroform, and the solution was washed with water, and dried. The solvent was distilled off and the residue was purified by column chromatography (eluent:hexane/ethyl acetate=1:1 to ethyl acetate) to give 1.49 g of the desired compound (80.2% yield, pale yellow crystals).

NMR (200 MHz, CDCl$_3$) δ:1.67–1.94 (4H, m), 3.02 (2H, t, J=7.0 Hz), 3.80 (2H, t, J=6.6 Hz), 7.10 (2H, dd, J=1.4, 4.8 Hz), 7.28 (1H, ddd, J=1.0, 4.8, 7.8 Hz), 7.51 (1H, d, J=7.8 Hz), 7.78 (1E, ddd, H=1.8, 7 6, 7.8 Hz), 7.79 (1H, s), 8.38 (2H, d, J=4.8 Hz), 8.75 (1H, d, J=4.6 Hz).

IR (KBr) cm$^{-1}$: 3040, 2950, 1730, 1670, 1575, 1390, 1130, 800, 710, 540.

EXAMPLE 187

Synthesis of 4-[4-(5-nonylmethylene-2,4-thiazolidinedione)-butylthio]pyridine hydrochloride i) Synthesis of 4-[4-(5-nonylmethylene-2,4-thiazolidinedione)butylthio]pyridine To a solution of 1.41 g (5.0 mmol) of 4-[4-(2,4-thiazolidinedione)butylthio]pyridine and 0.94 ml (5.0 mmol) of 1-decanal in 50 ml of ethanol, 0.05 ml (0.5 mmol) of piperidine was added, and the mixture was heated under reflux for 2 hours. After cooling, the solvent was distilled off. The residue was dissolved in ethyl acetate, and the solution was washed with saturated aqueous sodium bicarbonate, and dried. The solvent was distilled off and the residue was purified by column chromatography (eluent:hexane/ethyl acetate=5:1 to 1:1) to give 1.97 g of the desired compound (93.7% yield, yellow oil)

NMR (200 MHz, CDCl$_3$) δ:0.88 (3H, t, J=7.2 Hz), 1.22–1.30 (12H, m), 1.46–1.60 (2H, m), 1.68–1.88 (4H, m), 2.23 (2H, q, J=7.6 Hz), 3.02 (2H, t, J=7.0 Hz), 3.74 (2H, t, J=6.8 Hz), 7.09 (1H, t, J=7.8 Hz), 7.12 (2H, d, J=4.6 Hz), 8.40 (2H, s).

IR (neat) cm$^{-1}$: 3030, 2925, 2850, 1740, 1690, 1580, 1480, 1350, 800, 735, 710.

ii) Synthesis of 4-[4-(5-nonylmethylene-2,4-thiazolidinedione)butylthio]pyridine hydrochloride To a solution of 1.83 g (4.35 mmol) of the above free amine in 40 ml of methanol, 200 ml of 10% hydrochloric acid/methanol was added, and the mixture was stirred at room temperature for 2 hours. The solvent was distilled off and the residue was washed with ether to give 1.50 g of the desired product (75.4% yield, white solid).

NMR (200 MHz, D$_2$O) δ:0.93 (3H, m), 1.32 (12H, m), 1.55 (2H, m), 1.77 (4H, m), 2.21 (2H, m), 3.21 (2H, m), 3.74 (2H, m), 7.04 (1H, t, J=7.4 Hz), 7.68 (2H, d, J=6.6 Hz), 8.45 (2H, d, J=6.0 Hz).

EXAMPLE 188

Synthesis of 2-[4-[5-(2-thienyl)methylene-2,4-thiazolidinedione]-butylthio]pyridine To a solution of 2.11 g (10.0 mmol) of 5-(2-thienyl)methylene- 2,4-thiazolidinedione and 2.02 g (10.0 mmol) of 2-(4-chlorobutylthio)pyridine in 100 ml of dimethylformamide, 1.50 ml (10.0 mmol) of 1,8-diazabicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:hexane/ethyl acetate=3:1 to 2:1 ) to give 1.40 g of the desired compound (37.3% yield, pale yellow crystals).

NMR (200 MHz, CDCl$_3$) δ:1.68–1.94 (4H, m), 3.22 (2H, t, J=7.0 Hz), 3.79 (2H, t, J=6.8 Hz), 6.97 (1H, ddd, J=1.0, 4.8, 7.2 Hz), 7.14–7.22 (2H, m), 7.41 (1H, d, J=3.8 Hz), 7.47 (1H, ddd, J=1.6, 8.0, 8.0 Hz), 7.66 (1H, d, J=5.2 Hz), 8.06 (1H, s), 8.42 (1H, dd, J=1.4, 4.0 Hz).

IR (KBr) cm$^{-1}$: 1730, 1665, 1600, 1350, 1130, 755.

EXAMPLE 189

Synthesis of 3-[4-[5-(2-thienyl)methylene-2,4-thiazolidinedione]-butylthio]pyridine i) 3-(4-chlorobutylthio)pyridine To a solution of 2.73 g (15 mmol) of 3-(N,N-dimethylaminocarbamoylthio)pyridine in 30 ml of methanol, 16.5 ml (33 mmol) of 2N aqueous sodium hydroxide was added, and the mixture was heated under reflux for 30 minutes. After cooling, the pH of the reaction mixture was adjusted to about 5 with 1N hydrochloric acid, and the solvent was distilled off.

To a solution of this crude product (3-mercaptopyridine) and 4.18 ml (30 mmol) of triethylamine in 30 ml of ethanol, 3.46 ml (30 mmol) of 4-bromo-1-chlorobutane was added, and the mixture was stirred at room temperature for 4 hours. The solvent was distilled off and the residue was dissolved in methylene chloride. The solution was washed with saturated aqueous sodium bicarbonate, and dried. The solvent was distilled off and the residue was purified by column chromatography (eluent:hexane/ethyl acetate=5:1 to 1:1) to give 2.09 g of the desired compound (69.1% yield, yellow oil).

NMR (200 MHz, CDCl$_3$) δ:1.74–2.01 (4H, m), 2.97 (2H, t, J=7.0 Hz), 3.56 (2H, t, J=6.2 Hz), 7.25 (1H, dd, J=4.8, 8.0 Hz), 7.68 (1H, ddd, J=1.4, 1.8, 8.0 Hz), 8.44 (1H, dd, J=1.4, 4.8 Hz), 8.59 (1H, d, J=1.8 Hz).

IR (neat) cm$^{-1}$: 3035, 2955, 2865, 1560, 1465, 1405, 1110, 1020, 795, 705, 650, 620.

ii) 3-[4-[5-(2-thienyl)methylene-2,4-thiazolidinedione]butylthio]pyridine

To a solution of 2.11 g (10.0 mmol) of 5-(2-thienyl)methylene-2,4-thiazolidinedione and 2.02 g (10.0 mmol) of 3-(4-chlorobutylthio)pyridine in 100 ml of dimethylformamide, 1.50 ml (10.0 mmol) of 1,8-diazabicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by recrystallization (solvent:chloroform/ethyl acetate/diethyl ether) to give 2.18 g of the product (57.9% yield, pale brown crystals).

NMR (200 MHz, CDCl$_3$) δ:1.62–1.94 (4H, m), 2.97 (2H, t, J=7.0 Hz), 3.69 (2H, t, J=7.0 Hz), 7.18–7.22 (2H, m), 7.42 (1H, d, J=3.8 Hz), 7.63–7.69 (2H, m), 8.07 (1H, s), 8.43 (1H, s), 8.59 (1H, s).

IR (KBr) cm$^{-1}$: 1740, 1670, 1600, 1350, 1120, 720.

EXAMPLE 190

Synthesis of 4-[4-(5-isopropyridene-2,4-thiazolidinedione)-butylthio]pyridine i) 5-isopropyridene-2,4-thiazolidinedione In a 300 ml flask equipped with an apparatus for dehydration, 10.0 g (90 mmol) of 2,4-thiazolidinedione and 15 ml (225 mmol) of acetone was placed, and 100 ml of benzene was added thereto. To this suspension, 0.5 ml (5 mmol) of piperidine and 0.25 ml (4 mmol) of glacial acetic acid were successively added, and the mixture was heated under reflux for 22 hours. After cooling, the solvent was distilled off. Although the residue was recrystallized from ethanol/chloroform/ether, it was not possible to separate the product from the starting material (2,4-thiazolidinedione). In the subsequent reaction, this mixture (starting material:desired product=1:1.14, 4.55 g) was used without further purification.

NMR (200 MHz, DMSO-d$_6$) δ:1.94 (3H, s), 2.34 (3H, s), 12.06 (1H, s).

ii) 4-[4-(5-isopropyridene-2,4-thiazolidinedione)buthylthio]pyridine

To a solution of 2.60 g (18.8 mmol) of the above mixture and 3.79 g (18.8 mmol) of 4-(4-chlorobutylthio)pyridine in 100 ml of dimethylformamide, 2.81 ml (18.8 mmol) of 1,8-diazabicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:hexane/ethyl acetate=2:1 to 1:1 to 1:2 to ethyl acetate) to give 1.98 g of the desired product (61.4% yield, pale yellow powder).

NMR (200 MHz, CDCl$_3$) δ:1.68–1.86 (4H, m), 2.00 (3H, s), 2.45 (3H, s), 3.01 (2H, t, J=7.0 Hz), 3.71 (2H, t, J=6.8 Hz), 7.11 (2H, d, J=6.2 Hz), 8.38 (2H, s).

EXAMPLE 191

Synthesis of 4-[(isoindolin-1-on-2-yl)methylthio]pyridine

To a solution of 681 mg (2.5 mmol) of 4-[(3-hydroxyisoindolin-1-on-2-yl)methylthio]pyridine in 6 ml of trifluoroacetic acid, 0.30 g (7.93 mmol) of sodium borohydride was added in small portions, and the mixture was stirred for 15 minutes. The reaction mixture was poured into cold water and aqueous ammonia was added to make the mixture basic, followed by extraction with methylene chloride. The extract was dried over anhydrous magnesium sulfate and the solvent was distilled off. The residue was purified by recrystallization (solvent:ethyl acetate) to give 350 mg of the desired product (54.6% yield, colorless columns), mp. 131°–132° C.

Anal. for C$_{14}$H$_{12}$N$_{12}$OS,

Calcd.: C; 65.60, H; 4.72, N; 10.93.

Found: C; 65.31, H; 4.64, N; 10.71.

EXAMPLE 192

Synthesis of 3-[4-(4-pyridylthio)butyl]quinazoline 2(1H)-thion-4(3H)-one

In a solution of 1.50 g (4.0 mmol) of 4-[4-(2-aminobenzoylamino)butylthio]pyridine dihydrochloride in 10 ml of methanol, 4.2 ml (8.4 mmol) of 2N aqueous sodium hydroxide was added, and the mixture was stirred at room temperature for 1 hour. Water was added to the reaction mixture, and the mixture was extracted with chloroform. The extract was dried and the solvent was distilled off. The resulting free amine was used in the subsequent reaction without further purification.

Under nitrogen atmosphere, to a solution of the above free amine in 20 ml of tetrahydrofuran, 1.43 g (8.0 mmol) of 1,1'-thiocarbonyldiimidazole was added, and the mixture was stirred at room temperature for 16 hours. The solvent was distilled off and the residue was dissolved in chloroform. The solution was washed with water and dried. The solvent was distilled off and the residue was washed with chloroform/ethyl acetate to give 614 mg (44.8% yield, pale brown powder).

NMR (200 MHz, DMSO-d6) δ:1.64–1.94 (4H, m), 3.12 (2H, t, J=6.8 Hz), 4.44 (2H, t, J=7.4 Hz), 7.25 (2H, dd, J=1.4, 4.6 Hz), 7.29–7.41 (2H, m), 7.74 (1H, dt, J=1.4, 8.2 Hz), 7.96 (1H, dd, J=1.2, 8.0 Hz), 8.34 (2H, dd, J=1.4, 4.6 Hz).

IR (KBr) cm$^{-1}$:1675, 1590, 1405, 1160, 760, 720.

EXAMPLE 193

Synthesis of 3-[3-(4-pyridylthio)propyl]-quinazoline-2,4(1H,3H)-dione

Under nitrogen atmosphere, to a solution of 718 mg (2.5 mmol) of 4-[3-(2-aminobenzoylamino)propylthio]pyridine in 15 ml of tetrahydrofuran, 811 mg (5.0 mmol) of 1,1'-carbonyldiimidazole was added, and the mixture was stirred at room temperature for 16 hours. The solvent was distilled off and the residue was dissolved in chloroform. The solution was washed with water and dried. The solvent was distilled off and the residue was recrystallized from ethanol/chloroform/ether to give 514 mg of the desired product (65.7% yield, white crystals).

NMR (200 MHz, DMSO-d$_6$) δ:1.97 (2H, quint., J=7.2 Hz), 3.12 (2H, t, J=7.4 Hz), 4.05 (2H, t, J=7.0 Hz), 7.16–7.27 (4H, m), 7.65 (1H, dt, J=1.4, 6.6 Hz), 8.35 (2H, d, J=6.0 Hz), 11.43(1H, s).

IR (KBr) cm$^{-1}$: 1710, 1660, 1585, 1460, 1410, 805, 760, 720.

EXAMPLE 194

Synthesis of 3-[3-(4-pyridylthio)propyl]-quinazoline-2(1H)-thion-4(3H)-one

Under nitrogen atmosphere, to a solution of 1.48 g (5.15 mmol) of 4-[3-(2-aminobenzoylamino)propylthio]pyridine in 30 ml of tetrahydrofuran, 1.84 g (10.3 mmol) of 1,1'-thiocarbonyldiimidazole was added, and the mixture was stirred at room temperature for 64 hours. The solvent was distilled off and the residue was washed with chloroform/ether to give 1.16 g of the desired product (68.5% yield, pale brown crystals).

NMR (200 MHz, DMSO-d$_6$) δ:2.09 (2H, quint., J=7.6 Hz), 3.16 (2H, t, J=7.2 Hz), 4.56 (2H, t, J=7.6 Hz), 7.27 (2H, dd, J=1.6, 4.6 Hz), 7.30–7.42 (2H, m), 7.74 (1H, ddd, J=1.5, 7.0, 7.2 Hz), 7.67 (1H, dd, J=1.4, 8.0 Hz), 8.36 (2H, dd, J=1.6, 4.6 Hz).

IR (KBr) cm$^{-1}$: 2920, 2850, 1685, 1625, 1585, 1410, 1140, 760, 720.

EXAMPLE 195

Synthesis of 3-[4-(2-pyridylthio)butyl]-quinazoline-2,4(1H,3H)-dione

Under nitrogen atmosphere, to a solution of 452 mg (1.5 mmol) of 2-[4-(2-aminobenzoylamino)butylthio]pyridine in 20 ml of tetrahydrofuran, 486 mg (3.0 mmol) of 1,1'-carbonyldiimidazole was added, and the mixture was stirred at room temperature for 16 hours. The solvent was distilled off and the residue was dissolved in chloroform. The solution was washed with water and dried. The solvent was distilled off and the residue was recrystallized from chloroform/ether to give 337 mg of the desired product (68.8% yield, white crystals).

NMR (200 MHz, CDCl$_3$) δ:1.75–1.99 (4H, m), 3.25 (2H, t, J=6.8 Hz), 4.15 (2H, t, J=7.0 Hz), 6.94 (1H, ddd, J=1.2, 5.0, 7.2 Hz), 7.12–7.23 (3H, m), 7.44 (1H, ddd, J=2.0, 7.8, 8.0 Hz), 7.96 (1H, m), 8.13 (1H, dd, J=1.4, 8.0 Hz), 8.39 (1H, m), 10.32 (1H, s).

IR (KBr) cm$^{-1}$: 3190, 1720, 1635, 765.

EXAMPLE 196

Synthesis of 3-[4-[2-pyridylthio)butyl]quinazoline-2(1H)-thion-4(3H)-one

In a solution of 1.94 g (5.18 mmol) of 2-[4-(2-aminobenzoylamino)butylthio]pyridine dihydrochloride in 10 ml of methanol, 6.5 ml (13.0 mmol) of 2N aqueous sodium hydroxide was added, and the mixture was stirred at room temperature for 1 hour. Water was added to the reaction mixture, and the mixture was extracted with chloroform. The extract was dried and the solvent was distilled off. The resulting free amine was used in the subsequent reaction without further purification.

Under nitrogen atmosphere, to a solution of the above free amine in 20 ml of tetrahydrofuran, 1.43 g (8.0 mmol) of 1,1'-thiocarbonyldiimidazole was added, and the mixture was stirred at room temperature for 16 hours. The solvent was distilled off and the residue was dissolved in chloroform. The solution was washed with water and dried. The solvent was distilled off and the residue was recrystallized from chloroform/ether to give 0.856 g (62.2% yield, pale brown solid).

NMR (200 MHz, CDCl$_3$) δ:1.76–2.08 (4H, m), 3.25 (2H, t, J=7.0 Hz), 4.56 (2H, t, J=7.8 Hz), 6.95 (1H, ddd, J=1.0, 5.0, 7.2 Hz), 7.09–7.18 (2H, m), 7.27–7.35 (1H, m), 7.45 (1H, ddd, J=1.4, 7.4, 8.0 Hz), 7.61–7.70 (1H, m), 8.13 (1H, dd, J=1.6, 8.0 Hz), 8.39–8.43 (1H, m), 10.82 (1H, s).

EXAMPLE 197

Synthesis of 1,3-bis[3-(4-pyridylthio)propyl]-quinazoline-2,4(1H,3H)-dione dihydrochloride i) Synthesis of 1,3-bis[3-(4-pyridylthio)propyl]-quinazoline- 2,4(1H,3H)-dione To a solution of 1.62 g (10 mmol) of benzoylene urea and 1.88 g (10 mmol) of 4-(3-chloropropylthio)pyridine in 50 ml of dimethylformamide, 1.65 ml (11 mmol) of 1,8-diazabicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:ethyl acetate/ethanol=25:1 to 10:1 to 2:1). First, 0.973 g of 3-[3-(4-pyridylthio)propyl]quinazoline-2, 4-(1H,3H)-dione (31.1% yield, pale yellow crystals) was obtained, and then, 0.487 g of the desired product was obtained (10.4% yield, yellow oil).

NMR (200 MHz, CDCl$_3$) δ:2.04–2.24 (4H, m), 3.02–3.16 (4H, m), 4.27–4.35 (4H, m), 7.08–7.30 (6H, m), 7.62 (1H, ddd, J=1.8, 7.0, 7.2 Hz), 8.23 (1H, dd, J=1.6, 8.0 Hz), 8.35–8.41 (4H, m).

ii) Synthesis of 1,3-bis[3-(4-pyridylthio)propyl]-quinazoline- 2,4(1H,3H)-dione dihydrochloride To a solution of 150 mg (0.323 mmol) of the above free amine in 15 ml of methanol, 30 ml of 10% hydrochloric acid/methanol was added, and the mixture was stirred at room temperature for 2 hours. The solvent was distilled off and the residue was purified by recrystallization (solvent:ethanol/ether) to give 80.0 mg of the desired product (46.1% yield, pale yellow crystals).

NMR (200 MHz, D₂O) δ:2.11–2.30 (4H, m), 3.27–3.50 (4H, m), 4.10–4.40 (4H, m), 7.32–7.48 (2H, m), 7.73–7.82 (5H, m), 8.02 (1H, t, J=7.0 Hz), 8.39 (4H, d, J=6.6 Hz).

EXAMPLE 198

Synthesis of 1,3-bis[4-(2-pyridylthio)butyl]-quinazoline-2,4(1H,3H)-dione

To a solution of 1.62 g (10 mmol) of benzoylene urea and 2.02 g (10 mmol) of 2-(4-chlorobutylthio)pyridine in 50 ml of dimethylformamide, 1.65 ml (11mmol) of 1,8-diazabicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:hexane/ethyl acetate=2:1 to 1:2 ). First, 221 mg of the desired product was obtained (4.6% yield, yellow oil), and then, 292 mg of 3-[4-(2-pyridylthio)butyl]quinazoline-2,4(1H,3H)-dione was obtained (8.9% yield, white crystals).

NMR (200 MHz, CDCl₃) δ:1.76–1.94 (8H, m), 3.18–3.29 (4H, m), 4.08–4.20 (4H, m), 6.90–7.00 (2H, m), 7.12–7.23 (4H, m), 7.39–7.51 (2H, m), 7.63 (1H, ddd, J=1.6, 7.0, 7.4 Hz), 8.22 (1H, dd, J=1.8, 8.0 Hz), 8.37–8.42 (2H, m).

EXAMPLE 199

Synthesis of 1-(4-pyridylthio)methyl-3-[4-(4-pyridylthio)butyl]-quinazoline-2,4(1H,3H)-dione dihydrochloride i) Synthesis of 1-(4-pyridylthio)methyl-3-[4-(4-pyridylthio)butyl]quinazoline-2,4(1H,3H)-dione To a solution of 491 mg (1.5 mmol) of 3-[4-(4-pyridylthio)butyl]quinazoline-2,4(1H,3H)-dione and 287 mg (1.8 mmol) of 4-chloromethylthiopyridine in 15 ml of dimethylformamide, 0.27 ml (1.8 mmol) of 1,8-diazabicyclo[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by flash column chromatography (eluent:ethyl acetate/hexane=2:1 to 4:1 to ethyl acetate) to give 0.315 g of the desired product (46.7% yield, colorless oil).

NMR (200 MHz, CDCl₃) δ:1.68–1.90 (4H, m), 3.02 (2H, t, J=7.0 Hz), 4.10 (2H, t, J=7.2 Hz), 5.72 (2H, s), 7.10 (2H, dd, J=1.5, 4.8 Hz), 7.20 (1H, d, J=8.6 Hz), 7.33 (1H, dt, J=1.0, 7.0 Hz), 7.42 (2H, dd, J=1.6, 4.6 Hz), 7.72 (1H, ddd, J=1.8, 7.0, 7.4 Hz), 8.25 (1H, dd, J=1.4, 8.0 Hz), 8.35 (2H, dd, J=1.4, 4.8 Hz), 8.48 (2H, dd, J=1.6, 4.6 Hz).

IR (neat) cm⁻¹: 3030, 2960, 1705, 1660, 1575, 1480, 1400, 1260, 805, 760, 710.

ii) Synthesis of 1-(4-pyridylthio)methyl-3-[4-(4-pyridylthio)butyl]quinazoline-2,4(1H,3H)-dione dihydrochloride To a solution of 200 mg (0.44 mmol) of the above free amine in 10 ml of methanol, 50 ml of 10% hydrochloric acid/methanol was added, and the mixture was stirred at room temperature for 2 hours. The solvent was distilled off and the residue was purified by recrystallization (solvent:ethanol/ether) to give 183 mg of the desired product (78.8% yield, white crystals), mp. 148°–150° C.

EXAMPLE 200

Synthesis of 1,3-bis[4-(4-pyridylthio)butyl]-quinazoline-2(1H)-thion-4(3H)-one dihydrochloride i) Synthesis of 1,3-bis[4,4-pyridylthio)butyl]quinazoline-2(1H)-thion-4(3H)-one To a solution of 515 mg (1.5 mmol) of 3-[4-(4-pyridylthio)butyl] quinazoline-2(1H)-thion-4(3H)-one and 332 mg (1.65 mmol) of 4-(4-chlorobutylthio)pyridine in 15 ml of dimethylformamide, 0.25 ml (1.65 mmol) of 1,8-diazabicyclo-[5.4.0]-7-undecene was added, and the mixture was stirred at 80° C. for 16 hours. After cooling, water was added to the reaction mixture, and the mixture was extracted with ethyl acetate. The extract was dried and the solvent was distilled off. The residue was purified by flash column chromatography (eluent:ethyl acetate/ethanol=25:1 to 10:1) to give 0.694 mg of the desired product (97.1% yield; colorless oil).

NMR (200 MHz, CDCl₃) δ:1.78–2.06 (8H, m), 3.02–3.11 (4H, m), 3.34 (2H, t, J=7.0 Hz), 4.17 (2H, t, J=7.0 Hz), 7.12 (4H, d, J=5.4 Hz), 7.35–7.52 (2H, m), 7.69 (1H, ddd, J=1.4, 7.0, 7.0 Hz), 8.22 (1H, dd, J=1.4, 8.0 Hz), 8.40 (4H, s).

IR (neat) cm⁻¹: 2960, 1700, 1655, 1610, 1480, 1400, 1100, 760, 695.

ii) Synthesis of 1,3-bis[4-(4-pyridylthio)butyl]quinazoline- 2(1H)-thion-4(3H)-one dihydrochloride To a solution of 449 mg (0.94 mmol) of the free amine in 30 ml of methanol, 100 ml of 10% hydrochloric acid/methanol was added, and the mixture was stirred at room temperature for 2 hours. The solvent was distilled off and the residue was purified by recrystallization (solvent:ethanol/ether) to give 450 mg of the desired product (86.9% yield, white crystals), mp. 87°–89° C.

EXAMPLE 201

Synthesis of 1,3-bis[3-(4-pyridylthio)propyl]quinazoline-2(1H)-thion-4(3H)-one

To a solution of 494 mg (1.5 mmol) of 3-[4-(4-pyridylthio)propyl]quinazoline-2(1H)-thion-4(3H)-one and 338 mg (1.8 mmol) of 4-(3-chloropropylthio)pyridine in 15 ml of dimethylformamide, 0.27 ml (1.8 mmol) of 1,8-diazabicyclo [5.4.0]-7-undecene was added, and the mixture was stirred at room temperature for 3 hours and at 80° C. for 16 hours. After cooling, the solvent was distilled off and the residue was dissolved in chloroform. The solution was washed with water and dried. The solvent was distilled off and the residue was purified by column chromatography (eluent:ethyl acetate/ethanol=25:1 to 10:1 to 5:1) to give 0.73 g of the desired product (100% yield, yellow, oil).

NMR (200 MHz, CDCl₃) δ:2.21 (4H, quint., J=6.8 Hz), 3.12 (4H, q, J=7.2 Hz), 3.42 (2H, t, J=7.0 Hz), 4.30 (2H, t, J=7.2 Hz), 7.12 (4H, s), 7.35–7.51 (2H, m), 7.70 (1H, ddd, J=1.6, 7.0, 7.2 Hz), 8.20 (1H, dd, J=1.6, 7.8 Hz), 8.38 (4H, s).

EXAMPLE 202

Synthesis of 1,3-bis[4-(4-pyridylthio)butyl]-5,5-dimethylhydantoin dihydrochloride i) Synthesis of 1,3-bis[4-(4-pyridylthio)butyl]-5,5-dimethylhydantoin To a suspension of 96 mg (2.4 mmol) of 60% sodium hydride (oily) in 15 ml of dimethylformamide, 587 mg (2.0 mmol) of 3-[4-(4-pyridylthio)butyl]-5,5-dimethylhydantoin was added, and the mixture was stirred at room temperature for 10 minutes. To this reaction mixture, 807 mg (4.0 mmol) of 4-(4-chlorobutylthio)pyridine was added with stirring under ice-cooling, and the mixture was stirred at 80° C. for 16 hours. After cooling, water was added to the reaction mixture, and the mixture was extracted with ethyl acetate. The extract was dried and the solvent was distilled off. The residue was purified by column chromatography (eluent:-ethyl acetate/ethanol=10:1) to give 0.74 g of the desired product (80.7% yield, yellow oil).

NMR (200 MHz, CDCl$_3$) δ:1.37 (6H, s), 1.68–1.88 (8H, m), 2.98–3.07 (4H, m), 3.29 (2H, t, J=7.0 Hz), 3.55 (2H, t, J=6.6 Hz), 7.12 (4H, d, J=4.6 Hz), 8.39 (4H, s).

IR (neat) cm$^{-1}$: 3030, 2935, 1760, 1700, 1575, 1455, 800, 710.

ii) Synthesis of 1,3-bis[4-(4-pyridylthio)butyl]-5,5-dimethylhydantoin dihydrochloride To a solution of 0.68 g (1.48 mmol) of the above free amine in 30 ml of methanol, 50 ml of 10% hydrochloric acid/methanol was added, arid the mixture was stirred at room temperature for 2 hours. The solvent was distilled off to give 0.91 g of the desired product (100% yield, yellow oil).

NMR (200 MHz, D$_2$O) δ:1.40 (6H, ), 1.76–1.88 (8H, m), 3.23–3.32 (4H, m), 3.35–3.42 (2H, m), 3.57 (2H, t, J=6.2 Hz), 7.80 (4H, dd, J=1.4, 7.2 Hz), 8.42 (4H, d, J=7.0 Hz).

EXAMPLE 203

Synthesis of 1,2-bis[N-[4-(4-pyridylthio)butyl]-N-propionylamino]benzene dihydrochloride i) Synthesis of 1,2-dipropionylaminobenzene To a solution of 3.24 g (30 mmol) of O-phenylenediamine in 9.7 ml (120 mmol of pyridine, 11.54 ml (90 mmol) of propionic anhydride was added at room temperature, and the mixture was stirred for 16 hours. The resulting precipitate was filtered and washed with other, followed by drying to give 5.24 of the desired product (80.1% yield, white crystals).

NMR (200 MHz, DMSO-d$_6$) δ:1.09 (6H, t, J=7.8 Hz), 2.35 (4H, q, J=7.6 Hz), 7.12 (2H, dd, J=3.4, 6.0 Hz), 7.51 (2H, dd, J=3.4, 6.0 Hz), 9.25 (2H, s).

ii) Synthesis of 1,2-bis[N-(4-chlorobutyl)-N-propionylamino]benzene

To a suspension of 3.27 g (15 mmol) of 1,2-dipropionylaminobenzene, 4.32 ml (37.5 mmol) of 4-bromo-1-chlorobutane, and 0.96 g (3.0 mmol) of tetrabutylammonium bromide in 25 ml of toluene, 5.6 ml of 50% aqueous sodium hydroxide was added at room temperature, and the mixture was stirred for 16 hours. The organic layer was separated, washed with saturated aqueous sodium chloride, and dried. The solvent was distilled off and the residue was purified by column chromatography (eluent:hexane/ethyl acetate=2:1 to 1:1 to 1:2 to 1:4) to give 0.76 g of the desired product (12.6% yield, white crystals).

NMR (200 MHz, CDCl$_3$) δ:1.09 (6H, t, J=7.8 Hz), 1.58–1.90 (10H, m), 2.07–2.26 (2H, m), 2.69–2.83 (2H, m), 3.51 (4H, t, J=5.5 Hz), 4.24–4.40 (2H, m), 7.20 (2H, dd, J=3.6, 6.0 Hz), 7.43 (2H, dd, J=3.6, 6.0 Hz).

iii) Synthesis of 1,2-bis[N-[4-(4-pyridylthio)butyl]-N-propionylamino]benzene

To a solution of 525 mg (4.7 mmol) of 4-mercaptopyridine and 265 mg (4.7 mmol) of potassium hydroxide in 20 ml of dimethyl sulfoxide, 760 mg (1.89 mmol) of 1,2-bis[N-(4-chlorobutyl)-N-propionylamino]benzene was added at room temperature, and the mixture was stirred for 2 hours. The reaction mixture was poured into water and the mixture was extracted with ethyl acetate. The extract was dried and the solvent was distilled off. The residue was purified by column chromatography (eluent:ethyl acetate to ethyl acetate/ethanol=20:1 to 10:1 to 5:1) to give 0.84 g of the desired product (81.0% yield, pale yellow crystals).

NMR (200 MHz, CDCl$_3$) δ:1.62–1.74 (8H, m), 1.82 (6H, s), 2.84–2.99 (6H, m), 2.84–2.99 (6H, m), 4.22–4.38 (2H, m), 7.08 (4H, d, J=5.8 Hz), 7.14 (2H, dd, J=3.6, 5.8 Hz), 7.42 (2H, dd, J=3.6, 5.8 Hz), 8.38 (4H, s).

iv) Synthesis of 1,2-bis[N-[4-(4-pyridylthio)butyl]-N-propionylamino] benzene dihydrochloride To a solution of 840 mg (1.53 mmol) of 1,2-bis[N-[4-(4-pyridylthio)butyl]-N-propionylamino]benzene in 20 ml of methanol, 80 ml of 10% hydrochloric acid/methanol was added, and the mixture was stirred for 30 minutes. The solvent was distilled off and the residue was recrystallized from ethanol/ether to give 707 mg of the desired product (74.1% yield, pale yellow crystals).

NMR (200 MHz, D$_2$O) δ:0.95 (3H, t, J=7.2 Hz), 1.80–1.15 (3H, m), 1.62–1.95 (10H, m), 2.10–2.30 (2H, m), 2.74–2.90 (2H, m), 3.10–3.20 (4H, m), 4.04–4.36 (2H, m), 7.22–7.52 (4H, m), 7.69–7.73 (4H, m), 8.32–8.37 (4H, m).

REFERENCE EXAMPLE 1

Synthesis of 4-[3-(t-butoxycarbonylamino)propylsulfinyl]pyridine

To a solution of 4.03 g (15.0 mmol) of 4-[3-(t-butoxycarbonylamino)propylthio]pyridine in 100 ml of methylene chloride, 3.05 g (15.0 mmol) of m-chloroperbenzoic acid was added with stirring under ice-cooling, and the mixture was stirred at the same temperature for 1 hour. The reaction mixture was washed two times with saturated aqueous sodium bicarbonate and dried over anhydrous magnesium sulfate. The solvent was distilled off and the residue was purified by column chromatography (eluent:ethyl acetate/ethanol=10:1) to give 3.37 g of the desired compound (78.9% yield, colorless crystals).

NMR (90 MHz, CDCl$_3$) δ:1.43 (9H, s), 1.50–2.30 (2H, m), 2.60–3.10 (2H, m), 3.26 (2H, m), 4.84 (1H, br), 7.54 (2H, m), 8.78 (2H, m).

REFERENCE EXAMPLE 2

Synthesis of 4-[3-(t-butoxycarbonylamino)propylsulfonyl]pyridine

To a solution of 4.03 g (15.0 mmol) of 4-[3-(t-butoxycarbonylamino)propylthio]pyridine in 100 ml of methylene chloride, 6.70 g (33.0 mmol) of m-chloroperbenzoic acid was added with stirring under ice-cooling, and the mixture was stirred at room temperature for 18 hour. The reaction mixtures was washed two times with saturated aqueous sodium bicarbonate and dried over anhydrous magnesium sulfate. The solvent was distilled off and the residue was purified by column chromatography (eluent:ethyl acetate) to give 3.68 g of the desired compound (81.6% yield, colorless crystals).

NMR (90 MHz, CDCl$_3$) δ:1.40 (9H, s), 1.75–2.13 (2H, m), 3.06–3.38 (4H, m), 4.70 (1H, br), 7.75 (2H, m), 8.90 (2H, m).

REFERENCE EXAMPLE 3

Synthesis of 4-(4-chlorobutylthio)pyridine

To a suspension of 33.35 g (0.30 mol) of 4-mercaptopyridine and 51.44 g (0.30 mol) of 1-bromo-4-chlorobutane in 500 ml of ethanol, 41.9 ml (0.30 mol) of triethylamine was added, and the mixture was stirred at room temperature for 5 hours. The solvent was distilled off and chloroform was added to the residue. The mixture was washed with water and dried over anhydrous magnesium sulfate. The solvent was distilled off and the residue was purified by column chromatography (eluent:ethyl acetate/n-hexane=1:1 ) to give 54.27 g of the desired compound (89.7% yield, colorless oil).

NMR (200 MHz, CDCl$_3$) δ:1.92 (4H, m), 3.02 (2H, t, J=6.8 Hz), 3.59 (2H, t, J=6.2 Hz), 7.12 (2H, dd, J=4.6, 1.6 Hz), 8.40 (2H, dd, J=4.0, 1.6 Hz).

REFERENCE EXAMPLE 4

Synthesis of 4-(3-chloropropylthio)pyridine

The desired compound was synthesized in the same manner as described in Reference Example 3.

NMR (200 MHz, CDCl$_3$) δ:2.17 (2H, m), 3.17 (2H, t, J=7 Hz), 3.70 (2H, t, J=6 Hz), 7.14 (2H, dd, J=4.6, 1.6 Hz), 8.42 (2H, dd, J=4.6, 1.6 Hz).

REFERENCE EXAMPLE 5

Synthesis of 4-(2-chloroethylthio)pyridine

The desired compound was synthesized in the same manner as described in Reference Example 3.

NMR (200 MHz, CDCl$_3$) δ:3.34 (2H, t, J=8.4 Hz), 3.70 (2H, t, J=8.0 Hz), 7.15 (2H, dd, J=1.6, 4.4 Hz), 8.45 (2H, dd, J=1.4, 4.4 Hz).

REFERENCE EXAMPLE 6

Synthesis of 2-(4-chlorobutylthio)pyridine

This compound was synthesized by the same method as used in Reference Example 3.

NMR (200 MHz, CDCl$_3$) δ:1.70–2.05 (4H, m), 3.21 (2H, t, J=6.8 Hz), 3.58 (2H, t, J=6.2 Hz), 6.98 (1H, ddd, J=1.2, 5.0, 7.4 Hz), 7.17 (1H, d, J=8.0 Hz), 7.48 (1H, ddd, J=1.8, 7.2, 7.8 Hz), 8.40–8.45 (1H, m).

REFERENCE EXAMPLE 3

Synthesis of 4-[3-(2-aminobenzoylamino)propylthio]pyridine dihydrochloride i) Synthesis of 4-[3-(2-aminobenzoylamino)propylthio] pyridine To a solution of 4.82 g (20 mmol) of 4-(3-aminopropylthio)pyridine dihydrochloride in 20 ml of methanol, 25 ml (50 mmol) of 2N aqueous sodium hydroxide was added, and the mixture was stirred at room temperature for 1 hour. Water was added to the reaction mixture and the mixture was extracted with chloroform. The extract was dried and the solvent was distilled off. The resulting free amine was used in the subsequent reaction without further purification.

To a solution of the above free amine in 30 ml of dimethylformamide, 3.26 g (20 mmol) of isotonic anhydride was added, and the mixture was stirred at 80° C. for 30 minutes. After cooling, the solvent was distilled off. The residue was dissolved in chloroform, and the solution was washed with aqueous sodium bicarbonate and dried. The solvent was distilled off and the residue was purified by column chromatography (eluent:chloro- form/methanol= 20:1) to give 5.49 g of the desired product (95.5% yield, yellow oil).

NMR (200 MHz, CDCl$_3$) δ:2.04 (2H quint., J=7.0 Hz), 3.08 (2H, t, J=7.2 Hz), 3.58 (2H, q, J=6.2 Hz), 5.51 (2H, s), 6.25 (1H, s), 6.1–6.71 (2H, m), 7.12 (2H, dd, J=1.4, 4.6 Hz), 7.18–7.32 (2H, m), 8.39 (2H, dd, J=1.6, 4.8 Hz).

ii) Synthesis of 4-[3-(2-aminobenzoylamino)propylthio] pyridine dihydrochloride

To a solution of 2.39 g (8.32 mmol) of the above free amine in 30 ml of methanol, 200 ml of 10% hydrochloric acid/methanol was added, and the mixture was stirred at room temperature for 2 hours. The solvent was distilled off and the residue was purified by recrystallization (solvent:ethanol/ether) to give 2.23 g of the desired product (74.4% yield, white crystals).

NMR (200 MHz, D$_2$O) δ:2.15 (2H, quint., J=7.0 Hz), 3.36 (2H, t, J=7.2 Hz), 3.60 (2H, t, J=6.6 Hz), 7.45–7.59 (2H, m), 7.65–7.74 (1H, m), 7.79–7.85 (3H, m), 8.41 (2H, d, J=7.4 Hz).

IR (KBr) cm$^{-1}$: 1625, 1600, 1480, 1120, 815, 100, 740.

REFERENCE EXAMPLE 8

Synthesis of 2-[4-(2-aminobenzoylamino)butylthio]pyridine dihydrochloride i) Synthesis of 2-[4-(2-aminobenzoylamino)butylthio]pyridine To a suspension of 6.25 g (20 mmol) of 2-(4-phthalimidobutylthio)pyridine in 150 ml of ethanol, 2.91 ml (60 mmol) of hydrazine monohydrate was added, and the mixture was heated under reflux for 2 hours. After cooling, water was added to the reaction mixture, and the mixture was extracted with chloroform. The extract was dried and the solvent was distilled off. The resulting free amine was used in the subsequent reaction without further purification.

To a solution of the above free amine in 30 ml of dimethylformamide, 3.26 g (20 mmol) of isatoic acid anhydride was added, and the mixture was stirred at 80° C. for 1 hour. After cooling, the solvent was distilled off. The residue was dissolved in chloroform, and the solution was washed with aqueous sodium bicarbonate and dried. The solvent was distilled off and the residue was purified by column chromatography (eluent:hexane/ethyl acetate=1:1) to give 2.61 g (43.5% yield, yellow oil).

NMR (200 MHz, CDCl$_3$) δ:1.70–1.82 (4H, m), 3.22 (2H, t, J=7.0 Hz), 3.48 (2H, q, J=6.6 Hz), 5.50 (2H, s), 6.29 (1H, s), 6.57–6.70 (2H, m), 6.95 (1H, ddd, J=1.2, 4.8, 7.4 Hz), 7.15–7.31 (3H, m), 7.46 (1H, dt, J=1.8, 7.4 Hz), 8.37 (1H, dd, J=1.2, 5.2 Hz).

ii) Synthesis of 2-[4-(2-aminobenzoylamino)butylthio] pyridine dihydrochloride

125

To a solution of 606 mg (2.01 mmol) of the above free amine in 10 ml of methanol, 50 ml of 10% hydrochloric acid and methanol was added, and the mixture was stirred at room temperature for 2 hours. The solvent& was distilled off and the residue was purified by recrystallization (solvent:isopropylalcohol/methanol/ether) to give 710 mg of the desired product (94.5% yield, white crystals).

NMR (200 MHz, $D_2O$) δ:1.84–1.92 (4H, m), 3.37–3.49 (4H, m), 7.42–7.54 (2H, m), 7.61–7.74 (3H, m), 7.91 (1H, d, J=8.4 Hz), 8.29 (1H, dt, J=1.6, 8.0 Hz), 8.49 (1H, d, J=5.8 (Hz).

IR (KBr) $cm^{-1}$: 1645, 1590, 1545, 1320, 1140, 760.

REFERENCE EXAMPLE 9

Synthesis of 4-[4-(2-aminobenzoylamino)butylthio]pyridine dihydrochloride i) Synthesis of 4-[4-(2-aminobenzoylamino)butylthio]pyridine To a suspension of 6.25 g (20 mmol) of 4-(4-phthalimidobutylthio)pyridine in 150 ml of ethanol, 2.91 ml (60 mmol) of hydrazine monohydrate was added, and the mixture was heated under reflux for 2 hours. After cooling, water was added to the reaction mixture, and the mixture was extracted with chloroform. The extract was dried and the solvent was distilled off. The resulting free amine was used in the subsequent reaction without further purification.

To a solution of the above free amine in 30 ml of dimethylformamide, 3.26 g (20 mmol) of isatoic anhydride was added, and the mixture was stirred at 80° C. for 1 hours. After cooling, the solvent was distilled off and the residue was dissolved in chloroform. The solution was washed with aqueous sodium bicarbonate and dried. The solvent was distilled off and the residue was purified by column chromatography (eluent:hexane/ethyl acetate=1:1) to give 1.74 g of the desired product (28.9% yield, pale orange solid).

NMR (200 MHz, $CDCl_3$) δ:1.76–1.83 (4H, m), 3.03 (2H, t, J=7.0 Hz), 3.46 (2H, q, J=6.2 Hz), 5.49 (2H, s), 6.18 (1H, s), 6.58–6.70 (2H, m), 7.10 (2H, dd, J=1.6, 4.6 Hz), 7.15–7.29 (2H, m), 8.37 (2H, dd, J=1.4, 6.2 Hz).

ii) Synthesis of 2-[4-(2-aminobenzoylamino)butylthio]pyridine dihydrochloride

To a solution of 1.74 g (5.77 mmol) of the above free amine in 30 ml of methanol, 100 ml of 10% hydrochloric acid and methanol was added, and the mixture was stirred at room temperature for 2 hours. The solvent was distilled off and the residue was purified by recrystallization (solvent:ethanol/ether) to give 1.68 g of the desired product (77.8% yield, white crystals).

NMR (200 MHz, $D_2O$) δ:1.85–1.90 (4H, m), 3.31 (2H, t, J=6.8 Hz), 3.47 (2H, t, J=6.4 Hz), 7.45–7.56 (2H, m), 7.64–7.73 (2H, m), 7.79 (2H, d, J=7.2 Hz), 8.37 (2H, d, J=7.2 Hz).

IR (KBr) $cm^{-1}$: 3315, 1620, 1540, 1110, 800, 754.

What is claimed is:

1. A pyridine derivative of the formula (III):

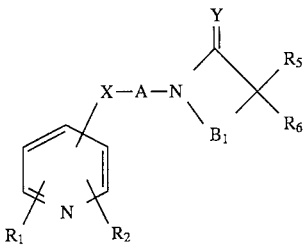

wherein $R_1$ and $R_2$ are the same or different and are a hydrogen atom, a halogen atom, a lower alkyl group, a lower alkenyl group, a lower alkoxy group, hydroxy group, nitro group, cyano group, amino group, carbamoyl group, an acylamino group, a lower alkylamino group, a lower alkenylamino group or an aralkylamino group, X is an oxygen atom or —S(O)n—, wherein n is 0, 1 or 2; A is a bivalent $C_{1-15}$ hydrocarbon residue whose branched moiety may have a substituent, Y is an oxygen atom, $R_5$ and $R_6$ are the same or different and are a hydrogen atom, a lower alkyl group, a lower alkenyl group, a halogeno lower alkyl group, a halogeno lower alkenyl group, an optionally substituted aralkyl group or an optionally substituted aryl group, or $R_5$ and $R_6$ are joined to form a group of the formula:

wherein $R_7$ and $R_8$ are the same or different and are a hydrogen atom, a lower alkyl group, a lower alkenyl group, a halogeno lower alkyl group, a halogeno lower alkenyl group, an optionally substituted aralkyl group or an optionally substituted aryl group, or $R_7$ and $R_8$ are linked together to form a ring, $B_1$ is

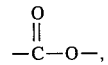

or a salt or solvate thereof.

2. A pyridine derivative according to claim 1, wherein $R_1$ and $R_2$ are the same or different and are a hydrogen atom, amino group or an acylamino group, X is an oxygen or sulfur atom, A is a bivalent $C_{1-6}$ hydrocarbon residue, $R_5$ and $R_6$ are the same or different and are a hydrogen atom or a lower alkyl, or $R_5$ and $R_6$ are joined to form a group of the formula:

wherein $R_7$ and $R_8$ are the same or different and are a hydrogen atom, a lower alkyl group, an optionally substituted aralkyl group or an optionally substituted aryl group.

3. The pyridine derivative according to claim 1 which is 4-(5,5-dimethyloxazolidine-2,4-dione)methylthiopyridine.

4. A pharmaceutical composition which comprises a pharmaceutically effective amount of the compound of claim 1 and a pharmaceutically acceptable carrier.

5. A method for providing anti-inflammatory activity which comprises administering an effective amount of the pharmaceutical composition of claim 4.

* * * * *